(12) United States Patent
Bregman et al.

(10) Patent No.: US 9,663,508 B2
(45) Date of Patent: May 30, 2017

(54) BIARYL ACYL-SULFONAMIDE COMPOUNDS AS SODIUM CHANNEL INHIBITORS

(71) Applicant: AMGEN INC., Thousand Oaks, CA (US)

(72) Inventors: Howard Bregman, Melrose, MA (US); Nagasree Chakka, Lexington, MA (US); Erin F. Dimauro, Cambridge, MA (US); Hua Gao, Canton, MA (US); Hakan Gunaydin, Somerville, MA (US); Hongbing Huang, Bellarie, TX (US); Philip R. Olivieri, Charlestown, MA (US); Laurie Schenkel, Boston, MA (US); Matthew Weiss, Boston, MA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 15/026,740

(22) PCT Filed: Oct. 1, 2014

(86) PCT No.: PCT/US2014/058699
§ 371 (c)(1),
(2) Date: Apr. 1, 2016

(87) PCT Pub. No.: WO2015/051043
PCT Pub. Date: Apr. 9, 2015

(65) Prior Publication Data
US 2016/0214971 A1   Jul. 28, 2016

Related U.S. Application Data

(60) Provisional application No. 61/885,372, filed on Oct. 1, 2013.

(51) Int. Cl.
| | |
|---|---|
| *C07D 417/12* | (2006.01) |
| *C07D 213/64* | (2006.01) |
| *C07D 213/26* | (2006.01) |
| *C07D 213/643* | (2006.01) |
| *C07D 213/70* | (2006.01) |
| *C07D 401/04* | (2006.01) |
| *C07D 405/12* | (2006.01) |

(52) U.S. Cl.
CPC ......... *C07D 417/12* (2013.01); *C07D 213/26* (2013.01); *C07D 213/64* (2013.01); *C07D 213/643* (2013.01); *C07D 213/70* (2013.01); *C07D 401/04* (2013.01); *C07D 405/12* (2013.01)

(58) Field of Classification Search
CPC .. C07D 417/12; C07D 213/26; C07D 213/70; C07D 213/643; C07D 405/12; C07D 401/04; C07D 213/64
See application file for complete search history.

(56) References Cited

U.S. PATENT DOCUMENTS 8,101,647 B2   1/2012  Chafeev et al.
8,772,343 B2 *  7/2014  Bell ..................... C07C 311/51
                                                    514/601

FOREIGN PATENT DOCUMENTS

| WO | 2009/065406 | 5/2009 |
| WO | 2012/007868 A2 | 1/2012 |
| WO | 2012/007869 A2 | 1/2012 |
| WO | 2012/0078777 A2 | 1/2012 |

OTHER PUBLICATIONS

Berge, et al., 1977, Pharmaceutical Salts, J Pharm Sci, 66: 1-19.
Binder et al., 2008, Nature Clinical Practice Neurology, 4:329-337.
Cox, et al, Nature, 2006, An SCN9A channelopathy causes congenital inability to experience pain, 444:894-898.
Devigili, et. al., 2014, Pain, Paroxysmal itch caused by gain-of-function Nav1.7 mutation, 155:9, 1702-1707.
Dib-Hajj, S.D., et al., 1998, Proc. Natl. Academy of Science US, 95:15, 8963-8968.
Do and Bean, 2003 Neuron, 39:109-120.
Drenth J.P. et al. 2004, J. Med. Genet., 41:171-174.
Ettinger and Argoff, 2007, Neurotherapeutics, 4:75-83.
Fertleman C. R., et al., 2006, SCN9A mutations in paroxysmal extreme pain disorder: allelic variants underlie distinct ahannel defects and phenotypes, Neuron 52:767-774.
Gillet L., et. al., 2009 J Biol Chem, 284:13, 8680-8691.
Goldberg Y. P., et al., 2007, Loss-of-function mutations in the Nav1.7 gene underlie congenital indifference to pain in multiple human populations, Clin Genet, 71:311-319.
Goldin, A. L., 2001, Resurgence of sodium channel research, Ann Rev Physiol, 63:871-894.
Gonzalez, et al., 2006, Methods and Principles in Medicinal Chemistry, 29:168-192.

(Continued)

*Primary Examiner* — Sudharkar Katakam
(74) *Attorney, Agent, or Firm* — Elsa D. Lemoine

(57) ABSTRACT

The present invention provides compounds of Formula (Ia), and pharmaceutically acceptable salts thereof. The compounds are useful as inhibitors of voltage-gated sodium channels, in particular Nav 1.7.

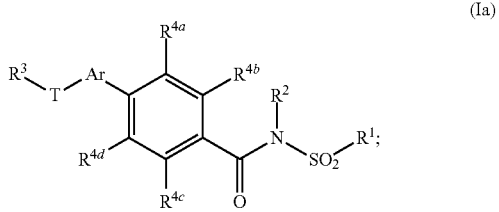

(Ia)

as described in the specification. The compounds are useful for the treatment of diseases treatable by inhibition of sodium channels such as pain disorders. Also provided are pharmaceutical compositions containing compounds of the present invention, as well as intermediates and processes useful for making the compounds.

20 Claims, No Drawings

(56) References Cited

OTHER PUBLICATIONS

Hains, B.D., et al., 2003, J. Neuroscience 23:26, 8881-8892.
Halford, B., 2014, Changing the Channel, C&E News, 92:12, 10-14.
Hamann M., et. al., 2003, Exp. Neurol. 184:2, 830-838.
Haufe V., et. al., .J Mol. Cell Cardiol. 42(3):469-477, 2007.
Ikoma et al., 2006, Nature Reviews Neuroscience, 7:535-547.
Inan et al., 2009, Euorpean Journal of Pharmacology 616:141-146.
Johannessen L. C., 2008, CNS Drugs 22:1, 27-47.
Jun-Ho, L. et. al., 2014, Cell, 157:6, 1393-404.
Kim D. Y., et. al., 2007, Nat. Cell. Biol. 9:7, 755-764.
Liu, H., et al., 2003, Am. J. Pharmacogenomics, 3:3, 173-179.
Morinville et al., 2007, J Comp Neurol., 504:680-689.
Puopolo et al.,2007, J. Neurosci. 27 :645-656.
Raymond, C.K., et al., 2004, J. Biol.Chem., 279 :44, 46234-46241.
Ross et al., 2010, Neuron 65:886-898.
Tamaoka A.,2003, Internal Medicine, 9:769-770.
Villamil et al., 1997, American Journal of Medicine, 102:584-585.
Waxman, 2006, Nature Neuroscience, 7 :932-941.
Wood, J. N. et al., 2005, Voltage-gated sodium channel blockers; target validation and therapeutic potential, Curr. Top Med. Chem., 5:529-537.
Woodruff-Pak D. S., et. al., 2006, Behav. Neurosci. 120:2, 229-240.
Yang Y et al., 1998, "Mutations in SCN9A, encoding a sodium channel alpha subunit, in patients with primary erythermalgia" J Med Genet 41:171-174.
Yu, F.H., et al., 2006, Nat. Neuroscience, 9:9, 1142-1149.

* cited by examiner

BIARYL ACYL-SULFONAMIDE COMPOUNDS AS SODIUM CHANNEL INHIBITORS

RELATED APPLICATIONS

This application claims the benefit of U.S. Provisional Patent Application No. 61/885,372, filed on Oct. 1, 2013, which specification is incorporated herein by reference in its entirety.

FIELD OF THE INVENTION

The present invention provides compounds that are inhibitors of voltage-gated sodium channels (Nav), in particular Nav 1.7, and are useful for the treatment of diseases treatable by inhibition of sodium channels such as pain disorders. Also provided are pharmaceutical compositions containing compounds of the present invention.

BACKGROUND OF THE INVENTION

A 2011 report of the institute of medicine estimates that 100 million adults in the US, roughly 30% of the population, suffer from chronic pain (*C & E News*, Bethany Halford, "Changing the Channel", published Mar. 24, 2014). Chronic pain by definition involves abnormal electrical spiking of neurons in the pain pathways: peripheral sensory neurons, spinal cord neurons, neurons in the pain matrix of the brain (e.g., somatosensory cortex, insular cortex, anterior cingular cortex), and/or neurons in brainstem. Although firing of these neurons is modulated and governed by many different receptors, enzymes, and growth factors, in most neurons the fast upstroke of the electrical spike is produced by entry of sodium ions through voltage-gated sodium channels (Hille B, Ion Channels of Excitable Membranes. Sinauer Associates, Inc.: Sunderland Mass., 3$^{rd}$ Ed. 2001). There are nine different isoforms of voltage-gated sodium channel (Nav 1.1-Nav 1.9), and they have distinct expression patterns in tissues including neurons and cardiac and skeletal muscle (Goldin, A. L, "Resurgence of sodium channel research," *Ann Rev Physiol* 63:871-894, 2001; Wood, J. N. and, Boorman, J. "Voltage-gated sodium channel blockers; target validation and therapeutic potential" *Curr. Top Med. Chem.* 5:529-537, 2005).

Nav1.1 and Nav1.2 are highly expressed in the brain (Raymond, C. K., et al., J. Biol. Chem. (2004) 279 (44): 46234-41) and are vital to normal brain function. Some loss of function due to Nav 1.1 mutations in humans, have resulted in epilepsy, presumably as these channels are expressed in inhibitory neurons (Yu, F. H., et al., Nat. Neuroscience (2006), 9 (9) 1142-1149). Nav 1.1 is also expressed in the peripheral nervous system and inhibition of Nav1.1 in the periphery may provide relief of pain. Hence, while inhibiting Nav1.1 may provide use for treating pain, it may also be undesirable possibly leading to anxiety and over excitability. Nav1.3 is expressed primarily in the fetal central nervous system, and expression was found to be upregulated after nerve injury in rats (Hains, B. D., et al., J. Neuroscience (2030) 23(26):8881-8892). Nav1.4 is expressed primarily in skeletal muscle. Mutations of the gene and its' product have significant impact on muscle function, including paralysis (Tamaoka A., Internal Medicine (2003), (9):769-770). Nav1.5 is expressed mainly in cardiac myocytes, including atria, ventricles, the sino-atrial node, atrio-ventircular node and cardiac Purkinje fibers. The rapid upstroke of the cardiac action potential and the rapid impulse condution through cardiac tissue is due to the opening of the Nav1.5 channel. Mutations of the Nav1.5 channel have resulted in arrhythmic syndromes, including QTc prolongation, Brugada syndrome (BS), sudden unexpected nocturnal death syndrome (SUNDS) and sudden infant death syndrome (SIDS) (Liu, H., et al., Am. J. Pharmacogenomics (2003), 3(3): 173-179). Nav1.6 is widely distributed voltage-gated sodium channel expressed throughout the central and peripheral nervous system. Nav1.8 is expressed primarily in sensory ganglia of the peripheral nervous system, such as the dorsal root ganglia. There are no identified Nav1.8 mutations that produce varied pain responses in humans. Nav1.8 differs from most neuronal Nav isotypes in that it is insensitive to inhibition by tetrodotoxin. Nav1.9, similar to Nav1.8, is also a tetrodotoxin insensitive sodium channel expressed primarily in dorsal root ganglia neurons (Dib-Hajj, S. D., et al., Proc. Natl. Acad. Sci. USA (1998), 95(15):8963-8968).

Recent evidence from several independent genetic studies has shown that the tetrodotoxin-sensitive voltage-gated sodium ion channel Nav 1.7 (SCN9A) is required to sense pain. Rare genetic forms of severe chronic pain, Primary Erythromelalgia and Paroxysmal Extreme Pain Disorder, result from mutations that increase the activity of Nav 1.7 (Fertleman C. R., Baker M. D., Parker K. A., Moffatt S., et al., "SCN9A mutations in paroxysmal extreme pain disorder: allelic variants underlie distinct channel defects and phenotypes," *Neuron* 52:767-774, 2006; Yang Y., Wang Y., Li S, et al., "Mutations in SCN9A, encoding a sodium channel alpha subunit, in patients with primary erythermalgia," J. Med. Genet. 41:171-174, 2004; Drenth J. P. H., te Morsche R. H. M., Guillet G., Taieb A., et al., "SCN9A mutations define primary erythermalgia as a neuropathic disorder of voltage gated sodium channels," *J Invest Dermatol* 124:1333-1338). Conversely, two separate clinical studies have determined that the root cause of the genetic disorder Congenital Indifference to Pain (CIP) is a loss of function of Nav 1.7 via mutations that truncate the protein and destroy function (Cox J. J., Reimann F, Nicholas A. K., et al. "An SCN9A channelopathy causes congenital inability to experience pain," *Nature* 444:894-898, 2006; Goldberg Y. P., MacFarlane J., MacDonald M. L., Thompson J., et al. "Loss-of-function mutations in the Nav1.7 gene underlie congenital indifference to pain in multiple human populations," *Clin Genet* 71:311-319, 2007). The disorder is inherited in Mendelian recessive manner with 100% penetrance. The phenotype associated with CIP is extreme: affected individuals are reported to have experienced painless burns, childbirth, appendicitis, and bone fractures, as well as to have insensitivity to clinical measures of pain such as pinprick or tendon pressure. Yet sensory, motor, autonomic, and other measured functions are normal, with the only reported abnormality being anosmia (inability to smell). These studies indicate that among the many possible targets in the pain pathway, Nav 1.7 governs one or more control points critical for pain perception.

Nonselective sodium channel inhibitors such as lidocaine, mexiletine, and carbamazepine show clinical efficacy in chronic pain, including neuropathic pain, but they are limited in dose and in use, likely due to effects on sodium channels outside the pain pathway. Lidocaine is a local anesthetic doctors use for minor surgery. So is the dentists office staple novocaine. But these compounds don't distinguish between the various sodium channel subtypes, making them unsuitable for use as systemic pain killers. "If you give a drug that blocks Nav1.7 but also blocks Nav1.5, the patient will die of heart failure," says Glenn F. King, a professor at Australia's University of Queensland who studies venoms that block ion channels. "It will be a completely painless death, but the patient will die nonetheless." Thus, selectivity for Nav1.7 is desired, particularly over Nav1.5. Researchers have tailored their efforts to find a molecule that inhibitors or block the activity of only Nav 1.7. To compound this problem, the identity, every location, every function and/or the tertiary structures of each subtype of voltage gated sodium channel proteins are not known or completely understood.

Consequently, a number of researchers are attempting to identify small molecule inhibitors of Nav1.7. For example, Chafeev et al disclose spiro-oxindole compound for the treatment and/or prevention of sodium channel-mediated diseases, such as pain, in U.S. Pat. No. 8,101,647. Thus, there is a need to identify Nav 1.7 inhibitors selective over at least Nav 1.5 to treat pain. The present invention provides compounds that are selective inhibitors of Nav 1.7, over at least Nav 1.5.

International Publications WO 2012/007868 and WO 2009/065406 disclose sulfonamide derivatives which are different from the sulfonamide derivatives of the present invention.

SUMMARY OF THE INVENTION

The present invention provides compounds, or pharmaceutically acceptable salts thereof, of Formula (I):

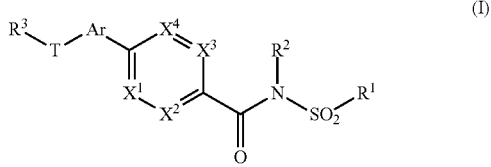

(I)

wherein:

$X^1$, $X^2$, $X^3$, and $X^4$ are independently N or $CR^4$, provided that only 0, 1 or 2 of $X^1$, $X^2$, $X^3$, and $X^4$ are N;

optionally, $X^1$ and $X^2$ may form a 5- to 6-membered carbocyclic or a 5- to 6-membered heterocyclic monocyclic ring fused to the ring containing $X^1$, $X^2$, $X^3$, and $X^4$; wherein said monocyclic ring is independently substituted by 0, 1, 2, 3, or 4 $R^5$ groups;

Ar is 5- to 10-membered aryl group, a 5- to 10-membered heteroaryl group, a 3- to 6-membered cycloalkyl group, or a 3- to 10-membered heterocycloalkyl group, wherein the heteroaryl or heterocycloalkyl group includes 1 to 3 heteroatoms independently selected from O, N or S, and wherein the aryl, heteroaryl, cycloalkyl or heterocycloalkyl group is independently substituted by 0, 1, 2, 3, or 4 $R^5$ groups;

T is absent, —O—, —(C=O)—, —N($R^d$)—, —(C=O)—N($R^d$)—, —($CR^dR^d$)$_p$—O—($CR^dR^d$)$_p$—, —O—($CR^dR^d$)$_p$—O—($CR^dR^d$)$_p$—, —O—($CR^dR^d$)$_p$—N($R^d$)—, —N($R^d$)—($CR^dR^d$)$_p$—, —N($R^d$)—($CR^dR^d$)$_p$—O—($CR^dR^d$)$_p$—, —(C=O)N($R^d$)($CR^dR^d$)$_p$—, S, S(=O), or S(=O)$_2$;

$R^1$ is $C_{1-6}$alkyl or a 4-, 5- to 6-membered heterocyclyl or heteroaryl group having from 1- to 3-heteroatoms independently selected from O, N or S, wherein each $C_{1-6}$alkyl is independently substituted by 0, 1, 2, 3, or 4 $R^7$ groups; and each said heterocyclyl or heteroaryl group is independently substituted by 0, 1, 2, 3, or 4 $C_{1-6}$alkyl or $R^7$ groups;

$R^2$ is H or $C_{1-6}$alkyl;

$R^3$ is absent, $C_{1-6}$ alkyl, a 6- to 10-membered aryl group, a 5- to 10-membered heteroaryl group, a 3- to 6-membered cycloalkyl group or a 3- to 10-membered heterocycloalkyl group, wherein the heteroaryl or heterocycloalkyl group includes 1 to 3 heteroatoms independently selected from O, N or S, wherein each $R^3$ $C_{1-6}$alkyl, aryl, heteroaryl, cycloalkyl or heterocycloalkyl group is independently substituted by 0, 1, 2, 3, or 4 $R^8$ substituents independently selected from an A group, halo, —$CF_3$, —$CF_2H$, —$CFH_2$, —OH, —$OCF_3$, —$OCHF_2$, —$OCH_2F$, $C_{1-6}$alkyl, —$OC_{1-6}$alkyl, —CN, —$(CH_2)_n NR^cR^c$, —$O(CR^dR^d)_p OR^c$, —$N(R^c)_2$, —$NR^d(CH_2)_m$5- to 10-membered aryl, —$NR^d(CH_2)_m$5- to 10-membered heteroaryl, —$(CH_2)_m O(CH_2)_m$6-membered aryl, —$NR^d(CH_2)_m OR^c$, or oxo; and wherein each occurrence of $R^8$ heteroaryl group includes 1 to 3 heteroatoms independently selected from O, N or S, and each occurrence of $R^8$ $C_{1-6}$alkyl, —$OC_{1-6}$alkyl, aryl, or heteroaryl group is independently substituted by 0, 1, 2, 3, or 4 $R^9$ substituents independently selected from a B group, halo, $C_{1-6}$alkyl, —CN, —$CF_3$, —OH, —$OCHF_2$, —$OCH_2F$, —$OCF_3$, —$OC_{1-6}$alkyl, or —$(CH_2)_n NR^dR^d$;

$R^4$ is H, halo, —CN, —$OC_{1-6}$alkyl, $C_{1-6}$alkyl, —$CF_3$; —OH, —$CF_2H$, —$OCF_3$, —$OCF_2H$, —$OCFH_2$, —O—$CH_2CF_3$, $C_{1-6}$alkyl-O—$C_{1-6}$alkyl-, —$O(CR^cR^c)_m OR^d$, —(C=O)$NR^dR^d$, —S(=O)$_2 NR^dR^d$, —S(=O)$_2$ $C_{1-6}$alkyl, a B group, or a —O—B group; wherein each occurrence of said $R^4C_{1-6}$alkyl is independently substituted by 0, 1, 2, 3, or 4 halo, CN, $C_{1-6}$alkyl, —$OC_{1-6}$alkyl, —$O(CR^dR^d)_p OR^c$, $NH_2$, OH, or —C(=O)$NH_2$;

each $R^5$ is independently halo, —CN, —$OC_{1-6}$alkyl, $C_{1-6}$alkyl, —$CF_3$; —OH, —$CF_2H$, —$CFH_2$, —$OCF_3$, —$OCF_2H$, —$OCFH_2$, $NR^dR^d$, or oxo;

each $R^6$ is independently halo, halo$C_{1-6}$alkyl, CN, OH, $NO_2$, $NH_2$, acetyl, —C(O)$NHCH_3$, OXO, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, —$OC_{1-6}$alkyl, —O—B group, —$O(CH_2)_m$B group, —$(CH_2)_n NR^dR^d$, —$O(CR^dR^d)_p OR^c$, —(C=O)$NR^dR^d$, —S(=O)$_2 NR^d$, —N($R^d$)$_2$, —$NR^d$(C=O)$NR^dR^d$, —$NR^d$S(=O)$_2 NR^d$, —S(=O)$_2 R^d$, —$NR^d(CH_2)_m OR^c$ or —$SC_{1-6}$alkyl, wherein each occurrence of $R^6$ $C_{1-6}$alkyl, $C_{2-6}$alkenyl, $C_{2-6}$alkynyl, or $C_{3-6}$cycloalkyl is independently substituted by 0, 1, 2, 3, 4, or 5 substituents independently selected from F, Cl, CN, $NO_2$, $NH_2$, OH, OXO, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or oxetan-3-yl;

$R^7$ is a B group, halo, —CN, or —$C_{1-6}$alkyl-$OC_{1-6}$alkyl;

an A group is a 5- to 6-membered aryl group, a 5- to 6-membered heteroaryl group, a 3- to 6-membered cycloalkyl group, or a 3- to 6-membered heterocycloalkyl group, wherein the heteroaryl or heterocycloalkyl group includes 1 to 3 heteroatoms independently selected from O, N or S, and wherein the aryl, heteroaryl, cycloalkyl, or heterocycloalkyl group is independently substituted by 0, 1, 2, 3, or 4 substituents independently selected from a B group or $R^6$;

a B group is a 5- to 6-membered aryl group, a 5- to 6-membered heteroaryl group, a 3- to 6-membered cycloalkyl group or a 3- to 6-membered heterocycloalkyl group, wherein the heteroaryl or heterocycloalkyl group includes 1 to 3 heteroatoms independently selected from O, N or S, and wherein the aryl, heteroaryl, cycloalkyl, or heterocycloalkyl group is independently substituted by 0, 1, 2, 3, or 4 substituents independently selected from $R^6$;

each $R^c$ is independently H or $C_{1-6}$alkyl, and wherein the $C_{1-6}$alkyl is independently substituted by 0, 1, 2, 3, or 4 substituents independently selected from halo, —OH or —CN;

each $R^d$ is independently H or $C_{1-6}$alkyl, and wherein the $C_{1-6}$alkyl is independently substituted by 0, 1, 2, 3, or 4 substituents independently selected from halo, —OH or —CN;

each m is independently 0, 1, 2 or 3;
each n is independently 0, 1, 2 or 3; and
each p is independently 1, 2, 3, or 4;

provided that the compound of Formula (I) is not: any one of the excluded compounds as listed in the priority document of the present application, i.e., U.S. Provisional Patent Application No. 61/885,372, pages 6 to 22, filed Oct. 1, 2013.

In embodiment 2, the present invention provides compounds of Formula (I), or pharmaceutically acceptable salts thereof, in accordance with embodiment 1 wherein:

$X^1$, $X^2$, $X^3$, and $X^4$ are independently N or $CR^4$, provided that only 0 or 1 of $X^1$, $X^2$, $X^3$, and $X^4$ are N;

Ar is 5- to 6-membered aryl group, or a 5- to 10-membered heteroaryl group;

T is absent, —O—, —$(CR^dR^d)_p$—O—$(CR^dR^d)_p$—, —N($R^d$)—, —N($R^d$)—$(CR^dR^d)_p$—O—$(CR^dR^d)_p$—, or S(=O)$_2$;

$R^1$ is $C_{1-6}$alkyl;
$R^2$ is H or $CH_3$;
$R^3$ is $C_{1-6}$alkyl, a 6- to 10-membered aryl group, a 5- to 10-membered heteroaryl group, a 3- to 6-membered cycloalkyl group, or a 3- to 10-membered heterocycloalkyl group, wherein the heteroaryl or heterocycloalkyl group includes 1 to 3 heteroatoms independently selected from O, N or S, wherein the aryl, heteroaryl, cycloalkyl, or heterocycloalkyl group is independently substituted by 0, 1, 2, 3, or 4 $R^8$ substituents independently selected from an A group, halo, —$CF_3$, —OH, —$OCF_3$, $C_{1-6}$alkyl, —$OC_{1-6}$alkyl, —CN, —$(CH_2)_nNR^cR^c$, —$O(CR^dR^d)_pOR^c$, —N($R^c$)$_2$, —$NR^d(CH_2)_m$5- to 10-membered aryl, —$NR^d(CH_2)_m$5- to 10-membered heteroaryl, —$(CH_2)_mO(CH_2)_m$6-membered aryl or —$NR^d(CH_2)_mOR^c$, and heteroaryl group includes 1 to 3 heteroatoms independently selected from O, N or S, and the $C_{1-6}$alkyl, —$OC_{1-6}$alkyl, aryl, or heteroaryl group is independently substituted by 0, 1, 2, 3, or 4 $R^9$ substituents independently selected from a B group, halo, $C_{1-6}$alkyl, —CN, —$CF_3$, —OH, —$OCHF_2$, —$OCH_2F$, —$OCF_3$, —$OC_{1-6}$alkyl or —$(CH_2)_nNR^dR^d$; and $R^4$ is H, halo, —CN, $C_{1-6}$alkyl, —$OC_{1-6}$alkyl, —C(=O)$OC_{1-6}$alkyl, —OH, —$OCF_3$, —$OCF_2H$, —$OCFH_2$, —$O(CR^cR^c)_mOR^d$, a B group selected from cyclopropyl, thienyl, thiazolyl, thiadiazolyl, pyrrolyl, pyrazolyl, imidazolyl, triazolyl, furanyl, dihydrofuranyl, tetrahydrofuranyl, piperidinyl, phenyl, pyridyl, pyrimidyl, pyrazinyl or pyridazinyl, or a —O—B group selected from oxetanyloxy, tetrahydrofuranyloxy, dihydropyranyloxy, tetrahydropyranyloxy, pyridyloxy, or pyridazinyloxy; wherein each occurrence of said $C_{1-6}$alkyl, B group, and —O—B group is independently substituted by 0, 1, 2, 3, or 4 substituents independently selected from halo, CN, $C_{1-6}$alkyl, —$OC_{1-6}$alkyl, —$O(CR^dR^d)_pOR^c$, $NH_2$, or OH.

In embodiment 3, the present invention provides compounds of Formula (I), or pharmaceutically acceptable salts thereof, in accordance with any one of embodiments 1 or 2 wherein $R^2$ is H.

In embodiment 4, the present invention provides compounds of Formula (I), or pharmaceutically acceptable salts thereof, in accordance with any one of embodiments 1 to 3 wherein Ar is 5- to 6-membered aryl group.

In embodiment 5, the present invention provides compounds of Formula (I), or pharmaceutically acceptable salts thereof, in accordance with any one of embodiments 1 to 4 wherein $R^3$ is $C_{1-6}$alkyl, a 6- to 10-membered aryl group, a 5- to 10-membered heteroaryl group, a 3- to 6-membered cycloalkyl group, or a 3- to 10-membered heterocycloalkyl group, wherein the heteroaryl or heterocycloalkyl group includes 1 to 3 heteroatoms independently selected from O, N or S, wherein the aryl, heteroaryl, cycloalkyl or heterocycloalkyl group is independently substituted by 0, 1, 2, or 3 $R^8$ substituents independently selected from halo, —$CF_3$, —$OCF_3$, $C_{1-6}$alkyl, —$OC_{1-6}$alkyl, or CN; and the $C_{1-6}$alkyl or —$OC_{1-6}$alkyl $R^8$ group is independently substituted by 0, 1, or 2 $R^9$ substituents independently selected from a B group, halo, $C_{1-6}$alkyl, —CN, —$CF_3$, —OH, —$OCHF_2$, —$OCH_2F$, —$OCF_3$, —$OC_{1-6}$alkyl or —$(CH_2)_nNR^dR^d$.

In embodiment 6, the present invention provides compounds of Formula (I), or pharmaceutically acceptable salts thereof, in accordance with any one of embodiments 1 to 3, or 5 wherein Ar is phenyl, naphthyl, pyrazolyl, pyridyl, triazolyl, thiazolyl, oxadiazolyl, pirazinyl, indolyl, imidazolyl, benzimidazolyl, benzthiazolyl, benzodioxepinyl, or pyrazolo[3,4-b]pyridinyl; wherein each Ar is substituted by 0, 1, or 2 $R^5$ groups.

In embodiment 7, the present invention provides compounds of Formula (I), or pharmaceutically acceptable salts thereof, in accordance with any one of embodiments 1 to 6 wherein each $R^5$ is independently halo, —CN, —$CF_3$; or —$CF_2H$.

In embodiment 8, the present invention provides compounds of Formula (I), or pharmaceutically acceptable salts thereof, in accordance with any one of embodiments 1 to 7 wherein $X^1$, $X^2$, $X^3$, and $X^4$ are independently $CR^4$; and $R^4$ is H, halo, $C_{1-6}$alkyl, —$OC_{1-6}$alkyl, —$OCF_3$, —$OCF_2H$, —$OCFH_2$, oxetanyloxy, or a ring selected from thiazolyl, pyrazolyl, imidazolyl, triazolyl, furanyl, dihydrofuranyl, pyridyl or pyrimidyl.

In embodiment 9, the present invention provides compounds of Formula (I), or pharmaceutically acceptable salts thereof, in accordance with any one of embodiments 1 to 8, wherein $R^1$ is $CH_3$ or $CH_2CH_3$.

In embodiment 10, the present invention provides compounds of Formula (I), or pharmaceutically acceptable salts thereof, in accordance with any one of embodiments 1 to 9, wherein $R^3$ is selected from phenyl, naphthyl, pyridyl, pyrimidyl, pyrazinyl, pyridazinyl, pyrazolyl, pyridazinyl, triazolyl, piperidinyl, piperazinyl, pyrrolidinyl or azetidinyl, wherein each $R^3$ is independently substituted by 0, 1, 2, or 3 $R^8$ substituents independently selected from halo, —$CF_3$, —$OCF_3$, $C_{1-6}$alkyl, or —$OC_{1-6}$alkyl; and the $C_{1-6}$alkyl or —$OC_{1-6}$alkyl $R^8$ group is independently substituted by 0, 1, or 2 $R^9$ substituents independently selected from a B group, halo, $C_{1-6}$alkyl, —CN, —$CF_3$, —OH, —$OCHF_2$, —$OCH_2F$, —$OCF_3$, —$OC_{1-6}$alkyl, or —$(CH_2)_nNR^dR^d$.

In embodiment 11, the present invention provides compounds, or pharmaceutically acceptable salts thereof, in accordance with any one of embodiments 1 to 9, wherein $R^3$ is $C_{1-6}$alkyl, phenyl, naphthyl, pyrrolidinyl, pyridyl, piperidinyl, morpholinyl, thiomorpholinyl, quinolinyl, benzimidazolyl, oxetanyl, thiophenyl, thiazolyl, furanyl, tetrahydrofuranyl, pyranyl, tetrahydropyranyl, benzothiazolyl, oxadiazolyl, azetidinyl, azabicyclo[2.2.1]heptyl, azaspiro[3.3]heptyl, imidazo[1,2-a]pyridinyl, cyclopropyl, cyclobutyl, cyclopentyl, or cyclohexyl, wherein each $R^3$ is substituted by 0, 1, 2, or 3 $R^8$ substituents independently selected from halo, —$CF_3$, —$OCF_3$, $C_{1-6}$alkyl, or —$OC_{1-6}$alkyl.

In embodiment 12, the present invention provides compounds, or pharmaceutically acceptable salts thereof, in accordance with any one of embodiments 1 to 11, wherein $R^3$ is phenyl substituted by 2 $R^8$ substituents independently selected from halo, —$CF_3$, —$OCF_3$, $C_{1-6}$alkyl, or —$OC_{1-6}$alkyl.

In embodiment 13, the present invention provides compounds, or pharmaceutically acceptable salts thereof, in accordance with any one of embodiments 1 to 9 or 11 to 12, wherein $X^1$, $X^2$, $X^3$, and $X^4$ are independently $CR^4$; and $R^4$ is H, halo, $C_{1-6}$alkyl, —$OC_{1-6}$alkyl, —$OCF_3$, —$OCF_2H$, —$OCFH_2$, oxetanyloxy, or a B group selected from thiazolyl, pyrazolyl, imidazolyl, triazolyl, furanyl, dihydrofuranyl, pyridyl or pyrimidyl;

Ar is pyridyl substituted by 0, 1, or 2 $R^5$ groups;
T is absent, —O—, or —$(CR^dR^d)_p$—O—$(CR^dR^d)_p$—;
$R^1$ is $C_{1-6}$alkyl;
$R^2$ is H;
$R^3$ is a $C_{1-6}$alkyl, phenyl, naphthyl, pyrrolidinyl, or pyridyl ring, wherein the ring is independently substituted by 0, 1, 2, or 3 $R^8$ substituents independently selected from halo, —$CF_3$, —$OCF_3$, $C_{1-6}$alkyl, or —$OC_{1-6}$alkyl; and
$R^4$ is H, halo, CN, —$OC_{1-6}$alkyl, —$OCF_3$, —$OCF_2H$, —$OCFH_2$, oxetanyloxy or a ring selected from thiazolyl, pyrazolyl, imidazolyl, triazolyl, furanyl, dihydrofuranyl, pyridyl, pyrimidyl, pyrazinyl or pyridazinyl, wherein said ring is independently substituted by 0, 1, 2, or 3 halo, $C_{1-6}$alkyl, $NH_2$ or OH.

In embodiment 14, the present invention provides compounds of Formula (I), or pharmaceutically acceptable salts thereof, in accordance with any one of embodiments 1 to 13 wherein T is —O—.

In embodiment 15, the present invention provides compounds of Formula (I), or pharmaceutically acceptable salts thereof, in accordance with any one of embodiments 1 to 14, wherein $R^1$ is methyl.

In embodiment 16, the present invention provides compounds of Formula (I), or pharmaceutically acceptable salts thereof, in accordance with any one of embodiments 1 to 15, wherein $R^4$ is H, —O-methyl, —O—$CF_2H$, oxetanyloxy, or imidazolyl.

In embodiment 17, the present invention provides compounds of Formula (I), or pharmaceutically acceptable salts thereof, in accordance with any one of embodiments 1 to 16, wherein $R^5$ is halo, CN, —$CF_3$, or —$CF_2H$; and T is —O—, —$N(R^d)$—, —$(CR^dR^d)_p$—O—$(CR^dR^d)_p$—, —O—$(CR^dR^d)_p$—O—$(CR^dR^d)_p$—, —$N(R^d)(CR^dR^d)_p$—, —$N(R^d)(CR^dR^d)_p$—O—$(CR^dR^d)_p$— or —$(C=O)N(R^d)$—$(CR^dR^d)_p$—; wherein $R^5$ is ortho to T.

In embodiment 18, the present invention provides compounds of Formula (I), or pharmaceutically acceptable salts thereof, in accordance with any one of embodiments 1 to 17, wherein $X^1$ and $X^2$ form a 5- to 6-membered carbocyclic or heterocyclic monocyclic ring fused to the ring containing $X^1$, $X^2$, $X^3$, and $X^4$; and wherein said monocyclic ring is independently substituted by 0, 1, 2, 3, or 4 $R^5$ groups.

In embodiment 19, the invention provides a sub-set of compounds of formula

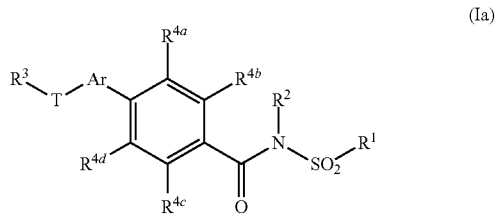

(Ia)

wherein:
Ar is a pyridinyl ring substituted by 0, 1, 2, or 3 $R^5$ groups;
T is absent, —$N(R^f)$—, —$(CR^dR^d)_r$—O—$(CR^dR^d)_r$—, —O—$(CR^dR^d)_p$—O—$(CR^dR^d)_p$—, —$N(R^d)$—$(CR^dR^d)_p$—, S, S(=O), or S(=O)$_2$;
$R^1$ is —$NHR^e$, $C_{1-6}$alkyl, a 3- to 6-membered cycloalkyl group, a 4-, 5- to 6-membered heterocyclyl group, or a 4-, 5- to 6-membered heteroaryl group, wherein each $C_{1-6}$alkyl is independently substituted by 0, 1, 2, 3, or 4 $R^7$ groups; and each said heterocyclyl or heteroaryl group is independently substituted by 0, 1, 2, 3, or 4 $C_{1-6}$alkyl or $R^7$ groups;
$R^2$ is H or $C_{1-6}$alkyl;
$R^3$ is $C_{1-6}$alkyl, a —$(CR^eR^e)_q$(6- to 10-membered aryl) group, a —$(CR^eR^e)_q$(5- to 10-membered heteroaryl) group, a —$(CR^eR^e)_q$(3- to 8-membered cycloalkyl) group, or a —$(CR^eR^e)_q$(3- to 10-membered heterocycloalkyl) group;
wherein each $R^3$ $C_{1-6}$alkyl, aryl, heteroaryl, cycloalkyl or heterocycloalkyl group is independently substituted by 0, 1, 2, 3, or 4 $R^8$ substituents independently selected from an A group, —O-A group, halo, —$CF_3$, —$CF_2H$, —$CFH_2$, —OH, —$OCF_3$, —$OCHF_2$, —$OCH_2F$, $C_{1-6}$alkyl, —$OC_{1-6}$alkyl, —CN, —$(CH_2)_nNR^cR^c$, —$O(CR^dR^d)_pOR^c$, —$N(R^c)_2$, —$NR^d(CH_2)_m$5- to 10-membered aryl, —$NR^d(CH_2)_m$5- to 10-membered heteroaryl, —$(CH_2)_mO(CH_2)_m$6-membered aryl, —$NR^d(CH_2)_mOR^c$, or oxo;
and each occurrence of $R^8$ $C_{1-6}$alkyl, —$OC_{1-6}$alkyl, aryl, or heteroaryl group is independently substituted by 0, 1, 2, 3, or 4 $R^9$ substituents independently selected from a B group, halo, $C_{1-6}$alkyl, —CN, —$CF_3$, —OH, —$OCHF_2$, —$OCH_2F$, —$OCF_3$, —$OC_{1-6}$alkyl, or —$(CH_2)_nNR^dR^d$;
Each $R^{4a}$, $R^{4b}$, $R^{4c}$, and $R^{4d}$ is independently H, halo, —CN, —$OC_{1-6}$alkyl, $C_{1-6}$alkyl, —$CF_3$, $CF_2H$, $CFH_2$, —$OCF_3$, —$OCF_2H$, —$OCFH_2$, —O—$CH_2CF_3$, a B group, or an —O—B group; wherein each occurrence of said $R^{4a}$, $R^{4b}$, $R^{4c}$, and $R^{4d}$ $C_{1-6}$alkyl group is independently substituted by 0, 1, 2, 3, or 4 halo, CN, $C_{1-6}$alkyl, —$OC_{1-6}$alkyl, —$O(CR^dR^d)_pOR^c$, $NH_2$, OH, or —C(=O)$NH_2$;
each $R^5$ is independently halo, —CN, —$OC_{1-6}$alkyl, $C_{1-6}$alkyl, —$CF_3$; —OH, —$CF_2H$, —$CFH_2$, —$OCF_3$, —$OCF_2H$, or —$OCFH_2$;
an A group is a 5- to 6-membered aryl group, a 5- to 6-membered heteroaryl group, a 3- to 6-membered cycloalkyl group, or a 3- to 6-membered heterocycloalkyl group, wherein the aryl, heteroaryl, cycloalkyl, or heterocycloalkyl group is independently substituted by 0, 1, 2, 3, or 4 substituents independently selected from a B group or $R^6$;
a B group is a 5- to 6-membered aryl group, a 5- to 6-membered heteroaryl group, a 3- to 6-membered cycloalkyl group or a 3- to 6-membered heterocycloalkyl group, wherein the aryl, heteroaryl, cycloalkyl, or heterocycloalkyl group is independently substituted by 0, 1, 2, 3, or 4 substituents independently selected from $R^6$;
each $R^6$ is independently halo, halo$C_{1-6}$alkyl, CN, OH, $NO_2$, $NH_2$, acetyl, —C(O)$NHCH_3$, OXO, $C_{1-6}$alkyl, $C_{2-6}$alkenyl, $C_{2-6}$alkynyl, $C_{3-6}$Cycloalkyl, $C_{1-6}$alkylamino-, $C_{1-6}$dialkylamino-, —$OC_{1-6}$alkyl, —O—B group, —O(CH$_2$)$_m$B group, —(CH$_2$)$_n$NR$^d$R$^d$, —O(CR$^d$R$^d$)$_p$OR$^c$, —(C=O)NR$^d$R$^d$, —S(=O)$_2$NR$^d$, —N(R$^d$)$_2$, —NR$^d$(C=O)NR$^d$R$^d$, —NR$^d$S(=O)$_2$NR$^d$, —S(=O)$_2$R$^d$, —NR$^d$(CH$_2$)$_m$OR$^c$ or —$SC_{1-6}$alkyl;

wherein each occurrence of R$^6$ $C_{1-6}$alkyl, $C_{2-6}$alkenyl, $C_{2-6}$alkynyl, or $C_{3-6}$cycloalkyl is independently substituted by 0, 1, 2, 3, 4, or 5 substituents independently selected from F, Cl, CN, NO$_2$, NH$_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or oxetan-3-yl;

R$^7$ is a B group, halo, —CN, or —$C_{1-6}$alkyl-O$C_{1-6}$alkyl;

each R$^c$ and R$^d$ is independently H or $C_{1-6}$alkyl, and wherein the $C_{1-6}$alkyl is independently substituted by 0, 1, 2, 3, or 4 substituents independently selected from halo, —OH or —CN;

each R$^e$ is independently H, $C_{1-6}$alkyl or a 3- to 6-membered cycloalkyl group; wherein each of the $C_{1-6}$alkyl and the 3- to 6-membered cycloalkyl group is independently substituted by 0, 1, 2, 3, or 4 substituents independently selected from halo, —OH or —CN;

each R$^f$ is independently H or $C_{1-6}$alkyl, and wherein the $C_{1-6}$alkyl is independently substituted by 0, 1, 2, 3, or 4 substituents independently selected from halo, —OH or —CN;

or alternatively, R$^f$ and R$^3$ together with the nitrogen atom they attach to may form a four-membered, five-membered, or six-membered heterocycloalkyl or heteroaryl ring, each of which is independently substituted by 0, 1, 2, 3, or 4 substituents independently selected from halo, —OH or —CN;

each m is independently 0, 1, 2 or 3;
each n is independently 0, 1, 2 or 3;
each p is independently 1, 2, 3, or 4;
each q is independently 0, 1, 2 or 3; and
each r is independently 0, 1, 2 or 3.

In embodiment 20, the invention provides a sub-set of compounds of formula (Ia), or a pharmaceutically acceptable salt thereof, wherein Ar is:

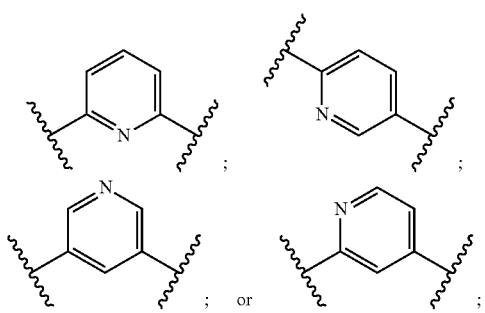

each of which is substituted by 0, 1, 2, or 3 R$^5$ groups.

In embodiment 21, the invention provides a sub-set of compounds of formula (Ia), or a pharmaceutically acceptable salt thereof, wherein: T is absent, —(CR$^d$R$^d$)$_r$—O—(CR$^d$R$^d$)$_r$—, —N(R$^f$)—, or S, wherein r is 0, 1, or 2.

In embodiment 22, the invention provides a sub-set of compounds of formula (Ib):

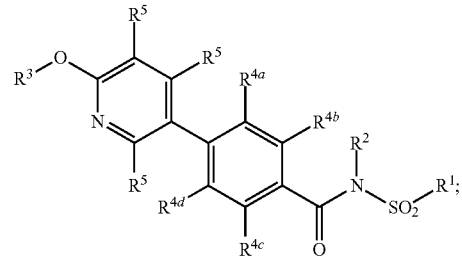

wherein R$^1$, R$^2$, R$^3$, R$^{4a}$, R$^{4b}$, R$^{4c}$, and R$^{4d}$, and R$^5$ are as defined in compounds of Formula (Ia) above.

In embodiment 23, the invention provides a sub-set of compounds of formula (Ia), or a pharmaceutically acceptable salt thereof, wherein: R$^2$ is H.

In embodiment 24, the invention provides a sub-set of compounds of formula (Ia), or a pharmaceutically acceptable salt thereof, wherein: at least one of R$^{4a}$, R$^{4b}$, R$^{4c}$, and R$^{4d}$ is not H. In a sub-embodiment, each R$^{4a}$, R$^{4b}$, R$^{4c}$, and R$^{4d}$ is independently H, F, Cl, Br, methyl, ethyl, propyl, isopropyl, methoxy, ethoxy, cyclopropyl, CN, CF$_3$, —OCF$_2$H, —O— oxetanyl, or —O—CF$_2$H, wherein at least one of R$^{4a}$, R$^{4b}$, R$^{4c}$, and R$^{4d}$ is not H.

In embodiment 25, the invention provides a sub-set of compounds of formula (Ia), or a pharmaceutically acceptable salt thereof, wherein: R$^{4a}$ is H, Br, —O—CF$_2$H, methoxy, or oxetanyl.

In embodiment 26, the invention provides a sub-set of compounds of formula (Ia), or a pharmaceutically acceptable salt thereof, wherein: R$^{4b}$ is H or F.

In embodiment 27, the invention provides a sub-set of compounds of formula (Ia), or a pharmaceutically acceptable salt thereof, wherein: R$^{4c}$ is H or F.

In embodiment 28, the invention provides a sub-set of compounds of formula (Ia), or a pharmaceutically acceptable salt thereof, wherein: R$^{4d}$ is H, F, Cl, methyl, isopropyl, or methoxy.

In embodiment 29, the invention provides a sub-set of compounds of formula (Ia), or a pharmaceutically acceptable salt thereof, wherein: R$^5$ is Cl, CN, CF$_3$, CHF$_2$, or methyl.

In embodiment 30, the invention provides a sub-set of compounds of formula (Ia), or a pharmaceutically acceptable salt thereof, wherein: R$^1$ is methyl, ethyl, propyl, cyclopropyl, cyclobutyl, —NH$_2$, —NHCH$_3$, —NHCH$_2$CH$_3$, —NHCH(CH$_3$)$_2$, —NH-cyclopropyl, azetidinyl, or thiazolyl.

In embodiment 31, the invention provides a sub-set of compounds of formula (Ia), or a pharmaceutically acceptable salt thereof, wherein: R$^f$ and R$^3$ together with the nitrogen atom they attach to form a four-membered or five-membered heterocycloalkyl or heteroaryl ring, each of which is independently substituted by 0, 1, 2, 3, or 4 substituents independently selected from halo, —OH or —CN.

In embodiment 32, the invention provides a sub-set of compounds of formula (Ia), or a pharmaceutically acceptable salt thereof, wherein: Ar is:

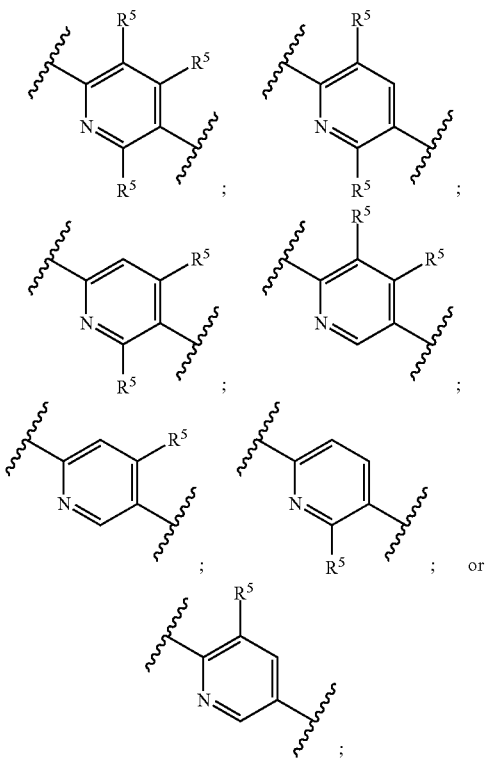

and
$R^5$ is independently Cl, F, methyl, —CN, —CF$_3$ or —CF$_2$H.
In a sub embodiment, Ar is

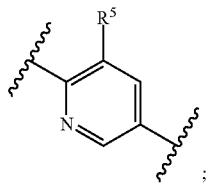

and $R^5$ is independently Cl, F, —CN, —CF$_3$; or —CF$_2$H.

In embodiment 30, the invention provides a sub-set of compounds of formula (Ia), or a pharmaceutically acceptable salt thereof, wherein: $R^3$ is selected from:
(a) 1-ethylpropyl, 1,3-dimethylbutyl, isopentyl, or CF$_3$,
(b) phenyl, naphthyl, or benzyl,
(c) pyridyl, pyrimidyl, pyrazinyl, pyridazinyl, pyrazolyl, pyridazinyl, triazolyl, piperazinyl, quinolinyl, or benzothiazolyl,
(d) cyclopropyl, cyclobutyl, cyclopentyl, cyclohexyl, spiro[2.4]heptyl, spiro[3.3]heptyl, —CH$_2$-cyclobutyl, —CH$_2$—CH$_2$-cyclopentyl, dihydroindenyl, tetrahydronaphthyl or bicyclo[2.2.1]heptyl,
(e) piperidinyl, pyrrolidinyl, or azetidinyl,
wherein each $R^3$ is substituted by 0, 1, 2, or 3 $R^8$ substituents independently selected from F, Cl, Br, methyl, ethyl, isopropyl, tert-butyl, CF$_3$, methoxy, ethoxy, isopropoxy, —O—CF$_3$, —O-oxetanyl, or phenyl.

In embodiment 33, the invention provides a sub-set of compounds of formula (Ia), or a pharmaceutically acceptable salt thereof, wherein: $R^3$ is
(a) a —(CR$^e$R$^e$)$_q$(6- to 10-membered aryl) group selected from phenyl, naphthyl, or benzyl;

(b) a —(CR$^e$R$^e$)$_q$(5- to 10-membered heteroaryl) group selected from furanyl, thiophenyl, thiazolyl, oxadiazolyl, pyridyl, pyrimidyl, pyrazinyl, pyridazinyl, pyrazolyl, pyridazinyl, triazolyl, piperazinyl, quinolinyl, imidazo[1,2-a]pyridinyl, benzimidazolyl, or benzothiazolyl;
(c) a —(CR$^e$R$^e$)$_q$(3- to 8-membered cycloalkyl) group selected from cyclopropyl, cyclobutyl, cyclopentyl, cyclohexyl, spiro[2.4]heptyl, spiro[3.3]heptyl, —CH$_2$-cyclobutyl, —CH$_2$—CH$_2$-cyclopentyl, dihydroindenyl, tetrahydronaphthyl or bicyclo[2.2.1]heptyl; or
(d) a —(CR$^e$R$^e$)$_q$(3- to 10-membered heterocycloalkyl) group selected from oxetanyl, tetrahydrofuranyl, pyranyl, tetrahydropyranyl, morpholinyl, thiomorpholinyl, piperidinyl, pyrrolidinyl, azetidinyl, azabicyclo[2.2.1]heptyl, azaspiro[3.3]heptyl;
wherein each q is 0, 1, or 2; and
wherein each $R^3$ is substituted by 0, 1, 2, or 3 $R^8$ substituents.

In embodiment 34, the invention provides a sub-set of compounds of formula (Ia), or a pharmaceutically acceptable salt thereof, wherein: $R^3$ is phenyl or pyridyl substituted by 1, 2, or 3 $R^8$ substituents independently selected from F, Cl, Br, methyl, ethyl, isopropyl, tert-butyl, CF$_3$, methoxy, ethoxy, isopropoxy, —O—CF$_3$, —O-oxetanyl, or phenyl.

In embodiment 35, the invention provides a sub-set of compounds of formula (Ia), or a pharmaceutically acceptable salt thereof, wherein: $R^9$ is CF$_3$, methyl, or chloro.

In embodiment 36, the invention provides a sub-set of compounds of formula (Ia), or a pharmaceutically acceptable salt thereof, wherein: T is —N(R$^f$)—, wherein R$^f$ is H or methyl.

In embodiment 37, the invention provides a sub-set of compounds of formula (Ia), or a pharmaceutically acceptable salt thereof, wherein: T is —C(R$^d$R$^d$)$_r$OC(R$^d$R$^d$)$_r$—, wherein R$^d$ is independently H, methyl, ethyl, propyl, or CF$_3$, and wherein each r is independently 0, 1, or 2.

In embodiment 38, the invention provides a sub-set of compounds of formula (Ia), or a pharmaceutically acceptable salt thereof, wherein: T is —O—.

In embodiment 39, the invention provides a sub-set of compounds of formula (Ia), or a pharmaceutically acceptable salt thereof, wherein: $R^1$ is methyl.

In embodiment 40, the invention provides a sub-set of compounds of formula (I), (Ia), or (Ib), or a pharmaceutically acceptable salt thereof, wherein $R^1$ is methyl or ethyl; $R^2$ is H; $R^3$ is phenyl, benzthiazolyl, cyclopropyl, cyclobutyl, or pyrrolidinyl; $R^{4a}$ is H, methoxy, or oxetanyloxy; $R^{4b}$ is H or F; $R^{4c}$ is H or F; $R^{4d}$ is H, Cl, methyl, methoxy, or —O—CHF$_2$; $R^5$ is Cl, CN, CF$_3$, or —CHF$_2$; T is absent, —O—, —O—CH$_2$—; or —O—(CH)(CH$_3$)—; and $R^8$ is H, F, Cl, methyl, methoxy, CF$_3$, or isopropyl.

In embodiment 41, the present invention provides compounds of Formula (I), and sub-Formulas thereof, as defined above, or pharmaceutically acceptable salts thereof, selected from any of the compounds of Examples No. 1 to No. 565 and Intermediate K, as listed in the priority document of the present application, i.e., U.S. Provisional Patent Application No. 61/885,372, pages 85 to 291, filed Oct. 1, 2013.

In embodiment 42, the present invention provides compounds of Formula (I), and sub-Formulas thereof, as defined above, or pharmaceutically acceptable salts thereof, selected from: Examples No. 1-841 disclosed in the present application and priority document thereof.

In embodiment 43, the present invention provides compounds of Formula (I), and sub-Formulas thereof, as defined above, or pharmaceutically acceptable salts thereof, selected from:

| EX. NO. | NAME |
|---|---|
| 576 | 4-(5-chloro-6-((4-chlorobenzyl)oxy)-3-pyridinyl)-3-methoxy-N-(methylsulfonyl)benzamide |
| 579 | 4-(5-chloro-6-(3-chloro-2-methylphenoxy)-3-pyridinyl)-3-methoxy-N-(methylsulfonyl)benzamide |
| 589 | 5-chloro-4-(5-chloro-6-(2,3,5-trifluorophenoxy)-3-pyridinyl)-2-fluoro-N-(methylsulfonyl)benzamide |
| 598 | 5-chloro-4-(5-chloro-6-(2,4-dichloro-6-methylphenoxy)-3-pyridinyl)-2-fluoro-N-(methylsulfonyl)benzamide |
| 623 | 4-(5-chloro-6-(3-fluoro-4-methylphenoxy)-3-pyridinyl)-2-fluoro-5-methyl-N-(methylsulfonyl)benzamide |
| 673 | 4-(5-chloro-6-((1R)-1-(2,5-dichlorophenyl)ethoxy)-3-pyridinyl)-2-fluoro-5-methyl-N-(methylsulfonyl)benzamide |
| 690 | 4-(6-(3-chloro-2-methylphenoxy)-5-cyano-3-pyridinyl)-3-methoxy-N-(methylsulfonyl)benzamide |
| 694 | 4-(5-cyano-6-(3,6-dichloro-2-methylphenoxy)-3-pyridinyl)-3-methoxy-N-(methylsulfonyl)benzamide |
| 702 | 4-(5-chloro-6-(cyclobutyloxy)-3-pyridinyl)-2-fluoro-5-methoxy-N-(methylsulfonyl)benzamide |
| 704 | 4-(5-chloro-6-(3-chloro-2-methylphenoxy)-3-pyridinyl)-2-fluoro-5-methoxy-N-(methylsulfonyl)benzamide |
| 705 | 4-(5-chloro-6-((1-methylcyclopropyl)methoxy)-3-pyridinyl)-2-fluoro-5-methoxy-N-(methylsulfonyl)benzamide |
| 706 | 4-(5-chloro-6-(2,5-difluorophenoxy)-3-pyridinyl)-2-fluoro-5-methoxy-N-(methylsulfonyl)benzamide |
| 709 | 4-(6-(1,3-benzothiazol-2-ylmethoxy)-5-chloro-3-pyridinyl)-2-fluoro-5-methoxy-N-(methylsulfonyl)benzamide |
| 734 | 4-(5-chloro-6-((1-(trifluoromethyl)cyclobutyl)oxy)-3-pyridinyl)-2-fluoro-5-methoxy-N-(methylsulfonyl)benzamide |
| 735 | 4-(5-chloro-6-((trans-3-methylcyclobutyl)oxy)-3-pyridinyl)-2-fluoro-5-methoxy-N-(methylsulfonyl)benzamide |
| 769 | 4-(5-chloro-6-((1R)-1-cyclobutylethoxy)-3-pyridinyl)-2-fluoro-5-methoxy-N-(methylsulfonyl)benzamide |
| 752 | 4-(5-chloro-6-(2-chloro-5-methylphenoxy)-3-pyridinyl)-2-fluoro-5-methoxy-N-(methylsulfonyl)benzamide |
| 777 | 3-chloro-4-(5-chloro-6-(3,5-dichlorophenoxy)-3-pyridinyl)-N-(methylsulfonyl)benzamide |
| 782 | 4-(5-chloro-6-(2,4-dichloro-6-methylphenoxy)-3-pyridinyl)-5-(difluoromethoxy)-2-fluoro-N-(methylsulfonyl)benzamide |
| 784 | 4-(5-chloro-6-(3,5-dichlorophenoxy)-3-pyridinyl)-5-(difluoromethoxy)-2-fluoro-N-(methylsulfonyl)benzamide |
| 791 | 4-(5-chloro-6-(2,3,6-trifluorophenoxy)-3-pyridinyl)-N-(ethylsulfonyl)-3-methoxybenzamide |
| 825 | 4-(6-(3,5-dichlorophenoxy)-5-(trifluoromethyl)-3-pyridinyl)-3-methoxy-N-(methylsulfonyl)benzamide |
| 826 | 4-(5-chloro-6-(3-chloro-4-methylphenoxy)-3-pyridinyl)-N-(methylsulfonyl)-3-(3-oxetanyloxy)benzamide |
| 827 | 4-(5-chloro-6-(3,5-dichlorophenoxy)-3-pyridinyl)-3-methoxy-N-(methylsulfonyl)benzamide |
| 828 | 4-(5-chloro-6-(2-chloro-5-methylphenoxy)-3-pyridinyl)-N-(methylsulfonyl)-3-(3-oxetanyloxy)benzamide |
| 829 | 4-(6-(3-chloro-4-methylphenoxy)-5-cyano-3-pyridinyl)-3-methoxy-N-(methylsulfonyl)benzamide |
| 830 | 4-(6-(3,5-dichlorophenoxy)-5-(difluoromethyl)-3-pyridinyl)-3-methoxy-N-(methylsulfonyl)benzamide |
| 831 | 4-(5-chloro-6-(2,3,6-trifluorophenoxy)-3-pyridinyl)-3-methoxy-N-(methylsulfonyl)benzamide |
| 832 | 4-(5-chloro-6-((3-chloro-2-methoxy-4-pyridinyl)oxy)-3-pyridinyl)-3-methoxy-N-(methylsulfonyl)benzamide |
| 833 | 4-(5-chloro-6-((2R)-2-(1-methylethyl)-1-pyrrolidinyl)-3-pyridinyl)-3-(difluoromethoxy)-N-(methylsulfonyl)benzamide |
| 833 | 4-(5-chloro-6-((2S)-2-(1-methylethyl)-1-pyrrolidinyl)-3-pyridinyl)-3-(difluoromethoxy)-N-(methylsulfonyl)benzamide |

In embodiment 44, the present invention provides pharmaceutical compositions comprising a compound, or a pharmaceutically acceptable salt thereof, in accordance with any one of embodiments 1 to 43, or a pharmaceutically acceptable salt thereof, and a pharmaceutically acceptable excipient.

In embodiment 45, the present invention provides methods of treating pain, the methods comprising administering to a patient in need thereof a therapeutically effective amount of a compound, or a pharmaceutically acceptable salt thereof, in accordance with any one of embodiments 1 to 43, or a pharmaceutically acceptable salt thereof.

In embodiment 46, the present invention provides methods of embodiment 45 wherein the treatment is for chronic pain, acute pain, neuropathic pain, pain associated with rheumatoid arthritis, pain associated with osteoarthritis, pain associated with cancer or a cough selected from the group consisting of post viral cough, viral cough, and acute viral cough. See Nature Reviews Neuroscience|AOP, published online 12 Dec. 2012; doi: 10.1038/nrn3404.

In embodiment 47, the present invention provides methods of embodiment 45 wherein the treatment is for pain, cough, or itch, comprising administering to a patient in need thereof a therapeutically effective amount of the compound in accordance with any of the preceding claims, or a pharmaceutically acceptable salt thereof, wherein the pain is selected from chronic pain, acute pain, neuropathic pain, pain associated with rheumatoid arthritis, pain associated with osteoarthritis, or pain associated with cancer; wherein the cough is selected from post viral cough, viral cough, or acute viral cough; and wherein the itch is selected from a) psoriatic pruritis, itch due to hemodyalisis, aguagenic pruritis, and itching caused by skin disorders (e.g., contact dermatitis), systemic disorders, neuropathy, psychogenic factors or a mixture thereof; b) itch caused by allergic reactions, insect bites, hypersensitivity (e.g., dry skin, acne, eczema, psoriasis), inflammatory conditions or injury; c) itch associated with vulvar vestibulitis; d) skin irritation or inflammatory effect from administration of another therapeutic selected from antibiotics, antivirals and antihistamines; or e) itch due to activation of PAR-2 G-protein coupled receptors.

In embodiment 48, the invention provides each individual compound, or a pharmaceutically acceptable salt thereof, or a sub-set of compounds, as described in the examples herein.

In embodiment 49, the invention provides a method of preparing a compound of Formula (Ia) as described above. In a sub embodiment, said method is as described in any of Schemes A, A1, B, C, F, G, and H below.

In embodiment 50, the invention provides an intermediate compound used in the method of preparing a compound of Formula (Ia) as described above. In a sub embodiment, said intermediate compound is as described in any of Schemes A, A1, B, C, F, G, and H below.

The present invention provides compounds of Formula (I), and sub-Formulas thereof, as defined above, and pharmaceutically acceptable salts thereof. The present invention also provides pharmaceutical compositions comprising a compound of Formula (I), or a sub-Formula thereof, as a free base or a pharmaceutically acceptable salt thereof, and methods of treating diseases and/or conditions, such as pain, cough, or itch, by using compounds of Formula (I), or pharmaceutically acceptable salts thereof.

The term "alkyl" means a straight or branched chain hydrocarbon. Representative examples of alkyl groups include methyl, ethyl, propyl, isopropyl, butyl, isobutyl, tert-butyl, sec-butyl, pentyl and hexyl. Typical alkyl groups are alkyl groups having from 1 to 8 carbon atoms, which groups are commonly represented as $C_{1-8}$-alkyl.

The term "alkoxy" means an alkyl group bonded to an oxygen atom. Representative examples of alkoxy groups include methoxy, ethoxy, tert-butoxy, propoxy and isobutoxy. Common alkoxy groups are $C_{1-8}$alkoxy.

The term "halogen" or "halo" means chlorine, fluorine, bromine or iodine.

The term "alkenyl" means a branched or straight chain hydrocarbon having one or more carbon-carbon double bonds. Representative examples alkenyl groups include ethenyl, propenyl, allyl, butenyl and 4-methylbutenyl. Common alkenyl groups are $C_{2-8}$alkenyl.

The term "alkynyl" means a branched or straight chain hydrocarbon having one or more carbon-carbon triple bonds. Representative examples of alkynyl groups include ethynyl, propynyl (propargyl) and butynyl. Common alkynyl groups are $C_{2-8}$ alkynyl.

The term "cycloalkyl" means a cyclic, nonaromatic hydrocarbon. Examples of cycloalkyl groups include cyclopropyl, cyclobutyl, cyclopentyl, cyclohexyl, cycloheptyl, bicyclo[2.2.1]heptanyl, bicyclo[4.4.0]decanyl, spiro[2.2]pentyl, spiro[2.4]heptyl, and spiro[2.5]octyl. A cycloalkyl group can contain one or more double bond. Examples of cycloalkyl groups that contain double bonds include cyclopentenyl, cyclohexenyl, cyclohexadienyl and cyclobutadienyl. Common cycloalkyl groups are $C_{3-8}$ cycloalkyl groups.

The term "perfluoroalkyl" means an alkyl group in which all of the hydrogen atoms have been replaced with fluorine atoms. Common perfluoroalkyl groups are $C_{1-8}$perfluoroalkyl. An example of a common perfluoroalkyl group is $CF_3$.

The term "acyl" means a group derived from an organic acid by removal of the hydroxy group (—OH). For example, the acyl group $CH_3C(=O)$ is formed by the removal of the hydroxy group from $CH_3C(=O)OH$.

The term "aryl" means a cyclic, aromatic hydrocarbon. Examples of aryl groups include phenyl and naphthyl. Common aryl groups are six to thirteen membered rings.

The term "heteroatom" as used herein means an oxygen, nitrogen or sulfur atom.

The term "heteroaryl" means a cyclic, aromatic hydrocarbon in which one or more carbon atoms of an aryl group have been replaced with a heteroatom independently selected from O, N or S. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, indolyl, triazolyl, pyridazinyl, indazolyl, purinyl, quinolizinyl, isoquinolyl, quinolyl, naphthyridinyl, quinoxalinyl, isothiazolyl and benzo[b]thienyl. Common heteroaryl groups are five to thirteen membered rings that contain from 1 to 4 heteroatoms. Heteroaryl groups that are five and six membered rings that contain 1 to 3 heteroatoms are particularly common.

The term "heterocycloalkyl" means a cycloalkyl group in which one or more of the carbon atoms has been replaced with a heteroatom. If the heterocycloalkyl group contains more than one heteroatom, the heteroatoms may be the same or different. Examples of heterocycloalkyl groups include tetrahydrofuryl, morpholinyl, piperazinyl, piperidinyl and pyrrolidinyl. It is also possible for the heterocycloalkyl group to have one or more double bonds, but is not aromatic. Examples of heterocycloalkyl groups containing double bonds include dihydrofuran. Common heterocycloalkyl groups are three to ten membered rings containing from 1 to 4 heteroatoms. Heterocycloalkyl groups that are five and six membered rings that contain 1 to 2 heteroatoms are particularly common.

It is also noted that the cyclic ring groups, i.e., aryl, heteroaryl, cycloalkyl, and heterocycloalkyl, can comprise more than one ring. For example, the naphthyl group is a fused bicyclic ring system. It is also intended that the present invention include ring groups that have bridging atoms, or ring groups that have a spiro orientation.

Representative examples of five to six membered aromatic rings, optionally having one or two heteroatoms, are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl, and pyrazinyl.

Representative examples of partially saturated, fully saturated or fully unsaturated five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-di oxazolyl, 1,3,4-di oxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyndazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-(3 oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, optionally having one to four heteroatoms, are indolizinyl, indolyl, isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)pyridinyl, pyrido(3,2-b)pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "hydroxyalkyl" means an "alkyl" group wherein one or more of the carbon atoms are substituted with a hydroxyl (—OH) group. Similarly the term "dihydroxyalkyl" means an alkyl group in which two (2) hydrogen atoms have been replaced by two (2) hydroxyl groups, ie., the alkyl has 2 hydroxyl substituents.

The term "substituted" means that a hydrogen atom on a molecule or group is replaced with a group or atom. Typical substituents include: halogen, $C_{1-8}$alkyl, hydroxyl, $C_{1-8}$alkoxy, —$NR^xR^x$, nitro, cyano, halo or perhalo$C_{1-8}$alkyl, $C_{2-8}$alkenyl, $C_{2-8}$alkynyl, —$SR^x$, —$S(=O)_2R^x$, —$C(=O)OR^x$, —$C(=O)R^x$, wherein each $R^x$ is independently hydrogen or $C_1$-$C_8$ alkyl. It is noted that when the substituent is —NR$^x$R$^x$, the R$^x$ groups may be joined together with the nitrogen atom to form a ring.

The term "oxo", when used as a substituent, means the =O group, which is typically attached to a carbon atom.

A group or atom that replaces a hydrogen atom is also called a substituent.

Any particular molecule or group can have one or more substituent depending on the number of hydrogen atoms that can be replaced.

The symbol "—" represents a covalent bond and can also be used in a radical group to indicate the point of attachment to another group. In chemical structures, the symbol is commonly used to represent a methyl group in a molecule.

The term "therapeutically effective amount" means an amount of a compound that ameliorates, attenuates or eliminates one or more symptom of a particular disease or condition, or prevents or delays the onset of one of more symptom of a particular disease or condition.

The term "patient" means animals, such as dogs, cats, cows, horses, sheep and humans. Particular patients are mammals. The term patient includes males and females.

The term "pharmaceutically acceptable" means that the referenced substance, such as a compound of the present invention or a formulation containing a compound of the present invention, or a particular excipient, are suitable for administration to a patient.

The terms "treating", "treat" or "treatment" and the like include preventative (e.g., prophylactic) and palliative treatment.

The term "patient in need thereof" means a patient who has or is at risk of having a disease and/or condition that can be treated by inhibition of Nav 1.7, such as chronic pain.

The term "excipient" means any pharmaceutically acceptable additive, carrier, diluent, adjuvant, or other ingredient, other than the active pharmaceutical ingredient (API), which is typically included for formulation and/or administration to a patient.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered by a tablet, while another is administered by injection or orally as a syrup. All combinations, delivery methods and administration sequences are contemplated.

The compounds of the present invention may be used in the manufacture of a medicament for the treatment of a disease and/or condition mediated by Nav 1.7, such as pain, chronic cough or itch.

Pain is typically divided into primary types: chronic and acute pain based on the duration of the pain. Typically, chronic pain lasts for longer than 3 months. Examples of chronic pain include pain associated with rheumatoid arthritis, osteoarthritis, lumbosacral radiculopathy or cancer. Chronic pain also includes idiopathic pain, which is pain that has no identified cause. An example of idiopathic pain is fibromyalgia.

Another type of pain is nociceptive pain. Nociceptive pain is caused by stimulation of peripheral nerve fibers that respond to highly noxious events such as thermal, mechanical or chemical stimuli.

Still another type of pain is neuropathic pain. Neuropathic pain is pain that is caused by damage or disease affecting a part of the nervous system. Phantom limb pain is a type of neuropathic pain. In phantom limb pain, the body detects pain from a part of a body that no longer exists. For example, a person who has had a leg amputated may feel leg pain even though the leg no longer exists.

In one embodiment of the methods of treatment provided by the present invention using the compounds of Formula I, or pharmaceutically acceptable salts thereof, the disease is chronic pain. In another aspect, the chronic pain is associated with, but are not limited to, post-herpetic neuralgia (shingles), rheumatoid arthritis, osteoarthritis, diabetic neuropathy, complex regional pain syndrome (CRPS), cancer or chemotherapy-induced pain, chronic back pain, phantom limb pain, trigeminal neuralgia, HIV-induced neuropathy, cluster headache disorders, and migraine, primary erythromelalgia, and paroxysmal extreme pain disorder. Other indications for Nav 1.7 inhibitors include, but are not limited to, depression (Morinville et al., *J Comp Neurol.*, 504:680-689 (2007)), bipolar and other CNS disorders (Ettinger and Argoff, *Neurotherapeutics*, 4:75-83 (2007)), epilepsy: ibid., and Gonzalez, Termin, Wilson, *Methods and Principles in Medicinal Chemistry*, 29:168-192 (2006)), multiple sclerosis (Waxman, *Nature Neurosci.* 7:932-941 (2006)), Parkinson's (Do and Bean, *Neuron* 39:109-120 (2003); Puopolo et al., *J. Neurosci.* 27:645-656 (2007)), restless legs syndrome, ataxia, tremor, muscle weakness, dystonia, tetanus (Hamann M., et. al., *Exp. Neurol.* 184(2):830-838, 2003), anxiety, depression: McKinney B. C, et. al., *Genes Brain Behav.* 7(6):629-638, 2008), learning and memory, cognition (Woodruff-Pak D. S., et. al., *Behav. Neurosci.* 120(2):229-240, 2006), cardiac arrhythmia and fibrillation, contractility, congestive heart failure, sick sinus syndrome (Haufe V., et. al., *J Mol. Cell Cardiol.* 42(3):469-477, 2007), schizophrenia, neuroprotection after stroke, drug and alcohol abuse (Johannessen L. C., *CNS Drugs* 22(1)27-47, 2008), Alzheimer's (Kim D. Y., et. al., *Nat. Cell. Biol.* 9(7):755-764, 2007), and cancer (Gillet L., et. *J Biol Chem* 2009, January 28 (epub)).

Another aspect of the invention relates to a method of treating acute and/or chronic inflammatory and neuropathic pain, dental pain, general headache, migraine, cluster headache, mixed-vascular and non-vascular syndromes, tension headache, general inflammation, arthritis, rheumatic diseases, rheumatoid arthritis, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound according to the present invention. A preferred type of pain to be treated is chronic neuropathic pain. Another preferred type of pain to be treated is chronic inflammatory pain.

In another aspect of the invention, the compounds of the present invention can be used in combination with other compounds that are used to treat pain. Examples of such other compounds include, but are not limited to aspirin, celecoxib, hydrocodone, oxycodone, codeine, fentanyl, ibuprofen, ketoprofen, naproxen, acetaminophen, gabapentin and pregabalin. Examples of classes of medicines that contain compounds that can be used in combination with the compounds of the present invention include non-steroidal anti-inflammatory compounds (NSAIDS), steroidal compounds, cycloxogenase inhibitors and opiod analgesics.

In another aspect of the invention, the compounds of the present invention can be used in combination with other compounds that are used to treat itch. Pruritus, commonly known as itch, is a common dermatological condition. There exist two broad categories of itch based upon the etiology: inflammatory skin itch and neuropathic itch (Binder et al., Nature Clinical Practice, 4:329-337, 2008). In the former case, inflammatory mediators activate cutaneous pruriceptors, a subset of dermal afferent nerve fibers, primarily unmyelinated C fibers. Treatments for this type of itch consist of either blocking receptors for the inflammatory agents (such as anti-histamines) or blocking the ensuing electrical activity. Voltage-gated sodium channels have a central role in the transmission of electrical activity in neurons and modulation of voltage-gated sodium channels is a well established means of modulating this signalling. Although the causes of neuropathic pruritus are complex and less well understood, there is well established evidence of central sensitization and hypersensitivity of input from sensory neuron C fibers in the dermis. As for inflammatory itch, sodium channels likely are essential for propagating electrical signals from the skin to the CNS. Transmission of the itch impulses results in the unpleasant sensation that elicits the desire or reflex to scratch.

Both inflammatory and neuropathic itch can be blocked by known voltage-gated sodium channel blockers, most commonly lidocaine (Villamil et al., American Journal of Medicine 118:1160-1163, 2005; Inan et al., European Journal of Pharmacology 616: 141-146, 2009; Fishman et al., American Journal of Medicine 102: 584-585, 1997; Ross et al., Neuron 65: 886-898, 2010). The doses of lidocaine needed to relieve itch are comparable to those effective in treating pain. Both sensory circuits share common mediators and related neuronal pathways (Ikoma et al., Nature Reviews Neuroscience, 7:535-547, 2006). However, other treatments for pain are ineffective against itch and can exacerbate pruritis rather than relieve it. For example, opioids, in particular, are effective at relieving pain, yet can generate severe pruritus. Thus, voltage-gated sodium channel block is a particularly promising therapy for both pain and itch. See also Devigili, et. al., *Pain* (2014), 155(9), 1702-1707; and Lee Jun-Ho et. al., *Cell* (2014), 157(6), 1393-404.

Compounds of the present invention have been shown to have analgesic effects in a number of animal models at oral doses ranging from 1 mg/Kg to 100 mg/Kg. The compounds of the invention can also be useful for treating pruritis.

The types of itch or skin irritation, include, but are not limited to:
a) psoriatic pruritis, itch due to hemodyalisis, aguagenic pruritis, and itching caused by skin disorders (e.g., contact dermatitis), systemic disorders, neuropathy, psychogenic factors or a mixture thereof; b) itch caused by allergic reactions, insect bites, hypersensitivity (e.g., dry skin, acne, eczema, psoriasis), inflammatory conditions or injury; c) itch associated with vulvar vestibulitis; d) skin irritation or inflammatory effect from administration of another therapeutic such as, for example, antibiotics, antivirals and antihistamines; and e) itch due to activation of PAR-2 G-protein coupled receptors.

The compounds of the present invention may also be used to treat diabetes, obesity and/or to facilitate weight loss.

The compounds of the present invention may be used in combination with other pharmaceutically active compounds. It is noted that the term "pharmaceutically active compounds" can include biologies, such as proteins, antibodies and peptibodies.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed by said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or fit compounds are admixed under sterile condition with a physiologically acceptable carrier, and any preservatives, buffers, or propellants that may be required. Opthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

The compounds of the present invention can be administered as pharmaceutically acceptable salts, cocrystyals, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$-$C_{12}$) alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

In addition, if a compound of the present invention comprises a sulfonamide moiety, a prodrug can be formed by replacement of the sulfonamide N(H) with a group such as —CH$_2$P(O)(O($C_1$-$C_6$)alkyl)$_2$ or —CH$_2$OC(O)($C_1$-$C_6$) alkyl.

The compounds of the present invention also include tautomeric forms of prodrugs.

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as S and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can can also be separated by converting the enantiomeric mixture into a diastereomeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls that are stereoisomeric due to hindered rotation around a bond).

The compounds of the present invention may exist in unsolvated as well as solvated forms with pharmaceutically acceptable solvents such as water (hydrate), ethanol, and the like. The present invention contemplates and encompasses both the solvated and unsolvated forms.

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{16}O$, $^{17}O$, $^{31}P$, $^{32}P$, $^{35}S$, $^{18}F$, and $^{36}Cl$. In another aspect, the compounds of the present invention contain one or more deuterium atoms (2H) in place of one or more hydrogen atoms.

Compounds of the present invention that contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detection. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

In synthesizing compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxysuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

All patents and other publications recited herein are hereby incorporated by reference in their entirety.

The examples presented below illustrate specific embodiments of the present invention. These examples are meant to be representative and are not intended to limit the scope of the claims in any manner.

It is noted that when a percent (%) is used with regard to a liquid, it is a percent by volume with respect to the solution. When used with a solid, it is the percent with regard to the solid composition. Materials obtained from commercial suppliers were typically used without further purification. Reactions involving air or moisture sensitive reagents were typically performed under a nitrogen or argon atmosphere. Purity was measured using high performance liquid chromatography (HPLC) system with UV detection at 254 nm and 215 nm (System A: Agilent Zorbax Eclipse XDB-C8 4.6×150 mm, 5 μm, 5 to 100% $CH_3CN$ in $H_2O$ with 0.1% TFA for 15 min at 1.5 mL/min; System B: Zorbax SB-C8, 4.6×75 mm, 10 to 90% $CH_3CN$ in $H_2O$ with 0.1% formic acid for 12 min at 1.0 mL/min) (Agilent Technologies, Santa Clara, Calif.). Silica gel chromatography was generally performed with prepacked silica gel cartridges (Biotage, Uppsala, Sweden or Teledyne-Isco, Lincoln, Nebr.). $^1H$ NMR spectra were recorded on a Bruker AV-400 (400 MHz) spectrometer (Bruker Corporation, Madison, Wis.) or a Varian (Agilent Technologies, Santa Clara, Calif.) 400 MHz spectrometer at ambient temperature. All observed protons are reported as parts per million (ppm) downfield from tetramethylsilane (TMS) or other internal reference in the appropriate solvent indicated. Data are reported as follows: chemical shift, multiplicity (s=singlet, d=doublet, t=triplet, q=quartet, br=broad, m=multiplet), coupling constants, and number of protons. Low-resolution mass spectral (MS) data were determined on an Agilent 1100 Series (Agilent Technologies, Santa Clara, Calif.) LC/MS with UV detection at 254 nm and 215 nm and a low resonance electrospray mode (ESI).

The following abbreviations may be used herein:
AmPhos 4-(di-tert-butylphosphino)-N,N-dimethylaniline
AcCl acetyl chloride
ACN Acetonitrile
AcOH acetic acid
aq or aq. Aqueous
BOC or Boc tert-butyloxycarbonyl
Bn Benzyl
DBU 1,8-diazabicyclo[5.4.0]undec-7-ene
DCM Dichloromethane
DMAP 4-dimethylaminopyridine
DMB Dimethoxybenzyl
DME Dimethoxyethane
DMF N,N-dimethylformamide
DMSO dimethyl sulfoxide
Dppf, DPPFordppf 1,1'-bis(diphenylphosphino)ferrocene
ESI or ES electrospray ionization
Et Ethyl
$Et_2O$ diethyl ether
$Et_3N$ Triethylamine
EtOAc ethyl acetate
eq or eq. Equivalent
g Grams
h Hour
HPLC high pressure liquid chromatography
iPr Isopropyl
$iPr_2NEt$ N-ethyl diisopropylamine (Hunig's base)
KOAc potassium acetate
LC MS, LCMS, LC-MS or LC/MS liquid chromatography mass spectroscopy
LHMDS or LiHMDS lithium hexamethyldisilazide
m/z mass divided by charge
Me Methyl
MeOH Methanol
MeCN or ACN Acetonitrile
mg Milligrams
min Minutes
mL Milliliters
MPLC medium pressure liquid chromatography
MS mass spectra
NBS N-bromosuccinimide
NCS N-chlorosuccinimide
n-BuLi n-butyllithium NMR nuclear magnetic resonance
Pd₂(dba)₃ tris(dibenzylideneacetone)dipalladium(0)
Ph Phenyl
PMB p-methoxybenzyl
RT or rt room temperature
SEM 2-(trimethylsilyl)ethoxymethyl
SFC supercritical fluid chromatography
TBAF tetra-n-butylammonium fluoride
t-BuOH tert-butanol
TIPS-Cl triisopropylsilyl chloride
TFA trifluoroacetic acid
THF tetrahydrofuran
UV ultraviolet
Xantphos 4,5-bis(diphenylphosphino)-9,9-dimethylxanthene
X-Phos 2-dicyclohexylphosphino-2',4',6'-triisopropyl-1,1'-biphenyl General Synthetic Scheme Compounds of the present invention can be made by the methods depicted in the general reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds of Formula (I) and subgenus thereof, i.e., Formulae (Ia) and (Ib), as defined in the Summary of the Invention can be prepared as illustrated and described in Schemes A1 and A2 below.

SCHEME A1

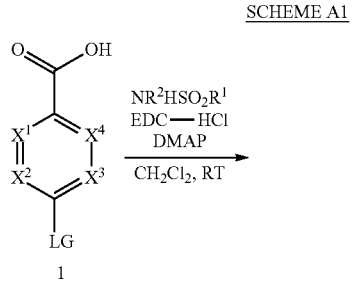

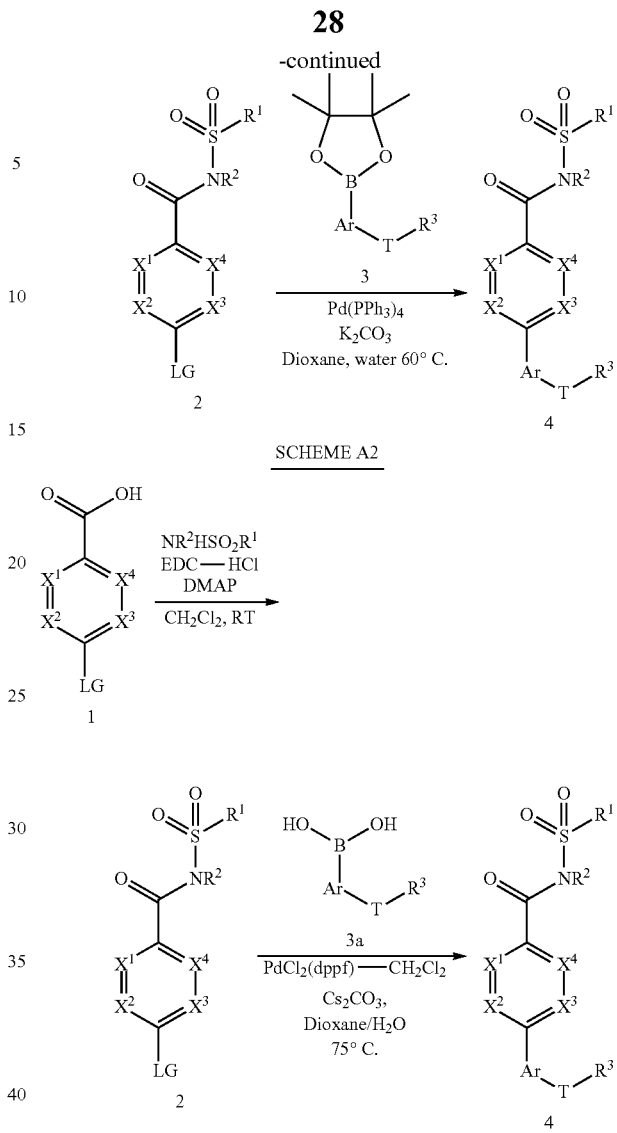

Step 1: Sulfonamidation of carboxylic acid step. In step 1, a carboxylic acid reagent 1, wherein LG is a leaving group, such as halo, more specifically bromo or chloro, can be reacted with a sulfonylation agent, such as NH₂SO₂Me, in the presence of a coupling reagent, such as EDC-HCl, and a base, such as DMAP, in a solvent such as methylene chloride, CCl₄, or neat, at room temperature, to form a sulfonamide intermediate compound 2.

Step 2: Coupling of sulfonamide intermediate compound 2 with a boronate reagent 3 or 4 to form compound 4. In step 2 of Scheme A1, compound 2 can be reacted with a boronate reagent 3, in the presence of a catalyst, such as Pd(PPh₃)₄ and potassium carbonate, in various solvents, such as dioxane/water, THF, diethyl ether, DME or dioxane, at an elevated temperature, such as 60° C., to form a biaryl acyl sulfonyl compound 4. The boronate reagents are commercially available or can be made by processes known to those skilled in the art, for example by reacting an aryl halide with 4,4,4',4',5,5,5',5'-octamethyl-2,2'-bi(1,3,2-dioxaborolane).

Alternatively, in step 2 of Scheme A2, compound 2 can be reacted with a boronate reagent 3a, in the presence of a catalyst, such as PdCl$_2$(dppf)-CH$_2$Cl$_2$ and Cs$_2$CO$_3$, in various solvents, such as dioxane/water, THF, diethyl ether, DME or dioxane, at an elevated temperature, such as 75° C., to form a biaryl acyl sulfonyl compound 4.

Yet alternatively, compounds of formula I and subgenus thereof wherein T is —O— can be prepared as described in Scheme B below.

SCHEME B

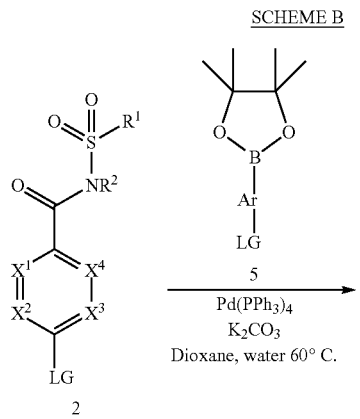

2

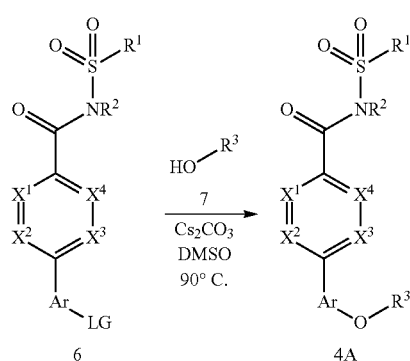

6  4A

Step 1: Coupling of sulfonamide intermediate compound 2 with a boronate reagent 5, wherein LG is a leaving group, such as halo, to form sulfonamide intermediate compound 6. In step 1, compound 2 can be reacted with a boronate reagent 5, in the presence of a catalyst, such as Pd(PPh$_3$)$_4$ and potassium carbonate, in various solvents, such as dioxane/water, THF, diethyl ether, DME or dioxane, at an elevated temperature, such as 60° C., to form a sulfonamide intermediate compound 6, wherein LG is a leaving group, such as halo. The boronate reagents are commercially available or can be made by processes known to those skilled in the art, for example by reacting an aryl halide with 4,4,4',4',5,5,5', 5'-octamethyl-2,2'-bi(1,3,2-dioxaborolane).

Step 2: Coupling of sulfonamide intermediate compound 6 with alcohol reagent 7 to form compound 4A. In step 2, compound 6 can be reacted with HT-R$^3$ agent, for example, when T is —O—, the corresponding HT-R$^3$ agent is an alcohol, in the presence of a base, such as Cs$_2$CO$_3$, in various solvents, such as DMSO, at an elevated temperature, such as 90° C., to form a sulfonamide compound 4A.

Furthermore, compounds 4 or 4A, wherein X$^4$ is CR$^4$ and R$^4$ s a group capable of undergoing palladium mediated oxidative addition, such as a bromide, can be reacted in a second coupling step with a coupling reagent, such as boronate reagent 8 as described in Scheme C below.

SCHEME C

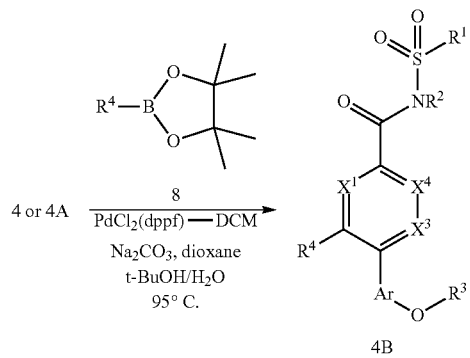

4 or 4A  4B

In Scheme C, compound 4 or 4A can be reacted with a second boronate agent compound 8 containing an R$^4$ group, such as 2-(C$_{1-6}$alkyl)-4,4,5,5-tetramethyl-1,3,2-dioxaborolane or 2-(B group)-4,4,5,5-tetramethyl-1,3,2-dioxaborolane, in the presence of a catalyst, such as PdCl$_2$(dppf)-CH$_2$Cl$_2$ and a base such as sodium carbonate, in various solvents, such as dioxane/tert-butanol, and water, at an elevated temperature, such as 95° C., to form a sulfonamide compound 4B, which is compound 4, wherein X$^2$ is CR$^4$ and R$^4$ is C$_{1-6}$alkyl, C$_{1-6}$alkyl-O—C$_{1-6}$alkyl-, or a B group.

Yet alternatively, compounds of formula I wherein T is absent and Ar is an oxadiazolyl group or pyrazolyl group can be prepared as described in Schemes D, E1, and E2 as described in the of the present application, i.e., U.S. Provisional Patent Application No. 61/885,372, pages 6 to 22, filed Oct. 1, 2013.

Yet alternatively, compounds of formula I and subgenus thereof (Compound 4E) wherein T is NR$^d$R$^3$ can be prepared as described in Scheme F below:

SCHEME F

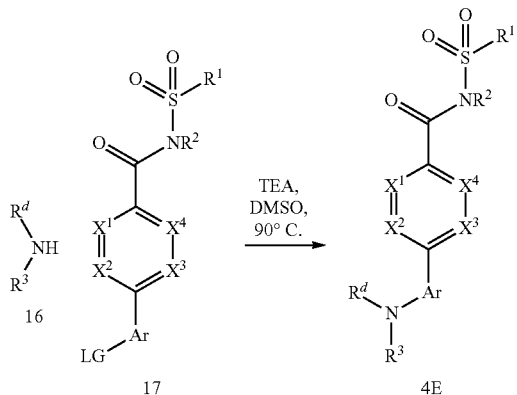

16  4E

Yet alternatively, compounds of formula I (Compound 4 above) can be prepared as described in Scheme G below:

SCHEME G

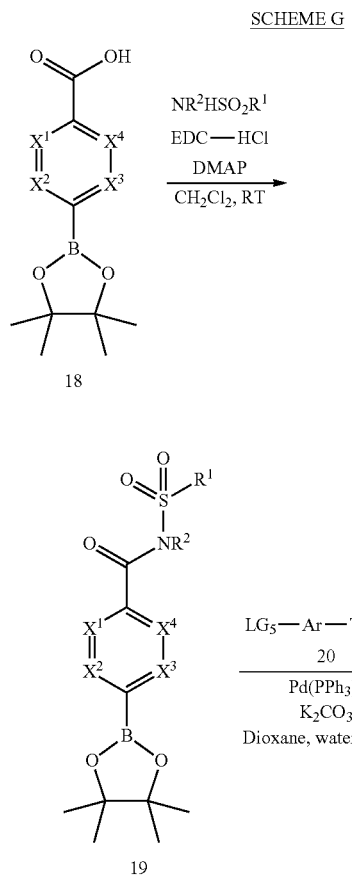

In step 1 of Scheme G, a carboxylic acid reagent 18 can be reacted with a sulfonylamine agent, such as NH$_2$SO$_2$Me, in the presence of a coupling reagent, such as EDC-HCl, in a solvent, such as DMAP and methylene chloride, CCl$_4$, or neat, at room temperature, to form compound 19. In step 2, compound 19 can be reacted with a coupling agent LG$_5$-Ar-T-R$^3$ 20, wherein LG$_5$ is substituent capable of undergoing oxidative addition, such as bromide, in the presence of a catalyst, such as Pd(PPh$_3$)$_4$ and potassium carbonate, in various solvents, such as dioxane/water, THF, diethyl ether, DME or dioxane, at an elevated temperature, such as 60° C., to form a sulfonamide compound 4.

Yet alternatively, compounds of formula I and subgenus thereof (Compound 4F) can be prepared as described in Scheme H below:

SCHEME H

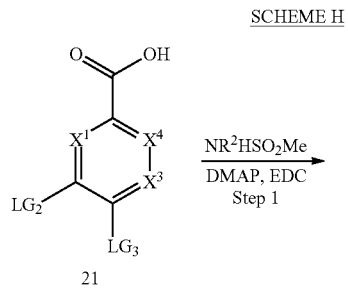

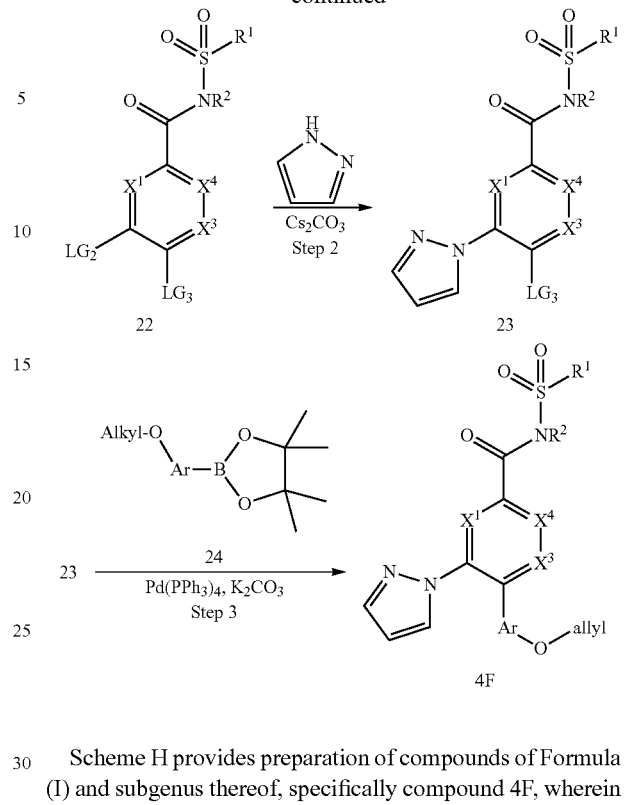

Scheme H provides preparation of compounds of Formula (I) and subgenus thereof, specifically compound 4F, wherein X$^2$ is CR$^4$, R$^4$ is pyrazolyl, T is —O—, and R is an alkyl group. In step 1 of Scheme H, a carboxylic acid reagent 21, wherein LG$_2$ and LG$_3$ are two different leaving groups, such as two different halo groups, for example fluoro and bromo, respectively, can be reacted with a sulfonylation agent, such as NH$_2$SO$_2$Me, in the presence of a coupling reagent, such as EDC, in a solvent, such as DMAP, DCM, CCl$_4$, or neat, at room temperature, to form compound 22. In step 2, compound 22 can be reacted with pyrazole, in the presence of a base, such as Cs$_2$CO$_3$, in various solvents, such as DMF, NMP, DMSO, or p-dioxanes, at an elevated temperature, such as 75° C., to form compound 23. In step 3, compound 23 can be reacted with a boronate reagent 24, in the presence of a catalyst, such as Pd(PPh$_3$)$_4$ and potassium carbonate, in various solvents, such as dioxane/water, THF, diethyl ether, DME or dioxane, at an elevated temperature, such as 60° C., to form a compound 4F.

EXAMPLES

Examples No. 1 to No. 565 and Intermediate K, as listed in the priority document of the present application, i.e., U.S. Provisional Patent Application No. 61/885,372, pages 85 to 291, filed Oct. 1, 2013, are included herein as examples of compounds of the Formula (I) and sub genus thereof. Examples Nos. 1 (Method I), 91 (Method II), 327, 329, 344, 348, 350, 355, 357, 361-365, 368-374, 376-377, 379, 382, 402, 412-413, 419, 422-426, 436, 446, 449, 452-453, 455-457, 459-462, 464-468, 539, 547, and 549 are reproduced herein.

Method I (Example 1): 4-(5-Chloro-6-Isobutoxy-pyridin-3-yl)-2,5-Difluoro-N-(Methylsulfonyl)Benzamide

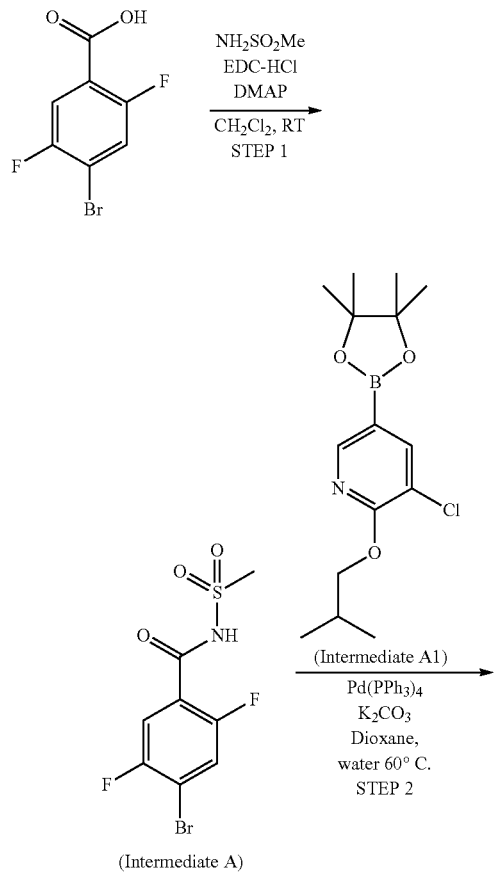

Step 1: 4-Bromo-2,5-Difluoro-N-(Methylsulfonyl)Benzamide (Intermediate A)

A round bottom flask was charged with 4-bromo-2,5-difluorobenzoic acid (10.00 g, 42.2 mmol, Aces Pharma), methanesulfonamide (4.82 g, 50.6 mmol), N,N-dimethyl-pyridin-4-amine (11.34 g, 93 mmol), and $N^1$-((ethylimino)methylene)-$N^3$,$N^3$-dimethylpropane-1,3-diamine hydrochloride (16.18 g, 84 mmol) and DCM (150 mL) was added. After stirring for 2 d at RT, the mixture was concentrated under reduced pressure to afford the crude material which was dissolved in 500 mL DCM and 10 mL methanol and filtered over 25 micron filter paper. The crude solution was injected onto a 1500 g silica gel cartridge (40-63 micron) and eluted at 300 mL/min with a gradient over ten column volumes (15 L total volume) from 2/98/0.1 methanol/DCM/HCOOH to 20/80/1 methanol/DCM/HCOOH to afford 4-bromo-2,5-difluoro-N-(methylsulfonyl)benzamide (Intermediate A) (9.78 g, 73.8%). MS (ESI, negative ion) m/z 311.

Step 2: 4-(5-Chloro-6-Isobutoxypyridin-3-yl)-2,5-Difluoro-N-(Methylsulfonyl)Benzamide A resealable 2 dram round bottom reaction tube was charged with 4-bromo-2,5-difluoro-N-(methylsulfonyl)benzamide (Intermediate A; 100 mg, 0.318 mmol), potassium carbonate (132 mg, 0.955 mmol), tetrakis(triphenylphosphine)palladium(0) (36.8 mg, 0.032 mmol), and 3-chloro-2-isobutoxy-5-(4,4,5,5-tetramethyl-1,3,2-dioxaborolan-2-yl)pyridine (Intermediate A1, 146 mg, 0.637 mmol). The vial was flushed with Ar (g), then 1,4-dioxane (2 mL) and water (0.67 mL) were added. The vial was purged with Ar (g), sealed and heated with shaking at 60° C. overnight. The crude reaction mixture was filtered through a CELITE plug and purified by Preparative LC/MS (2 System Column: XBridge 19×100 mm; Mobile phase: 0.1% $NH_4OH$ in water/acetonitrile; Flow rate: 40 ml/min Inj: 2000 uL, Gradient: 10 min 10-40% LV $NH_3$; 10 min 10-30% LV $NH_3$; 10 min 20-50% LV $NH_3$; 10 min 10-20% LV $NH_3$) to afford 4-(5-chloro-6-isobutoxypyridin-3-yl)-2,5-difluoro-N-(methylsulfonyl)benzamide as a white solid. MS (ESI, positive ion) m/z 419.0. $^1$H NMR (500 MHz, DMSO-$d_6$) δ ppm 1.00 (d, J=6.76 Hz, 6H) 1.97-2.19 (m, 1H) 3.09 (s, 3H) 4.19 (d, J=6.64 Hz, 2H) 7.48-7.70 (m, 2H) 8.18 (s, 1H) 8.37 (s, 1H)

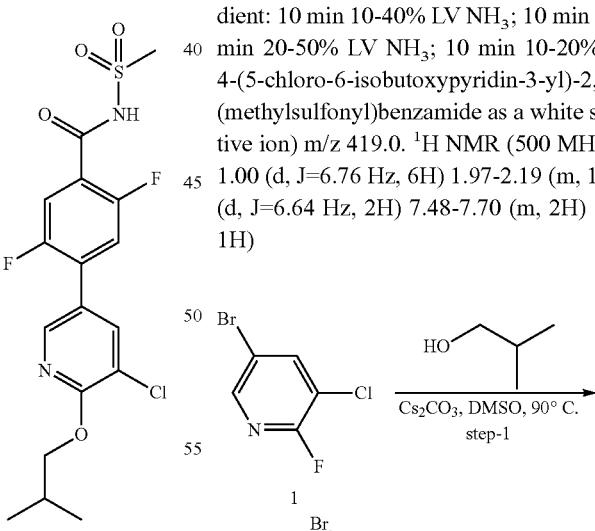

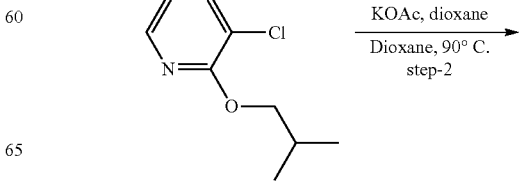

35

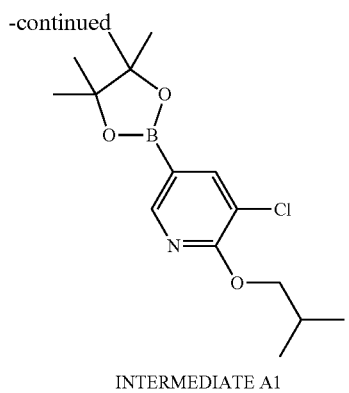

INTERMEDIATE A1

Preparation of Intermediate A1: 3-Chloro-2-Isobutoxy-5-(4,4,5,5-Tetramethyl-1,3,2-Dioxaborolan-2-yl)Pyridine Step-1: 5-Bromo-3-Chloro-2-Isobutoxypyridine To a solution of 5-bromo-3-chloro-2-fluoropyridine (5.0 g, 23.7 mmol, LLB Chem) and 2-methylpropan-1-ol (5.28 g, 71.3 mmol, Spectrochem) in DMSO (100 mL) was added $Cs_2CO_3$ (23.0 g, 71.3 mmol, GLR) and the reaction was heated at 90° C. for 3 h. The reaction mixture was allowed to cool to room temperature, water (500 mL) was added and the aqueous layer was extracted with diethyl ether (2×500 mL). The combined organic extract was dried over sodium sulfate and concentrated under reduced pressure to obtain the crude material which was purified by column chromatography (silica gel 100-200 mesh and 0-5% ethyl acetate in hexanes) to obtain compound-3 (5.0 g, 86%) as colorless oil. TLC solvent system: 10%) ethyl acetate in hexanes, product's $R_f$: 0.8. MS (ESI, positive ion): No ionization. $^1H$ NMR (400 MHz, $CDCl_3$) δ 8.06 (d, J=2.2 Hz, 1H), 7.74 (d, J=2.2 Hz, 1H), 4.11 (d, J=6.7 Hz, 2H), 2.12 (dp, J=13.4, 6.7 Hz, 1H), 1.03 (d, J=6.7 Hz, 6H).

Step-2: 3-Chloro-2-Isobutoxy-5-(4,4,5,5-Tetramethyl-1,3,2-Dioxaborolan-2-yl)-Pyridine To a solution 5-bromo-3-chloro-2-isobutoxypyridine (11.0 g, 41.5 mmol) and bis(pinacolato)diboron (13.6 g, 54.1 mmol, GLR) in 1,4-dioxan (100 mL) was added KOAc (10.1 g, 104 mmol, Spectrochem). The reaction mixture was degassed with nitrogen for 10 min. Pd(dppf)Cl$_2$:DCM (3.3 g, 4.15 mmol, GLR) was added to the reaction mixture and the mixture was allowed to stir at 90° C. for 3 h. The reaction mixture was diluted with ethyl acetate (300 mL) and filtered through a CELITE bed. The filtrate was concentrated under reduced pressure to obtain the crude material which was purified by column chromatography (neutral alumina, 0-10%) ethyl acetate in hexanes) to obtain 3-chloro-2-isobutoxy-5-(4,4,5,5-tetramethyl-1,3,2-dioxaborolan-2-yl) pyridine (6.0 g, 47%) as colorless oil. TLC solvent system: 10%> ethyl acetate in hexanes, product's $R_f$: 0.7. MS (ESI, positive ion) m/z; No ionization. $^1H$ NMR (400 MHz, $CDCl_3$) δ 8.36 (d, J=1.6 Hz, 1H), 7.96 (d, J=1.6 Hz, 1H), 4.17 (d, J=6.7 Hz, 2H), 2.14 (dt, J=13.4, 6.7 Hz, 1H), 1.35 (s, 12H), 1.03 (d, J=6.7 Hz, 6H).

36

Method II (Example 91): 4-(5-Chloro-6-Isopropoxypyridin-3-yl)-2,5-Difluoro-N-(Methylsulfonyl)Benzamide

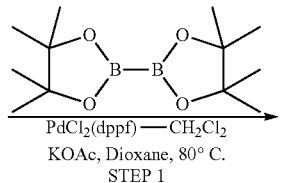

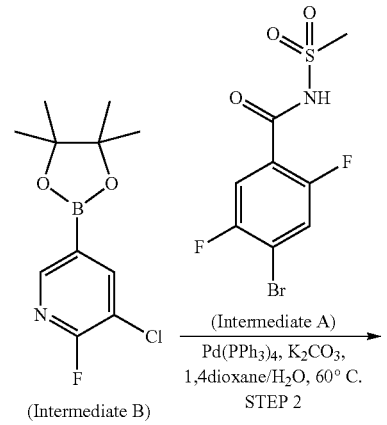

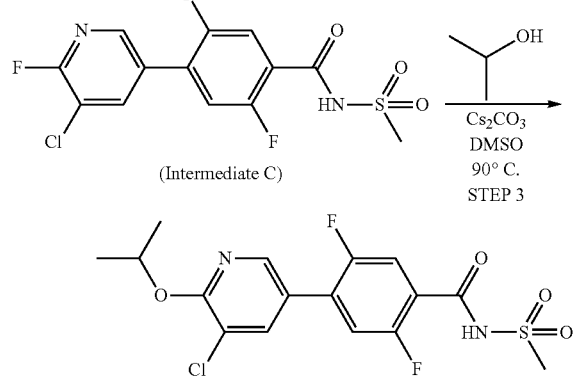

Step 1 (Intermediates): 3-Chloro-2-Fluoro-5-(4,4,5,5-Tetramethyl-1,3,2-Dioxaborolan-2-yl)Pyridine A mixture of 5-bromo-3-chloro-2-fluoropyridine (25.0 g, 118.8 mmol, Ark Pharma), 4,4,4',4',5,5,5',5'-octamethyl-2,2'-bi(1,3,2-dioxaborolane) (36.2 g, 142.5 mmol) and potassium acetate (23.3 g, 237.6 mmol) in dioxane (250 mL) was degassed with nitrogen for 10 min. PdCl$_2$(dppf)-CH$_2$Cl$_2$ (4.85 g, 5.94 mmol) was added to the reaction mixture and it was again degassed for 10 min. The reaction mixture was heated at 90° C. for 4 h. After completion, the reaction mixture was filtered through CELITE and the CELITE bed was washed with EtOAc (200 mL). The filtrate was concentrated under reduced pressure to afford the crude material which was purified by column chromatography (neutral alumina; elution: hexane) to afford Intermediate B as a white solid (22.0 g, 72.1%). MS (ESI, positive ion) m/z; No ionization. $^1H$ NMR (400 MHz, $CDCl_3$) δ 8.43 (s, 1H), 8.16 (dd, J=9.6, 1.5 Hz, 1H), 1.34 (s, 12H).

Step 2 (Intermediate C): 4-(5-Chloro-6-Fluoropyridin-3-yl)-2,5-Difluoro-N-(Methylsulfonyl)Benzamide A solution of Intermediate B (5.4 g, 17.19 mmol), Intermediate A (4.4 g, 17.19 mmol) and potassium carbonate (7.1 g, 51.7 mmol) in dioxane:water (90 mL: 30 mL) was degassed with nitrogen for 10 min. Tetrakis(triphenylphosphine) palladium(O) (1.9 g, 1.71 mmol) was added and the reaction mixture was again degassed for 10 min. The reaction mixture was heated at 60° C. for 16 h. After completion, reaction mixture was concentrated under reduced pressure and the crude material was purified by column chromatography (silica: 100-200 mesh; elution: 7.5% methanol in DCM). The semi-pure product thus obtained was stirred with diethyl ether and pentane (2:1, 100 mL) and filtered to afford Intermediate C as a white solid (2.2 g, 35.2%). MS (ESI, negative ion) m/z 363; $^1$H NMR (400 MHz, DMSO) δ 8.53 (d, J=8.6 Hz, 1H), 8.48 (s, 1H), 7.71 (td, J=11.1, 6.0 Hz, 2H), 3.25 (s, 3H).

Step 3: 4-(5-Chloro-6-Isopropoxypyridin-3-yl)-2,5-Difluoro-N-(Methylsulfonyl)Benzamide Intermediate C (0.110 g, 0.302 mmol), cesium carbonate (0.295 g, 0.905 mmol), and isopropanol (0.036 g, 0.603 mmol) were combined in a 2 dram resealable reaction tube and DMSO (2 mL) was added. The mixture was heated at 90° C. for 2 d with shaking. After cooling, the mixture was filtered through a frit, washing with MeOH and purified by Preparative LC/MS (2 System Column: XBridge 19×100 mm 12230326114 03 Mobile phase: 0.1% NH$_4$OH in water/acetonitrile Flow rate: 40 ml/min Inj: 2000 uL, Gradient: 10 min 10-40% LV NH$_3$; 10 min 10-30% LV NH$_3$; 10 min 20-50% LV NH$_3$; 10 min 10-20% LV NH$_3$) to afford the title compound as a white solid. MS (ESI, positive ion) m/z 405. $^1$H NMR (500 MHz, DMSO-d$_6$) δ ppm 1.36 (d, J=6.20 Hz, 6H) 2.91 (s, 3H) 5.32-5.45 (m, 1H) 7.40-7.50 (m, 1H) 7.53 (dd, J=10.90, 6.20 Hz, 1H) 8.15 (s, 1H) 8.36 (s, 1H).

Method VIII: Preparation by Using Intermediate J

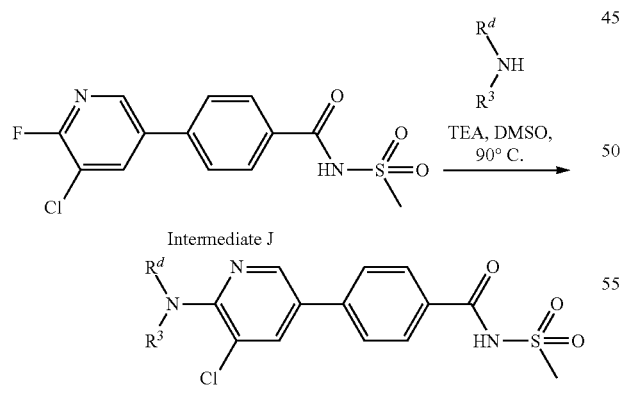

To a vial charged with Intermediate J (Prepared according to the procedure for Intermediate N, see Method XIII below), was added about 1 equivalent of amine reagent, DMSO, and about 3 equivalents of TEA. The vessel was sealed and shaken at 90° C. for 16 hrs. The solution was purified directly via preparative LC/MS (2 System Column: XBridge 19×100 mm; Mobile phase: 0.1% NH$_4$OH in water/acetonitrile Flow rate: 40 ml/min Inj: 2000 μL, Gradient (one of): 10 min 10-40% 0.1% NH$_4$OH; 10 min 0.1% NH$_4$OH; 0.1% NH$_4$OH; 0.1% NH$_4$OH) to afford the product.

Alternatively, an aniline reagent can be used in place of the amine reagent, as follows:

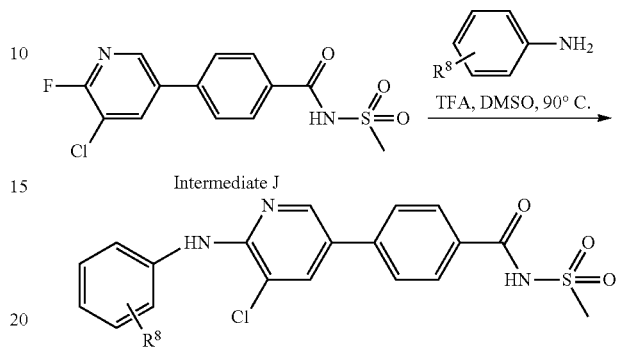

To a vial charged with Intermediate J (Prepared according to the procedure for Intermediate N, see Method XIII below), was added about 3 equivalents of aniline reagent, DMSO, and about 3 equivalents of TFA. The vessel was sealed and shaken at 90° C. for 16 hrs. The solution was purified directly via preparative LC/MS (2 System Column: XBridge 19×100 mm; Mobile phase: 0.1% NH$_4$OH in water/acetonitrile Flow rate: 40 ml/min Inj: 2000 μL, Gradient (one of these): 10 min 10-40% 0.1% NH$_4$OH; 10 min 0.1% NH$_4$OH; 0.1% NH$_4$OH; 0.1% NH$_4$OH) to afford the product.

Method XI: Preparation by Using Intermediate L

Intermediate L was prepared using a two-step procedure below:

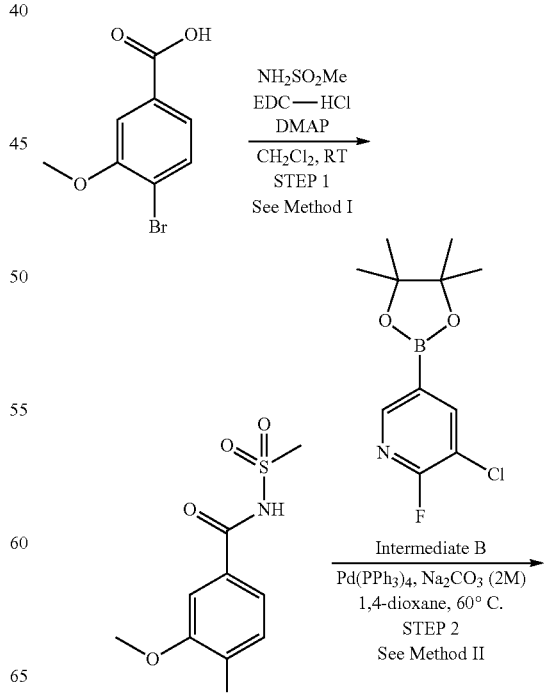

39
-continued

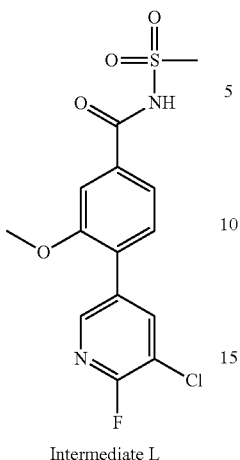

Intermediate L

Step 1: 4-bromo-3-methoxy-N-(methylsulfonyl)benzamide: The protocol described in Method I was used.

Step 2: 4-(5-Chloro-6-Fluoropyridin-3-yl)-3-Methoxy-N-(Methylsulfonyl)Benzamide

The protocol described in Method II was used using 2M Na$_2$CO$_3$ (5 eq) as the base in 0.25M 1,4-dioxane. The crude reaction mixture was cooled in an ice water bath and the pH adjusted to <2 by the careful addition of 6N HCl. The resulting slurry was stirred for 15 mins affording an off-white precipitate which was collected via vacuum filtration and washed with water, affording product as a white solid (70%). $^1$H NMR (400 MHZ, DMSO-d$_6$) δ=12.27 (br. s., 1H), 8.41-8.35 (m, 2H), 7.71 (d, J=1.6 Hz, 1H), 7.66 (dd, J=1.7, 7.9 Hz, 1H), 7.59 (d, J=1.9 Hz, 1H), 3.90 (s, 3H), 3.40 (s, 3H). MS m/z: [M+1]$^+$=359.1

Example 576

4-(5-Chloro-6-((4-Chlorobenzyl)Oxy)Pyridin-3-yl)-3-Methoxy-N-(Methylsulfonyl)Benzamide

40
-continued

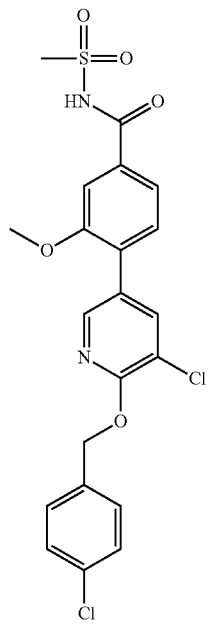

To a vial charged with 4-(5-chloro-6-fluoropyridin-3-yl)-3-methoxy-N-(methylsulfonyl)benzamide (50 mg, 0.139 mmol) and Cs$_2$CO$_3$ (136 mg, 0.418 mmol) was added (4-chlorophenyl)methanol (0.348 mmol, 2.5 eq) and DMSO (0.3 M). The resulting suspension was heated with shaking at 90° C. overnight. The resulting suspension was filtered through a frit, rinsing with isopropanol. The isopropanol was removed in-vacuo and the crude material was purified by reverse phase HPLC (Waters-Xbridge C18, 19×100 mm, 10 μm column with a gradient 5-95% acetonitrile and water with 0.1% NH$_4$OH) to afford 4-(5-chloro-6-((4-chlorobenzyl)oxy)pyridin-3-yl)-3-methoxy-N-(methylsulfonyl)benzamide (39 mg, 58%). LC-MS m/z (ESI, negative ion) 479.0. $^1$H NMR (500 MHz, DMSO-d$_6$) δ ppm 2.88 (s, 3H) 3.82 (s, 3H) 5.48 (s, 2H) 7.34 (d, J=7.80 Hz, 1H) 7.44-7.55 (m, 4H) 7.62 (d, J=7.75 Hz, 1H) 7.67 (s, 1H) 8.07 (d, J=2.04 Hz, 1H) 8.27 (d, J=1.98 Hz, 1H).

Example 578

4-(5-Chloro-6-(2,4-Dichloro-6-Methylphenoxy)-Pyridin-3-yl)-3-Methoxy-N-(Methylsulfonyl)Benzamide

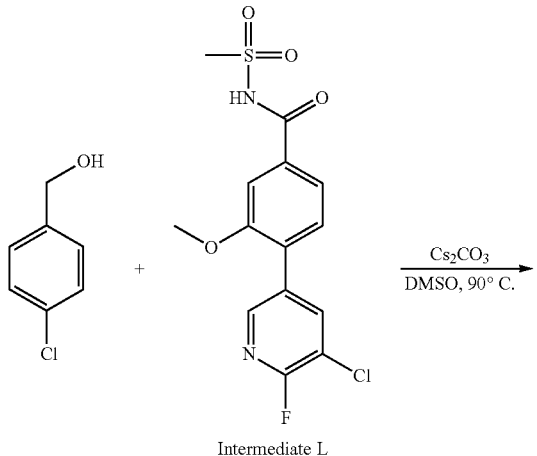

Intermediate L

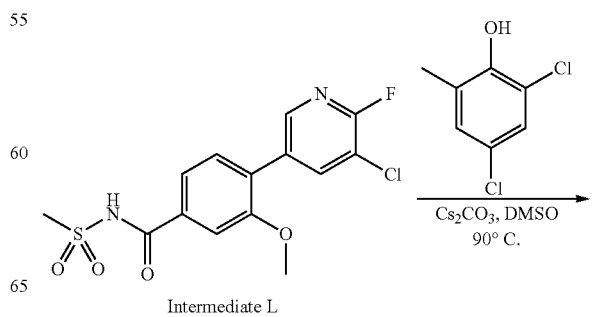

Intermediate L

-continued

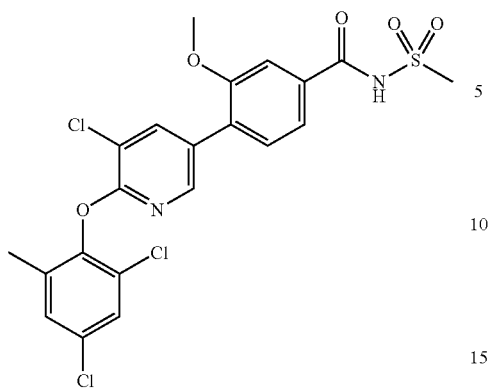

2,4-dichloro-6-methylphenol (80 mg, 0.452 mmol), cesium carbonate (276 mg, 0.847 mmol), and 4-(5-chloro-6-fluoropyridin-3-yl)-3-methoxy-N-(methylsulfonyl)benzamide (INTERMEDIATE L, see above Method XI, 101 mg, 0.282 mmol) were combined in a 2 dram resealable reaction vessel and DMSO (2 mL) was added. The vial was sealed and heated at 90° C. for 40 h. The crude reaction mixture was then filtered through a frit and washed with DCM, then MeOH. After concentration, the crude residue was purified using preparative reverse phase HPLC (0.1% NH$_4$OH in water/acetonitrile; Flow rate: 40 ml/min; Gradient: 10 min 20-50% NH$_3$) to afford 4-(5-chloro-6-(2,4-dichloro-6-methylphenoxy)pyridin-3-yl)-3-methoxy-N-(methylsulfonyl)benzamide (51.6 mg). LC-MS m/z (ESI, negative ion) 514.0. $^1$H NMR (500 MHz, DMSO-d$_6$) δ 8.24-8.28 (m, 1H), 8.15-8.19 (m, 1H), 7.66-7.70 (m, 1H), 7.59-7.65 (m, 2H), 7.46-7.50 (m, 1H), 7.38-7.43 (m, 1H), 3.84 (s, 3H), 3.01 (s, 3H), 2.15 (s, 3H).

Example 579

4-(5-Chloro-6-(3-Chloro-2-Methylphenoxy)-3-Pyridinyl)-3-Methoxy-N-(Methylsulfonyl)Benzamide

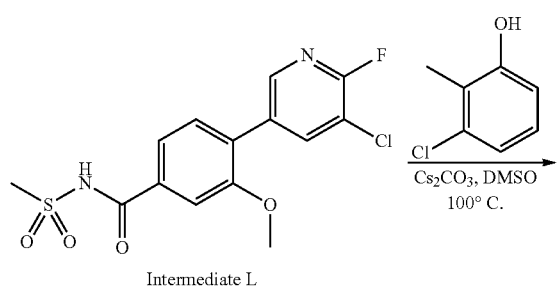

-continued

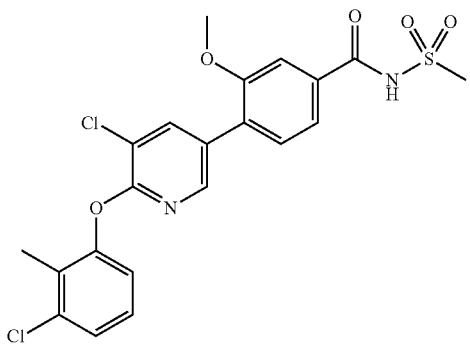

3-chloro-2-methylphenol (80 mg, 0.561 mmol), cesium carbonate (343 mg, 1.052 mmol), and 4-(5-chloro-6-fluoropyridin-3-yl)-3-methoxy-N-(methylsulfonyl)benzamide (INTERMEDIATE L, see above Method XI, 126 mg, 0.351 mmol) were combined in a 2 dram resealable reaction vessel and DMSO (2 mL) was added. The vial was sealed and heated at 100° C. for 48 h. The crude reaction mixture was then filtered through a frit and washed with DCM then MeOH. After concentration, the crude residue was purified using preparative reverse phase HPLC (0.1% NH$_4$OH in water/acetonitrile; Flow rate: 40 ml/min; Gradient: 10 min 20-50% NH$_3$) to afford 4-(5-chloro-6-(3-chloro-2-methylphenoxy)-3-pyridinyl)-3-methoxy-N-(methylsulfonyl)benzamide (44.5 mg). LC-MS m/z (ESI, positive ion) 481.0. $^1$H NMR (500 MHz, DMSO-d$_6$) δ 8.20 (dd, J=1.98, 19.43 Hz, 2H), 7.67 (s, 1H), 7.61 (dd, J=1.07, 7.82 Hz, 1H), 7.29-7.42 (m, 3H), 7.18 (d, J=8.04 Hz, 1H), 3.82 (s, 3H), 2.88 (s, 3H), 2.16 (s, 3H).

Example 583

4-(5-Chloro-6-(2,3-Dichlorophenoxy)Pyridin-3-yl)-3-Methoxy-N-(Methylsulfonyl)Benzamide

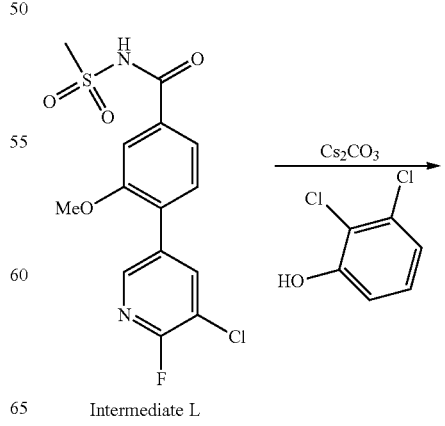

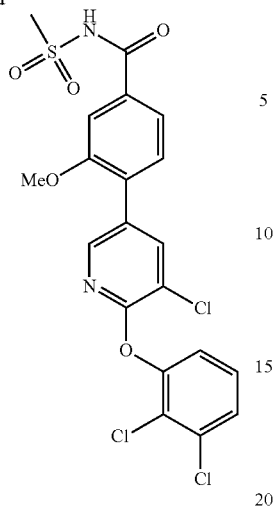

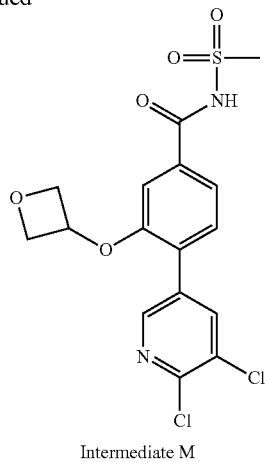

Intermediate M

To a vial containing 2,3-dichlorophenol (0.13 g, 0.3 mmol) was added cesium carbonate (0.143 g, 0.440 mmol) and 1-(5,6-dichloropyridin-3-yl)-N-(methylsulfonyl)isoquinoline-6-carboxamide (0.079 g, 0.2 mmol) in DMSO (1.000 ml). The reaction mixture was heated at 100° C. in a with shaking overnight. The crude material was then purified by reverse phase HPLC using PREP LC/MS-2 System Column (XBridge Prep Shield RP18 19×100 mm 104|131331GG 03) with 0.1% $NH_4OH$ in water/acetonitrile as mobile phase. Flow rate: 40 ml/min Inj: 2800 uL Gradient: 10 min 10-40%_LV_$NH_3$. $^1H$ NMR (500 MHz, DMSO-$d_6$) δ ppm 2.94 (s, 3H), 3.79-3.88 (m, 3H), 7.38 (d, J=1.96 Hz, 1H), 7.42-7.51 (m, 2H), 7.58-7.64 (m, 2H), 7.67 (s, 1H), 8.20 (d, J=1.88 Hz, 1H), 8.25 (s, 1H). MS m/z [M+1]$^+$=503.0.

Method XII: Preparation by Using Intermediate M

Intermediate M was prepared using a two-step procedure below:

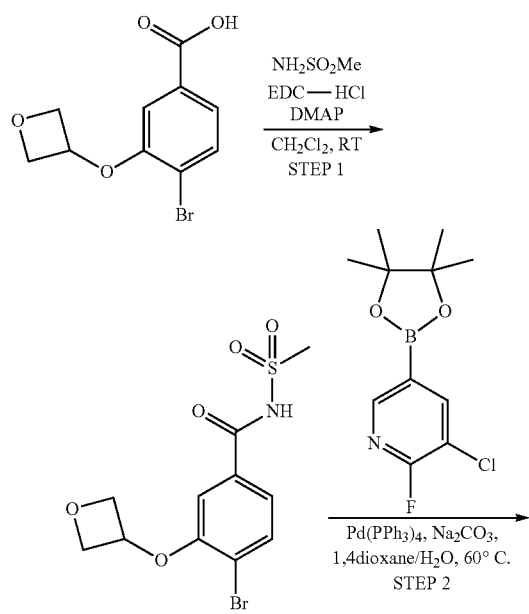

Step 1: 4-Bromo-N-(Methylsulfonyl)-3-(Oxetan-3-yloxy)Benzamide

A round bottom flask was charged with 4-bromo-3-(oxetan-3-yloxy)benzoic acid (HDH Pharma) (5.0 g, 18.31 mmol), methanesulfonamide (3.48 g, 36.6 mmol), 4-dimethylaminopyridine (6.71 g, 54.9 mmol), and EDC (7.02 g, 36.6 mmol) and $CH_2Cl_2$ (100 mL) was added. After stirring for 2 d at RT, the crude reaction solution was poured into sat $NaHCO_3$, and extracted with DCM. The organics were then washed 3× with sat. $NaHCO_3$. The combined aqueous layers were then acidified with conc. HCl affording a white precipitate the product crashed out as a white solid. The mixture was extracted 3× with DCM then 1× with EtOAc. Concentration afforded 4-bromo-N-(methylsulfonyl)-3-(oxetan-3-yloxy)benzamide (4.76 g, 13.59 mmol, 74.2% yield) as a white solid. MS m/z: [M+1]$^+$=350.1

Step 2: 4-(5-Chloro-6-Fluoropyridin-3-yl)-N-(Methylsulfonyl)-3-(Oxetan-3-yloxy)Benzamide To a flask charged with 4-bromo-N-(methylsulfonyl)-3-(oxetan-3-yloxy)benzamide (4.76 g, 13.59 mmol), (5-chloro-6-fluoropyridin-3-yl)boronic acid (2.384 g, 13.59 mmol), Pd(Ph$_3$P)$_4$ (0.785 g, 0.680 mmol) was added 1,4-dioxane (54.4 ml) and Na$_2$CO$_3$ (2M) (34.0 ml, 68.0 mmol). The mixture was purged with nitrogen for 5 mins then heated to 110° C. overnight affording about 75% conversion. To the mixture was added additional 5-chloro-6-fluoropyridin-3-yl)boronic acid (0.5 eq, 1.2 g) and Pd(PPh$_3$)$_4$ (0.025 eq, 392 mg) and heating continued at 110° C. for 2 hrs affording complete conversion according to LC-MS. The mixture was cooled in an ice water bath and brought to pH <2 by the addition of 2N HCl affording an orange precipitate which was collected by vacuum filtration. The solid obtained was impure and combined with the filtrate. The mixture was transferred to a sep funnel with the aid of DCM and extracted with DCM (2×). The combined organics were dried with Na$_2$SO$_4$, filtered and dried under reduced pressure. The aqueous layer still contained product and was dried under reduced pressure and combined with the organic extracted material. The mixture was adsorbed onto silica gel and purified with chromatography using a 100 g ultra snap column ramping EtOAc in heptane (0-100%, then DCM: MeOH (90:10) in DCM (0-100%) to affording the product (2.61 g, 48%). $^1H$ NMR (400 MHz, DMSO-$d_6$) δ 8.43-8.51

(m, 2H), 7.67-7.73 (m, 1H), 7.59-7.67 (m, 1H), 7.25 (s, 1H), 5.45 (t, J=5.28 Hz, 1H), 4.95 (t, J=6.60 Hz, 2H), 4.47-4.61 (m, 2H), 3.38 (s, 3H). MS m/z: [M+1]$^+$=401.1.

Method XIII: Preparation by Using Intermediate N

INTERMEDIATE N was prepared using a two step procedure below:

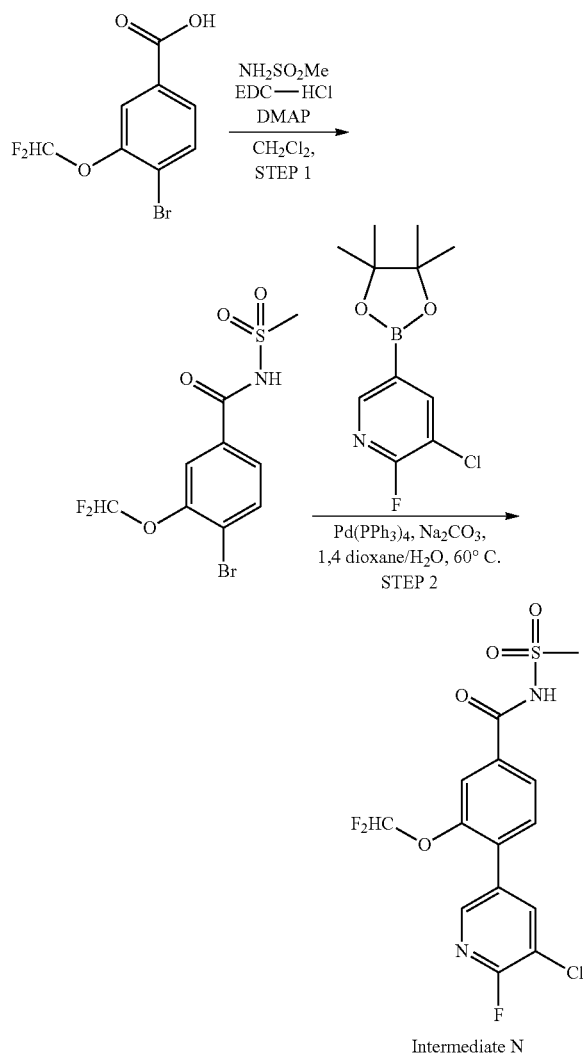

Preparation of Intermediate N, 4-(5-Chloro-6-Fluoropyridin-3-yl)-3-(Difluoromethoxy)-N-(Methylsulfonyl)Benzamide Step 1: 4-Bromo-3-(Difluoromethoxy)-N-(Methylsulfonyl)Benzamide To a flask charged with 4-bromo-3-(difluoromethoxy) benzoic acid (HDH Pharma) (5.00 g, 18.72 mmol) was added N,N-dimethylpyridin-4-amine (3.43 g, 28.1 mmol), methanesulfonamide (2.137 g, 22.47 mmol), DCM (74.9 ml) and N$^1$-((ethylimino)methylene)-N$^3$,N$^3$-dimethylpropane-1,3-diamine hydrochloride (5.38 g, 28.1 mmol) respectively. The mixture was stirred overnight at room temperature affording the desired product cleanly as the main species according to LC-MS. The solution was transferred to a sep funnel, diluted with DCM and extracted with 2N HCl. The DCM layer was dried with Na$_2$SO$_4$, filtered, and dried under reduced pressure affording 4-bromo-3-(difluoromethoxy)-N-(methylsulfonyl)benzamide (6.45 g, 18.74 mmol, 100% yield)) as an off-white solid. MS m/z: [M+1]$^+$=345.9

Step 2: 4-(5-Chloro-6-Fluoropyridin-3-yl)-3-(Difluoromethoxy)-N-(Methylsulfonyl)Benzamide To a flask charged with 4-bromo-3-(difluoromethoxy)-N-(methylsulfonyl)benzamide (6.45 g, 18.74 mmol), (5-chloro-6-fluoropyridin-3-yl)boronic acid (3.29 g, 18.74 mmol), Pd(Ph$_3$P)$_4$ (1.083 g, 0.937 mmol) was added 1,4-dioxane (75.0 ml) and Na$_2$CO$_3$ (2M) (46.9 ml, 94 mmol) and the mixture purged with nitrogen for 5 mins then heated overnight at 110° C. affording conversion to the desired product as the major species. The mixture was cooled in an ice water bath and the pH adjusted to <2 by the addition of 2N HCl. The resulting mixture was transferred to a separatory funnel and extracted with DCM (2×). The combined organics were dried with Na$_2$SO$_4$, filtered, and dried under reduced pressure. The crude residue was purified with a 100 g ultra snap column ramping DCM:MeOH (90:10) in DCM (0-100%). Product eluted in three different main peaks coeluting with a minor impurity with each peak. The peaks were all combined and dried under reduced pressure affording a white solid which was triturated with MeOH affording the product 4-(5-chloro-6-fluoropyridin-3-yl)-3-(difluoromethoxy)-N-(methylsulfonyl)benzamide (4.65 g, 11.78 mmol, 62.8% yield) with an aromatic impurity present. The filtrate and this solid were combined and repurified using the following conditions: System: Prep SFC-3, Whelk-O, 2×25 cm column, 20% methanol, 80 mL/min (column backpressure=52 bar), 100 bar BPR, 254 nm, Dissolution: 200 mL 3:2 MeOH:DCM, Test Injections: 0.1, 0.25, 0.5, 1.0, 2.0, and 4.0 mL, Sample processed with 4.0 mL injections and 3.3 minute cycle time. The product was obtained as a yellow solid 4-(5-chloro-6-fluoropyridin-3-yl)-3-(difluoromethoxy)-N-(methylsulfonyl)benzamide (4.65 g, 11.78 mmol, 62.8% yield) with about 85% purity. $^1$H NMR (400 MHz, DMSO-d$_6$) δ=$^1$H NMR (400 MHz, DMSO-d$_6$) δ 8.40-8.46 (m, 1H), 8.35-8.40 (m, 1H), 7.94 (d, J=7.73 Hz, 1H), 7.88 (s, 1H), 7.76 (d, J=8.12 Hz, 1H), 7.21 (t, J=71 Hz, 1H), 3.41 (s, 3H). MS m/z: [M+1]$^+$=395.1

Method XV: Preparation by Using Intermediate P

INTERMEDIATE P was prepared as follows:

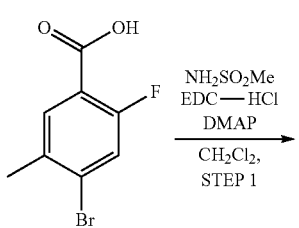

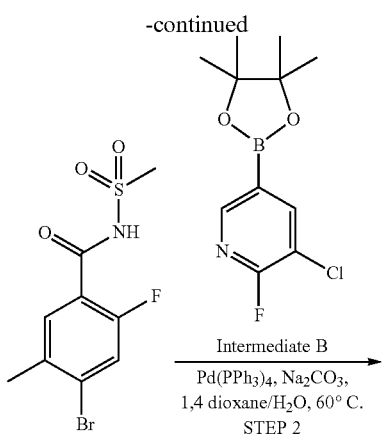

Intermediate B

Pd(PPh₃)₄, Na₂CO₃,
1,4 dioxane/H₂O, 60° C.
STEP 2

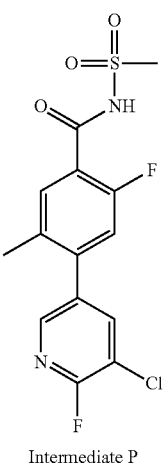

Intermediate P

Step 1: 4-Bromo-2-Fluoro-5-Methyl-N-(Methylsulfonyl)Benzamide

To a flask charged with 4-bromo-2-fluoro-5-methylbenzoic acid (Ark Pharm) (9.93 g, 42.6 mmol) was added N,N-dimethylpyridin-4-amine (7.81 g, 63.9 mmol), methanesulfonamide (4.86 g, 51.1 mmol), DCM (170 ml) and $N^1$-((ethylimino)methylene)-$N^3$,$N^3$-dimethylpropane-1,3-diamine hydrochloride (12.25 g, 63.9 mmol). The mixture was stirred overnight at room temp overnight affording the desired product cleanly as the main species according to LCMS. The mixture was cooled in an ice water bath prior to the addition of 2N HCl (about 150 ml) and the resulting mixture was stirred for 10 mins. The mixture was transferred to a sep funnel, the DCM layer collected and the aqueous layer washed again with DCM. The combined organics were collected, dried with Na₂SO₄, filtered, and dried under reduced pressure affording 4-bromo-2-fluoro-5-methyl-N-(methylsulfonyl)benzamide (13.02 g, 42.0 mmol, 99% yield) as an off-white foamy solid. MS m/z: [M+1]⁺=309.9

Step 2: 4-(5-Chloro-6-Fluoropyridin-3-yl)-2-Fluoro-5-Methyl-N-(Methylsulfonyl)Benzamide To a flask charged with 4-bromo-2-fluoro-5-methyl-N-(methylsulfonyl)benzamide (13.05 g, 42.1 mmol), 3-chloro-2-fluoro-5-(4,4,5,5-tetramethyl-1,3,2-dioxaborolan-2-yl)pyridine (10.83 g, 42.1 mmol), Pd(Ph₃P)₄ (2.431 g, 2.104 mmol) was added 1,4-dioxane (168 ml) and Na₂CO₃ (2M) (105 ml, 210 mmol) and the mixture purged with nitrogen for 5 mins then heated to 110° C. overnight affording a suspension with product as the main species according to LCMS. The mixture was cooled in an ice water bath and brought to pH <2 by the addition of 6N HCl with stirring. The product appeared to oil out with stirring. Additional 1N HCl was added (about 100 mL) with stirring affording no precipitate. The mixture was brought to 80° C., then the heat was removed and the oiled out product was still present. IPA was added (about 10 mL) with stirring affording the formation of a precipitate which was collected by vacuum filtration. The light yellow solid obtained was triturated with MeOH to affording product 4-(5-chloro-6-fluoropyridin-3-yl)-2-fluoro-5-methyl-N-(methylsulfonyl)benzamide (11.14 g, 30.9 mmol, 73.4% yield) as a white solid. ¹H NMR (400 MHz, DMSO-d₆) δ=12.33 (br. s., 1H), 8.37 (dd, J=2.2, 8.9 Hz, 1H), 8.27 (dd, J=1.3, 2.2 Hz, 1H), 7.65 (d, J=12 Hz, 1H), 7.38 (d, J=10.9 Hz, 1H), 6.80 (br. s., 1H), 3.42-3.36 (m, 3H), 2.26 (s, 3H). MS m/z: [M+1]⁺=360.9.

Example 623

4-(5-Chloro-6-(3-Fluoro-4-Methylphenoxy)Pyridin-3-yl)-2-Fluoro-5-Methyl-N-(Methylsulfonyl)Benzamide

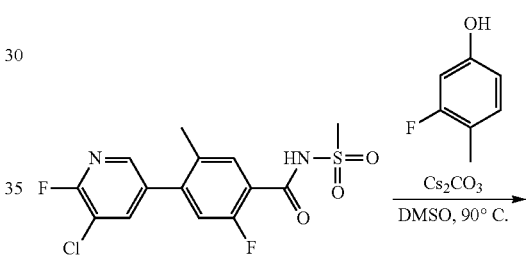

Intermediate P

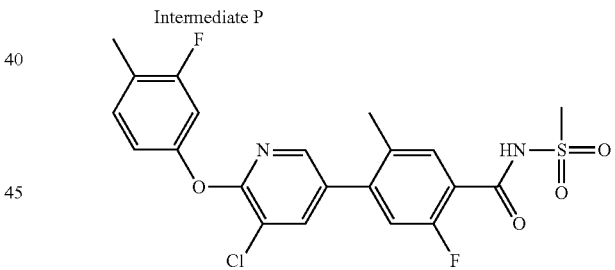

To a vial charged with 4-(5-chloro-6-fluoropyridin-3-yl)-2-fluoro-5-methyl-N-(methylsulfonyl)benzamide (INTERMEDIATE P, 65 mg, 0.180 mmol) and Cs₂CO₃ (176 mg, 0.541 mmol) was added 3-fluoro-4-methylphenol (0.252 mmol, 1.4 eq, Sigma Aldrich) and DMSO (0.3 M). The resulting suspension was heated with shaking at 90° C. overnight. The resulting suspension was filtered through a frit, rinsing with isopropanol. The isopropanol was removed in-vacuo and the crude material purified by reverse phase HPLC (Waters-Xbridge C18, 19×100 mm, 10 μm column with a gradient 5-95% acetonitrile and water with 0.1% NH₄OH) to afford 4-(5-chloro-6-(3-fluoro-4-methylphenoxy)pyridin-3-yl)-2-fluoro-5-methyl-N-(methylsulfonyl) benzamide (46 mg, 70%). LC-MS m/z (ESI, negative ion) 465.0. ¹H NMR (500 MHz, DMSO-d₆) δ ppm 2.25 (s, 3H) 2.22 (s, 3H) 2.87 (s, 3H) 6.98 (dd, J=8.26, 2.04 Hz, 1H) 7.01-7.17 (m, 2H) 7.34 (t, J=8.57 Hz, 1H) 7.59 (d, J=7.58 Hz, 1H) 8.09 (d, J=2.04 Hz, 1H) 8.15 (d, J=2.04 Hz, 1H).

Example 673

4-(5-Chloro-6-((1R)-1-(2,5-Dichlorophenyl)Ethoxy)-3-Pyridinyl)-2-Fluoro-5-Methyl-N-(Methylsulfonyl)Benzamide

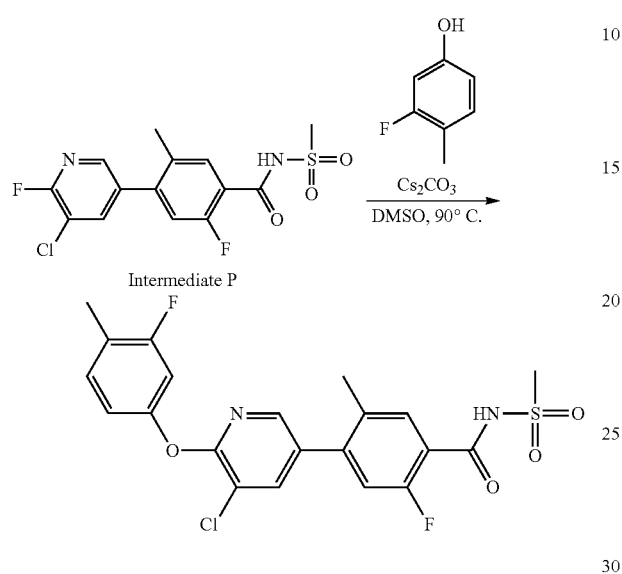

(R)-1-(2,5-dichlorophenyl)ethanol (48 mg, 0.252 mmol), cesium carbonate (176 mg, 0.541 mmol), and 4-(5-chloro-6-fluoropyridin-3-yl)-2-fluoro-5-methyl-N-(methylsulfonyl)benzamide (INTERMEDIATE P) (65 mg, 0.180 mmol) were combined in a 2 dram resealable reaction vessel, and DMSO (2 mL) was added. The vial was sealed and heated at 100° C. for 48 h. The crude reaction mixture was then filtered through a frit and washed with DCM then MeOH. After concentration, the crude residue was purified using preparative reverse phase HPLC (0.1% NH$_4$OH in water/acetonitrile; Flow rate: 40 ml/min; Gradient: 10 min 20-50% NH$_3$) to afford 4-(5-chloro-6-((1R)-1-(2,5-dichlorophenyl)ethoxy)-3-pyridinyl)-2-fluoro-5-methyl-N-(methylsulfonyl)benzamide (54 mg). LC-MS m/z (ESI, positive ion) 531.0. 1H NMR (500 MHz, DMSO-d$_6$) δ 8.09 (d, J=2.08 Hz, 1H), 8.03 (d, J=2.08 Hz, 1H), 7.50-7.60 (m, 3H), 7.42 (dd, J=2.53, 8.56 Hz, 1H), 7.03 (d, J=11.09 Hz, 1H), 6.49 (q, J=6.36 Hz, 1H), 2.87 (s, 3H), 2.18 (s, 3H), 1.64 (d, J=6.42 Hz, 3H).

Method XVI: Preparation by Using Intermediate Q 4-(5-Cyano-6-fluoropyridin-3-yl)-3-methoxy-N-(methylsulfonyl)benzamide (INTERMEDIATE Q) was prepared as follows:

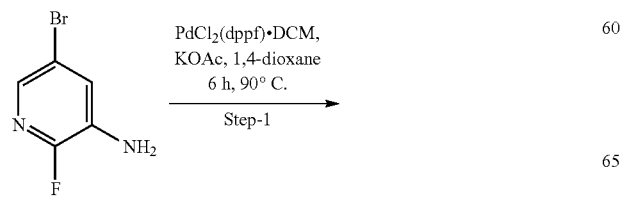

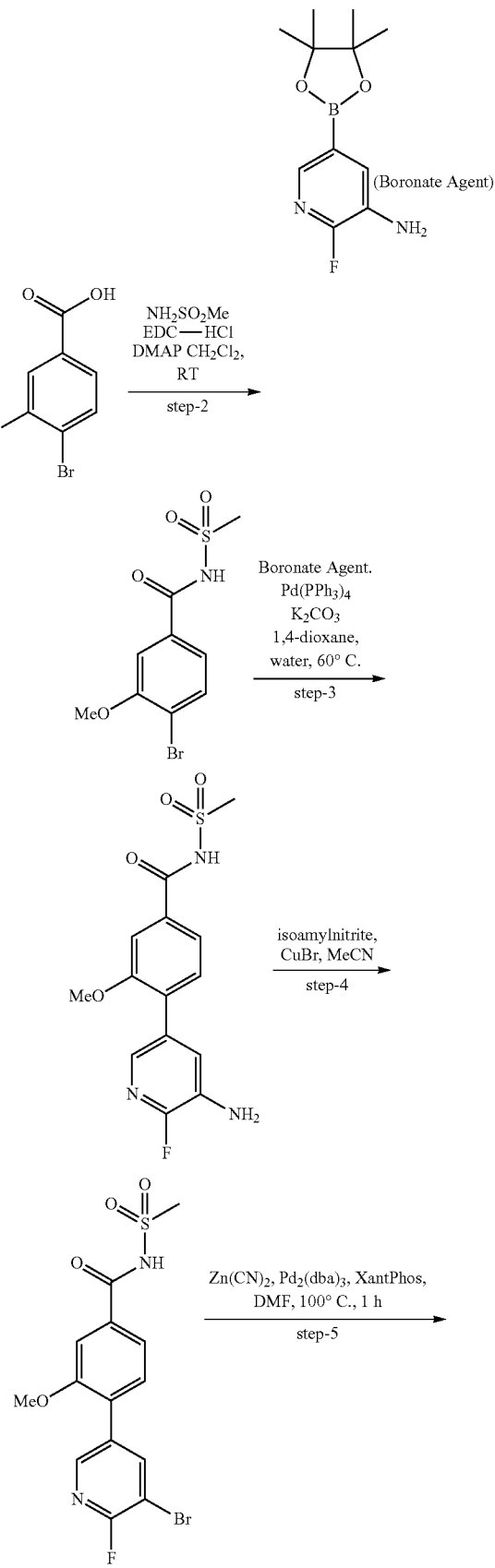

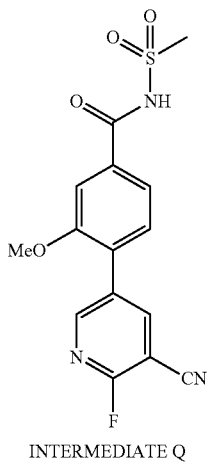

INTERMEDIATE Q

Step-1: 2-Fluoro-5-(4,4,5,5-Tetramethyl-1,3,2-Dioxaborolan-2-yl)Pyridin-3-Amine A mixture of 3-amino-5-bromo-2-fluoropyridine (50.0 g, 262 mmol, Combi-Blocks), bispinacolatodiborane (79.7 g, 314 mmol, Spectrochem) and potassium acetate (77.1 g, 785 mmol) in 1,4-dioxane (500 mL, Spectrochem) was degassed with nitrogen for 10 minutes. PdCl$_2$(dppf)-CH$_2$Cl$_2$ (21.2 g, 26.1 mmol, Hindustan platinum) was added to the reaction mixture and again the mixture was degassed for 10 minutes. The reaction mixture was heated at 90° C. overnight. After completion (monitored by TLC), the reaction mixture was filtered through CELITE and the CELITE bed was washed with ethyl acetate (2×100 mL). The combined filtrate was concentrated under reduced pressure to get the crude material which was purified by column chromatography (silica gel 230-400, elution 0-10% ethyl acetate in hexanes) to get 2-fluoro-5-(4,4,5,5-tetramethyl-1,3,2-dioxaborolan-2-yl)pyridin-3-amine (52.0 g, 84%). TLC solvent system: 30% EtOAc in hexanes, Product's R$_f$: 0.9. MS (ESI +ve ion) m/z: [M+1]=239.1. $^1$H NMR (300 MHz, Chloroform-d) δ 7.94 (s, 2H), 7.48 (d, J=11.0 Hz, 2H), 1.33 (s, 12H).

Step-2: 4-Bromo-3-Methoxy-N-(Methylsulfonyl)Benzamide

To a solution of 4-bromo-3-methoxybenzoic acid (50.0 g, 216 mmol, F-Chemicals) and methane sulfonamide (24.6 g, 259 mmol, Apollo) in DCM (1.0 L) was added DMAP (79.0 g, 648 mmol) and EDC.HCl (82.5, 432 mmol, Spectrochem). The reaction mixture was stirred at room temperature for 12 h. The reaction mass was washed with 1.5 N aqueous HCl (200 mL) and the organic layers were separated. The aqueous layer was washed with DCM (2×200 mL). The combined organic layer was washed with saturated brine (200 mL), dried over anhydrous sodium sulphate and concentrated under reduced pressure. The crude product was dissolved in minimum DCM (100 mL) and added hexanes (about 200 mL) dropwise. The precipitates thus obtained were filtered and dried to get pure 4-bromo-3-methoxy-N-(methylsulfonyl)benzamide (51 g, 77%). TLC solvent system: 10% MeOH in EtOAc. Product's R$_f$: 0.1. MS (ESI +ve ion) m/z: [M+1]=307.9. $^1$H NMR (300 MHz, Chloroform-d) δ 9.05 (s, 1H), 7.67 (d, J=8.2 Hz, 1H), 7.43 (d, J=1.9 Hz, 1H), 7.30 (d, J=2.0 Hz, 1H), 3.98 (s, 3H), 3.45 (s, 3H).

Step-3: 4-(5-Amino-6-Fluoropyridin-3-yl)-3-Methoxy-N-(Methylsulfonyl)Benzamide A solution of 2-fluoro-5-(4,4,5,5-tetramethyl-1,3,2-dioxaborolan-2-yl)pyridin-3-amine (46.4 g, 194 mmol), 4-bromo-3-methoxy-N-(methylsulfonyl)benzamide (50 g, 162 mmol) and potassium carbonate (55.9 g, 406 mmol) in 1,4-dioxane:water (750 mL:150 mL) was degassed with nitrogen for 10 minutes. Tetrakis(triphenylphosphine) palladium(O) (18.7 g, 16.23 mmol, Hindustan platinum) was added and the reaction mixture was again degassed with nitrogen for 10 minutes. The reaction mixture was heated at 90° C. for 16 h. After completion of reaction (monitored by TLC), the reaction mixture was concentrated under reduced pressure to get the crude material which was purified by column chromatography (silica: 60-120 mesh; elution: 15% methanol in DCM) to obtain the desired 4-(5-amino-6-fluoropyridin-3-yl)-3-methoxy-N-(methylsulfonyl)benzamide (25 g, 46%). TLC solvent system: 20% methanol in DCM, Product's R$_f$: 0.1. MS (ESI +ve ion) m/z: [M+1]=340.0. $^1$H NMR (300 MHz, DMSO-d$_6$) δ 7.63 (s, 1H), 7.61-7.55 (m, 1H), 7.39 (d, J=1.9 Hz, 1H), 7.28 (dd, J=10.7, 2.1 Hz, 1H), 7.21 (d, J=7.8 Hz, 1H), 5.42 (s, 2H), 3.78 (s, 3H), 2.84 (s, 3H). Note: NH proton not observed.

Step-4: 4-(5-Bromo-6-Fluoropyridin-3-yl)-3-Methoxy-N-(Methylsulfonyl)Benzamide Isoamylnitrite (17.3 g, 147.4 mmol, Aldrich) was added to a solution of 4-(5-amino-6-fluoropyridin-3-yl)-3-methoxy-N-(methylsulfonyl)benzamide (25 g, 73.7 mmol) in acetonitrile (160 mL) and the reaction mixture was stirred at room temperature for 10 minutes. Copper bromide (21.1 g, 147 mmol) was added portion-wise and the reaction mixture was stirred at room temperature for 3 h. The reaction mixture was quenched with saturated aqueous ammonium chloride solution (100 mL) and the aqueous layer was extracted with ethyl acetate (3×500 mL). The combined organic layer was washed with brine (250 mL), dried over anhydrous sodium sulphate and concentrated under reduced pressure to obtained the crude product which was purified by column chromatography (silica gel 60-120 mesh, elution 0-10% methanol in DCM) to obtained 4-(5-bromo-6-fluoropyridin-3-yl)-3-methoxy-N-(methylsulfonyl)benzamide (12.0 g, 40%). TLC solvent system: 20% methanol in DCM, Product's R$_f$: 0.3. MS (ESI +ve ion) m/z: [M+1]=402.9. $^1$H NMR (400 MHz, DMSO-d$_6$) δ 12.3 (s, 1H), 8.49 (dd, J=8.7, 2.0 Hz, 1H), 8.40 (s, 1H), 7.70 (s, 1H), 7.66 (d, J=8.1 Hz, 1H), 7.59 (d, J=7.9 Hz, 1H), 3.90 (s, 3H), 3.41 (s, 3H).

Step-5: 4-(5-Cyano-6-Fluoropyridin-3-yl)-3-Methoxy-N-(Methylsulfonyl)Benzamide A suspension of 4-(5-bromo-6-fluoropyridin-3-yl)-3-methoxy-N-(methylsulfonyl)benzamide (1.0 g, 2.48 mmol), zinc cyanide (580 mg, 4.96 mmol, Aldrich), Xantphos (120 mg, 0.248 mmol, GLR) and Pd$_2$(dba)$_3$ (114 mg, 0.124 mmol, Hindustan platinum) in DMF (10 mL) was degassed with nitrogen for 5 minutes. The reaction mixture was heated at 100° C. for 70 minutes in the microwave. The reaction mixture was filtered through CELITE and the CELITE bed was washed with ethyl acetate and the mixture was concentrated under reduced pressure to obtain the crude material which was purified by column chromatography (silica gel 60-120 mesh, elution 0-8% Methanol in DCM) to get 4-(5-cyano-6-fluoropyridin-3-yl)-3-methoxy-N-(methylsulfonyl)benzamide (Intermediate Q, see method XVI, 545 mg, 63%). TLC solvent system: 10% methanol in DCM, Product's R$_f$: 0.1. MS (ESI +ve ion) m/z: [M+1]=350.1. $^1$H NMR (400 MHz, DMSO-d$_6$) δ 12.30 (s, 1H), 8.79-8.71 (m, 2H), 7.73-7.64 (m, 2H), 7.61 (d, J=7.9 Hz, 1H), 3.90 (s, 3H), 3.41 (s, 3H).

Example 690

4-(6-(3-Chloro-2-Methylphenoxy)-5-Cyano-3-Pyridinyl)-3-Methoxy-N-(Methylsulfonyl)Benzamide

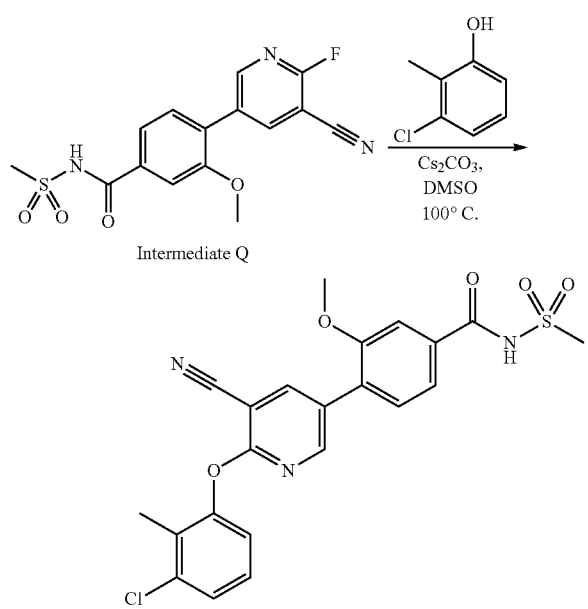

3-chloro-2-methylphenol (80 mg, 0.561 mmol), cesium carbonate (343 mg, 1.052 mmol), and 4-(5-cyano-6-fluoropyridin-3-yl)-3-methoxy-N-(methylsulfonyl)benzamide (INTERMEDIATE Q) (123 mg, 0.351 mmol) were combined in a 2 dram resealable reaction vessel and DMSO (2 mL) was added. The vial was sealed and heated at 100° C. for 48 h. The crude reaction mixture was then filtered through a frit and washed with DCM then MeOH. After concentration, the crude residue was purified using preparative reverse phase HPLC (0.1% NH$_4$OH in water/acetonitrile; Flow rate: 40 ml/min; Gradient: 10 min 20-50% NH$_3$) to afford 4-(6-(3-chloro-2-methylphenoxy)-5-cyano-3-pyridinyl)-3-methoxy-N-(methylsulfonyl)benzamide (60.7 mg). LC-MS m/z (ESI, positive ion) 472.0. $^1$H NMR (500 MHz, DMSO-d$_6$) δ 8.59 (d, J=2.34 Hz, 1H), 8.51 (d, J=2.34 Hz, 1H), 7.68 (s, 1H), 7.63 (d, J=7.90 Hz, 1H), 7.25-7.45 (m, 4H), 7.12 (br. s., 1H), 3.83 (s, 3H), 2.90 (s, 3H), 2.18 (s, 3H).

Example 694

4-(5-Cyano-6-(3,6-Dichloro-2-Methylphenoxy)-3-Pyridinyl)-3-Methoxy-N-(Methylsulfonyl)Benzamide

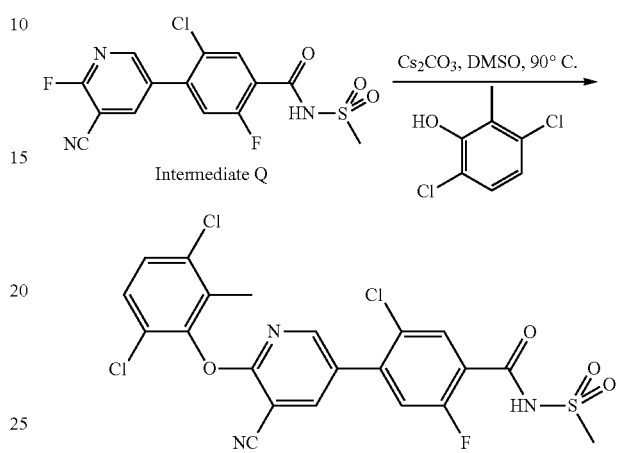

A vial was charged with 5-chloro-4-(5-cyano-6-fluoropyridin-3-yl)-2-fluoro-N-(methylsulfonyl)benzamide (Intermediate Q) (80 mg, 0.229 mmol), cesium carbonate (187 mg, 0.573 mmol), 3,6-dichloro-2-methylphenol (61 mg, 0.344 mmol) and 1.5 mL DMSO. The vial was sealed, and the reaction mixture was heated at 90° C. for 15 h. The mixture was filtered through a frit, which was washed with MeOH and DCM. The filtrate was concentrated, and the crude material was purified by reverse phase chromatography, PREP LC/MS-2 System Column: XBridge Prep Shield RP18 19×100 mm 104|131331GG 03 Mobile phase: 0.1% NH$_4$OH in water/acetonitrile Flow rate: 40 ml/min Inj: 2500 μL Gradient: 10 min, 10-40%_LV_NH$_3$ 4-(5-cyano-6-(3,6-dichloro-2-methylphenoxy)-3-pyridinyl)-3-methoxy-N-(methylsulfonyl)benzamide was isolated as an off-white solid (50 mg, 43% yield). MS (ESI, negative ionization) m/z 504.0; 1H NMR (500 MHz, DMSO-d$_6$) δ ppm 2.23 (s, 3H) 3.89 (s, 3H) 7.47-7.60 (m, 3H) 7.64 (d, J=7.77 Hz, 1H) 7.69 (s, 1H) 8.56 (d, J=2.27 Hz, 1H) 8.70 (d, J=2.27 Hz, 1H).

Method XVIII: Preparation by Using Intermediate V

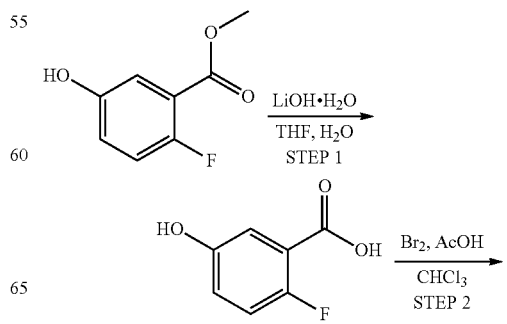

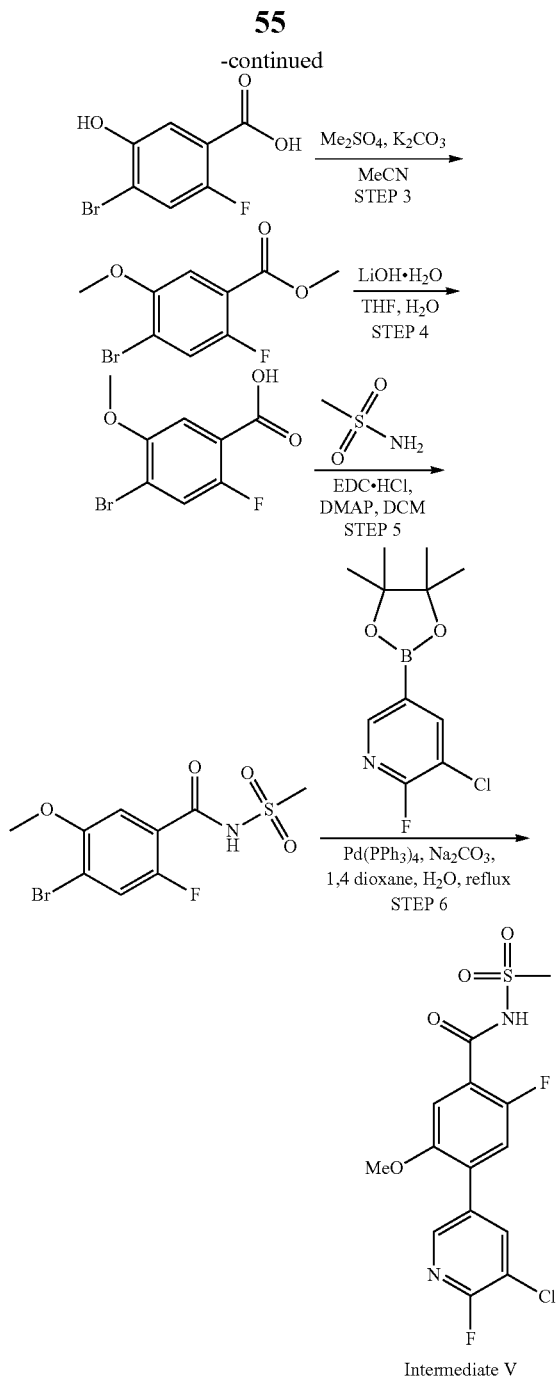

Step 2: 4-Bromo-2-Fluoro-5-Hydroxybenzoic Acid

To a solution of 2-fluoro-5-hydroxybenzoic acid (5.0 g, 32.03 mmol, 1.0 equiv) in CHCl₃ (50 mL) was added a solution of bromine (4.9 mL, 96.09 mmol, 3.0 equiv) in acetic acid (50 mL) at 0° C. and stirred for 20 h at room temperature. The reaction was quenched with saturated sodium sulfite solution (100 mL), extracted with EtOAc (3×150 mL). The combined extracts were washed with brine (200 mL), dried over anhydrous Na₂SO₄, filtered and evaporated to afford crude compound. The crude compound was triturated with n-hexane to afford 4-bromo-2-fluoro-5-hydroxybenzoic acid as an off white solid (3.5 g, impure). This compound was used for the next step without further purification. MS m/z: [M−1]⁻=235.2.

Step 3: 4-Bromo-2-Fluoro-5-Methoxybenzoate

To a solution of 4-bromo-2-fluoro-5-hydroxybenzoic acid (3.5 g, 14.89 mmol, 1.0 equiv) in acetonitrile (40 mL) were added K₂CO₃ (6.16 g, 44.68 mmol, 3.0 equiv) and dimethyl sulfate (5.63 g, 44.68 mmol, 3.0 equiv) at room temperature. The mixture was stirred for 5 h at 80° C. TLC showed (ethyl acetate: petroleum ether, 2:8) complete consumption of starting material. The reaction mixture was cooled to room temperature, diluted with water (250 mL), extracted with EtOAc (3×100 mL). The combined extracts were washed with brine (100 mL), dried with anhydrous Na₂SO₄, filtered and evaporated to afford crude compound. The crude compound was purified on column chromatography (silica gel, 60-120 mesh) using 5% ethyl acetate in pet-ether as gradient to afford impure compound. The impure compound was triturated with diethyl ether (20 mL) to afford methyl 4-bromo-2-fluoro-5-methoxybenzoate as an off white solid (1.5 g, 38% yield). MS m/z: [M+1]⁺=263.3.

Step 4: 4-Bromo-2-Fluoro-5-Methoxybenzoic Acid

To a solution of methyl 4-bromo-2-fluoro-5-methoxybenzoate (9.0 g, 34.22 mmol, 1.0 equiv, in THF:H₂O (6:1, 100 mL) was added LiOH.H₂O (4.3 g, 102.66 mmol, 3.0 equiv) at room temperature. The solution was stirred for 16 h at room temperature. The THF was removed from the reaction mixture, diluted with cold water; pH was adjusted to about 3 with 1.5 N aqueous HCl, extracted with EtOAc (3×250 mL). The combined extracts were washed with brine (150 mL), dried over anhydrous Na₂SO₄, filtered and evaporated to afford crude compound. The crude compound was triturated with n-hexane to afford 4-bromo-2-fluoro-5-methoxybenzoic acid as an off white solid (8.01 g, 94% yield). MS m/z: [M−1]⁻=249.2.

Step 5: 4-Bromo-2-Fluoro-5-Methoxy-N-(Methylsulfonyl)Benzamide

To a solution of methyl 4-bromo-2-fluoro-5-methoxybenzoic acid (8.0 g, 32.12 mmol, 1.0 equiv) in DCM (100 mL) were added methane sulfonamide (3.66 g, 38.55 mmol, 1.2 equiv), DMAP (5.88 g, 48.19 mmol, 1.5 equiv) and EDC.HCl (9.23 g, 48.19 mmol, 1.5 equiv) at room temperature and was stirred for 48 h at the same temperature. The reaction was quenched with 1.5 N aqueous HCl (150 mL), extracted with DCM (3×250 mL). The combined extracts were washed with brine (150 mL), dried over anhydrous Na₂SO₄, filtered and evaporated to afford crude compound. The crude compound was triturated with diethyl ether: n-hexane (2: 8) 100 mL to afford 4-bromo-2-fluoro-5-

Step 1: 2-Fluoro-5-Hydroxybenzoic Acid

To a solution of methyl 2-fluoro-5-hydroxybenzoate (30.0 g, 176.47 mmol, 1.0 equiv, F-chemicals) in THF:H₂O (3:1, 350 mL) was added LiOH.H₂O (22.2 g, 529.41 mmol, 3.0 equiv) at room temperature. The reaction mixture was stirred for 16 h at room temperature. The THF was removed from the reaction mixture, diluted with cold water; pH was adjusted to about 3 with 1.5 N aqueous HCl, extracted with EtOAc (3×250 mL). The combined extracts were washed with brine (150 mL), dried over anhydrous Na₂SO₄, filtered and evaporated to afford 2-fluoro-5-hydroxybenzoic acid as an off white solid (25.1 g, 91% yield). MS m/z: [M−1]⁻=155.4.

methoxy-N-(methylsulfonyl)benzamide as an off white solid (8.5 g, 81% yield). MS m/z: [M−1]⁻=324.2.

Step 6: 4-(5-Chloro-6-Fluoropyridin-3-yl)-2-Fluoro-5-Methoxy-N-(Methylsulfonyl)Benzamide (Intermediate V)

To a flask charged with 4-bromo-2-fluoro-5-methoxy-N-(methylsulfonyl)benzamide (5.00 g, 15.33 mmol), 3-chloro-2-fluoro-5-(4,4,5,5-tetramethyl-1,3,2-dioxaborolan-2-yl)pyridine (3.95 g, 15.33 mmol, Bellon), Pd(Ph$_3$P)$_4$ (0.886 g, 0.767 mmol) was added 1,4-dioxane (61.3 ml) and Na$_2$CO$_3$ (2M) (38.3 ml, 77 mmol) and the mixture purged with nitrogen for 5 mins then heated to 90° C. overnight affording ~25% conversion to product with starting material remaining. To the mixture was added additional 3-chloro-2-fluoro-5-(4,4,5,5-tetramethyl-1,3,2-dioxaborolan-2-yl)pyridine (2 g) and Pd(Ph$_3$P)$_4$ (0.886 g, 0.767 mmol) and the mixture heated to 130° C. for 16 hrs affording complete conversion to desired product according to LC-MS, with minor impurities present. The suspension was cooled in an ice water bath and brought to pH <2 by the addition of 6 N HCl affording a precipitate which was collected by vacuum filtration, washed with water, and dried under a vacuum/nitrogen sweep. The resulting solid was triturated with MeOH/H$_2$O (~1:1) and the solid washed with water affording a light yellow solid 4-(5-chloro-6-fluoropyridin-3-yl)-2-fluoro-5-methoxy-N-(methylsulfonyl)benzamide (5.26 g, 13.96 mmol, 91% yield). $^1$H NMR (400 MHz, DMSO-d$_6$) δ=12.36 (br. s., 1H), 8.38 (m, 2H), 7.40 (m, 2H), 3.83 (s, 3H), 3.13 (s, 3H). MS m/z: [M+1]⁺=376.8.

Example 704

4-(5-Chloro-6-(3-Chloro-2-Methylphenoxy)Pyridin-3-yl)-2-Fluoro-5-Methoxy-N-(Methylsulfonyl)Benzamide

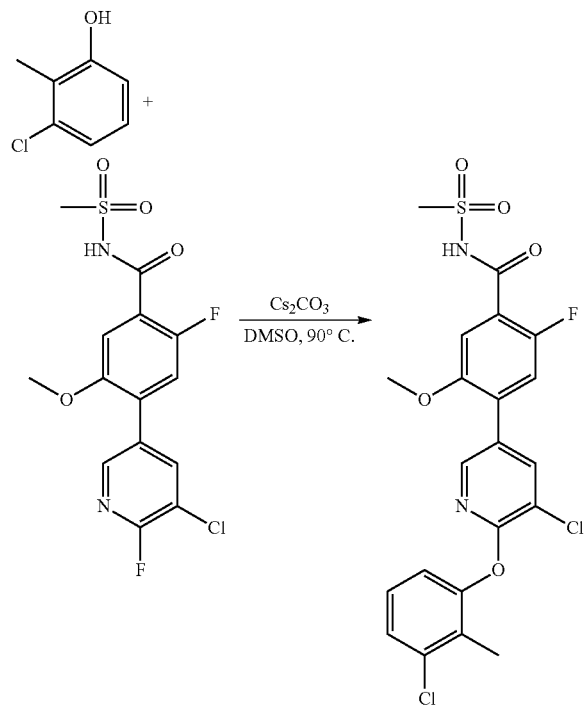

To a vial charged with 4-(5-chloro-6-fluoropyridin-3-yl)-2-fluoro-5-methoxy-N-(methylsulfonyl)benzamide (INTERMEDIATE V, 65 mg, 0.173 mmol) and Cs$_2$CO$_3$ (169 mg, 0.518 mmol) was added 3-chloro-2-methylphenol (0.242 mmol, 1.4 eq, Sigma Aldrich) and DMSO (0.3 M). The resulting suspension was heated with shaking at 90° C. overnight. The resulting suspension was filtered through a frit, rinsing with isopropanol. The isopropanol was removed in-vacuo and the crude material purified Waters-Xbridge C18, 19×100 mm, 10 μm column with a gradient 5-95% acetonitrile and water with 0.1% NH$_4$OH to afford 4-(5-chloro-6-(3-chloro-2-methylphenoxy)pyridin-3-yl)-2-fluoro-5-methoxy-N-(methylsulfonyl)benzamide (49 mg, 40%). LC-MS m/z (ESI, negative ion) 496.9. LC-MS m/z (ESI, negative ion) 496.9. $^1$H NMR (500 MHz, DMSO-d$_6$) δ ppm 2.15 (s, 3H) 2.99 (s, 3H) 3.81 (s, 3H) 7.18 (d, J=7.91 Hz, 2H) 7.25-7.41 (m, 4H) 8.21 (d, J=2.01 Hz, 1H) 8.26 (d, J=2.01 Hz, 1H).

Example 705

4-(5-Chloro-6-((1-Methylcyclopropyl)Methoxy)Pyridin-3-yl)-2-Fluoro-5-Methoxy-N-(Methylsulfonyl)Benzamide

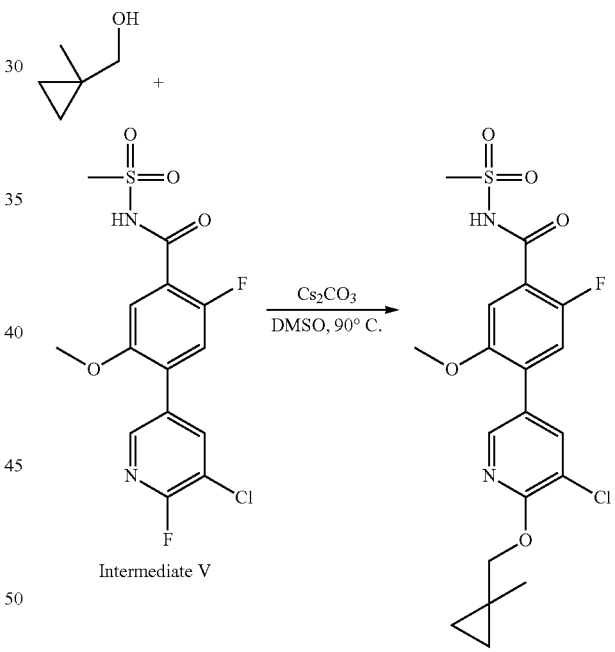

To a vial charged with 4-(5-chloro-6-fluoropyridin-3-yl)-2-fluoro-5-methoxy-N-(methylsulfonyl)benzamide (INTERMEDIATE V, 65 mg, 0.173 mmol) and Cs$_2$CO$_3$ (169 mg, 0.518 mmol) was added (1-methylcyclopropyl)methanol (0.242 mmol, 1.4 eq, Frontier Scientific) and DMSO (0.3 M). The resulting suspension was heated with shaking at 90° C. overnight. The resulting suspension was filtered through a frit, rinsing with isopropanol. The isopropanol was removed in-vacuo and the crude material purified Waters-Xbridge C18, 19×100 mm, 10 μm column with a gradient 5-95% acetonitrile and water with 0.1% NH$_4$OH to afford 4-(5-chloro-6-((1-methylcyclopropyl)methoxy)pyridin-3-yl)-2-fluoro-5-methoxy-N-(methylsulfonyl)benzamide (20 mg, 18%). LC-MS m/z (ESI, negative ion) 441.0. $^1$H NMR (500 MHz, DMSO-d₆) δ ppm 0.36-0.46 (m, 2H) 0.51-0.63 (m, 2H) 1.20 (s, 3H) 3.01 (s, 3H) 3.80 (s, 3H) 4.20 (s, 2H) 7.26 (d, J=10.70 Hz, 1H) 7.34 (d, J=6.10 Hz, 1H) 8.06 (d, J=2.08 Hz, 1H) 8.25 (d, J=2.08 Hz, 1H).

Example 706

4-(5-Chloro-6-(2,5-Difluorophenoxy)Pyridin-3-yl)-2-Fluoro-5-Methoxy-N-(Methylsulfonyl)Benzamide

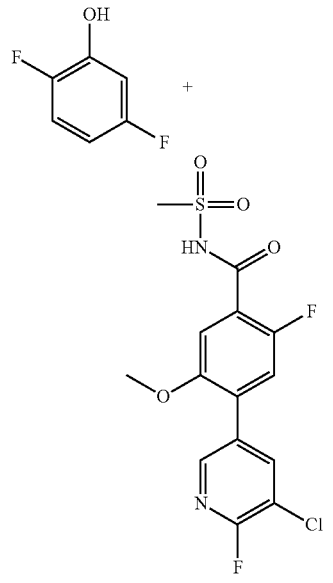

To a vial charged with 4-(5-chloro-6-fluoropyridin-3-yl)-2-fluoro-5-methoxy-N-(methylsulfonyl)benzamide (INTERMEDIATE V, 65 mg, 0.173 mmol) and Cs₂CO₃ (169 mg, 0.518 mmol) was added 2,5-difluorophenol (0.242 mmol, 1.4 eq) and DMSO (0.3 M). The resulting suspension was heated with shaking at 90° C. overnight. The resulting suspension was filtered through a frit, rinsing with isopropanol. The isopropanol was removed in-vacuo and the crude material purified Waters-Xbridge C18, 19×100 mm, 10 µm column with a gradient 5-95% acetonitrile and water with 0.1% NH₄OH to afford 4-(5-chloro-6-(2,5-difluorophenoxy)pyridin-3-yl)-2-fluoro-5-methoxy-N-(methylsulfonyl)benzamide (44 mg, 36%). LC-MS m/z (ESI, negative ion) 484.8. ¹H NMR (500 MHz, DMSO-d₆) δ ppm 2.95 (s, 3H) 3.80 (s, 3H) 7.17-7.31 (m, 2H) 7.35 (d, J=6.03 Hz, 1H) 7.40-7.54 (m, 2H) 8.23 (d, J=1.95 Hz, 1H) 8.27 (d, J=1.95 Hz, 1H).

Example 709

4-(6-(Benzo[D]Thiazol-2-Ylmethoxy)-5-Chloropyridin-3-yl)-2-Fluoro-5-Methoxy-N-(Methylsulfonyl)Benzamide

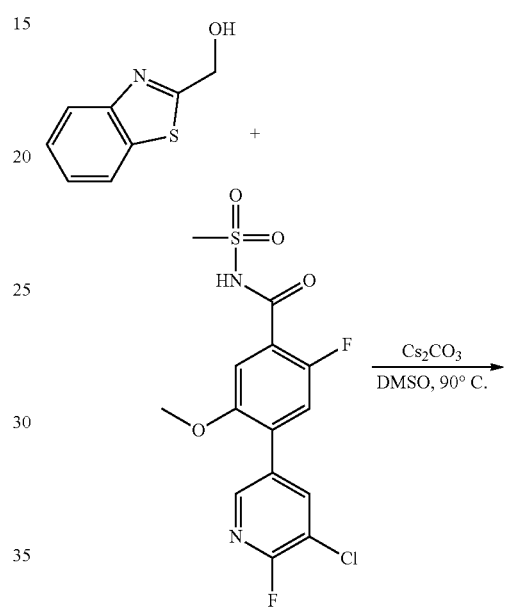

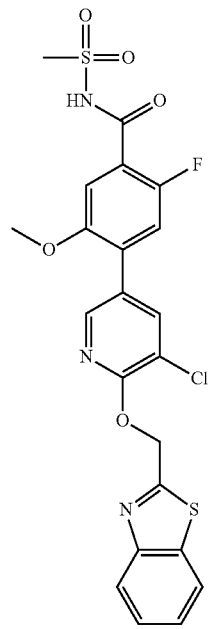

To a vial charged with 4-(5-chloro-6-fluoropyridin-3-yl)-2-fluoro-5-methoxy-N-(methylsulfonyl)benzamide (INTERMEDIATE V, 65 mg, 0.173 mmol) and Cs₂CO₃ (169 mg, 0.518 mmol) was added benzo[d]thiazol-2-ylmethanol (0.242 mmol, 1.4 eq, Frontier Scientific) and DMSO (0.3 M). The resulting suspension was filtered through a frit, rinsing with isopropanol. The isopropanol was removed in-vacuo and the crude material purified Waters-Xbridge C18, 19×100 mm, 10 μm column with a gradient 5-95% acetonitrile and water with 0.1% NH$_4$OH to afford 4-(6-(benzo[d]thiazol-2-ylmethoxy)-5-chloropyridin-3-yl)-2-fluoro-5-methoxy-N-(methylsulfonyl)benzamide (10 mg, 8%). LC-MS m/z (ESI, negative ion) 520.0. $^1$H NMR (500 MHz, DMSO-d$_6$) δ ppm 3.14 (s, 3H) 3.82 (s, 3H) 5.94 (s, 2H) 7.30-7.41 (m, 2H) 7.46 (t, J=7.70 Hz, 1H) 7.54 (t, J=7.10 Hz, 1H) 8.02 (d, J=8.04 Hz, 1H) 8.08-8.17 (m, 1H) 8.20 (d, J=2.01 Hz, 1H) 8.34 (d, J=2.01 Hz, 1H).

Examples 719, 767, and 769: 4-(5-Chloro-6-(1-Cyclobutylethoxy)Pyridin-3-yl)-2-Fluoro-5-Methoxy-N-(Methylsulfonyl)Benzamide, (S)-4-(5-Chloro-6-(1-Cyclobutylethoxy)Pyridin-3-yl)-2-Fluoro-5-Methoxy-N-(Methylsulfonyl)Benzamide, and (R)-4-(5-Chloro-6-(1-Cyclobutylethoxy)Pyridin-3-yl)-2-Fluoro-5-Methoxy-N-(Methylsulfonyl)Benzamide

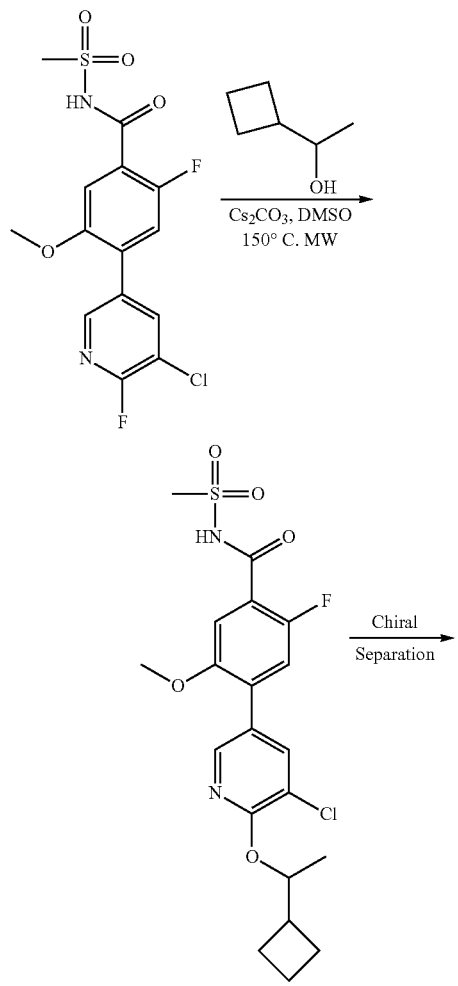

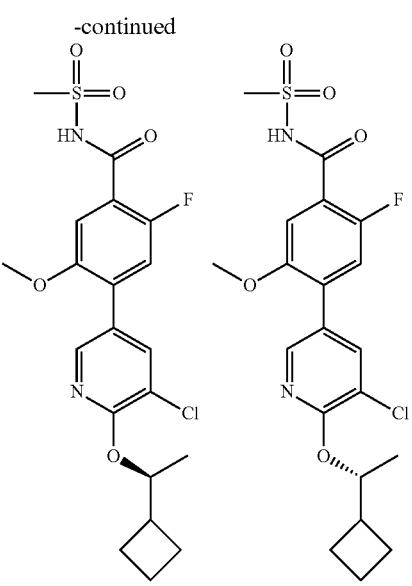

To a microwave vessel charged with 1-cyclobutylethanol (Matrix Scientific, 120 mg, 1.16 mmol) was added 4-(5-chloro-6-fluoropyridin-3-yl)-2-fluoro-5-methoxy-N-(methylsulfonyl)benzamide (Intermediate V) (0.080 g, 0.194 mmol) and DMSO (2 mL). Then cesium carbonate (0.253 g, 0.775 mmol) was added. The tube was sealed and heated at 150° C. in MW for 2 h. The crude reaction mixture was then filtered through a frit and washed with DCM then MeOH. After concentration, the crude residue was purified using preparative reverse phase LCMS (0.1% NH$_4$OH in water/acetonitrile; Flow rate: 40 ml/min; Gradient: 10 min 20-50% NH$_3$) to afford 4-(5-chloro-6-(1-cyclobutylethoxy)pyridin-3-yl)-2-fluoro-5-methoxy-N-(methylsulfonyl)benzamide (60 mg). LC-MS m/z (ESI, negative ion) 455.0. $^1$H NMR (500 MHz, DMSO-d$_6$) δ 8.25 (d, J=2.01 Hz, 1H), 8.03 (d, J=1.95 Hz, 1H), 7.33 (d, J=6.10 Hz, 1H), 7.18 (d, J=10.64 Hz, 1H), 5.21-5.26 (m, 1H), 3.78 (s, 3H), 2.86 (s, 3H), 2.60 (m, 1H), 1.83-2.03 (m, 6H), 1.2 (d, J=7.40 Hz, 3H). Chiral resolution of 4-(5-chloro-6-(1-cyclobutylethoxy)pyridin-3-yl)-2-fluoro-5-methoxy-N-(methylsulfonyl)benzamide by SFC (Chiracel OJ-H) provided 23 mg of peak 1, (S)-4-(5-chloro-6-(1-cyclobutylethoxy)pyridin-3-yl)-2-fluoro-5-methoxy-N-(methylsulfonyl)benzamide, (>98%) ee) and 20 mg of peak 2, (R)-4-(5-chloro-6-(1-cyclobutylethoxy)pyridin-3-yl)-2-fluoro-5-methoxy-N-(methylsulfonyl)benzamide (>98% ee). Absolute stereochemistry was arbitrarily assigned.

Example 734: 4-(5-Chloro-6-((1-(Trifluoromethyl)-Cyclobutyl)Oxy)-3-Pyridinyl)-2-Fluoro-5-Methoxy-N-(Methylsulfonyl)Benzamide Example 735: 4-(5-Chloro-6-((Trans-3-Methylcyclobutyl)Oxy)-3-Pyridinyl)-2-Fluoro-5-Methoxy-N-(Methylsulfonyl)Benzamide

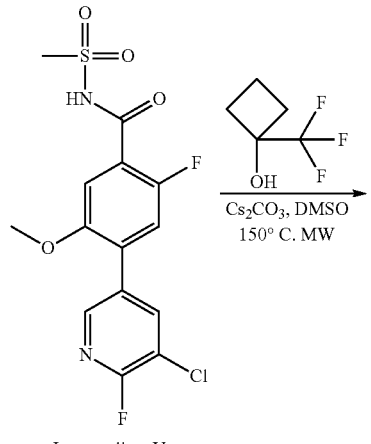

Intermediate V

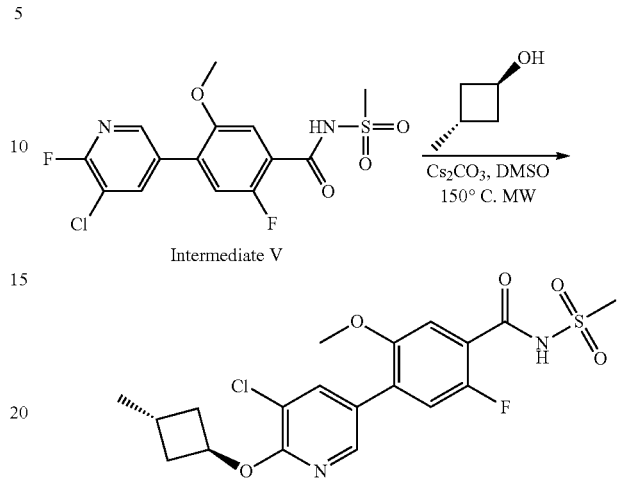

Intermediate V

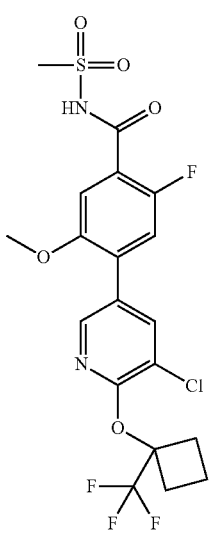

To a microwave vessel charged with 1-(trifluoromethyl)cyclobutanol (Enamine, 89 mg, 0.637 mmol) was added 4-(5-chloro-6-fluoropyridin-3-yl)-2-fluoro-5-methoxy-N-(methylsulfonyl)benzamide (INTERMEDIATE V) (0.080 g, 0.212 mmol), DMSO (2 mL), then cesium carbonate (0.277 g, 0.849 mmol). The tube was sealed and heated at 150° C. in the microwave for 2 h. The crude reaction mixture was then filtered through a frit and washed with DCM then MeOH. After concentration, the crude residue was purified using preparative reverse phase LCMS (0.1% NH₄OH in water/acetonitrile; Flow rate: 40 ml/min; Gradient: 10 min 20-50% NH₃) to afford 4-(5-chloro-6-((1-(trifluoromethyl)cyclobutyl)oxy)-3-pyridinyl)-2-fluoro-5-methoxy-N-(methylsulfonyl)benzamide (46 mg). LC-MS m/z (ESI, positive ion) 497.0. ¹H NMR (500 MHz, DMSO-d₆) δ 8.29 (d, J=2.08 Hz, 1H), 8.14 (d, J=2.01 Hz, 1H), 7.34 (d, J=6.03 Hz, 1H), 7.26 (d, J=10.70 Hz, 1H), 3.80 (s, 3H), 2.96 (s, 3H), 2.82-2.94 (m, 2H), 2.61-2.70 (m, 2H), 1.94-2.04 (m, 1H), 1.79-1.90 (m, 1H).

To a microwave vessel charged with trans-3-methylcyclobutanol (DSK Biopharma, 55 mg, 0.637 mmol) was added 4-(5-chloro-6-fluoropyridin-3-yl)-2-fluoro-5-methoxy-N-(methylsulfonyl)benzamide (INTERMEDIATE V) (0.080 g, 0.212 mmol), DMSO (2 mL), then cesium carbonate (0.277 g, 0.849 mmol). The tube was sealed and heated at 150° C. in the microwave for 2 h. The crude reaction mixture was then filtered through a frit and washed with DCM then MeOH. After concentration, the crude residue was purified using preparative reverse phase LCMS (0.1% NH₄OH in water/acetonitrile; Flow rate: 40 ml/min; Gradient: 10 min 20-50% NH₃) to afford 4-(5-chloro-6-((trans-3-methylcyclobutyl)oxy)-3-pyridinyl)-2-fluoro-5-methoxy-N-(methylsulfonyl)benzamide (48 mg). LC-MS m/z (ESI, positive ion) 443.0. ¹H NMR (500 MHz, DMSO-d₆) δ 8.24 (d, J=6.85 Hz, 1H), 8.03 (d, J=7.05 Hz, 1H), 7.33 (d, J=6.16 Hz, 1H), 7.17 (d, J=10.77 Hz, 1H), 5.07 (quin, J=7.43 Hz, 1H), 3.78 (s, 3H), 2.86 (s, 3H), 2.56-2.73 (m, 2H), 1.98-2.08 (m, 1H), 1.64-1.74 (m, 2H), 1.12 (d, J=6.55 Hz, 3H).

Example 752: 4-(5-Chloro-6-(2-Chloro-5-Methyl-phenoxy)-3-Pyridinyl)-2-Fluoro-5-Methoxy-N-(Methylsulfonyl)Benzamide

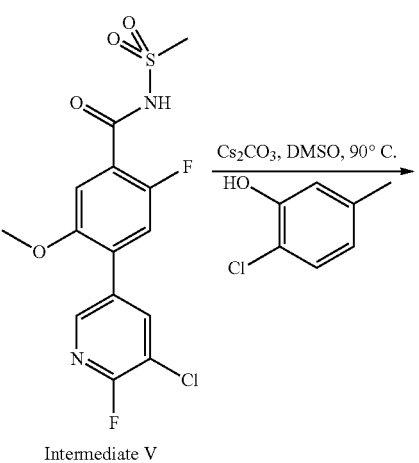

Intermediate V

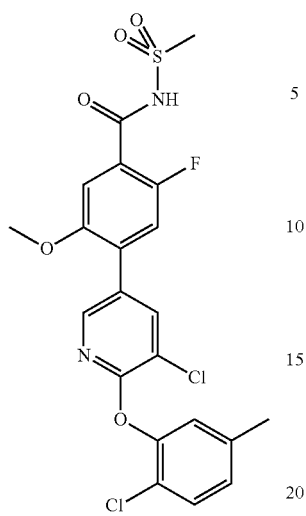

A vial was charged with 4-(5-chloro-6-fluoropyridin-3-yl)-2-fluoro-5-methoxy-N-(methylsulfonyl)benzamide (INTERMEDIATE V) (100 mg, 0.26 mmol), cesium carbonate (216 mg, 0.664 mmol), 2-chloro-5-methylphenol (57 mg, 0.400 mmol) and 1.5 mL DMSO. The vial was sealed, and the reaction mixture was heated at 90° C. for 15 h. The mixture was filtered through a frit, which was washed with MeOH and DCM. The filtrate was concentrated, and the crude material was purified by reverse phase chromatography, PREP LC/MS-2 System Column: XBridge Prep Shield RP18 19×100 mm 104I131331GG 03 Mobile phase: 0.1% NH$_4$OH in water/acetonitrile Flow rate: 40 ml/min Inj: 2500 µL Gradient: 10 min, 10-40%_LV_NH$_3$. 4-(5-chloro-6-(2-chloro-5-methylphenoxy)-3-pyridinyl)-2-fluoro-5-methoxy-N-(methylsulfonyl)benzamide was isolated as an off-white solid (90 mg, 68% yield). MS (ESI, negative ionization) m/z 497.0; $^1$H NMR (500 MHz, DMSO-d$_6$) δ ppm 2.33 (s, 3H) 2.87 (s, 3H) 3.76-3.83 (m, 3H) 7.04-7.18 (m, 2H) 7.18-7.27 (m, 1H) 7.35 (d, J=6.10 Hz, 1H) 7.47 (d, J=8.17 Hz, 1H) 8.17-8.27 (m, 2H).

Method XIX: Preparation by Using Intermediate W

Intermediate W was prepared using a two-step procedure below:

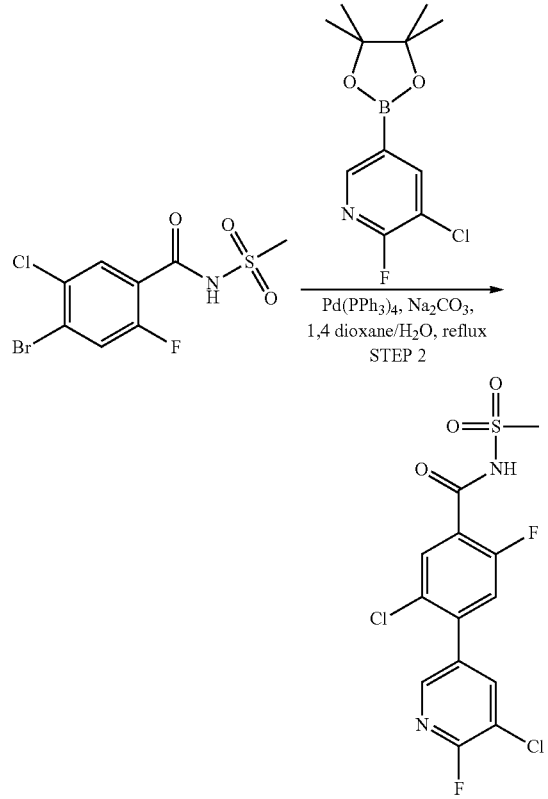

Step 1: 4-Bromo-5-Chloro-2-Fluoro-N-(Methylsulfonyl)Benzamide

To a solution of 4-bromo-5-chloro-2-fluorobenzoic acid (13.0 g, 51.29 mmol, 1.0 equiv, Oakwood) and methane sulfonamide (5.85 g, 61.55 mmol, 1.2 equiv) in DCM (1.0 L) was added DMAP (18.80 g, 153.87 mmol, 3.0 equiv) followed by EDC.HCl (19.66 g, 102.58 mmol, 2.0 equiv). The reaction mixture was stirred at ambient temperature for 12 h. After completion of reaction (monitored by TLC), the reaction mass was diluted with DCM (500 mL) and washed with 1.5 N aqueous HCl (2×250 mL). The organic layer was washed with saturated brine (2×250 mL), dried over anhydrous sodium sulfate and concentrated under reduced pressure. The crude product was dissolved in minimum DCM (20 mL) and hexane (250 mL) was added drop-wise with stirring. The precipitates thus obtained were filtered and dried to afford 4-bromo-5-chloro-2-fluoro-N-(methylsulfonyl)benzamide (13.2 g, 77.8%). MS m/z: [M−1]$^-$=329.8.

Step 2: 5-Chloro-4-(5-Chloro-6-Fluoropyridin-3-yl)-2-Fluoro-N-(Methylsulfonyl)Benzamide To a flask charged with 4-bromo-5-chloro-2-fluoro-N-(methylsulfonyl)benzamide (3.054 g, 9.24 mmol), 3-chloro-2-fluoro-5-(4,4,5,5-tetramethyl-1,3,2-dioxaborolan-2-yl)pyridine (2.379 g, 9.24 mmol), Pd(Ph$_3$P)$_4$ (0.534 g, 0.462 mmol) was added 1,4-dioxane (37.0 ml) and Na$_2$CO$_3$ (2M) (23.10 ml, 46.2 mmol) and the mixture purged with nitrogen for 5 mins then heated to 90° C. for 3 hrs affording only ~15% conversion to product. The mixture was heated to 120° C. overnight affording ~70% conversion (based on remaining SM) with other minor impurities. To the mixture was added additional 3-chloro-2-fluoro-5-(4,4,5,5-tetramethyl-1,3,2-dioxaborolan-2-yl)pyridine (800 mg) and Pd(Ph₃P)₄ (170 mg) and heating and stirring continued at 120° C. for 3 hrs affording complete conversion. The mixture was cooled in an ice water bath and brought to pH <2 by the careful addition of 6N HCl with vigorous stirring affording a partial oiling out of organic material. To the mixture was added IPA (~10 ml) and water (~25 ml) and stirring continued for 2 hrs (slowly warming to room temp) affording a precipitate which was collected by vacuum filtration and dried with a vacuum/nitrogen sweep. The material obtained was triturated with MeOH affording product as a yellow solid, 5-chloro-4-(5-chloro-6-fluoropyridin-3-yl)-2-fluoro-N-(methylsulfonyl)benzamide (1.96 g, 5.14 mmol, 55.7% yield). ¹H NMR (400 MHz, DMSO-d₆) δ=8.46 (dd, 0.7=2.2, 8.8 Hz, 1H), 8.37 (dd, J=1.2, 2.2 Hz, 1H), 7.96 (d, J=6.4 Hz, 1H), 7.69 (d, J=10.5 Hz, 1H), 3.38 (s, 3H). MS m/z: [M+1]⁺=380.8.

Example 589: 5-Chloro-4-(5-Chloro-6-(2,3,5-Trifluorophenoxy)Pyridin-3-yl)-2-Fluoro-N-(Methylsulfonyl)Benzamide

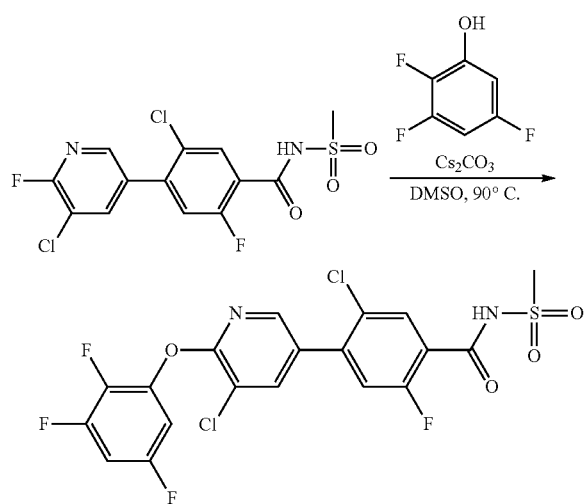

To a vial charged with 5-chloro-4-(5-chloro-6-fluoropyridin-3-yl)-2-fluoro-N-(methylsulfonyl)benzamide (65 mg, 0.171 mmol) and Cs₂CO₃ (167 mg, 0.512 mmol) was added 2,3,5-trifluorophenol (0.239 mmol, 1.4 eq) and DMSO (0.3 M). The resulting suspension was heated with shaking at 90° C. overnight. The resulting suspension was filtered through a frit, rinsing with isopropanol. The isopropanol was removed in-vacuo and the crude material purified Waters-Xbridge C18, 19×100 mm, 10 μm column with a gradient 5-95% acetonitrile and water with 0.1% NH₄OH to afford 5-chloro-4-(5-chloro-6-(2,3,5-trifluorophenoxy)pyridin-3-yl)-2-fluoro-N-(methylsulfonyl)benzamide (49 mg, 39%). LC-MS m/z (ESI, negative ion) 506.9. ¹H NMR (500 MHz, DMSO-d₆) δ ppm 2.91 (s, 3H) 7.38-7.47 (m, 2H) 7.55 (br. s., 1H) 7.82 (d, J=6.68 Hz, 1H) 8.22 (d, J=2.01 Hz, 1H) 8.33 (d, J=2.01 Hz, 1H).

Example 598: 5-Chloro-4-(5-Chloro-6-(2,4-Dichloro-6-Methylphenoxy)Pyridin-3-yl)-2-Fluoro-N-(Methylsulfonyl)Benzamide

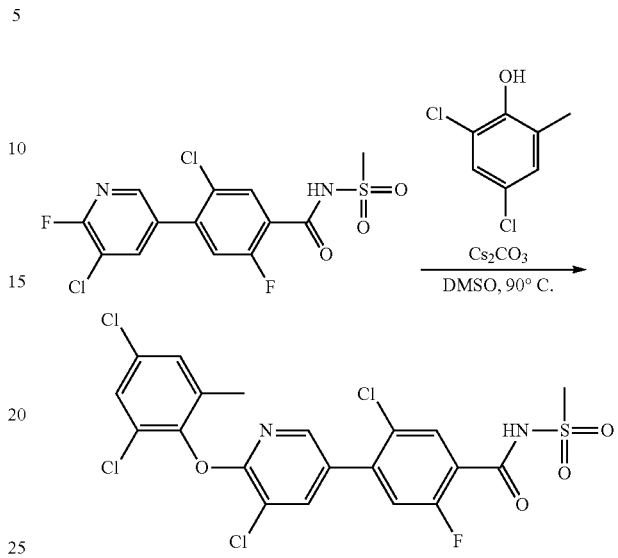

To a vial charged with 5-chloro-4-(5-chloro-6-fluoropyridin-3-yl)-2-fluoro-N-(methylsulfonyl)benzamide (65 mg, 0.171 mmol) and Cs₂CO₃ (167 mg, 0.512 mmol) was added 2,4-dichloro-6-methylphenol (0.239 mmol, 1.4 eq, Frontier Scientific) and DMSO (0.3 M). The resulting suspension was heated with shaking at 90° C. overnight. The resulting suspension was filtered through a frit, rinsing with isopropanol. The isopropanol was removed in-vacuo and the crude material purified Waters-Xbridge C18, 19×100 mm, 10 (μm column with a gradient 5-95% acetonitrile and water with 0.1% NH₄OH to afford 5-chloro-4-(5-chloro-6-(2,4-dichloro-6-methylphenoxy)pyridin-3-yl)-2-fluoro-n-(methylsulfonyl)benzamide (49 mg, 37%). LC-MS m/z (ESI, negative ion) 536.8. ¹H NMR (500 MHz, DMSO-d₆) δ ppm 2.15 (s, 3H) 2.89 (s, 3H) 7.40 (d, J=10.51 Hz, 1H) 7.45-7.54 (m, 1H) 7.63 (d, J=2.14 Hz, 1H) 7.81 (d, J=6.68 Hz, 1H) 8.15 (d, J=2.01 Hz, 1H) 8.30 (d, J=2.01 Hz, 1H).

Method XX: Preparation by Using Intermediate X

Example 772: 4-(5-Chloro-6-(3,5-Dichlorophenoxy)Pyridin-3-yl)-3-Methoxy-N—(N-Methylsulfamoyl)Benzamide

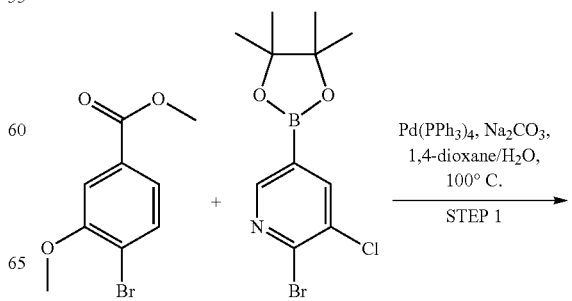

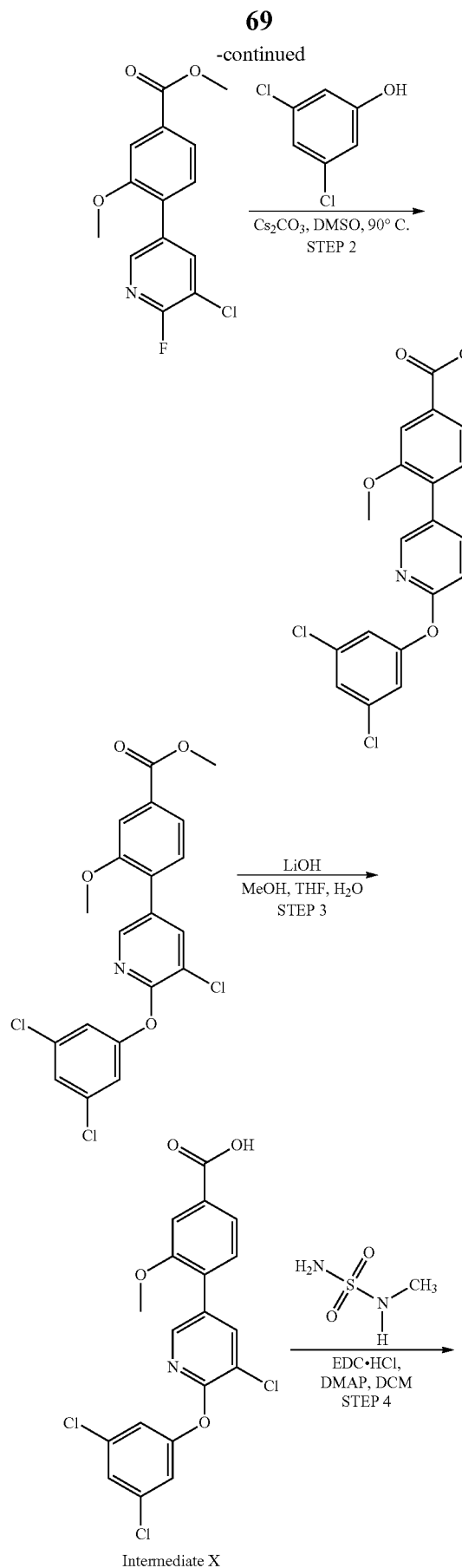

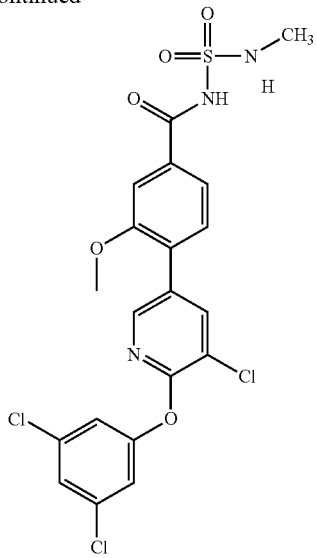

Step 1: Methyl 4-(5-Chloro-6-Fluoropyridin-3-yl)-3-Methoxybenzoate

To a flask charged with methyl 4-bromo-3-methoxybenzoate (2.00 g, 8.16 mmol, Astatech), 3-chloro-2-fluoro-5-(4,4,5,5-tetramethyl-1,3,2-dioxaborolan-2-yl)pyridine (2.206 g, 8.57 mmol), and Pd(Ph$_3$P)$_4$ (0.943 g, 0.816 mmol) was added cyclopentyl methyl ether (20.40 ml) and 2M Na$_2$CO$_3$ (20.40 ml, 40.8 mmol) and the mixture heated to 100° C. overnight and stirred under nitrogen affording a yellow solution. Upon cooling to room temperature a precipitate formed which was collected by vacuum filtration and washed with water. The solid was stirred in 30 ml MeOH for 1.5 hr and the solid was collected by vacuum filtration and washed with MeOH affording clean product as a white solid, methyl 4-(5-chloro-6-fluoropyridin-3-yl)-3-methoxybenzoate (2.41 g, 8.15 mmol, 100% yield). MS m/z: [M+1]$^+$=296.1.

Step 2: Methyl 4-(5-Chloro-6-(3,5-Dichlorophenoxy)Pyridin-3-yl)-3-Methoxybenzoate To a vial charged with methyl 4-(5-chloro-6-fluoropyridin-3-yl)-3-methoxybenzoate (1.0 g, 3.38 mmol) was added 3,5-dichlorophenol (0.579 g, 3.55 mmol), Cs$_2$CO$_3$ (1.322 g, 4.06 mmol) and DMSO (9.66 ml). The resulting mixture was heated to 90° C. for 4 hrs. The mixture was cooled to room temperature affording a precipitate which was collected by vacuum filtration and washed with water affording product. The yield was not determined and the material was used directly in the subsequent step. MS m/z: [M+1]$^+$=438.1.

Step 3: 4-(5-Chloro-6-(3,5-Dichlorophenoxy)Pyridin-3-yl)-3-Methoxybenzoic Acid To a flask charged with methyl 4-(5-chloro-6-(3,5-dichlorophenoxy)pyridin-3-yl)-3-methoxybenzoate (1.45 g, 3.31 mmol) was added THF (19.33 ml), MeOH (19.33 ml), water (19.33 ml). To the resulting slurry was added LiOH (0.396 g, 16.53 mmol) and the resulting mixture stirred overnight at room temperature affording a turbid light yellow suspension. To the mixture was added 2N HCl until the pH was 2, affording a white precipitate which was collected by vacuum filtration and washed with water. LC-MS of the solid indicated about 70% product purity with starting material still present as an impurity. The material was used without further purification. MS m/z: [M+1]+=423.9.

Step 4: 4-(5-Chloro-6-(3,5-Dichlorophenoxy)Pyridin-3-yl)-3-Methoxy-N—(N-Methylsulfamoyl)Benzamide To a vial charged with 4-(5-chloro-6-(3,5-dichlorophenoxy)pyridin-3-yl)-3-methoxybenzoic acid (100 mg, 0.235 mmol) was added N-methylsulfamide (26 mg, 0.235 mmol), DMAP (31.6 mg, 0.259 mmol), EDCI (49.7 mg, 0.259 mmol) and DCM (942 μl). The resulting mixtures were shaken overnight at room temperature. To the vessel was added 2N HCl (2 ml) and the mixture passed through a phase separator column, washing with DCM. The organics were dried under reduced pressure and the crude material was purified with a Waters-Xbridge C18, 19×100 mm, 10 μm column with a gradient 5-95% acetonitrile and water with 0.1% NH$_4$OH to afford 4-(5-chloro-6-(3,5-dichlorophenoxy)pyridin-3-yl)-3-methoxy-N—(N-methylsulfamoyl)benzamide (25 mg, 20%). LC-MS m/z (ESI, negative ion) 514.0. $^1$H NMR (500 MHz, DMSO-d$_6$) δ ppm 2.52 (d, J=4.64 Hz, 3H) 3.88 (m, 3H) 7.24 (br. s., 1H) 7.45 (d, J=1.70 Hz, 2H) 7.48-7.54 (m, 2H) 7.64 (d, J=7.92 Hz, 1H) 7.69 (s, 1H) 8.26 (dd, J=9.67, 1.98 Hz, 2H).

Method XXII (Example 806): 4'-Chloro-5-Fluoro-2-Methyl-N-(Methylsulfonyl)-3'-(Trifluoromethyl)-4-Biphenylcarboxamide

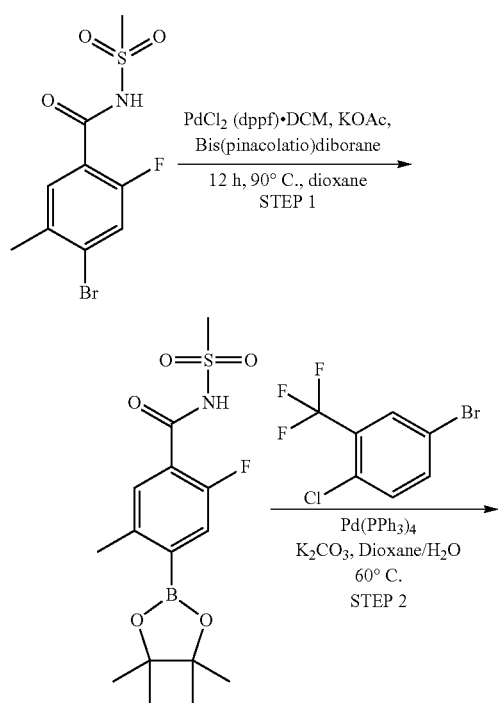

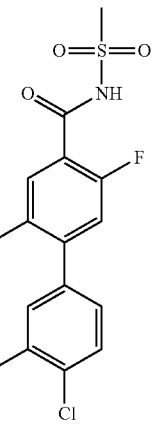

Step 1: 2-Fluoro-5-Methyl-N-(Methylsulfonyl)-4-(4,4,5,5-Tetramethyl-1,3,2-Dioxaborolan-2-yl)Benzamide To a solution of 4-bromo-2-fluoro-5-methyl-N-(methylsulfonyl)benzamide (prepared as described in Step 1 of METHOD XV) (20.0 g, 64.43 mmol) in 1,4-dioxane (400 mL) was added bis(pinacolato)diborane (24.5 g, 96.69 mmol) and KOAc (18.9 g, 193.29 mmol). The reaction mixture was degassed with nitrogen for 15 min. and PdCl$_2$(dppf)-DCM (2.6 g, 3.22 mmol) was added. The reaction mixture was again degassed with nitrogen for 15 min. and heated at 90° C. for 16 h. The reaction mixture was filtered through CELITE and the CELITE bed was washed with ethyl acetate (150 mL). The organic layer was washed with water (500 mL) and aqueous layer was extracted with ethyl acetate (2×150 mL). The combined organics were washed with a brine solution (150 mL), dried with sodium sulfate and concentrated under reduced pressure to obtain the crude material which was purified by column chromatography (silica gel 60-120 mesh, elution: 0-1% Methanol in DCM) to afford 2-fluoro-5-methyl-N-(methylsulfonyl)-4-(4,4,5,5-tetramethyl-1,3,2-dioxaborolan-2-yl)benzamide (15.3 g, 66.5%). MS m/z: [M+1]+=358.1. $^1$H NMR (400 MHz, DMSO-d$_6$) δ 12.32 (s, 1H), 7.47 (d, J=6.6 Hz, 1H), 7.37 (d, J=10.6 Hz, 1H), 3.37 (s, 3H), 2.46 (s, 3H), 1.31 (s, 12H).

Step 2: 4'-Chloro-5-Fluoro-2-Methyl-N-(Methylsulfonyl)-3'-(Trifluoromethyl)-4-Biphenylcarboxamide A resealable 2 dram round bottom reaction tube was charged with 4-bromo-1-chloro-2-(trifluoromethyl)benzene (72.5 mg, 0.280 mmol), potassium carbonate (116 mg, 0.840 mmol), tetrakis(triphenylphosphine)palladium(0) (32.4 mg, 0.028 mmol), and 2-fluoro-5-methyl-N-(methylsulfonyl)-4-(4,4,5,5-tetramethyl-1,3,2-dioxaborolan-2-yl)benzamide (120 mg, 0.336 mmol). The vial was flushed with Ar (g), then 1,4-dioxane (2 mL) and water (0.67 mL) were added. The vial was purged with Ar (g), sealed and heated with shaking at 60° C. for 2 d. The crude reaction mixture was filtered through a frit, concentrated and purified by PREP LC/MS-2 System Column: XBridge 19×100 mm 12230326114 03 Mobile phase: 0.1% NH$_4$OH in water/acetonitrile, Flow rate: 40 ml/min, Inj: 2200 uL, Gradient: 10 min 10-40%_LV_NH$_3$; 10 min 5-30%_LV_NH$_3$; 10 min 20-50%_LV_NH$_3$ to afford 4'-chloro-5-fluoro-2-methyl-N-

(methylsulfonyl)-3'-(trifluoromethyl)-4-biphenylcarboxamide as an off-white solid (86 mg, 0.21 mmol, 25%). MS m/z: [M−1]⁻=407.9.

Example 817: 4-(6-(3,5-Dichlorophenoxy)-5-(Trifluoromethyl)Pyridin-3-yl)-2-Fluoro-5-Methyl-N-(Methylsulfonyl)Benzamide

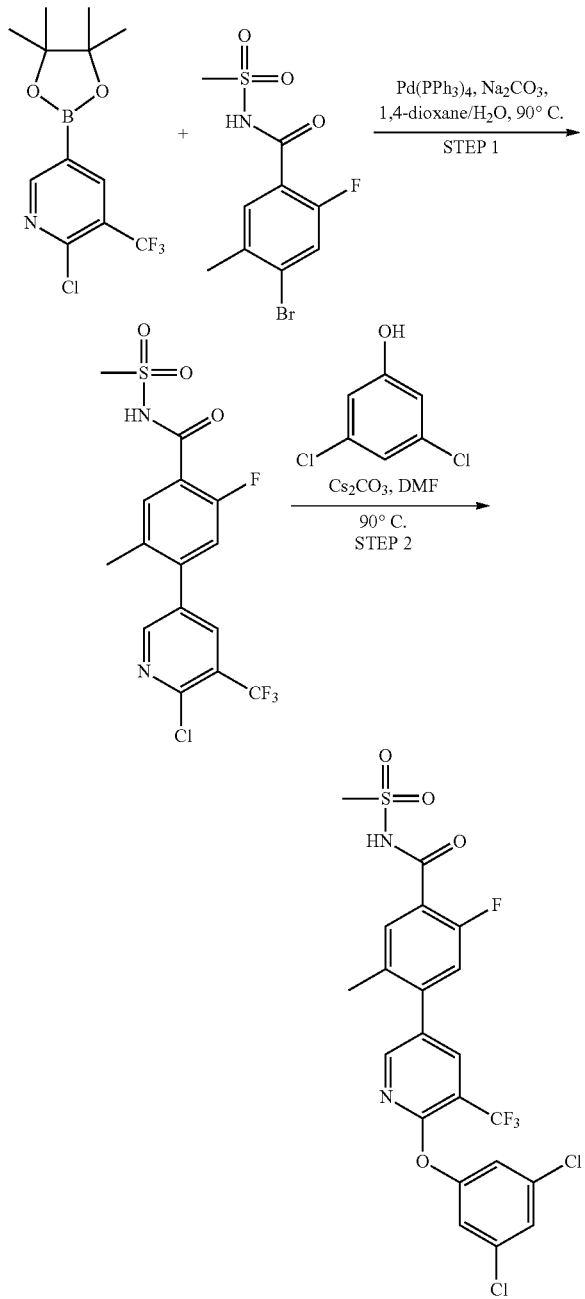

Step 1: 4-(6-Chloro-5-(Trifluoromethyl)Pyridin-3-yl)-2-Fluoro-5-Methyl-N-(Methylsulfonyl)Benzamide To a flask charged with 4-bromo-2-fluoro-5-methyl-N-(methylsulfonyl)benzamide (see INTERMEDIATE P preparation) (0.8 g, 2.58 mmol), 2-chloro-5-(4,4,5,5-tetramethyl-1,3,2-dioxaborolan-2-yl)-3-(trifluoromethyl)pyridine (0.952 g, 3.10 mmol, Combi-Blocks), Pd(Ph₃P)₄ (0.149 g, 0.129 mmol) was added CPME (10.32 ml) and Na₂CO₃ (2M) (6.45 ml, 12.90 mmol) and the mixture purged with argon, sealed and heated to 110° C. for 4 hrs. The mixture was diluted with water and EtOAc and the organic layer separated and the aqueous phase cooled in an ice water bath and acidified to pH <2 by the addition of 6N HCl affording a precipitate which became an oil with stirring. The mixture was extracted 2× with EtOAc and the combined organics were dried with Na₂SO₄, filtered, and dried under reduced pressure. The material was purified with a 50 g ultra snap column ramping DCM:MeOH (90:10) in DCM (0-50%). The product was isolated along with an impurity and was repurified with RP Isolera, 55 g, C18 HP column ramping ACN in H₂O (0-100%, 0.1% formic acid throughout) affording product as a yellow oil with minor impurities by LC-MS. The material was used without further purification. MS m/z: [M+1]⁺= 411.0.

Step 2: 4-(6-(3,5-Dichlorophenoxy)-5-(Trifluoromethyl)Pyridin-3-yl)-2-Fluoro-5-Methyl-N-(Methylsulfonyl)Benzamide To a vial charged with 4-(6-chloro-5-(trifluoromethyl)pyridin-3-yl)-2-fluoro-5-methyl-N-(methylsulfonyl)benzamide (60 mg, 0.146 mmol), 3,5-dichlorophenol (25.00 mg, 0.153 mmol) and Cs₂CO₃ (143 mg, 0.438 mmol) was added DMSO (584 µl) and the mixture heated to 120° C. for 3 hrs. The mixture was loaded onto a redisep load column and purified with RP-Isolera using a 55 g Interchim C-18, 30 um column ramping ACN in H₂O (35-100%, 0.1% formic acid) affording product co-elution with a close running impurity. The mixture was repurified with RP-HPLC ramping ACN in H₂O (5-95%, 0.1% NH₄OH throughout) affording the title compound (26 mg, 33%). ¹H NMR (500 MHz, DMSO-d₆) δ 8.49 (s, 1H), 8.38-8.28 (m, 1H), 7.64 (d, J=7.4 Hz, 1H), 7.60-7.52 (m, 1H), 7.47 (d, J=1.7 Hz, 2H), 7.26 (d, J=10.7 Hz, 1H), 3.15 (s, 3H), 2.25 (s, 3H). MS m/z: [M+1]⁺=537.0.

Method XXIX (Example 818): 4-(5-Chloro-6-((3-Methoxybenzyl)Thio)-Pyridin-3-yl)-2-Fluoro-5-Methyl-N-(Methylsulfonyl)Benzamide

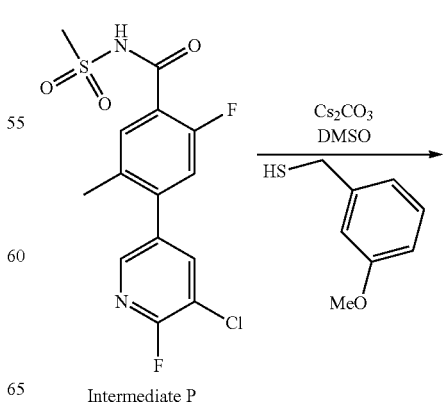

Intermediate P

-continued

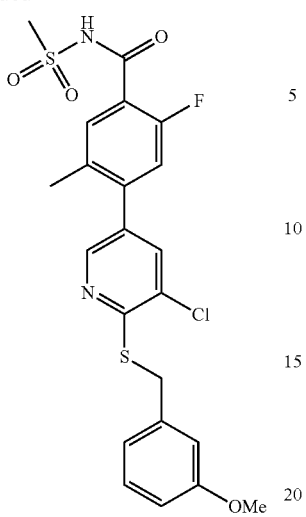

To a vial containing 4-(5-chloro-6-fluoropyridin-3-yl)-2-fluoro-5-methyl-N-(methylsulfonyl)benzamide (0.072 g, 0.2 mmol) was added DMSO (1.333 ml), cesium carbonate (0.143 g, 0.440 mmol), and (3-methoxyphenyl)methanethiol (0.043 ml, 0.300 mmol). The reaction mixture was heated at 100° C. in a heating block overnight. After cooling to rt, the reaction mixture was filtered and was purified by preparative HPLC using 0.1% $NH_4OH$ in ACN and water as mobile phase to provide 4-(5-chloro-6-((3-methoxybenzyl)thio)pyridin-3-yl)-2-fluoro-5-methyl-N-(methylsulfonyl)benzamide (33 mg, 31% yield). $^1$H NMR (500 MHz, DMSO-$d_6$) δ ppm 2.23 (s, 3H), 2.54 (s, 1H), 2.95 (s, 3H), 3.73 (s, 3H), 4.47 (s, 2H), 6.83 (d, J=8.01 Hz, 1H), 7.00-7.05 (m, 2H), 7.05-7.17 (m, 2H), 7.24 (t, J=7.82 Hz, 1H), 7.61 (d, J=7.53 Hz, 1H), 7.97 (d, J=1.82 Hz, 1H), 8.52 (d, J=1.82 Hz, 1H). MS m/z $[M+1]^+$=495.0.

Method XXIII (Example 834) (AMG 3101999)

4-(5-Chloro-6-(3,5-Difluorophenyl)-3-Pyridinyl)-2-Fluoro-5-Methyl-N-(Methylsulfonyl)Benzamide

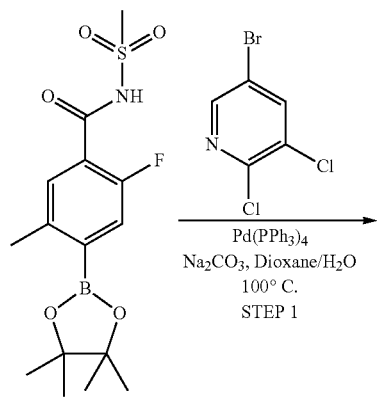

Step 1: 4-(5,6-Dichloropyridin-3-yl)-2-Fluoro-5-Methyl-N-(Methylsulfonyl)Benzamide (Intermediate Y)

To a solution of 2-fluoro-5-methyl-N-(methylsulfonyl)-4-(4,4,5,5-tetramethyl-1,3,2-dioxaborolan-2-yl)benzamide (15.6 g, 43.63 mmol) (prepared as described in Step 1 of Method XXII) in 1,4-dioxane (180 mL) was added 5-bromo-2,3-dichloropyridine (9.0 g, 39.66 mmol) and aqueous 2M aqueous $Na_2CO_3$ solution (99.2 mL, 198.32 mmol). The reaction mixture was degassed with nitrogen for 15 min and $Pd(PPh_3)_4$ (2.3 g, 1.98 mmol) was added. The mixture was again degassed with nitrogen for 15 minutes and then heated at 100° C. for 16 h. The reaction mixture was filtered through CELITE and the CELITE bed was washed with ethyl acetate (150 mL). The filtrate was concentrated under reduced pressure and the crude material was diluted with water (180 mL). The aqueous layer was acidified to pH 3 with 6N aqueous HCl solution and extracted with ethyl acetate (3×200 mL). The combined organic layers were washed with brine solution (150 mL), dried with sodium sulfate and concentrated under reduced pressure to obtain the crude material which was purified by column chromatography (silica gel 60-120 mesh, elution: 0-1% Methanol in DCM) to afford 4-(5,6-dichloropyridin-3-yl)-2-fluoro-5-methyl-N-(methylsulfonyl)benzamide (10.0 g, 66.8%). MS m/z: $[M+1]^+$=377.1. $^1$H NMR (400 MHz, DMSO-$d_6$) δ 12.38 (s, 1H), 8.48 (d, J=2.1 Hz, 1H), 8.32 (d, J=2.2 Hz, 1H), 7.67 (d, J=1.1 Hz, 1H), 7.41 (d, J=10.8 Hz, 1H), 3.39 (s, 3H), 2.28 (s, 3H).

Step 2: 4-(5-Chloro-6-(3,5-Difluorophenyl)-3-Pyridinyl)-2-Fluoro-5-Methyl-N-(Methylsulfonyl) Benzamide

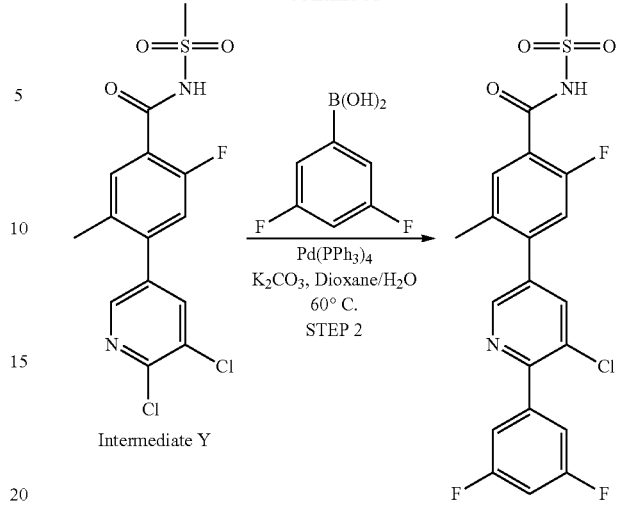

4-(5,6-dichloropyridin-3-yl)-2-fluoro-5-methyl-N-(methylsulfonyl)benzamide (0.100 g, 0.277 mmol), (3,5-difluorophenyl)boronic acid (0.044 g, 0.277 mmol), potassium carbonate (0.115 g, 0.832 mmol), and tetrakis(triphenylphosphine)palladium(0) (0.032 g, 0.028 mmol) were taken up in 1,4-dioxane (2.5 mL) and water (0.833 mL) and the mixture was purged with Argon and then heated at 60° C. overnight. The crude mixture was passed through a plug of CELITE and purified by reverse phase HPLC with 0.1% NH₄OH in ACN and water as the mobile phase to afford 4-(5-chloro-6-(3,5-difluorophenyl)pyridin-3-yl)-2-fluoro-5-methyl-N-(methylsulfonyl)benzamide (0.058 g, 0.128 mmol, 46% yield) as a white solid. MS m/z: [M−1]⁻=453.0.

Method XXIV

Example 836: 4-(5-Bromo-6-(2-Methylpropoxy)-3-Pyridinyl)-2,5-Difluoro-N-(Methylsulfonyl)Benzamide

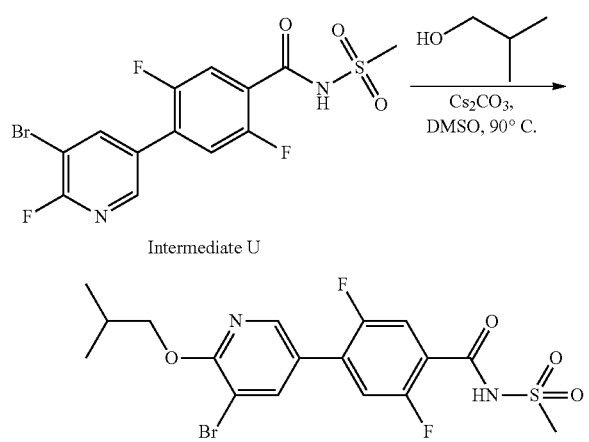

4-(5-bromo-6-fluoropyridin-3-yl)-2,5-difluoro-N-(methylsulfonyl)benzamide (Intermediate U) (0.400 g, 0.978 mmol), 2-methylpropan-1-ol (0.145 g, 1.955 mmol), and cesium carbonate (0.956 g, 2.93 mmol) were combined in a 2 dram resealable vial and DMSO (10 mL) was added. The mixture was heated at 90° C. for 24 h with shaking. After cooling to RT, the mixture was filtered through a CELITE plug, washing with DCM and concentrated. Purification by reverse phase HPLC with 0.1% NH₄OH in ACN and water as the mobile phase to afforded 4-(5-bromo-6-isobutoxy-pyridin-3-yl)-2,5-difluoro-N-(methylsulfonyl)benzamide (0.232 g, 0.501 mmol, 51.2% yield) as a white solid. MS m/z: [M−1]⁻=462.0.

Example 837: 2,5-Difluoro-4-(5'-Fluoro-2'-Methoxy-2-(2-Methylpropoxy)-3,3'-Bipyridin-5-yl)-N-(Methylsulfonyl)Benzamide

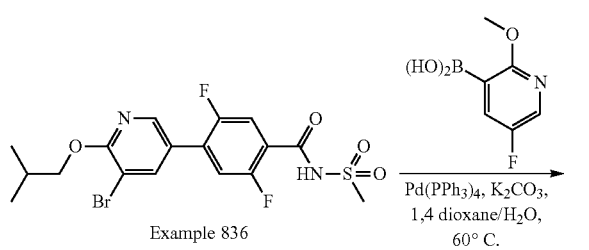

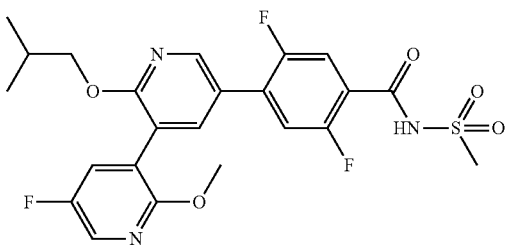

4-(5-bromo-6-isobutoxypyridin-3-yl)-2,5-difluoro-N-(methylsulfonyl)benzamide (Example 836, 0.100 g, 0.216 mmol), (5-fluoro-2-methoxypyridin-3-yl)boronic acid (0.044 g, 0.259 mmol, Aldrich), potassium carbonate (0.089 g, 0.648 mmol), and tetrakis(triphenylphosphine)palladium (0) (0.025 g, 0.022 mmol) were combined in a resealable 2 dram reaction tube and 1,4-dioxane (3 mL) and water (1 mL) were added. The mixture was purged with argon and heated at 60° C. overnight. After filtration through a CELITE plug and concentration, reverse phase HPLC with 0.1% NH₄OH in ACN and water as mobile phase afforded 2,5-difluoro-4-(5'-fluoro-2-isobutoxy-2'-methoxy-[3,3'-bipyridin]-5-yl)-N-(methylsulfonyl)benzamide (0.019 g, 0.037 mmol, 17.3% yield). MS m/z: [M−1]⁻=508.0.

Method XXV: Example 841

4-(6-(3,5-Dichlorophenoxy)-5-Methyl-3-Pyridinyl)-3-Methoxy-N-(Methylsulfonyl)Benzamide

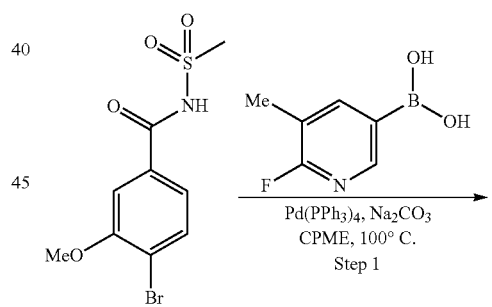

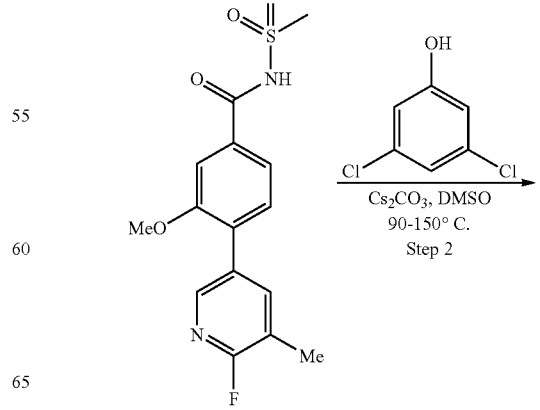

-continued

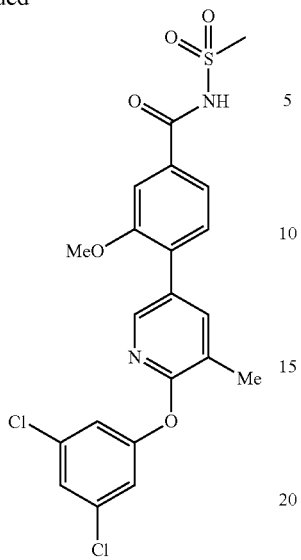

Step 1: 4-(6-Fluoro-5-Methylpyridin-3-yl)-3-Methoxy-N-(Methylsulfonyl)Benzamide A microwave vial was charged with (6-fluoro-5-methylpyridin-3-yl)boronic acid (0.084 g, 0.542 mmol, FSSI), 4-bromo-3-methoxy-N-(methylsulfonyl)benzamide (0.152 g, 0.493 mmol, Method XI, Step 1), and Pd(PPh$_3$)$_4$ (0.040 g, 0.035 mmol). The vial was sealed with septum cap and cyclopentylmethylether (CPME) (1.2 mL) was added followed by an aqueous solution of sodium carbonate (0.789 ml, 1.577 mmol, 2 N). The mixture was sparged with N$_2$ and heated in a microwave at 100° C. for 3 h. The mixture was cooled to rt and the organic and aqueous layers were separated. The aqueous layer was acidified with 6 N HCl (dropwise) and extracted with EtOAc (2×10 mL). The combined EtOAc extracts were concentrated to provide 4-(6-fluoro-5-methylpyridin-3-yl)-3-methoxy-N-(methylsulfonyl)benzamide, which was of sufficient purity for use in the subsequent reaction. MS m/z: [M−1]$^−$=337.2.

Step 2: 4-(6-(3,5-Dichlorophenoxy)-5-Methyl-3-Pyridinyl)-3-Methoxy-N-(Methylsulfonyl)Benzamide A microwave vial was charged with 3,5-dichlorophenol (0.077 g, 0.473 mmol, Aldrich) and cesium carbonate (0.462 g, 1.419 mmol). A solution of 4-(6-fluoro-5-methylpyridin-3-yl)-3-methoxy-N-(methylsulfonyl)benzamide (0.160 g, 0.473 mmol) in DMSO (2 mL) was transferred to the vial. The vial was sealed and the resulting slurry was heated in a microwave at 100° C. for 1 h, the resulting mixture was then heated in a microwave to 150° C. for 1 h, and then heated in the microwave at 155° C. for 1 h. The crude reaction mixture was taken up in minimal MeOH/DMSO and purified by preparative HPLC (Gilson, Phenomenex Luna column, 10 micron, C8(2), 100 Å, 150×30 mm 35-95% CH$_3$CN:H$_2$O (1% TFA modifier) over 15 min). Clean fractions were combined and concentrated to afford 4-(6-(3,5-dichlorophenoxy)-5-methylpyridin-3-yl)-3-methoxy-N-(methylsulfonyl)benzamide (70 mg, 0.145 mmol, 30.8% yield) as a tan amorphous solid. $^1$H NMR (400 MHz, DMSO-d$_6$) δ 12.22 (br. s., 1H), 8.14 (d, J=2.35 Hz, 1H), 7.89-7.96 (m, 1H), 7.68 (d, J=1.57 Hz, 1H), 7.61-7.66 (m, 1H), 7.50 (d, J=7.92 Hz, 1H), 7.48 (t, J=1.86 Hz, 1H), 7.35 (d, J=1.86 Hz, 2H), 3.88 (s, 3H), 3.41 (s, 3H), 2.32-2.39 (m, 3H); MS m/z [M+1]$^+$=480.9.

Method XXVI (Example 819): 4-(5-Chloro-6-((4-Cyanophenoxy)Methyl)-Pyridin-3-yl)-3-Methoxy-N-(Methylsulfonyl)Benzamide

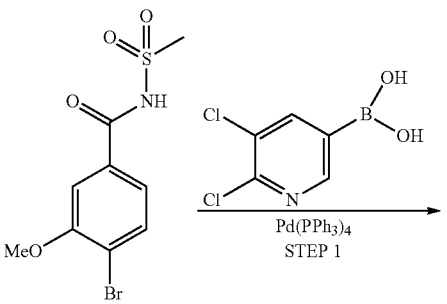

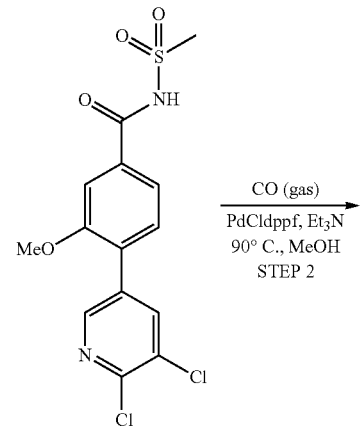

Intermediate Z

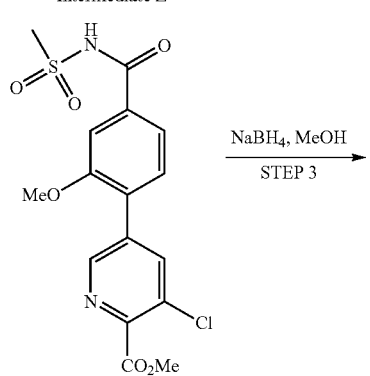

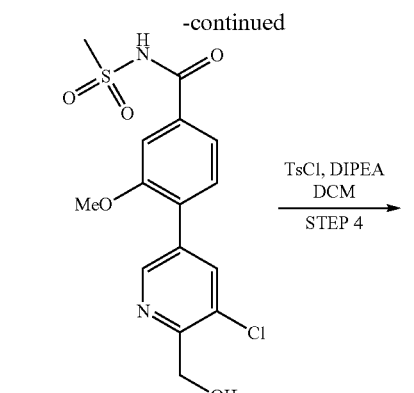

Intermediate AA

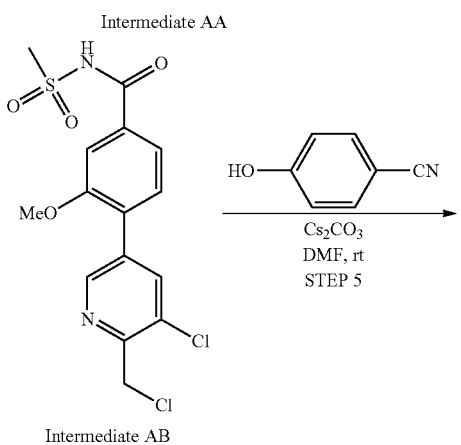

Intermediate AB

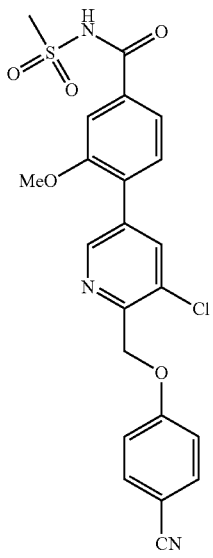

Step 1: 4-(5,6-Dichloropyridin-3-yl)-3-Methoxy-N-(Methyl-Sulfonyl)Benzamide (Intermediate Z)

A microwave vial was charged with (5,6-dichloropyridin-3-yl)boronic acid (3.11 g, 16.23 mmol) and 4-bromo-3-methoxy-N-(methylsulfonyl)benzamide (5 g, 16.23 mmol, synthesized via Step 1 for preparation of Intermediate L, see above Method XI), Pd(Ph$_3$P)$_4$ (1.313 g, 1.136 mmol). The vial was sealed with a septa cap and cyclopentylmethylether (CPME) (40.6 ml) then sodium carbonate (2N aq.) (26.0 ml, 51.9 mmol) were added. The vial was sparged with N$_2$ and heated in a microwave reactor at 100° C. for 3 h. The reaction layers were separated and the aqueous layer was acidified with 6 N HCl and was extracted with EtOAc. The organic layers were combined and concentrated in vacuo. The material was taken forward without further purification. MS m/z [M+1]$^+$=375.0.

Step 2: Methyl 3-Chloro-5-(2-Methoxy-4-((Methyl-sulfonyl)-Carbamoyl)-Phenyl)Picolinate A mixture of 4-(5,6-dichloropyridin-3-yl)-3-methoxy-N-(methylsulfonyl)benzamide (780 mg, 2.079 mmol), triethylamine (1.446 ml, 10.39 mmol) and 1,1'-bis(diphenylphosphino)ferrocene palladium(II)dichloride dichloromethane adduct (170 mg, 0.208 mmol) in methanol was flushed and refilled with CO. The mixture was exposed to 45 psi CO and heated to 50° C. and stirred for 4 h. After cooling to rt, the reaction mixture was filtered and the filtrate was concentrated in vacuo. The material was used without purification. MS m/z [M+1]$^+$=399.0.

Step 3: 4-(5-Chloro-6-(Hydroxymethyl)Pyridin-3-yl)-3-Methoxy-N-(Methylsulfonyl)Benzamide (Intermediate AA)

Sodium borohydride (201 mg, 5.32 mmol) was added slowly into a solution of methyl 3-chloro-5-(2-methoxy-4-((methylsulfonyl)carbamoyl)phenyl)picolinate (530 mg, 1.329 mmol) in MeOH (4430 µl) at rt. The reaction mixture was stirred for 2 days. Another portion of sodium borohydride (201 mg, 5.32 mmol) was added, the reaction mixture was stirred another day. The reaction mixture was concentrated in vacuo. The residue was dissolved in DCM, and was washed with water. The combined water layers were concentrated in vacuo, the crude material was absorbed onto a plug of silica gel and purified by chromatography through a Redi-Sep pre-packed silica gel column (12 g), eluting with a gradient of 0% to 10% MeOH in CH$_2$Cl$_2$, to provide 4-(5-chloro-6-(hydroxymethyl)pyridin-3-yl)-3-methoxy-N-(methylsulfonyl)benzamide (80 mg, 0.216 mmol, 16% yield) as off-white solid. MS m/z [M+1]$^+$=371.0.

Step 4: 4-(5-Chloro-6-(Chloromethyl)Pyridin-3-yl)-3-Methoxy-N-(Methylsulfonyl)Benzamide (Intermediate AB)

To a 50-mL round-bottomed flask was added INTERMEDIATE AA (612 mg, 1.650 mmol) in dichloromethane (8252 µl). Diisopropylethylamine (574 µl, 3.30 mmol) was added to the reaction mixture, followed by p-toluenesulfonyl chloride (378 mg, 1.981 mmol). The reaction was stirred at ambient temperature for 2 days. The crude material was absorbed onto a plug of silica gel and purified by chromatography through a Redi-Sep pre-packed silica gel column (12 g), eluting with a gradient of 0% to 10% MeOH in CH$_2$CL$_2$, to provide 4-(5-chloro-6-(chloromethyl)pyridin-3-yl)-3-methoxy-N-(methylsulfonyl)benzamide (400 mg, 1.028 mmol, 62.3% yield). MS m/z [M+1]$^+$=389.1.

Step 5: 4-(5-Chloro-6-((4-Cyanophenoxy)Methyl) Pyridin-3-yl)-3-Methoxy-N-(Methylsulfonyl)Benzamide To a 1 mL vial was added 4-hydroxybenzonitrile (35.2 mg, 0.295 mmol) and cesium carbonate (84 mg, 0.257 mmol) in 0.2 mL of DMF. The reaction mixture was stirred at rt for 10 min before 4-(5-chloro-6-(chloromethyl)pyridin-3-yl)-3-methoxy-N-(methylsulfonyl)benzamide (50 mg, 0.128 mmol) in 0.5 mL of DMF was added and the reaction was stirred overnight. The crude material was purified by preparative HPLC: PREP LC/MS-2 System Column: XBridge 19×100 mm 12230326114 03 Mobile phase: 0.1% NH₄OH in water/acetonitrile Flow rate: 40 ml/min Inj: 2000 uL Gradient: 10 min 10-40%_LV_NH₃; 10 min 5-30%_LV_NH₃ to provide 4-(5-chloro-6-((4-cyanophenoxy)methyl)pyridin-3-yl)-3-methoxy-N-(methylsulfonyl)benzamide (33 mg, 55% yield). ¹H NMR (500 MHz, DMSO-d₆) δ ppm 3.13 (s, 3H) 3.87 (s, 4H) 5.41 (s, 2H) 7.25 (d, J=8.76 Hz, 2H) 7.50 (d, J=7.92 Hz, 1H) 7.62-7.73 (m, 2H) 7.80 (d, J=8.76 Hz, 2H) 8.16 (d, J=1.64 Hz, 1H) 8.70 (d, J=1.58 Hz, 1H). MS m/z [M+1]⁺=471.8.

Method XXVII: Preparation by Using Intermediate AC

Preparation of Intermediate AA

INTERMEDIATE AA was prepared according to Method XXVI above.

Example 774: 4-(5-Chloro-6-((3,4-Dichlorophenoxy)-Methyl)Pyridin-3-yl)-3-Methoxy-N-(Methylsulfonyl)Benzamide

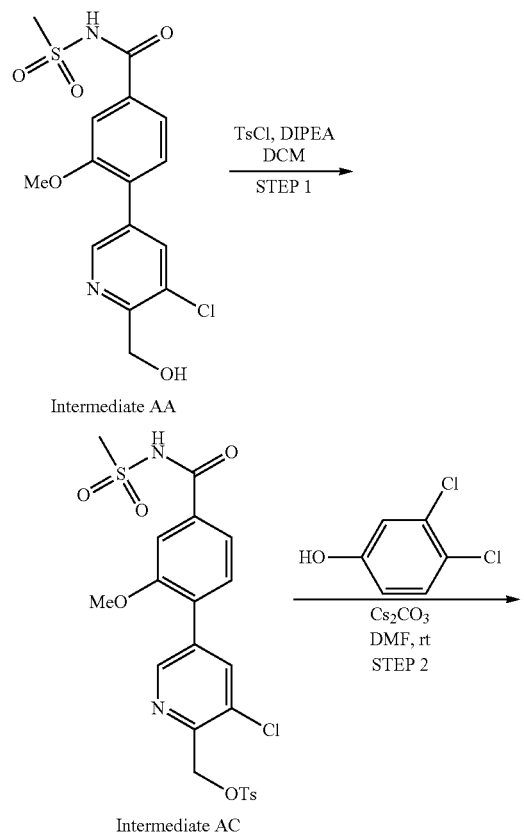

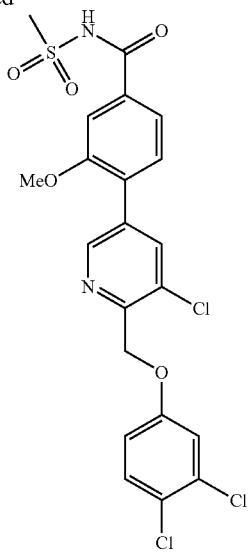

Step 1: (3-Chloro-5-(2-Methoxy-4-((Methylsulfonyl)Carbamoyl)-Phenyl)Pyridin-2-yl)Methyl 4-Methylbenzenesulfonate (Intermediate AC)

To a 5-mL round-bottomed flask was added 4-(5-chloro-6-(hydroxymethyl)pyridin-3-yl)-3-methoxy-N-(methylsulfonyl)benzamide (INTERMEDIATE AA, 50 mg, 0.135 mmol) in dichloromethane (674 µl). Diisopropylethylamine (46.9 µl, 0.270 mmol) was added to the reaction mixture, followed by p-toluenesulfonyl chloride (30.8 mg, 0.162 mmol). The reaction was stirred at ambient temperature for 15 hours. The crude material was absorbed onto a plug of silica gel and purified by chromatography through a Redi-Sep pre-packed silica gel column (12 g), eluting with a gradient of 0% to 10% MeOH in CH₂Cl₂, to provide (3-chloro-5-(2-methoxy-4-((methylsulfonyl)carbamoyl)phenyl)pyridin-2-yl)methyl 4-methylbenzenesulfonate (70 mg, 0.133 mmol, 99% yield). MS m/z [M+1]⁺=389.0.

Step 2: 4-(5-Chloro-6-((3,4-Dichlorophenoxy)Methyl)Pyridin-3-yl)-3-Methoxy-N-(Methylsulfonyl)Benzamide To a 1 mL vial was added 3,4-dichlorophenol (21.73 mg, 0.133 mmol) and cesium carbonate (87 mg, 0.267 mmol) in DMF (667 µl). The reaction mixture was stirred at rt for 10 min before 4-(5-chloro-6-((3,4-dichlorophenoxy)methyl)pyridin-3-yl)-3-methoxy-N-(methylsulfonyl)benzamide was added and the reaction was stirred overnight. The crude material was purified by preparative HPLC using 0.1% NH₄OH in ACN and water as mobile phase to provide 4-(5-chloro-6-((3,4-dichlorophenoxy)methyl)pyridin-3-yl)-3-methoxy-N-(methylsulfonyl)benzamide (33 mg, 36% yield). ¹H NMR (500 MHz, DMSO-d₆) δ ppm 1.14-1.30 (m, 2H), 3.01-3.20 (m, 4H), 3.86 (s, 2H) 5.33 (s, 2H), 7.09 (dd, J=8.93, 2.88 Hz, 2H), 7.41 (d, J=2.83 Hz, 1H), 7.48 (d, J=7.86 Hz, 1H) 7.55 (d, J=8.93 Hz, 1H), 7.62-7.68 (m, 1H), 7.70 (s, 1H), 8.15 (d, J=1.75 Hz, 1H), 8.69 (d, J=1.75 Hz, 1H). MS m/z [M+1]⁺=517.0.

Method XXVIII (Examples 820 and 821): 4-(5-Chloro-6-Isobutoxypyridin-3-yl)-3-(2-Methoxy-4-Methylpyridin-3-yl)-N-(Methylsulfonyl)Benzamide

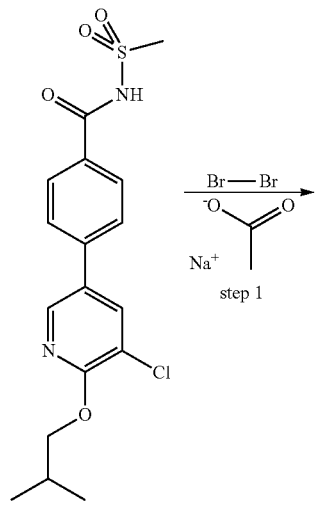

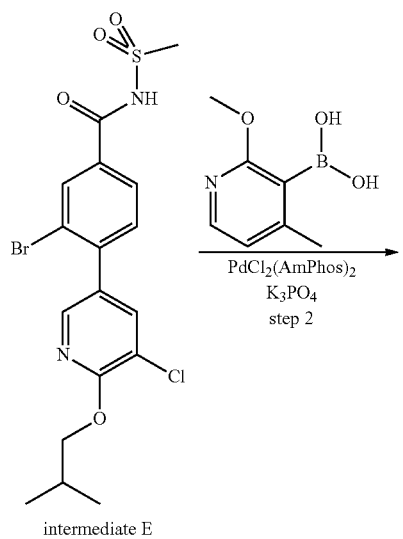

intermediate E

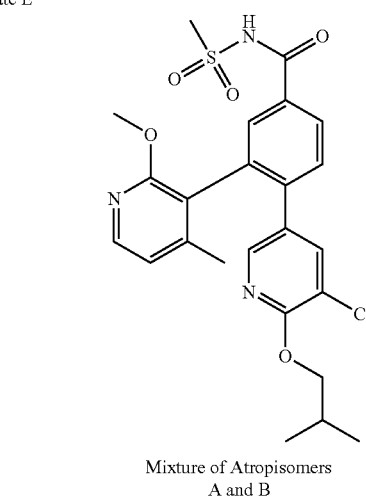

Mixture of Atropisomers A and B

Step 1: 3-Bromo-4-(5-Chloro-6-Isobutoxypyridin-3-yl)-N-(Methylsulfonyl)Benzamide (Intermediate E)

To a ice cold solution of 4-(5-chloro-6-isobutoxypyridin-3-yl)-N-(methylsulfonyl)benzamide (Intermediate E, Prepared according to Method III, 83.76 mg, 0.219 mmol) and sodium acetate (35.9 mg, 0.438 mmol) in DCM (768 µl) was added a solution of $Br_2$ (22.54 µl, 0.438 mmol) in DCM (768 µl) dropwise and warmed up to ambient temperature over 16 h. To the mixture was added sodium acetate (35.9 mg, 0.438 mmol) and $Br_2$ (22.54 µl, 0.438 mmol) and irradiated at 90° C. for 4 h in microwave. The reaction mixture was filtered through a frit and purified by RP-HPLC. Purification was done with 0.1% TFA in ACN and water as mobile phase to obtain 3-bromo-4-(5-chloro-6-isobutoxypyridin-3-yl)-N-(methylsulfonyl)benzamide (26.7 mg, 27% yield); MS (ESI, positive ion) m/z 462.8 (m/z).

Step 2: 4-(5-Chloro-6-Isobutoxypyridin-3-yl)-3-(2-Methoxy-4-Methylpyridin-3-yl)-N-(Methylsulfonyl) Benzamide A vial was charged with 3-bromo-4-(5-chloro-6-isobutoxypyridin-3-yl)-N-(methylsulfonyl)-benzamide (100 mg, 0.217 mmol), 2-methoxy-4-methylpyridin-3-ylboronic acid (36.2 mg, 0.217 mmol), $Pd(AmPhos)_2Cl_2$ (15.33 mg, 0.022 mmol), potassium phosphate (138 mg, 0.650 mmol), dioxane (541 µl), and water (180 µl). The vial was sealed and heated in a Biotage Initiator microwave reactor for 1 h at 100° C. The reaction mixture was filtered and was purified by preparative HPLC using 0.1% $NH_4OH$ in ACN and water as mobile phase. The atropisomers were separated by chiral SFC using Chiralpak AS-H, 25% methanol. Atropisomer A: $^1H$ NMR (500 MHz, DMSO-$d_6$) δ 8.04 (dd, J=1.66, 8.12 Hz, 1H), 8.01 (d, J=5.18 Hz, 1H), 7.82 (s, 1H), 7.80 (d, J=2.08 Hz, 1H), 7.61 (d, J=8.01 Hz, 1H), 7.57 (d, J=2.14 Hz, 1H), 6.88 (d, J=5.29 Hz, 1H), 4.05 (d, J=6.62 Hz, 2H), 3.66 (s, 3H), 3.28 (br. s., 3H), 2.00 (td, J=6.62, 13.25 Hz, 1H), 0.94 (d, J=6.68 Hz, 6H). MS m/z [M+1]$^+$=504.2. Atropisomer B: $^1H$ NMR (500 MHz, DMSO-$d_6$) δ 8.04 (dd, J=1.68, 8.04 Hz, 1H), 8.01 (d, J=5.18 Hz, 1H), 7.78-7.84 (m, 2H), 7.59 (d, J=8.01 Hz, 1H), 7.57 (d, J=2.14 Hz, 1H), 6.88 (d, J=5.18 Hz, 1H), 4.05 (d, J=6.62 Hz, 2H), 3.66 (s, 3H), 3.24 (br. s., 3H), 2.00 (td, J=6.69, 13.33 Hz, 1H), 1.91 (s, 3H), 0.94 (d, J=6.68 Hz, 7H). MS m/z [M+1]$^+$=504.2.

Example 822: 4-(6-(3,5-Dichlorophenoxy)-5-Formylpyridin-3-yl)-3-Methoxy-N-(Methylsulfonyl)Benzamide

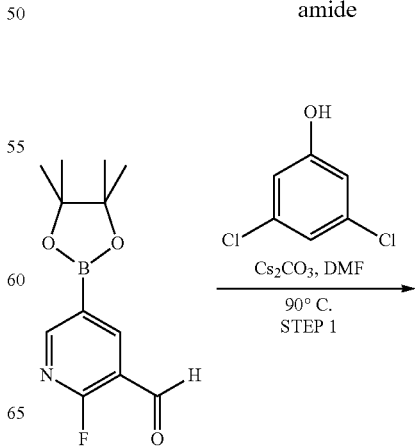

-continued

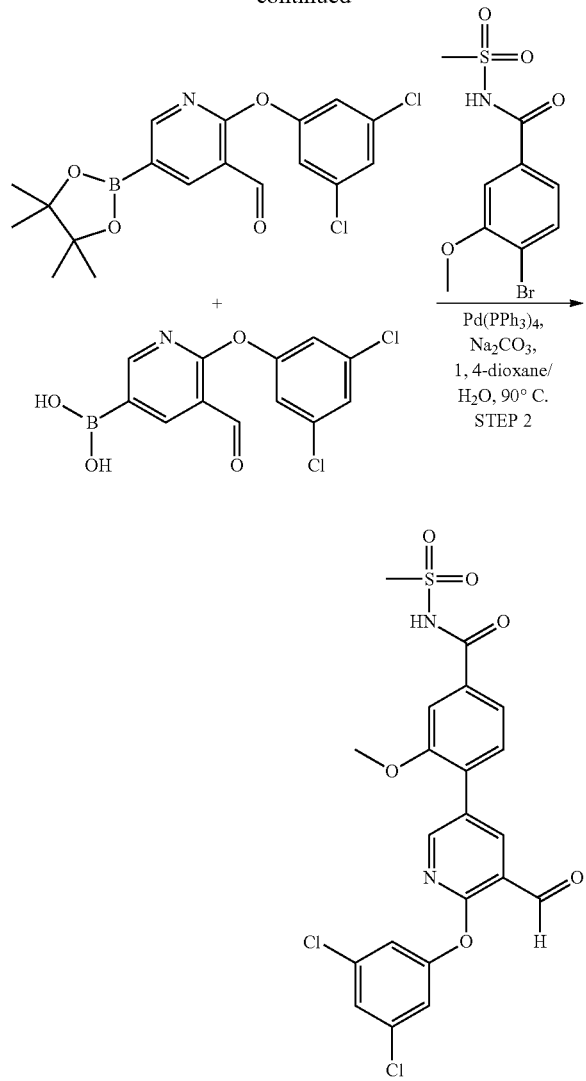

Step 1: 2-(3,5-Dichlorophenoxy)-5-(4,4,5,5-Tetramethyl-1,3,2-Dioxaborolan-2-yl)Nicotinaldehyde & (6-(3,5-Dichlorophenoxy)-5-Formylpyridin-3-yl) Boronic Acid To a vial charged with 2-fluoro-5-(4,4,5,5-tetramethyl-1,3,2-dioxaborolan-2-yl)nicotinaldehyde (Small Molecules, Inc.) (250 mg, 0.996 mmol) was added 3,5-dichlorophenol (162 mg, 0.996 mmol), $Cs_2CO_3$ (973 mg, 2.99 mmol) and DMF (3983 µl). The mixture was heated overnight at 50° C. affording a brown suspension. The mixture was filtered through CELITE washing with MeOH and the filtrate dried under reduced pressure affording a yellow oil, 2-(3,5-dichlorophenoxy)-5-(4,4,5,5-tetramethyl-1,3,2-dioxaborolan-2-yl) nicotinaldehyde (102 mg, 0.259 mmol, 26.0% yield). NMR indicated a mixture of boronate ester and boronic acid and was used without further purification. MS m/z: [M+1]+= 394.2.

Step 2: 4-(6-(3,5-Dichlorophenoxy)-5-Formylpyridin-3-yl)-3-Methoxy-N-(Methylsulfonyl)Benzamide To a flask charged with 4-bromo-3-methoxy-N-(methylsulfonyl)benzamide (see prep of Intermediate L) (296 mg, 0.962 mmol), (6-(3,5-dichlorophenoxy)-5-formylpyridin-3-yl)boronic acid (300 mg, 0.962 mmol), Pd(Ph$_3$P)$_4$ (55.6 mg, 0.048 mmol) was added 1,4-dioxane (3847 µl) and Na$_2$CO$_3$ (2M) (2405 µl, 4.81 mmol) and the mixture heated overnight at 90° C. affording conversion to desired product as the major species with many minor impurities present by LC-MS. The mixture was filtered through CELITE and the filtrate dried under reduced pressure. The crude residue was dissolved in DCM/MeOH and loaded onto CELITE and purified using RP-Isolera with a 55 g Interchim (30 um, C-18) column ramping ACN in H$_2$O (5-95%, 0.1% formic acid) affording product as a light yellow solid 4-(6-(3,5-dichlorophenoxy)-5-formylpyridin-3-yl)-3-methoxy-N-(methylsulfonyl)benzamide (199 mg, 0.402 mmol, 41.8% yield). $^1$H NMR (400 MHz, DMSO-d) 5=12.26 (br. s., 1H), 10.41 (s, 1H), 8.61 (d, J=2.5 Hz, 1H), 8.40 (d, J=2.5 Hz, 1H), 7.71 (d, J=1.6 Hz, 1H), 7.69-7.65 (m, 1H), 7.60-7.56 (m, 2H), 7.56-7.52 (m, 2H), 3.89 (s, 3H), 3.39 (s, 3H). MS m/z: [M+1]+=495.0.

Example 823: 4-(6-(3,5-Dichlorophenoxy)-5-(Difluoromethyl)Pyridin-3-yl)-2-Fluoro-5-Methyl-N-(Methyl Sulfonyl)Benzamide

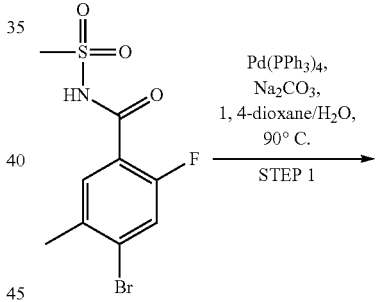

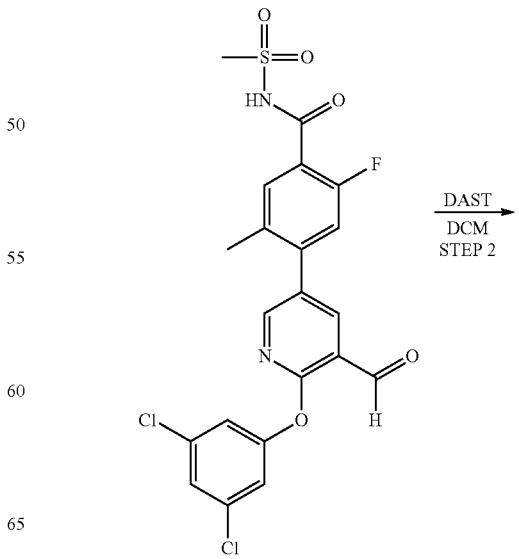

Step 1: 4-(6-(3,5-Dichlorophenoxy)-5-Formylpyridin-3-yl)-2-Fluoro-5-Methyl-N-(Methyl Sulfonyl) Benzamide

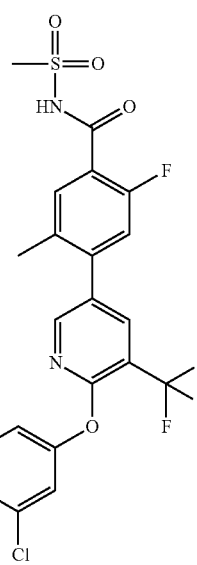

To a flask charged with 4-bromo-2-fluoro-5-methyl-N-(methylsulfonyl)benzamide (See Step 1 of Example 822, 711 mg, 2.292 mmol) and (6-(3,5-dichlorophenoxy)-5-formylpyridin-3-yl)boronic acid (715 mg, 2.292 mmol) was added dioxane (9169 μl) and 2M $Na_2CO_3$ (5731 μl, 11.46 mmol). The resulting mixture was purged with nitrogen for 5 mins prior to the addition of $Pd(PPh_3)_4$ (132 mg, 0.115 mmol). The resulting mixture was stirred overnight at 90° C. overnight. LC-MS of the resulting suspension indicated desired product as the major species. The mixture was cooled in an ice water bath and water followed by the addition 6N HCl was added until the pH was <2. The resulting white precipitate was collected by vacuum filtration and washed with water. The solid obtained was dried under reduced pressure and the solid obtained was over 2.5 g. The solid was triturated with MeOH/DCM (~4:1) and the solid obtained washed with minimal methanol affording product as a white solid (540 mg, 47%). MS m/z: $[M+1]^+$= 497.1.

Step 2: 4-(6-(3,5-Dichlorophenoxy)-5-(Difluoromethyl)Pyridin-3-yl)-3-Methoxy-N-(Methylsulfonyl) Benzamide To a suspension of 4-(6-(3,5-dichlorophenoxy)-5-formylpyridin-3-yl)-2-fluoro-5-methyl-N-(methylsulfonyl)benzamide (150 mg, 0.302 mmol) in DCM (1206 μl) was added (diethylamino)sulfur trifluoride (100 μl, 0.754 mmol). The mixture was shaken at 50° C. for 30 mins affording a yellowish solution. To the mixture was added MeOH (~1 ml) and the solution dried under reduced pressure and purified with a 25 g ultra snap column ramping EtOAc:EtOH (76:24) in heptane (0-100%) affording product with about 75% purity (75 mg) which was repurified with RP-HPLC ramping ACN in $H_2O$ (5-95%, 0.1% $NH_4OH$ throughout) affording product as a white solid 4-(6-(3,5-dichlorophenoxy)-5-(difluoromethyl)pyridin-3-yl)-2-fluoro-5-methyl-N-(methylsulfonyl)benzamide (34 mg, 0.065 mmol, 21.71% yield). MS m/z: $[M-1]^-$=517.0. $^1$H NMR (500 MHz, DMSO-$d_6$) δ ppm 2.23 (s, 3H) 2.98 (s, 3H) 6.95-7.16 (m, 1H) 7.19 (s, 1H) 7.29 (s, 1H) 7.45 (d, J=1.75 Hz, 1H) 7.54 (t, J=1.72 Hz, 1H) 7.62 (d, J=7.46 Hz, 1H) 8.16 (s, 1H) 8.36 (s, 1H).

Examples 839 and 840: 4-(3-Chloro-4'-Methoxy-2'-Methyl-[2,3'-Bipyridin]-5-yl)-2-Fluoro-5-Methyl-N-(Methylsulfonyl)Benzamide and 4-(3-Chloro-4'-Methoxy-2'-Methyl-[2,3'-Bipyridin]-5-yl)-2-Fluoro-5-Methyl-N-(Methyl Sulfonyl)Benzamide

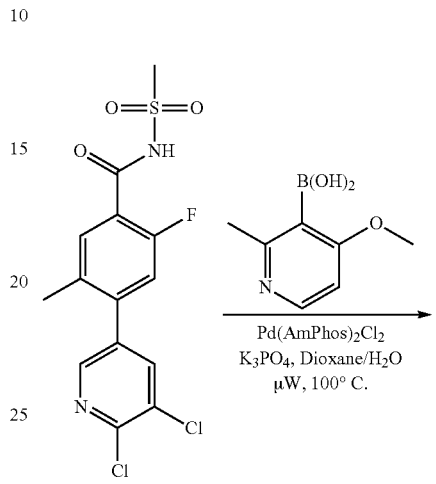

Intermediate Y

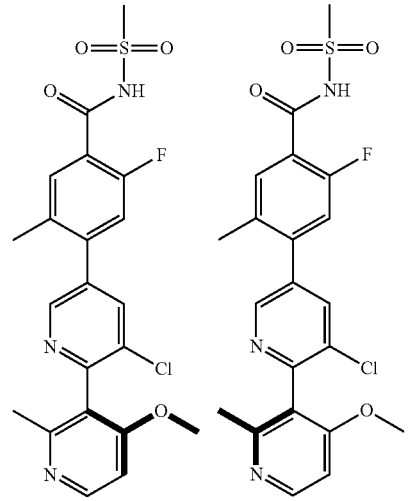

Mixture of atropisomers A & B

A microwave vial was charged with 4-(5,6-dichloropyridin-3-yl)-2-fluoro-5-methyl-N-(methylsulfonyl)benzamide (200 mg, 0.530 mmol), 2-methoxy-4-methylpyridin-3-ylboronic acid (89 mg, 0.530 mmol, Anisyn Inc.), Pd(AmPhos)$_2$Cl2 (37.5 mg, 0.053 mmol), potassium phosphate (338 mg, 1.591 mmol), 1,4-dioxane (1325 μl), and Water (442 μl). The vial as sealed and heated in a Biotage Initiator microwave reactor for 2 h at 100° C. After cooling and concentration, the mixture was purified by reverse phase HPLC with 0.1% TFA in ACN and water as mobile phase, then further purified by SFC: Chiralpak IC, 40% methanol to afford 4-(3-chloro-2'-methoxy-4'-methyl-2,3'-bipyridin-5-yl)-2-fluoro-5-methyl-N-(methylsulfonyl)benzamide (10 mg, >99% ee) and 4-(3-chloro-2'-methoxy-4'-methyl-2,3'-bipyridin-5-yl)-2-fluoro-5-methyl-N-(methylsulfonyl)benzamide (12 mg, >99% ee) as a mixture of A & B atropisomers. Absolute configuration was arbitrarily assigned. MS m/z: $[M-1]^-$= 462.0 for both isomers.

Method XXX (Example 775): 4-(5-Chloro-6-(2,4-Dichloro-6-Methylphenoxy)-3-Pyridinyl)-3-Methyl-N-(Methyl Sulfonyl)Benzamide

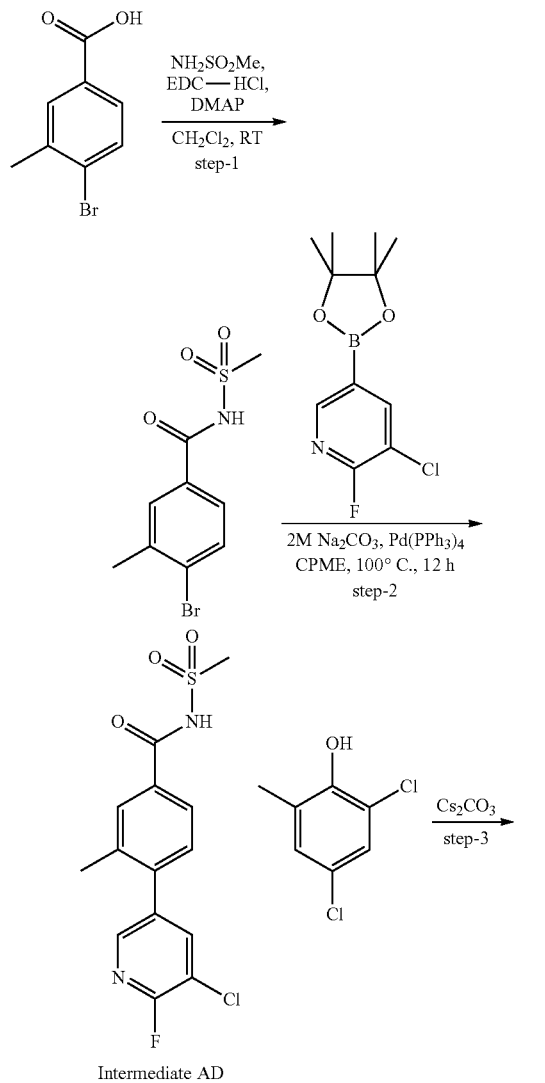

Intermediate AD

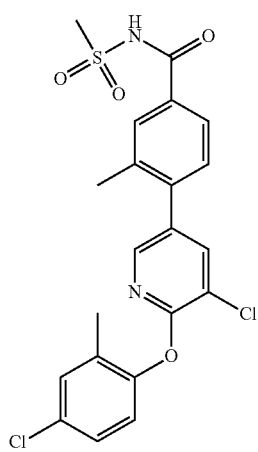

Step 1: 4-Bromo-3-Methyl-N-(Methylsulfonyl)Benzamide

To a solution of 4-bromo-3-methylbenzoic acid (20 g, 93.02 mmol, Combi-blocks) and methane sulfonamide (10.62 g, 111.63 mmol, Apollo) in DCM (1.0 L) was added DMAP (34.24 g, 279.07 mmol) followed by EDC.HCl (35.67 g, 186.05 mmol). The reaction mixture was stirred at RT for 12 h. The crude reaction mixture was diluted with DCM (500 mL) and washed with 1.5 N aqueous HCl (2×500 mL). The organic layer was washed with saturated brine (2×500 mL), dried over anhydrous sodium sulphate and concentrated under reduced pressure. The crude product was dissolved in DCM (50 mL) and hexane (250 mL) was added drop-wise with stirring. The precipitate thus obtained was filtered and dried to afford pure 4-bromo-3-methyl-N-(methylsulfonyl)benzamide (19.0 g, 70%). MS (ESI −ve ion) m/z: [M−1]=292.2. $^1$H NMR (400 MHz, DMSO-$d_6$) δ 12.25 (s, 1H), 7.93 (d, J=1.8 Hz, 1H), 7.74 (d, J=8.3 Hz, 1H), 7.67 (dd, J=8.3, 2.1 Hz, 1H), 2.51 (s, 3H).

Step-2: 4-(5-Chloro-6-Fluoropyridin-3-yl)-3-Methyl-N-(Methylsulfonyl)Benzamide To a solution of 4-bromo-3-methyl-N-(methylsulfonyl)benzamide (19.0 g, 65.04 mmol) in cyclopentyl methyl ether (100 mL) was added 3-chloro-2-fluoro-5-(4,4,5,5-tetramethyl-1,3,2-dioxaborolan-2-yl)pyridine (20.09 g, 78.04 mmol) followed by 2.0 M aqueous $Na_2CO_3$ solution (162.59 mL, 325.18 mmol). The reaction mixture was degassed with nitrogen for 15 min and added $Pd(PPh_3)_4$ (3.76 g, 3.25 mmol). The reaction mixture was again degassed with nitrogen for 15 min and heated at 100° C. for 16 h. After cooling to RT, the mixture was filtered through a CELITE pad, washing with water (50 mL). The filtrate was acidified with 1.5N HCl solution and extracted with ethyl acetate (3×500 mL). The combined organic layer was washed with brine solution (2×500 mL), dried with sodium sulfate and concentrated under reduced pressure to obtain the crude material which was purified by tituration with ethyl acetate and pet ether to afford 4-(5-chloro-6-fluoropyridin-3-yl)-3-methyl-N-(methylsulfonyl)benzamide (7.5 g, 33.70%). MS (ESI −ve ion) m/z: [M−1]=341.2. $^1$H NMR (400 MHz, DMSO-$d_6$) 12.15 (s, 1H), 8.32 (dd, J=9.0, 2.1 Hz, 1H), 8.23 (s, 1H), 7.91 (s, 1H), 7.84 (d, J=8.0 Hz, 1H), 7.37 (d, J=8.0 Hz, 1H), 3.18 (s, 3H), 2.29 (s, 3H).

Step 3: 4-(5-Chloro-6-(2,4-Dichloro-6-Methylphenoxy)-3-Pyridinyl)-3-Methyl-N-(Methylsulfonyl)Benzamide A 2 dram resealable vial was charged with 2,4-dichloro-6-methylphenol (80 mg, 0.452 mmol), cesium carbonate (276 mg, 0.847 mmol), and 4-(5-chloro-6-fluoropyridin-3-yl)-3-methyl-N-(methylsulfonyl)benzamide (97 mg, 0.282 mmol, Intermediate AD) and DMSO (2 mL) was added. The vial was sealed and heated at 90° C. for 40 h. The reaction mixture was then filtered through a frit, washing with DCM and MeOH. After concentration, the crude residue was purified using preparative reverse phase LCMS (0.1% $NH_4OH$ in water/acetonitrile; Flow rate: 40 ml/min; Gradient: 10 min 20-50% $NH_3$) to afford 4-(5-chloro-6-(2,4-dichloro-6-methylphenoxy)-3-pyridinyl)-3-methyl-N-(methylsulfonyl)benzamide. MS m/z (ESI, negative ion) 498.8.

93

Method XXXI: Preparation by Using Intermediate AE

Example 776: 3-Chloro-4-(5-Chloro-6-(2,4-Dichloro-6-Methylphenoxy)-3-Pyridinyl)-N-(Methylsulfonyl)Benzamide

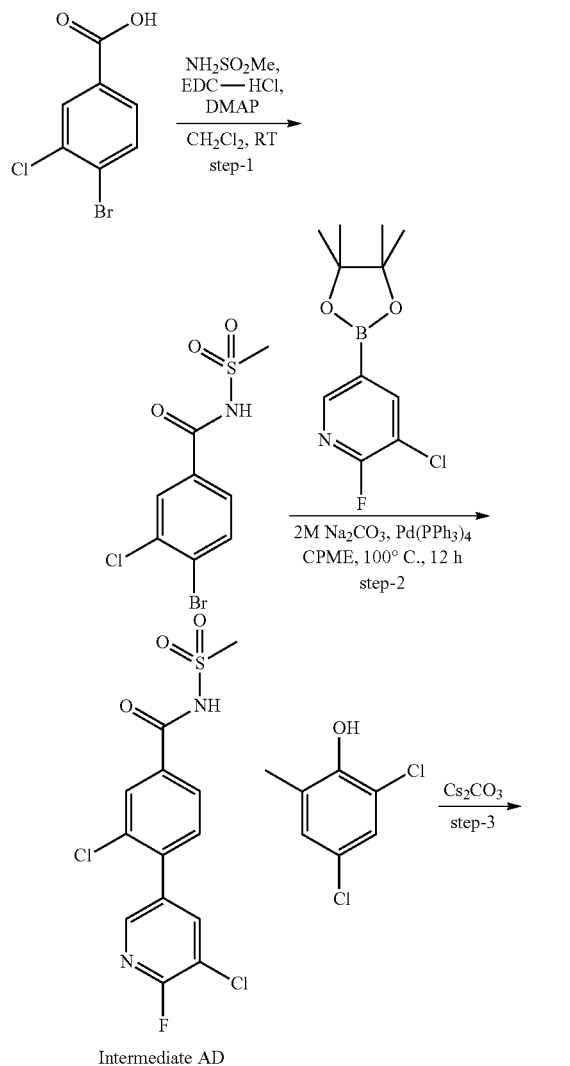

Intermediate AD

94

Step-1: 4-Bromo-3-Chloro-N-(Methylsulfonyl)Benzamide

To a solution of 4-bromo-3-chlorobenzoic acid (20 g, 84.94 mmol, Combi blocks) and methane sulfonamide (9.69 g, 101.93 mmol, Apollo) in DCM (150 mL) was added DMAP (31.26 g, 254.82 mmol) followed by EDC.HCl (32.56 g, 169.88 mmol). The reaction mixture was stirred at RT for 12 h. The crude reaction mixture was diluted with DCM (100 mL) and washed with 1.5 N aqueous HCl (50 mL). The organic layer was washed with saturated brine (50 mL), dried over anhydrous sodium sulphate and concentrated under reduced pressure. The crude product was dissolved in DCM (25 mL) and hexane (50 mL) was added drop-wise with stirring. The precipitate thus obtained was filtered and dried to afford 4-bromo-3-chloro-N-(methylsulfonyl)benzamide (22 g, 82.8%). MS (ESI −ve ion) m/z: [M−1]=310.12. $^1$H NMR (400 MHz, DMSO-$d_6$) δ 12.42 (s, 1H), 8.17 (d, J=2.0 Hz, 1H), 7.96 (d, J=8.4 Hz, 1H), 7.80 (dd, J=8.4, 2.0 Hz, 1H), 3.43 (s, 3H).

Step-2: 3-Chloro-4-(5-Chloro-6-Fluoropyridin-3-yl)-N-(Methylsulfonyl)Benzamide To a solution of 4-bromo-3-chloro-N-(methylsulfonyl)benzamide (22.0 g, 70.38 mmol) in cyclopentyl methyl ether (100 mL) was added 3-chloro-2-fluoro-5-(4,4,5,5-tetramethyl-1,3,2-dioxaborolan-2-yl)pyridine (21.75 g, 84.46 mmol) followed by 2.0 M aqueous $Na_2CO_3$ solution (175.94 mL, 351.93 mmol). The reaction mixture was degassed with nitrogen for 15 min. and Pd(PPh$_3$)$_4$ (4.06 g, 3.51 mmol) was added. The reaction mixture was again degassed with nitrogen for 15 min. and heated at 100° C. for 16 h. The reaction mixture was cooled to RT, then filtered through a CELITE pad, washing with water (50 mL). The filtrate was acidified with 1.5 N HCl to pH ~1 and extracted with ethyl acetate (3×50 mL). The organic layers were combined and washed with brine solution (50 mL), dried with sodium sulfate and concentrated under reduced pressure to obtain the crude material which was purified by stirring with ethyl acetate and pet ether (1:1, 100 mL) for 30 min. The precipitate thus obtained was filtered to afford 3-chloro-4-(5-chloro-6-fluoropyridin-3-yl)-N-(methylsulfonyl)benzamide (Intermediate AE) (17.2 g, 67.3%). MS (ESI −ve ion) m/z: [M−1]= 361.2 $^1$H NMR (400 MHz, DMSO-$d_6$) 12.40 (s, 1H), 8.44 (dd, J=8.9, 2.2 Hz, 1H), 8.34 (dd, J=2.1, 1.2 Hz, 1H), 8.18 (d, J=1.7 Hz, 1H), 8.00 (dd, J=8.0, 1.8 Hz, 1H), 7.70 (d, J=8.0 Hz, 1H), 3.45 (s, 3H).

Step 3: 3-Chloro-4-(5-Chloro-6-(2,4-Dichloro-6-Methylphenoxy)-3-Pyridinyl)-N-(Methylsulfonyl)Benzamide A 2 dram resealable vial was charged with 2,4-dichloro-6-methylphenol (80 mg, 0.452 mmol), cesium carbonate (276 mg, 0.847 mmol), and 3-chloro-4-(5-chloro-6-fluoropyridin-3-yl)-N-(methylsulfonyl)benzamide (103 mg, 0.282 mmol, Intermediate AE) and DMSO (2 mL) was added. The vial was sealed and heated at 90° C. for 40 h. The reaction mixture was then filtered through a frit, washing with DCM and MeOH. After concentration, the crude residue was purified using preparative reverse phase LCMS (0.1% NH$_4$OH in water/acetonitrile; Flow rate: 40 ml/min; Gradient: 10 min 20-50% NH$_3$) to afford 3-chloro-4-(5-chloro-6-(2,4-dichloro-6-methylphenoxy)-3-pyridinyl)-N-(methylsulfonyl)benzamide. MS m/z (ESI, negative ion) 518.8/520.8.

Example 777: 3-Chloro-4-(5-Chloro-6-(3,5-Dichlorophenoxy)-3-Pyridinyl)-N-(Methylsulfonyl)Benzamide

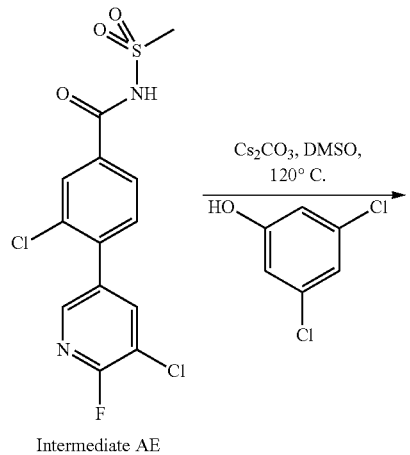

Intermediate AE

A vial was charged with 3-chloro-4-(5-chloro-6-(3,5-dichlorophenoxy)pyridine-3-yl)-N-(methylsufonyl)benzamide (INTERMEDIATE AE) (100 mg, 0.275 mmol), cesium carbonate (224 mg, 0.688 mmol), 3,5-dichlorophenol (67 mg, 0.413 mmol) and 1.5 mL DMSO. The vial was sealed, and the reaction mixture was heated at 120° C. for 15 h. The mixture was filtered through a frit, which was washed with MeOH and DCM. The filtrate was concentrated, and the crude material was purified by reverse phase chromatography, PREP LC/MS-2 System Column: XBridge Prep Shield RP18 19×100 mm 104|131331GG 03 Mobile phase: 0.1% NH$_4$OH in water/acetonitrile Flow rate: 40 ml/min Inj: 2500 μL Gradient: 10 min, 20-50%_LV_NH$_3$. 3-chloro-4-(5-chloro-6-(3,5-dichlorophenoxy)-3-pyridinyl)-N-(methylsulfonyl)benzamide was isolated as an off-white solid (100 mg, 72% yield). MS (ESI, MH+) m/z 507.0; $^1$H NMR (500 MHz, DMSO-d$_6$) δ ppm 2.87 (s, 3H) 7.45-7.50 (m, 3H) 7.53 (t, J=7.49 Hz, 1H) 7.94 (dd, J=7.91, 1.36 Hz, 1H) 8.05 (d, J=1.23 Hz, 1H) 8.21 (d, J=2.08 Hz, 1H) 8.25 (d, J=2.01 Hz, 1H).

Method XXXII: (Example 779): 4-(5-Chloro-6-(3-Chloro-2-Methylphenoxy)-3-Pyridinyl)-5-Ethoxy-2-Fluoro-N-(Methylsulfonyl)Benzamide

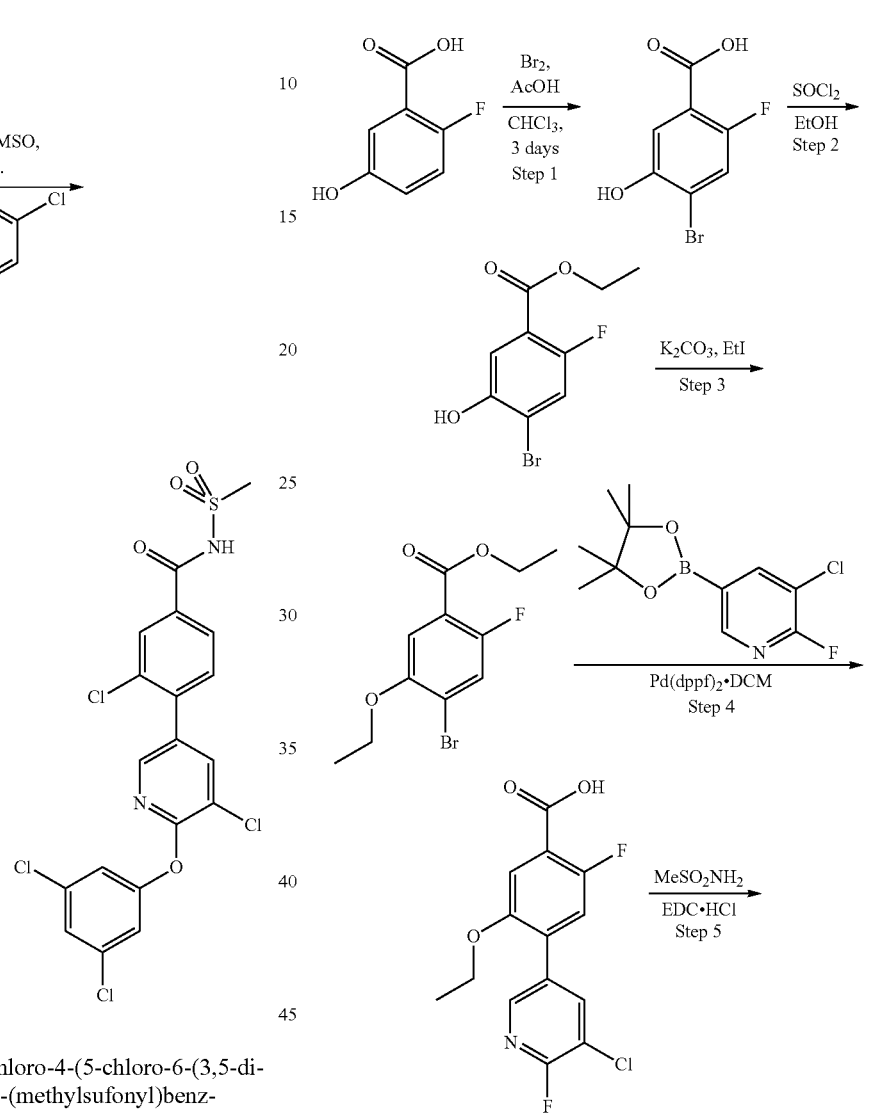

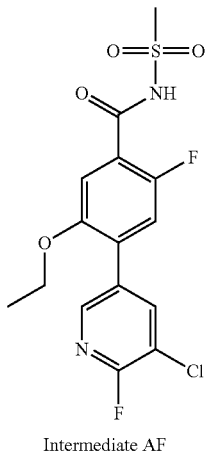

Intermediate AF

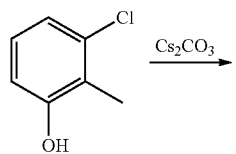

-continued

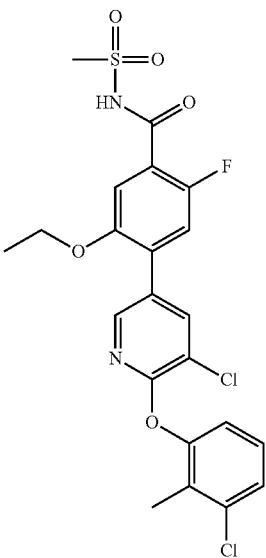 [SMILES: CCOc1cc(C(=O)NS(C)(=O)=O)c(F)cc1-c1cnc(Oc2cccc(Cl)c2C)c(Cl)c1]

Step 1: 4-Bromo-2-Fluoro-5-Hydroxybenzoic Acid

To a solution 2-fluoro-5-hydroxybenzoic acid (Alfa Aesar) (100 g, 644.3 mmol) in AcOH (800 mL) was added $Br_2$ (49.65 mL, 966 mmol) in AcOH (200 mL) at 0° C. drop wise and the mixture was stirred at RT for 24 h. The reaction mixture was quenched with sat. sodium sulfite solution until the reaction mixture was colorless and then was extracted with EtOAc (3×500 mL). The combined organic layers were washed with brine solution (2×500 mL), dried over sodium sulphate and evaporated under reduced pressure. The crude product was triturated with DCM (500 mL) and hexane to afford 4-bromo-2-fluoro-5-hydroxybenzoic acid (85 g, 56% yield) as an off white solid. MS (ESI negative ion) m/z: 234.0 (M−1). $^1$H NMR (300 MHz, DMSO-$d_6$) 10.62 (s, 1H), 7.53 (dd, J=10.0, 2.9 Hz, 1H), 7.39 (dd, J=6.7, 1.5 Hz, 1H).

Step 2: Ethyl 4-Bromo-2-Fluoro-5-Hydroxybenzoate

To a solution of 4-bromo-2-fluoro-5-hydroxybenzoic acid (25 g, 106.4 mmol) in ethanol (250 mL) was added thionyl chloride (15.5 mL, 212.8 mmol) at 0° C. drop wise and stirred at RT for 16 h. The solvent was evaporated under reduced pressure. To the obtained residue was added EtOAc (250 mL) and washed with saturated sodium bicarbonate solution (2×100 mL). The organic layer was dried over sodium sulphate and evaporated under reduced pressure to afford pure ethyl 4-bromo-2-fluoro-5-hydroxybenzoate (11 g, 39%) as an off-white solid. MS (ESI negative ion) m/z: 261.0 (M−2). $^1$H NMR (400 MHz, DMSO-$d_6$) δ 10.67 (s, 1H), 7.62 (d, J=10.1 Hz, 1H), 7.42 (d, J=6.5 Hz, 1H), 4.30 (q, J=7.1 Hz, 2H), 1.30 (t, J=7.1 Hz, 3H).

Step 3: Ethyl 4-Bromo-5-Ethoxy-2-Fluorobenzoate

To a solution of ethyl 4-bromo-2-fluoro-5-hydroxybenzoate (40 g, 152.1 mmol) in DMF (400 mL) was added potassium carbonate (63 g, 456 mmol) and ethyl iodide (24.3 mL, 304.2 mmol) and stirred at room temperature for 16 h. DMF was evaporated from the reaction mixture. To the obtained residue was added water (200 mL) and extracted with EtOAc (2×200 mL). The combined organic layers were washed with water (100 mL), dried over sodium sulphate and evaporated under reduced pressure to afford pure ethyl 4-bromo-5-ethoxy-2-fluorobenzoate (43 g, 95%) as an off-white solid. $^1$H NMR (400 MHz, Chloroform-d) δ 7.49-7.34 (m, 2H), 4.41 (q, J=7.2 Hz, 2H), 4.13 (q, J=7.0 Hz, 2H), 1.49 (t, J=7.0 Hz, 3H), 1.41 (t, J=7.1 Hz, 3H).

Step 4: 4-(5-Chloro-6-Fluoropyridin-3-yl)-5-Ethoxy-2-Fluorobenzoic Acid

To a solution of ethyl 4-bromo-5-ethoxy-2-fluorobenzoate (43 g, 148 mmol) in 1,4-dioxane (430 mL) was added 2-chloro-5-(4,4,5,5-tetramethyl-1,3,2-dioxaborolan-2-yl)-3-(trifluoromethyl)pyridine (41.8 g, 162.5 mmol) and 2M sodium carbonate solution (332.5 mL) at RT. Then the reaction mixture was degassed with $N_2$ gas for about 30 min. Then $PdCl_2$(dppf)DCM (6 g, 7.4 mmol) was added to the reaction mixture and again degassed with $N_2$ gas for about 30 min. Then the reaction mixture was heated to 90° C. for 16 h. The reaction mixture was cooled to RT, filtered through a CELITE pad and washed with EtOAc (400 mL). The filtrate was evaporated under reduced pressure. To the obtained residue was added water (200 mL) and extracted with EtOAc (2×200 mL). The combined organic layers were dried over sodium sulphate and evaporated under reduced pressure. The crude material was purified by flash column chromatography (silica gel, 230-400 mesh) using 5-10% EtOAc in petroleum ether gradient to afford pure ethyl 4-(5-chloro-6-fluoropyridin-3-yl)-5-ethoxy-2-fluorobenzoate (6.5 g, 13%) as an off white solid. The aqueous layer was acidified with 1.5N HCl and the precipitated solids were filtered and dried under vacuum to afford pure 4-(5-chloro-6-fluoropyridin-3-yl)-5-ethoxy-2-fluorobenzoic acid (17 g, 37%) as an off white solid. MS (ESI negative ion) m/z: 312.0 (M−1). $^1$H NMR (400 MHz, DMSO-$d_6$) δ 13.45 (s, 1H), 8.44 (d, J=7.2 Hz, 2H), 7.60-7.43 (m, 2H), 4.12 (q, J=6.9 Hz, 2H), 1.28 (t, J=6.9 Hz, 3H).

Step 5: 4-(5-Chloro-6-Fluoropyridin-3-Yl)-5-Ethoxy-2-Fluoro-N-(Methylsulfonyl)Benzamide To a solution of 4-(5-chloro-6-fluoropyridin-3-yl)-2-fluoro-5-ethoxybenzoic acid (4.0 g, 12.75 mmol) and methane sulfonamide (1.45 g, 15.3 mmol) in DCM (80 mL) under $N_2$ atm. was added DMAP (4.6 g, 38.25 mmol). Then EDC.HCl (4.9 g, 25.5 mmol) was added to the reaction mixture at RT and stirred for 16 h. The reaction mixture was quenched with 1.5N HCl (50 mL) and extracted with DCM (3×50 mL). The combined organic layers were washed with brine solution (2×50 mL), dried over sodium sulphate and evaporated under reduced pressure to afford a brown solid. The obtained brown solid was triturated with DCM (5 mL) and petroleum ether (20 mL) to afford Intermediate AF (1.6 g, 32%) as an off-white solid. MS (ESI negative ion) m/z: 389.0 (M−1). $^1$H NMR (400 MHz, DMSO-$d_6$) δ 12.60-12.15 (s, 1H), 8.44 (d, J=7.9 Hz, 2H), 7.56 (d, J=10.5 Hz, 1H), 7.36 (d, J=5.7 Hz, 1H), 4.14 (q, J=6.9 Hz, 2H), 3.39 (s, 3H), 1.29 (t, J=6.9 Hz, 3H).

Step 6: 4-(5-Chloro-6-(3-Chloro-2-Methylphenoxy)-3-Pyridinyl)-5-Ethoxy-2-Fluoro-N-(Methylsulfonyl)Benzamide To a microwave vessel charged with 3-chloro-2-methylphenol (0.088 g, 0.614 mmol) was added 4-(5-chloro-6-fluoropyridin-3-yl)-5-ethoxy-2-fluoro-N-(methylsulfonyl)benzamide (0.080 g, 0.205 mmol) and DMSO (2 mL), then cesium carbonate (0.267 g, 0.819 mmol) was added. The tube was sealed and heated at 150° C. in a microwave reactor for 2 h. The reaction was filtered though a frit, washing with DCM, and the crude reaction mixture was purified via reverse phase chromatography (PREP LC/MS-2 System Column: XBridge Prep Shield RP18 19×100 mm 104|131331GG 03 Mobile phase: 0.1% NH$_4$OH in water/acetonitrile Flow rate: 40 ml/min Inj: 2800 uL Gradient: 10 min 10-40%_LV_NH$_3$) to give 4-(5-chloro-6-(3-chloro-2-methylphenoxy)-3-pyridinyl)-5-ethoxy-2-fluoro-N-(methylsulfonyl)benzamide (50 mg). MS (ESI negative ion) m/z: 511.0 (M−1).

Method XXXIII: Preparation by Using Intermediate AG

Example 780: 4-(5-Chloro-6-(3-Chloro-2-Methylphenoxy)-3-Pyridinyl)-5-(Difluoromethoxy)-2-Fluoro-N-(Methylsulfonyl)Benzamide

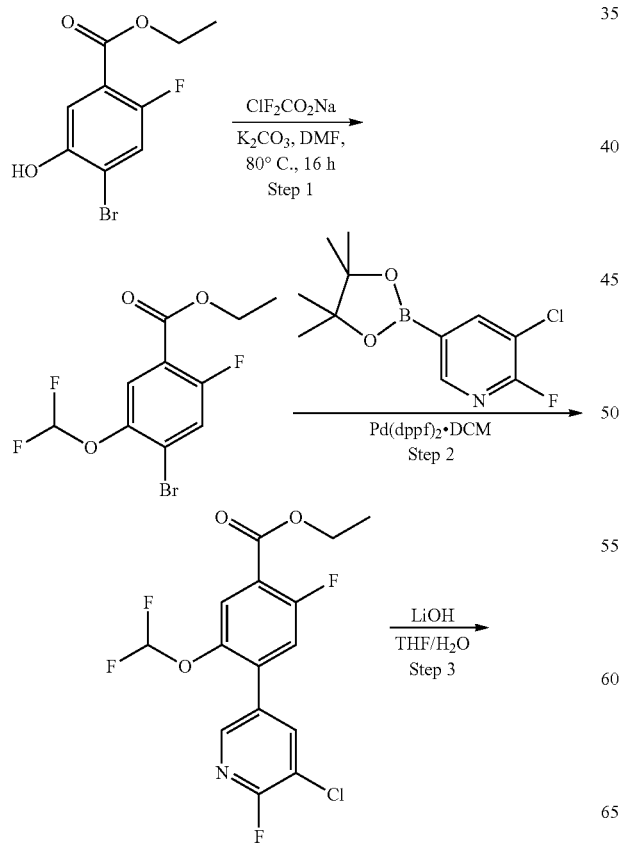

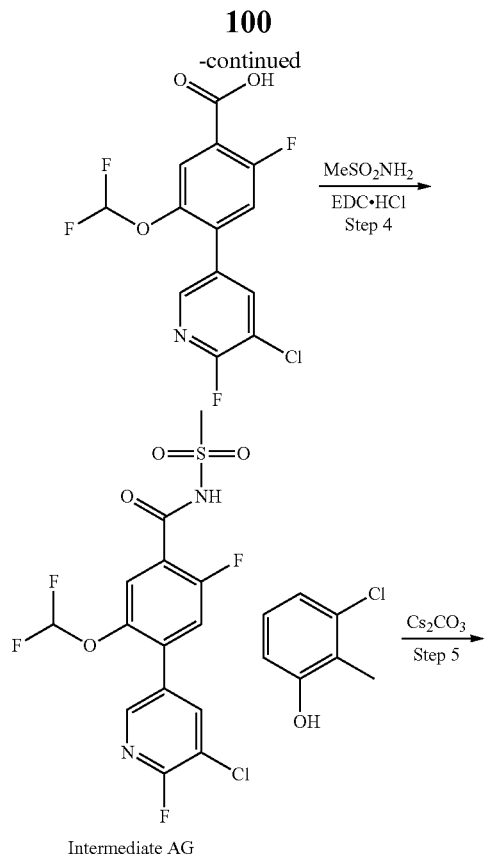

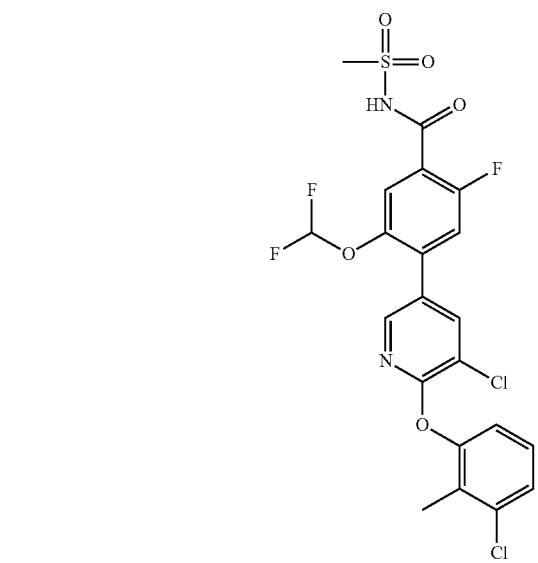 [SMILES: Cc1c(Cl)cccc1Oc1ncc(-c2cc(F)c(C(=O)NS(C)(=O)=O)cc2OC(F)F)cc1Cl]

Step 1: Ethyl 4-Bromo-5-(Difluoromethoxy)-2-Fluorobenzoate

To a solution of ethyl 4-bromo-2-fluoro-5-hydroxybenzoate (10 g, 38 mmol, see Intermediate AF prep, Step 2 above) in DMF (100 mL) was added potassium carbonate (15.76 g, 114 mmol), sodium difluorochloro acetate (8.69 g, 57 mmol) and stirred at 70° C. for 16 h. DMF was evaporated under reduced pressure and the residue was added water (100 mL) and extracted with EtOAc (2×100 mL). The combined organic layers were washed with water (100 mL), dried over sodium sulphate and evaporated under reduced pressure to afford pure ethyl 4-bromo-5-(difluoromethoxy)-

2-fluorobenzoate (8 g, 67%) as an off white solid. ¹H NMR (400 MHz, Chloroform-d) δ 7.82 (dq, J=6.5, 1.0 Hz, 1H), 7.51-7.44 (m, 1H), 6.77-6.37 (m, 1H), 4.50-4.39 (m, 2H), 1.42 (tdd, J=7.1, 2.2, 1.0 Hz, 3H).

Step 2: Ethyl 4-(5-Chloro-6-Fluoropyridin-3-yl)-5-(Difluoromethoxy)-2-Fluorobenzoate To a solution of ethyl 4-bromo-5-(difluoromethoxy)-2-fluorobenzoate (7.5 g, 23.96 mmol) in 1,4-dioxane (75 mL) was added 2-chloro-5-(4,4,5,5-tetramethyl-1,3,2-dioxaborolan-2-yl)-3-(trifluoromethyl)pyridine (6.8 g, 26.36 mmol) and saturated sodium carbonate solution (34.2 mL). The reaction mixture was degassed with Ar for about 20 min. Then PdCl$_2$(dppf)DCM (0.98 g, 1.2 mmol) was added to the reaction mixture and again it was degassed with Ar for about 20 min. Then the reaction mixture was heated to 70° C. for 1 h. After cooling to RT, filtration through a CELITE pad, washing with EtOAc (100 mL) was followed by evaporation under reduced pressure to obtained the crude residue. To this was added water (100 mL) and the mixture was extracted with EtOAc (2×100 mL). The combined organic layers were dried over sodium sulphate and evaporated under reduced pressure to afford the crude product. The crude was purified by flash column chromatography (silica gel, 230-400 mesh) using 5-10% EtOAc in petroleum ether gradient to give pure 4-(5-chloro-6-fluoropyridin-3-yl)-5-(difluoromethoxy)-2-fluorobenzoate (4.4 g, 51%) as an off-white solid. ¹H NMR (400 MHz, Chloroform-d) δ 8.24 (dd, J=2.2, 1.2 Hz, 1H), 8.00 (ddd, J=8.5, 2.2, 0.9 Hz, 1H), 7.88 (dd, J=5.9, 1.0 Hz, 1H), 7.32-7.13 (m, 1H), 6.48 (td, J=72.3, 1.1 Hz, 1H), 4.46 (qd, J=7.3, 1.1 Hz, 2H), 1.45 (td, J=7.3, 1.0 Hz, 3H).

Step 3: 4-(5-Chloro-6-Fluoropyridin-3-yl)-5-(Difluoromethoxy)-2-Fluorobenzoic Acid To a solution of ethyl 4-(5-chloro-6-fluoropyridin-3-yl)-5-(difluoromethoxy)-2-fluorobenzoate (4.9 g, 13.5 mmol) in THF:water (58.8 mL, 6:1 ratio, 12 vol.) was added LiOH.H$_2$O (1.7 g, 41 mmol) at RT and the mixture was stirred for 16 h. THF was removed under reduced pressure, and the residue was diluted with cold water (30 mL) and the pH was adjusted to ~3 using 1.5 N aqueous HCl solution. The crude product was extracted with ethyl acetate (3×20 mL). The combined organic layer was washed with brine (20 mL), dried over anhydrous Na$_2$SO$_4$, filtered and evaporated to afford 4-(5-chloro-6-fluoropyridin-3-yl)-5-(difluoromethoxy)-2-fluorobenzoic acid (3.3 g, 73%) as an off white solid. MS (ESI negative ion) m/z: 334 (M−1). ¹H NMR (400 MHz, DMSO-d$_6$) 13.74 (s, 1H), 8.44 (dd, J=8.8, 2.2 Hz, 1H), 8.39 (dd, J=2.2, 1.2 Hz, 1H), 7.75 (d, J=6.0 Hz, 1H), 7.68 (d, J=10.8 Hz, 1H), 7.24 (t, J=73.1 Hz, 1H).

Step 4: 4-(5-Chloro-6-Fluoropyridin-3-yl)-5-(Difluoromethoxy)-2-Fluoro-N-(Methylsulfonyl)Benzamide To a solution of 4-(5-chloro-6-fluoropyridin-3-yl)-5-(difluoromethoxy)-2-fluorobenzoic acid (3.3 g, 9.85 mmol) and methane sulfonamide (1.12 g, 11.8 mmol) in DCM (66 mL) under N$_2$ atm. was added DMAP (3.6 g, 29.55 mmol). Then EDC.HCl (3.76 g, 19.7 mmol) was added to the reaction mixture and it was stirred at RT for 16 h. The reaction mixture was quenched with 1.5N HCl (50 mL) and extracted with DCM (3×50 mL). The combined organic layers were washed with brine solution (2×50 mL), dried over sodium sulphate and evaporated under reduced pressure to afford the crude product, which was triturated with DCM (5 mL) and petroleum ether (20 mL) to afford pure compound 4-(5-chloro-6-fluoropyridin-3-yl)-5-(difluoromethoxy)-2-fluoro-N-(methylsulfonyl)benzamide (Intermediate AG) (2.1 g, 52%) as an off white solid. MS (ESI negative ion) m/z: 411.0 (M−1). ¹H NMR (400 MHz, DMSO-d$_6$) δ 12.54 (bs, 1H), 8.45 (dd, J=8.8, 2.1 Hz, 1H), 8.41-8.38 (m, 1H), 7.73 (d, J=10.4 Hz, 1H), 7.65 (d, J=5.7 Hz, 1H), 7.22 (t, J=73.1 Hz, 1H), 3.40 (s, 3H).

Step 5: 4-(5-Chloro-6-(3-Chloro-2-Methylphenoxy)-3-Pyridinyl)-5-(Difluoromethoxy)-2-Fluoro-N-(Methylsulfonyl)Benzamide To a microwave vessel charged with 3-chloro-2-methylphenol (0.088 g, 0.581 mmol) was added 4-(5-chloro-6-fluoropyridin-3-yl)-5-(difluoromethoxy)-2-fluoro-N-(methylsulfonyl)benzamide (0.080 g, 0.194 mmol) and DMSO (2 mL), then cesium carbonate (0.253 g, 0.775 mmol) was added. The tube was sealed and heated at 150° C. in a microwave reactor for 2 h. The reaction was filtered though a frit, washing with DCM, and the crude reaction mixture was purified via reverse phase chromatography (PREP LC/MS-2 System Column: XBridge Prep Shield RP18 19×100 mm 104l131331GG 03 Mobile phase: 0.1% NH$_4$OH in water/acetonitrile Flow rate: 40 ml/min Inj: 2800 uL Gradient: 10 min 10-40%_LV_NH3) to give 4-(5-chloro-6-(3-chloro-2-methylphenoxy)-3-pyridinyl)-5-(difluoromethoxy)-2-fluoro-N-(methylsulfonyl)benzamide (60 mg). MS (ESI negative ion) m/z: 535.0/537.0 (M−1).

Example 782: 4-(5-Chloro-6-(2,4-Dichloro-6-Methylphenoxy)-3-Pyridinyl)-5-(Difluoromethoxy)-2-Fluoro-N-(Methylsulfonyl)Benzamide

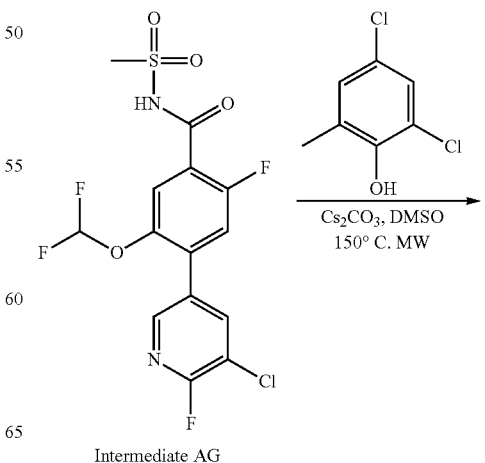

Intermediate AG

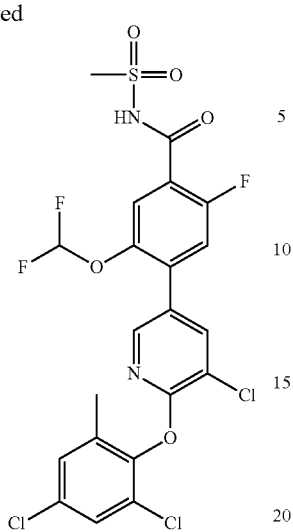

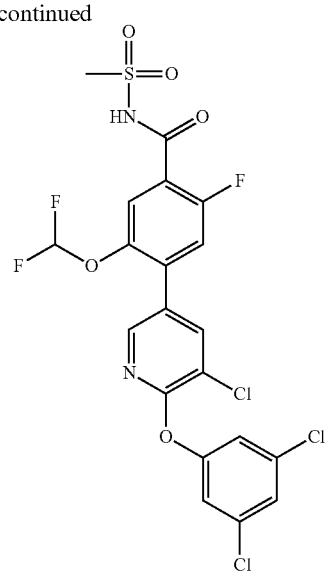

To a microwave vessel charged with 2,4-dichloro-6-methylphenol (103 mg, 0.581 mmol) was added 4-(5-chloro-6-fluoropyridin-3-yl)-5-(difluoromethoxy)-2-fluoro-N-(methylsulfonyl)-benzamide (INTERMEDIATE AG) (0.080 g, 0.194 mmol) and DMSO (2 mL). Then cesium carbonate (0.253 g, 0.775 mmol) was added. The tube was sealed and heated at 150° C. in the microwave for 2 h. The crude reaction mixture was then filtered through a frit and washed with DCM then MeOH. After concentration, the crude residue was purified using preparative reverse phase LCMS (0.1% NH$_4$OH in water/acetonitrile; Flow rate: 40 ml/min; Gradient: 10 min 20-50% NH$_3$) to afford 4-(5-chloro-6-(2,4-dichloro-6-methylphenoxy)-3-pyridinyl)-5-(difluoromethoxy)-2-fluoro-N-(methylsulfonyl)benzamide (50.6 mg). LC-MS m/z (ESI, positive ion) 569.0. $^1$H NMR (500 MHz, DMSO-d$_6$) δ 8.29 (d, J=2.01 Hz, 1H), 8.17 (d, J=1.95 Hz, 1H), 7.63 (d, J=2.14 Hz, 1H), 7.58 (d, J=6.10 Hz, 1H), 7.49 (d, J=1.82 Hz, 1H), 7.44 (d, J=10.51 Hz, 1H), 7.01-7.33 (m, 1H), 2.93 (s, 3H), 2.14 (s, 3H).

Example 784: 4-(5-Chloro-6-(3,5-Dichlorophenoxy)-3-Pyridinyl)-5-(Difluoromethoxy)-2-Fluoro-N-(Methylsulfonyl)Benzamide To a microwave vessel charged with 3,5-dichlorophenol (95 mg, 0.581 mmol) was added 4-(5-chloro-6-fluoropyridin-3-yl)-5-(difluoromethoxy)-2-fluoro-N-(methylsulfonyl)benzamide (Intermediate AG) (0.080 g, 0.194 mmol) and DMSO (2 mL). Then cesium carbonate (0.253 g, 0.775 mmol) was added. The tube was sealed and heated at 150° C. in the microwave for 2 h. The crude reaction mixture was then filtered through a frit and washed with DCM then MeOH. After concentration, the crude residue was purified using preparative reverse phase LCMS (0.1% NH$_4$OH in water/acetonitrile; Flow rate: 40 ml/min; Gradient: 10 min 20-50% NH$_3$) to afford 4-(5-chloro-6-(3,5-dichlorophenoxy)-3-pyridinyl)-5-(difluoromethoxy)-2-fluoro-N-(methylsulfonyl)benzamide (58 mg). LC-MS m/z (ESI, positive ion) 556.0. 1H NMR (500 MHz, DMSO-d$_6$) δ 8.28 (dd, J=2.01, 9.02 Hz, 2H), 7.60 (d, J=6.29 Hz, 1H), 7.54 (t, J=14.59 Hz, 1H), 7.39-7.51 (m, 3H), 7.03-7.35 (m, 1H), 3.01 (s, 3H).

Method XXXIV: Preparation by Using Intermediates U and AH

Preparation of Intermediate U: 4-(5-Bromo-6-Fluoropyridin-3-yl)-2,5-Difluoro-N-(Methylsulfonyl)Benzamide

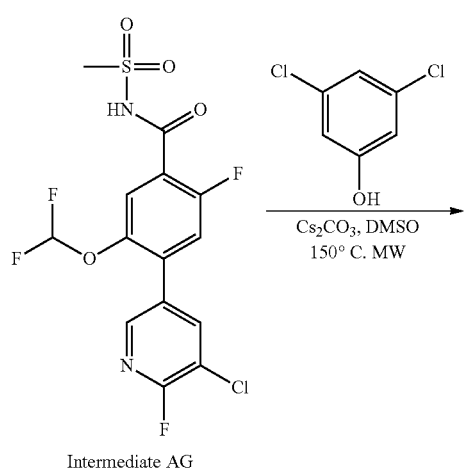

Intermediate AG

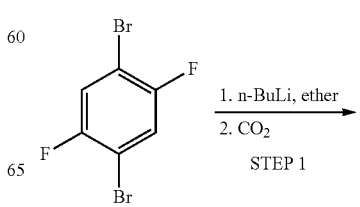

STEP 1

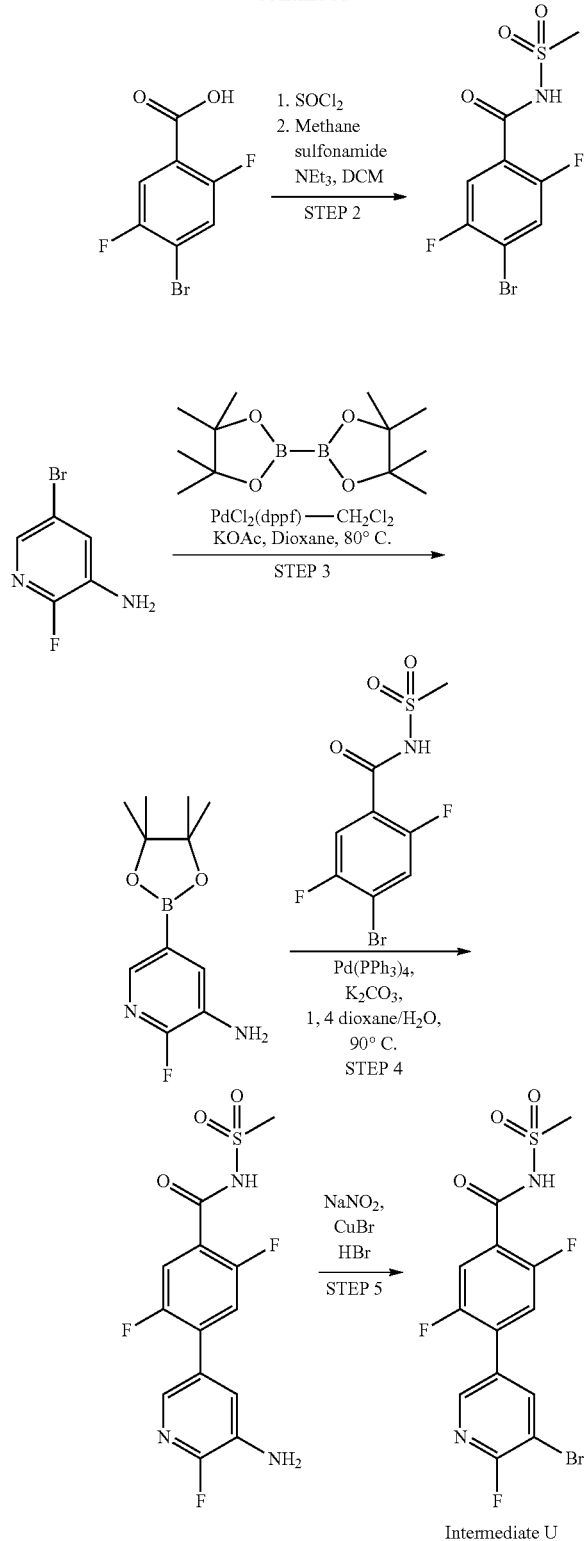

Intermediate U

Step 1: Synthesis of 4-Bromo-2,5-Difluorobenzoic Acid

To a solution of 1,4-dibromo-2,5-difluorobenzene (30.0 g, 110 mmol) in diethyl ether (300 mL), n-BuLi (1.6 M in hexanes, 44.1 mL, 110 mmol) was added dropwise at −78° C. over a period of 30 min. The reaction mixture was stirred at −78° C. for 2 h. Carbon dioxide gas was bubbled through the reaction mixture at the same temperature for 30 min. The reaction mixture was quenched with 1 N aqueous HCl (200 mL) and extracted with ethyl acetate (2×400 mL). The combined organic layer was washed with water, dried over sodium sulfate, filtered and concentrated under reduced pressure to obtain 4-bromo-2,5-difluorobenzoic acid (15.3 g, 58.5%) as off white solid. TLC solvent system: 30% EtOAc in hexanes. Product's $R_f$: 0.1. MS (ESI, positive ion) m/z; No ionization. $^1$H NMR (400 MHz, DMSO) δ 13.79 (s, 1H), 7.88 (dd, J=9.7, 5.6 Hz, 1H), 7.77 (dd, J=8.6, 6.3 Hz, 1H).

Step 2: Synthesis of 4-Bromo-2,5-Difluoro-N-(Methylsulfonyl)Benzamide

A solution of 4-bromo-2,5-difluorobenzoic acid (15.3 g, 64.6 mmol) in thionyl chloride (150 mL) and DMF (2 drops) was heated at 85° C. for 4 h. Reaction mixture was concentrated under reduced pressure and the crude was taken in DCM (50 mL). This solution was added dropwise to a pre-cooled solution of methane sulfonamide (6.13 g, 64.6 mmol) and TEA (22.5 mL, 161.4 mmol) in DCM (200 mL) at 0° C. The reaction mixture was allowed to stir at ambient temperature for 12 h. Reaction mixture was concentrated under reduced pressure to obtain the crude compound which was purified by column chromatography (silica gel 100-200 mesh and 0-1% MeOH in DCM as eluent) to obtain 4-bromo-2,5-difluoro-N-(methylsulfonyl)benzamide (7.8 g, 38.5%) as white solid. TLC solvent system: 10% MeOH in DCM. Product's $R_f$: 0.3. MS (ESI, negative ion) m/z; 312.0 (M−1). $^1$H NMR (400 MHz, DMSO) δ 12.46 (s, 1H), 7.94 (dd, J=9.2, 5.5 Hz, 1H), 7.75 (dd, J=8.3, 6.0 Hz, 1H), 3.37 (s, 3H).

Step 3: Synthesis of 2-Fluoro-5-(4,4,5,5-Tetramethyl-1,3,2-Dioxaborolan-2-yl)Pyridin-3-Amine A mixture of 5-bromo-2-fluoropyridin-3-amine (10.0 g, 52.6 mmol), 4,4,4',4',5,5,5',5'-octamethyl-2,2'-bi(1,3,2-dioxaborolane) (16.0 g, 63.1 mmol) and potassium acetate (15.4 g, 158 mmol) in 1,4-dioxane (100 mL) was degassed with nitrogen for 10 minutes. PdCl$_2$(dppf)-CH$_2$Cl$_2$ (4.29 g, 5.26 mmol) was added to the reaction mixture and again degassed for 10 min. The reaction mixture was heated at 90° C. for 24 h. After completion, the reaction mixture was filtered through CELITE and the CELITE bed was washed with ethyl acetate (200 mL). The filtrate was concentrated under reduced pressure to get the crude material which was purified by column chromatography (silica: 100-200; elution: 30% ethyl acetate in hexanes) to get desired 2-fluoro-5-(4,4,5,5-tetramethyl-1,3,2-dioxaborolan-2-yl)pyridin-3-amine as white solid (8.5 g, 68%). TLC solvent system: 40% ethyl acetate in hexanes, Product's R: 0.3. MS (ESI, positive ion) m/z; No ionization. $^1$H NMR (400 MHz, DMSO) δ 7.54 (s, 1H), 7.40 (dd, J=11.7, 1.5 Hz, 1H), 5.45 (s, 2H), 1.28 (s, 12H).

Step 4: Synthesis of 4-(5-Amino-6-Fluoropyridin-3-yl)-2,5-Difluoro-N-(Methylsulfonyl)Benzamide A solution of 2-fluoro-5-(4,4,5,5-tetramethyl-1,3,2-dioxaborolan-2-yl)pyridin-3-amine (7.20 g, 30.5 mmol), 4-bromo-2,5-difluoro-N-(methylsulfonyl)benzamide (8.00 g, 25.4 mmol) and potassium carbonate (8.80 g, 63.6 mmol) in dioxane: water (100 mL : 20 mL) was degassed with nitrogen for 10 minutes. Tetrakis(triphenylphosphine) palladium(0) (2.90 g, 2.54 mmol) was added and the reaction mixture was again degassed for 10 minutes. The reaction mixture was heated at 90° C. for 16 h. After completion, reaction mixture was concentrated under reduced pressure and the crude material was purified by column chromatography (silica: 60-120 mesh; elution: 15% methanol in DCM) to get the desired compound. The product thus obtained was stirred with diethyl ether and pentane (2:1, 100 mL) and filtered to get the pure 4-(5-amino-6-fluoropyridin-3-yl)-2,5-difluoro-N-(methylsulfonyl)benzamide (9.5 g, 91.3%). TLC solvent system: 10% methanol in DCM, Product's $R_f$: 0.5. MS (ESI, positive ion) m/z; No ionization. $^1$H NMR (400 MHz, DMSO) δ 12.21 (s, 1H), 7.61 (dd, J=10.6, 5.9 Hz, 1H), 7.53 (s, 1H), 7.47 (dd, J=10.5, 6.1 Hz, 1H), 7.38 (d, J=10.4 Hz, 1H), 5.67 (s, 2H), 3.13 (s, 3H).

Step 5: (Intermediate U): 4-(5-Bromo-6-Fluoropyridin-3-yl)-2,5-Difluoro-N-(Methyl Sulfonyl)Benzamide To a solution of 4-(5-amino-6-fluoropyridin-3-yl)-2,5-difluoro-N-(methylsulfonyl)benzamide (8.00 g, 23.74 mmol) in hydrobromic acid (48% in water) (150 mL) was added a solution of sodium nitrite (16.3 g, 237 mmol) in water (50 mL) keeping the temperature below 0° C. The reaction mixture was stirred at same temperature for 30 minutes. Copper (I) bromide (34.1 g, 237 mmol) was added in portions at same temperature and stirred for additional 15 minutes. The reaction mixture was allowed to stir for 16 h at ambient temperature. The reaction mixture was diluted with ethyl acetate (1000 mL) and neutralized with sodium bicarbonate. The organic layer was separated, dried over sodium sulphate and concentrated under reduced pressure to obtain crude material which was further purified by washing with ethyl acetate (100 mL) and hexanes (100 mL) to get pure 4-(5-bromo-6-fluoropyridin-3-yl)-2,5-difluoro-N-(methylsulfonyl)benzamide (3.0 g, 31.2%). TLC solvent system: 10% methanol in DCM, Product's $R_f$: 0.2. MS (ESI, negative ion) m/z; 406.9. $^1$H NMR (400 MHz, DMSO) δ 12.57 (s, 1H), 8.59 (d, J=8.4 Hz, 1H), 8.48 (s, 1H), 7.56 (dt, J=12.6, 6.4 Hz, 2H), 2.91 (s, 3H).

Example 787: 4-(5-Cyano-6-(2,4-Dichloro-6-Methylphenoxy)-3-Pyridinyl)-2,5-Difluoro-N-(Methylsulfonyl)Benzamide Example 787 was prepared from Intermediate AH, which was prepared from intermediate U, by using the conditions described below.

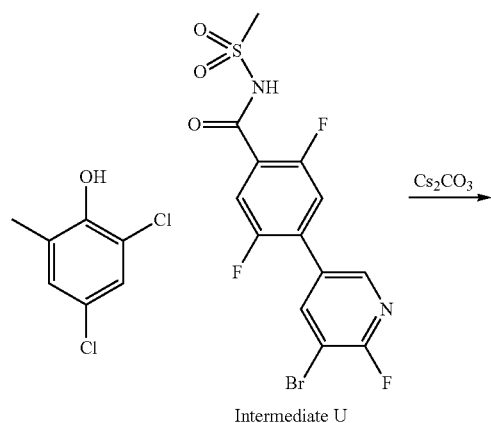

Intermediate U

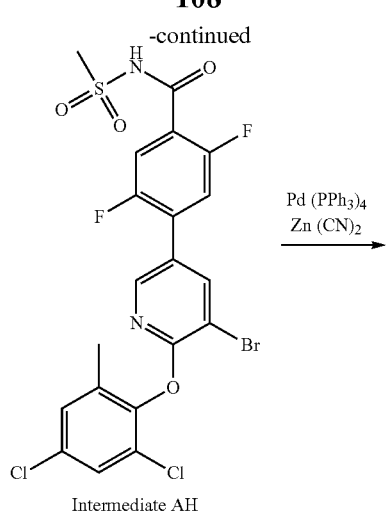

Intermediate AH

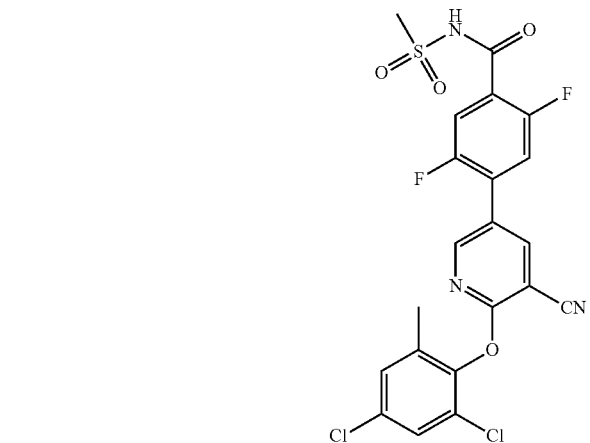

Step 1: 4-(5-Bromo-6-(2,4-Dichloro-6-Methylphenoxy)Pyridin-3-yl)-2,5-Difluoro-N-(Methylsulfonyl)Benzamide A 2 dram resealable vial was charged with 2,4-dichloro-6-methylphenol (80 mg, 0.452 mmol), cesium carbonate (276 mg, 0.847 mmol), and 4-(5-bromo-6-fluoropyridin-3-yl)-2,5-difluoro-N-(methylsulfonyl)benzamide (116 mg, 0.282 mmol, Intermediate U) and DMSO (2 mL) was added. The vial was sealed and heated at 90° C. for 40 h. The reaction mixture was then filtered through a frit, washing with DCM and MeOH. After concentration, the crude residue was purified using preparative reverse phase LCMS (0.1% NH$_4$OH in water/acetonitrile; Flow rate: 40 ml/min; Gradient: 10 min 20-50% NH$_3$) to afford 4-(5-bromo-6-(2,4-dichloro-6-methylphenoxy)pyridin-3-yl)-2,5-difluoro-N-(methylsulfonyl)benzamide (16 mg). LC-MS m/z (ESI, negative ion) 564.8.

Step 2: 4-(5-Cyano-6-(2,4-Dichloro-6-Methylphenoxy)Pyridin-3-yl)-2,5-Difluoro-N-(Methylsulfonyl)Benzamide In a 2-mL sealed tube, added 4-(5-bromo-6-(2,4-dichloro-6-methylphenoxy)pyridin-3-yl)-2,5-difluoro-N-(methylsulfonyl)benzamide (100 mg, 0.177 mmol), dicyanozinc (20.74 mg, 0.177 mmol) and Pd(Ph$_3$P)$_4$ (20.41 mg, 0.018 mmol) in DMF (589 μL). The tube was purged with nitrogen for 5 minutes, sealed. The vessel was heated to 100° C. in a microwave oven for 4 h.

After cooling to RT, the crude material was filtered. The crude material was purified by HPLC using 0.1% TFA in ACN and water as mobile phase to provide 4-(5-cyano-6-(2,4-dichloro-6-methylphenoxy)pyridin-3-yl)-2,5-difluoro-N-(methylsulfonyl)benzamide. $^1$H NMR (500 MHz, DMSO-$d_6$) δ ppm 2.19 (s, 3H) 3.35 (s, 3H), 7.67 (d, J=2.08 Hz, 1H), 7.69-7.80 (m, 2H), 8.65 (s, 1H) 8.83 (s, 1H). MS m/z [M+1]$^+$=514.0.

Method XXXV: Preparation by Using Intermediate AI

Example 793: 4-(5-Chloro-6-(3,4-Dichlorobenzyl) Pyridin-3-yl)-3-Methoxy-N-(Methylsulfonyl)Benzamide

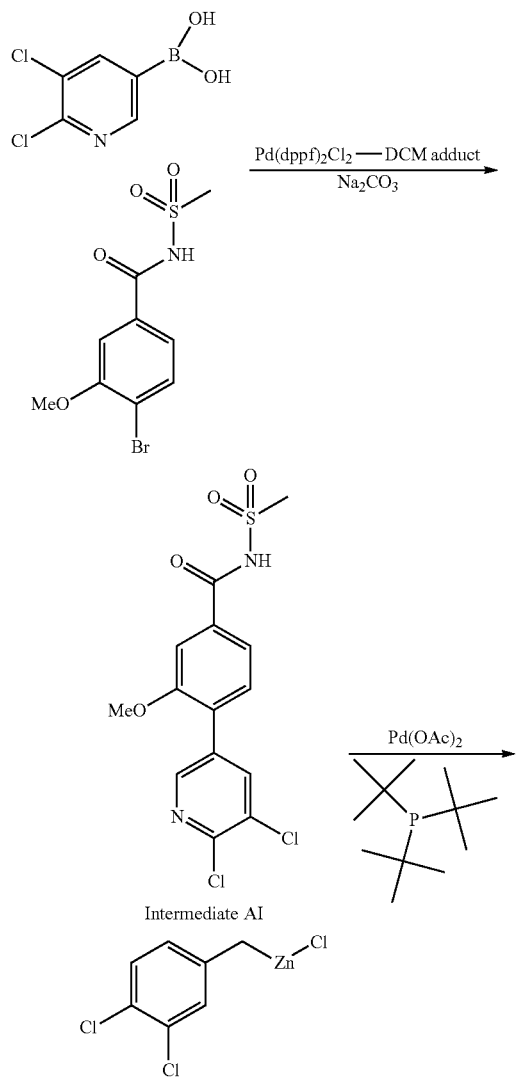

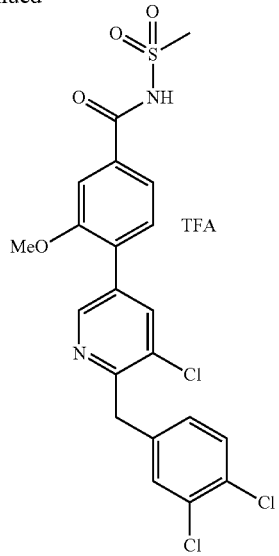

Step 1: 4-(5,6-Dichloropyridin-3-yl)-3-Methoxy-N-(Methylsulfonyl)Benzamide

A microwave vial was charged with (5,6-dichloropyridin-3-yl)boronic acid (1.245 g, 6.49 mmol), 4-bromo-3-methoxy-N-(methylsulfonyl)benzamide (1 g, 3.25 mmol), PdCl$_2$dppf (0.265 g, 0.325 mmol). Sealed with septa cap and added cyclopentylmethylether (CPME) (6.49 ml), then sodium carbonate (2N aq.) (5.19 ml, 10.38 mmol). Sparged with N$_2$ and heated in a heating block at 120° C. for 4 h. The reaction mixture was diluted with DCM. The layers were separated and the aqueous layer was washed with DCM (2×) and was acidified with 6 N HCl. The precipitate was filtered and washed with water. 4-(5,6-dichloropyridin-3-yl)-3-methoxy-N-(methylsulfonyl)benzamide was brought on to the next step without further purification. MS m/z [M]=375.0.

Step 2: 4-(5-Chloro-6-(3,4-Dichlorobenzyl)Pyridin-3-yl)-3-Methoxy-N-(Methylsulfonyl)Benzamide To a 5-mL round-bottomed flask was added 4-(5,6-dichloropyridin-3-yl)-3-methoxy-N-(methylsulfonyl)benzamide (100 mg, 0.267 mmol), tri-tert-butylphosphine, 1.0 M in toluene (53.3 μl, 0.053 mmol), palladium (II) acetate (8.97 mg, 0.040 mmol) and 3,4-dichlorobenzyl zinc chloride (800 μl, 0.400 mmol) in THF (666 μl). The reaction mixture was stirred at rt for 4H. The reaction mixture was quenched with sat. aq. NH$_4$Cl and the resulting mixture was transferred to a sep. funnel. The aqueous layer was washed 3× with EtOAc. The organic extract was dried over Na₂SO₄. The solution was filtered and concentrated in vacuo to give the crude material as a yellow solid. The crude material was purified by reverse-phase preparative HPLC using 0.1% TFA in CH₃CN/H₂O, gradient 10% to 90% over 20 min to provide 4-(5-chloro-6-(3,4-dichlorobenzyl)pyridin-3-yl)-3-methoxy-N-(methylsulfonyl)benzamide 2,2,2-trifluoroacetate as a yellow solid. $^1$H NMR (500 MHz, DMSO-d₆) δ ppm 8.75 (s, 1H), 8.13 (d, J=1.75 Hz, 1H), 7.89 (d, J=15.83 Hz, 1H), 7.78 (d, J=8.43 Hz, 2H), 7.72 (s, 1H), 7.60-7.70 (m, 3H), 7.49 (d, J=8.63 Hz, 2H), 3.92 (s, 2H). MS m/z [M−1]⁺=498.1.

Method XXXVI: Preparation by Using Intermediate AJ

Example 798: 4-(5-Chloro-6-Cyclobutoxypyridin-3-yl)-N-(Cyclopropylsulfonyl)-2-Fluoro-5-Methylbenzamide

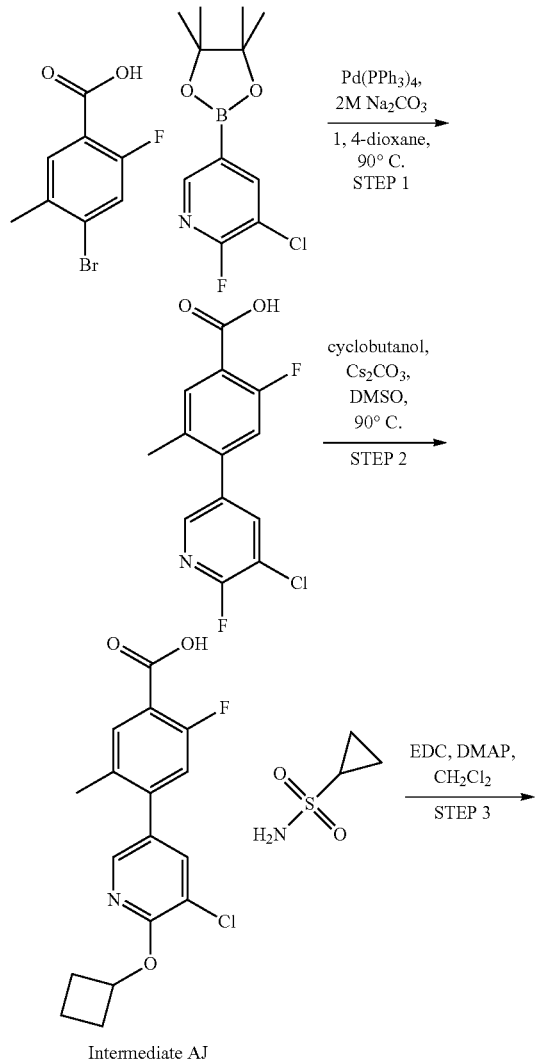

Intermediate AJ

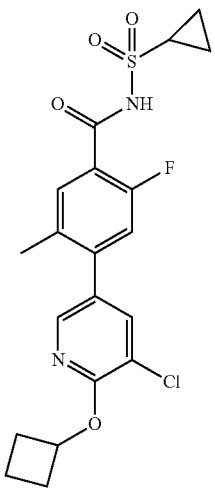

Step 1: Synthesis of 4-(5-Chloro-6-Fluoropyridin-3-yl)-2-Fluoro-5-Methylbenzoic Acid To a solution of 4-bromo-2-fluoro-5-methylbenzoic acid (25.0 g, 0.107 mol, 1.0 equiv, F-chemicals) and 3-chloro-2-fluoro-5-(4,4,5,5-tetramethyl-1,3,2-dioxaborolan-2-yl) pyridine (30.6 g, 0.128 mol, 1.2 equiv) in 1,4-dioxane (250 mL) was added 2.0 M aqueous Na₂CO₃ solution (268 mL, 0.536 mol, 3.0 equiv) at ambient temperature. The reaction mixture was degassed with nitrogen for 10 minutes and Pd(PPh₃)₄ (6.60 g, 0.005 mol, 0.05 equiv, GLR) was added. The reaction mixture was again degassed with nitrogen for 15 minutes and heated at 90° C. for 12 h. After completion of reaction, the reaction mixture cooled to rt and was filtrated over CELITE pad. The CELITE pad was washed with water (3×50 mL). The combined filtrate was acidified (pH ~3) with 1.5 N aqueous HCl and extracted with ethyl acetate (2×500 mL). The combined organic layer was dried over sodium sulphate and concentrated under reduced pressure to get crude product which was purified by column chromatography (elution 0-100% ethyl acetate in hexane) to obtain 4-(5-chloro-6-fluoropyridin-3-yl)-2-fluoro-5-methylbenzoic acid (11.6 g, 38%) as off white solid. MS (ESI −ve ion) m/z: [M−1]=281.8. $^1$H NMR (400 MHz, DMSO-d₆) 13.34 (s, 1H), 8.37-8.32 (m, 1H), 8.27 (dd, J=2.2, 1.2 Hz, 1H), 7.82 (d, J=7.4 Hz, 1H), 7.33 (d, J=11.3 Hz, 1H), 2.25 (s, 3H).

Step 2: 4-(5-Chloro-6-Cyclobutoxypyridin-3-yl)-2-Fluoro-5-Methylbenzoic Acid

A vial was charged with cyclobutanol (0.331 mL, 4.23 mmol), 4-(5-chloro-6-fluoropyridin-3-yl)-2-fluoro-5-methylbenzoic acid (1.0 g, 3.53 mmol), cesium carbonate (2.53 g, 7.76 mmol) and dimethyl sulfoxide (7.76 mL). The vial was capped and the mixture was heated at 90° C. for 21 h. The mixture was diluted with water and EtOAc, and the layers were separated. The aqueous portion was brought to pH 4 by addition of aq HCl and was extracted twice with EtOAc. These organic extracts were combined, dried, filtered, and concentrated. The crude material was purified by silica gel chromatography, 10-100% 90/10 DCM/MeOH in DCM to provide 4-(5-chloro-6-cyclobutoxypyridin-3-yl)-2-fluoro-5-methylbenzoic acid (0.640 g, 1.906 mmol, 54.1% yield) as a white solid. m/z (ESI) 336.0 (M+H)+. $^1$H NMR (400 MHz, DMSO-d$_6$) 13.26 (br. s., 1H), 8.14 (d, J=2.18 Hz, 1H), 8.02 (d, J=2.18 Hz, 1H), 7.79 (d, J=7.57 Hz, 1H), 7.26 (d, J=11.40 Hz, 1H), 5.20-5.29 (m, 1H), 2.39-2.48 (m, 2H), 2.25 (s, 3H), 2.07-2.19 (m, 2H), 1.76-1.88 (m, 1H), 1.59-1.73 (m, 1H).

Step 3: 4-(5-Chloro-6-Cyclobutoxypyridin-3-yl)-N-(Cyclopropylsulfonyl)-2-Fluoro-5-Methylbenzamide To a flask charged with 4-(5-chloro-6-cyclobutoxypyridin-3-yl)-2-fluoro-5-methylbenzoic acid (75 mg, 0.223 mmol, Intermediate AJ) was added cyclopropanesulfonamide (22.46 μL, 0.268 mmol), dichloromethane (851 μL), DMAP (5.46 mg, 0.045 mmol) and 1-(3-dimethylaminopropyl)-3-ethylcarbodiimide hydrochloride (64.2 mg, 0.335 mmol). The vessel was sealed and stirred at room temperature for 17 hours. The reaction was eluted through a silica gel column using 10-75% 3:1 EtOAc:EtOH/heptane. The desired fractions were combined and concentrated down to yield 4-(5-chloro-6-cyclobutoxypyridin-3-yl)-N-(cyclopropylsulfonyl)-2-fluoro-5-methylbenzamide (35 mg, 0.080 mmol, 35.7% yield) as an off-white solid. m/z (ESI) 437.1 (M−H)$^-$. $^1$H NMR (400 MHz, DMSO-d$_6$) δ ppm 1.09-1.18 (m, 3H) 1.23 (br. s., 1H) 1.59-1.74 (m, 1H) 1.82 (q, J=9.95 Hz, 1H) 2.07-2.19 (m, 2H) 2.25 (s, 3H) 2.39-2.48 (m, 2H) 3.02-3.15 (m, 1H) 5.24 (quin, J=7.23 Hz, 1H) 7.26-7.34 (m, 1H) 7.60 (d, J=7.26 Hz, 1H) 7.98-8.04 (m, 1H) 8.10-8.18 (m, 1H) 12.20 (br. s., 1H).

Method XXXVII: Preparation by Using Intermediate AK

Example 798: 4-(5-Chloro-6-(2,4-Dichloro-6-Methylphenoxy)Pyridin-3-yl)-N-(Cyclopropylsulfonyl)-2-Fluoro-5-Methylbenzamide

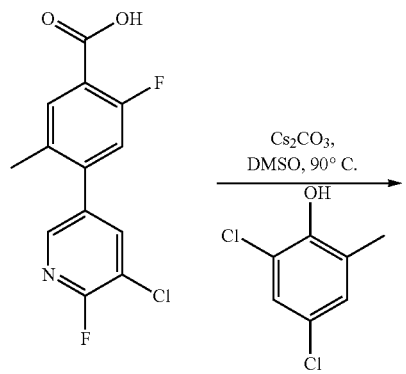

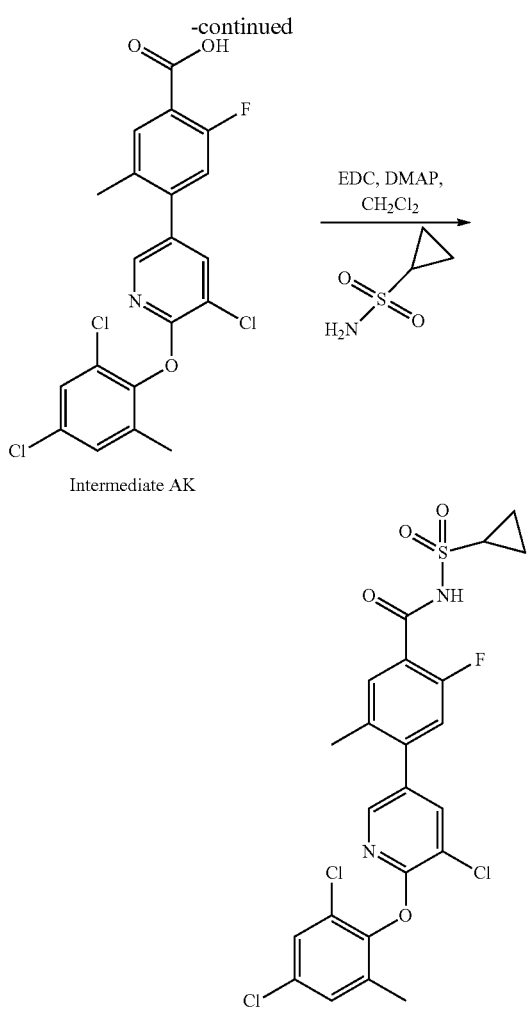

Step 1: 4-(5-Chloro-6-(2,4-Dichloro-6-Methylphenoxy)Pyridin-3-yl)-2-Fluoro-5-Methylbenzoic Acid 4-(5-chloro-6-(2,4-dichloro-6-methylphenoxy)pyridin-3-yl)-2-fluoro-5-methylbenzoic acid (Intermediate AK) was made in similar fashion to Intermediate AJ using 2,4-dichloro-6-methylphenol instead of cyclobutanol. 4-(5-chloro-6-(2,4-dichloro-6-methylphenoxy)pyridin-3-yl)-2-fluoro-5-methylbenzoic acid (1.45 g, 3.29 mmol, 85% yield) was isolated as a yellow solid. m/z (ESI) 439.8; 441.9 (M+H)$^+$. $^1$H NMR (400 MHz, DMSO-d$_6$) δ ppm 2.15 (s, 3H) 2.25 (s, 3H) 7.31 (d, J=11.30 Hz, 1H) 7.49 (dd, J=2.54, 0.78 Hz, 1H) 7.63 (dd, J=2.49, 0.62 Hz, 1H) 7.79 (d, J=7.57 Hz, 1H) 8.10 (d, J=2.18 Hz, 1H) 8.25 (d, J=2.07 Hz, 1H) 13.25-13.31 (m, 1H).

Step 2: 4-(5-Chloro-6-(2,4-Dichloro-6-Methylphenoxy)Pyridin-3-yl)-N-(Cyclopropylsulfonyl)-2-Fluoro-5-Methylbenzamide To a flask charged with 4-(5-chloro-6-(2,4-dichloro-6-methylphenoxy)pyridin-3-yl)-2-fluoro-5-methylbenzoic acid (Intermediate AK, 125 mg, 0.284 mmol) was added cyclopropanesulfonamide (41.2 mg, 0.340 mmol), CH$_2$Cl$_2$ (0.85 mL), DMAP (17.33 mg, 0.142 mmol) and 1-(3-dimethylaminopropyl)-3-ethylcarbodiimide hydrochloride (82 mg, 0.425 mmol). The vessel was sealed and stirred at room temperature for 17 hours. The reaction was extracted into dichloromethane, washed once with water, once with sodium chloride, dried with sodium sulfate, filtered through a fritted funnel, and concentrated down. The crude material was eluted through a silica gel column using 0-50% $CH_2Cl_2$: MeOH(90:10)/$CH_2Cl_2$. The desired fractions were collected and concentrated down to yield 4-(5-chloro-6-(2,4-dichloro-6-methylphenoxy)pyridin-3-yl)-N-(cyclopropylsulfonyl)-2-fluoro-5-methylbenzamide (100 mg, 0.184 mmol, 64.8% yield) as a light yellow solid. m/z (ESI) 544.8 (M+H)$^+$. $^1$H NMR (400 MHz, DMSO-d$_6$) 12.23 (br. s., 1H), 8.21-8.29 (m, 1H), 8.07-8.12 (m, 1H), 7.59-7.66 (m, 2H), 7.46-7.53 (m, 1H), 7.33-7.41 (m, 1H), 3.04-3.14 (m, 1H), 2.23-2.30 (m, 3H), 2.15 (s, 3H), 1.10-1.19 (m, 4H).

Method XXXVIII: Preparation by Using Intermediate AL

Example 802: 4-(5-Chloro-6-Cyclobutoxypyridin-3-yl)-5-Cyclopropyl-2-Fluoro-N-(Methylsulfonyl)Benzamide

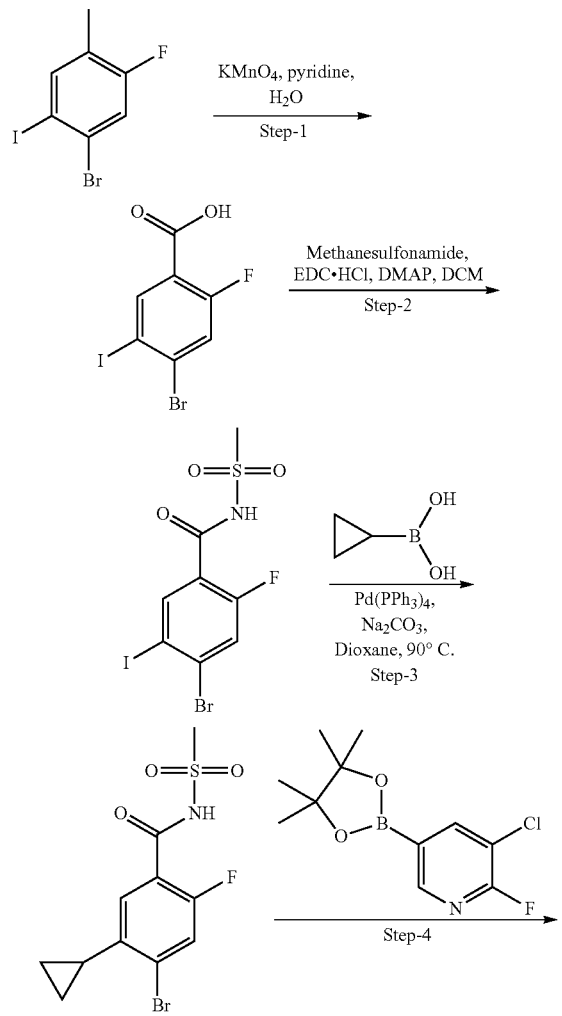

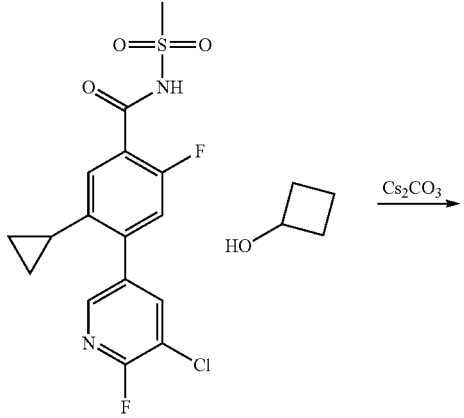

Intermediate AL

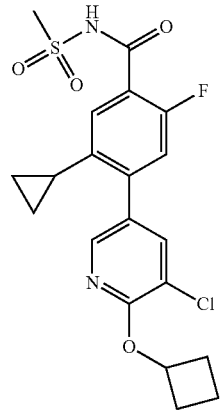 [SMILES: CS(=O)(=O)NC(=O)c1cc(C2CC2)c(-c2cnc(OC3CCC3)c(Cl)c2)cc1F]

Step 1: 4-Bromo-2-Fluoro-5-Iodobenzoic Acid

To a solution of 1-bromo-5-fluoro-2-iodo-4-methylbenzene (50 g, 159.23 mmol, 1.0 equiv) in pyridine (300 mL) and water (300 mL) was added KMnO$_4$ (100 g, 637.24 mmol, 4.0 equiv) portion-wise. The reaction mixture was heated at 85° C. for 6 h. After completion, the reaction mixture was filtered through CELITE and the CELITE bed was washed with ethanol (2×1.0 L). The filtrate was concentrated under reduced pressure to half of the volume. The mixture was acidified with 1.5N HCl solution (500 mL) to pH ~2. The precipitate thus obtained were collected by filtration and the washed with diethylether (2×150 mL) and dried under reduced pressure to obtain 4-bromo-2-fluoro-5-iodobenzoic acid (30 g, 55.0%) as white solid which was used in next step without purification. MS (ESI +ve ion) m/z: [M+1]: 345.0 $^1$H NMR (400 MHz, DMSO-d$_6$): δ 7.97 (d, J=7.4 Hz, 1H), 7.44 (d, J=9.4 Hz, 1H).

Step 2: 4-Bromo-2-Fluoro-5-Iodo-N-(Methylsulfonyl)Benzamide

To a solution of 4-bromo-2-fluoro-5-iodobenzoic acid (30.0 g, 86.96 mmol, 1.0 equiv) and methane sulfonamide (12.39 g, 130.04 mmol, 1.5 equiv) in DCM (500 mL) was added DMAP (31.82 g, 230.88 mmol, 3.0 equiv) and EDC.HCl (50.0 g, 260.88 mmol, 3.0 equiv). The reaction mixture was stirred at room temperature for 14 h. The reaction was diluted with DCM (500 mL) and washed with 4 N aqueous HCl (2×250 mL). The organic layer was washed with brine solution (200 mL), dried over sodium sulphate, filtered and concentrated under reduced pressure to obtain 4-bromo-2-fluoro-5-iodo-N-(methylsulfonyl)benzamide (18.0 g, 49%) as white solid. MS (ESI −ve ion) m/z: [M−1]: 420.0 $^1$H NMR (400 MHz, DMSO-d$_6$): δ 12.20 (s, 1H), 8.16 (d, J=7.3 Hz, 1H), 7.89 (d, J=9.9 Hz, 1H), 3.34 (s, 3H).

Step 3: 4-Bromo-5-Cyclopropyl-2-Fluoro-N-(Methylsulfonyl)-Benzamide

To a solution of 4-bromo-2-fluoro-5-iodo-N-(methylsulfonyl)benzamide (9.0 g, 21.38 mmol, 1.0 equiv) in cyclopentyl methyl ether (300 mL) was added cyclopropylboronic acid (4.54 g, 53.45 mmol, 2.5 equiv) and 2M aqueous Na$_2$CO$_3$ solution (32 mL, 64.14 mmol, 3.0 equiv). The reaction mixture was degassed with nitrogen for 15 min and Pd(PPh$_3$)$_4$ (2.47 g, 2.13 mmol, 0.1 equiv) was added. The reaction mixture was degassed with nitrogen for an additional 15 minutes and heated at 100° C. for 16 h. The reaction mixture was acidified with 4N aqueous HCl solution and concentrated under reduced pressure to obtain the crude material which was purified by column chromatography (0-25% Ethyl acetate in petroleum ether) to obtain 4-bromo-5-cyclopropyl-2-fluoro-N-(methylsulfonyl)benzamide (4.5 g, 31%) as off white solid. MS (ESI −ve ion) m/z: [M−1]: 334.1 $^1$H NMR (400 MHz, DMSO-d$_6$): δ 12.30 (s, 1H), 7.74 (d, J=9.8 Hz, 1H), 7.27 (d, J=7.4 Hz, 1H), 3.37 (s, 3H), 2.11-2.01 (m, 1H), 1.10-0.96 (m, 2H), 0.83-0.73 (m, 2H).

Step 4: 4-(5-Chloro-6-Fluoropyridin-3-yl)-5-Cyclopropyl-2-Fluoro-N-(Methylsulfonyl)Benzamide To a solution of 4-bromo-5-cyclopropyl-2-fluoro-N-(methylsulfonyl)benzamide (4.5 g, 13.39 mmol, 1.0 equiv) in cyclopentyl methyl ether (250 mL) was added 3-chloro-2-fluoro-5-(4,4,5,5-tetramethyl-1,3,2-dioxaborolan-2-yl)pyridine (4.56 g, 20.08 mmol, and 1.5 equiv) and 2M aqueous Na$_2$CO$_3$ solution (16.7 mL, 33.47 mmol, 2.5 equiv). The reaction mixture was degassed with nitrogen for 15 min and Pd(PPh$_3$)$_4$ (1.54 g, 3.22 mmol, 0.1 equiv) was added. The reaction mixture was degassed with nitrogen for 15 additional minutes and heated at 100° C. for 14 h. The reaction mixture was acidified with 4N aqueous HCl solution and concentrated under reduced pressure to obtain the crude material which was purified by column chromatography (0-25% Ethyl acetate in petroleum ether) to obtain 4-(5-chloro-6-fluoropyridin-3-yl)-5-cyclopropyl-2-fluoro-N-(methylsulfonyl)benzamide (4.2 g, 82%) as white solid. MS (ESI −ve ion) m/z: [M−1]: 385.0 $^1$H NMR (400 MHz, DMSO-d$_6$): δ 12.35 (s, 1H), 8.40 (dd, J=8.9, 2.2 Hz, 1H), 8.33 (t, J=1.7 Hz, 1H), 7.44-7.32 (m, 2H), 3.36 (s, 3H), 1.85 (tt, J=8.4, 5.3 Hz, 1H), 0.91-0.80 (m, 2H), 0.76-0.68 (m, 2H).

Step 5: 4-(5-Chloro-6-Cyclobutoxypyridin-3-yl)-5-Cyclopropyl-2-Fluoro-N-(Methylsulfonyl)Benzamide To a vial containing cyclobutanol (67 μL, 0.300 mmol) was added cesium carbonate (0.143 g, 0.440 mmol) and 1-(5,6-dichloropyridin-3-yl)-N-(methylsulfonyl)isoquinoline-6-carboxamide (0.079 g, 0.2 mmol) in DMSO (1.0 ml). The reaction mixture was heated at 120° C. in a heating block. After stirring overnight, the reaction was cooled to rt and filtered. The mixture was then purified by reverse phase HPLC with 0.1% NH$_4$OH in ACN and water as mobile phase to give 4-(5-chloro-6-cyclobutoxypyridin-3-yl)-5-cyclopropyl-2-fluoro-N-(methylsulfonyl)benzamide (185 mg). MS (ESI +ve ion) m/z: [M+1]: 439.0. $^1$H NMR (500 MHz, DMSO-d$_6$) δ ppm 0.58-0.69 (m, 2H) 0.84-0.94 (m, 2H) 1.68-1.82 (m, 1H) 1.82-1.96 (m, 2H) 2.14-2.27 (m, 2H) 2.54-2.59 (m, 1H) 2.62 (s, 1H) 2.93 (s, 3H) 5.33 (quin, J=7.31 Hz, 1H) 7.10 (d, J=10.96 Hz, 1H) 7.43 (d, J=7.46 Hz, 1H) 8.08 (d, J=2.08 Hz, 1H) 8.25 (d, J=2.01 Hz, 1H).

Method XXXIX: Preparation by Using Intermediate AM

Example 791: 4-(5-Chloro-6-(2,3,6-Trifluorophenoxy)Pyridin-3-yl)-(Ethylsulfonyl)-3-Methoxybenzamide

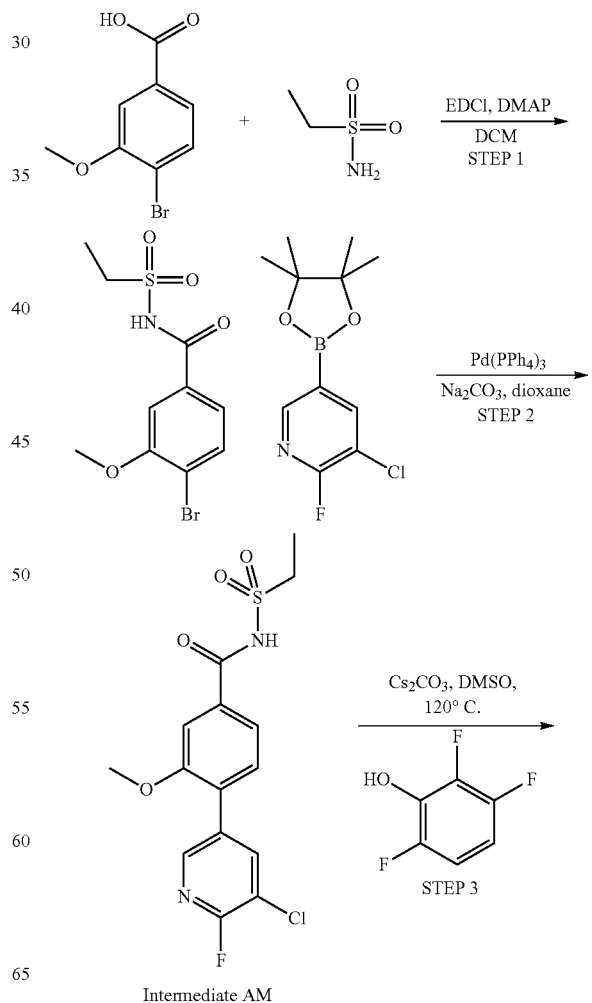

Intermediate AM

-continued

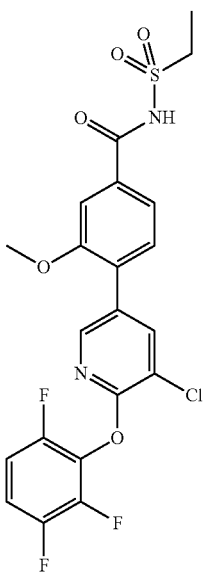

Step 1:
4-Bromo-N-(Ethylsulfonyl)-3-Methoxybenzamide

To a vial charged with 4-bromo-3-methoxybenzoic acid (1.00 g, 4.33 mmol, Astatech), ethanesulfonamide (0.567 g, 5.19 mmol), N,N-dimethylpyridin-4-amine (0.793 g, 6.49 mmol) and DCM (17.31 ml) was added $N^1$-((ethylimino)methylene)-$N^3,N^3$-dimethylpropane-1,3-diamine hydrochloride (1.245 g, 6.49 mmol) and the solution stirred overnight providing a light pink solution. The solution was transferred to a separatory funnel and washed with 2N HCl. The DCM layer was collected, dried with $Na_2SO_4$, filtered, and dried under reduced pressure affording product as a white solid 4-bromo-N-(ethylsulfonyl)-3-methoxybenzamide (1.27 g, 3.94 mmol, 91% yield). MS m/z: $[M+1]^+$= 321.9.

Step 2: 4-(5-Chloro-6-Fluoropyridin-3-yl)-N-(Ethylsulfonyl)-3-Methoxybenzamide

To a flask charged with 4-bromo-N-(ethylsulfonyl)-3-methoxybenzamide (1.22 g, 3.79 mmol), 3-chloro-2-fluoro-5-(4,4,5,5-tetramethyl-1,3,2-dioxaborolan-2-yl)pyridine (1.22 g, 3.79 mmol, Bellen), $Pd(PPh_3)_4$ (0.219 g, 0.189 mmol) was added 1,4-dioxane (15.15 ml) and $Na_2CO_3$ (2M) (9.47 ml, 18.93 mmol) and the mixture purged with nitrogen for 5 mins then heated to 80° C. overnight with stirring under nitrogen affording an orange suspension. The mixture was cooled in an ice water bath and brought to pH ~2 by the addition of 2N HCl. The slurry was stirred for an hr (warming slowly to room temp) affording a white precipitate which was collected by vacuum filtration and washed with water and dried under high vacuum affording product as a white solid, 4-(5-chloro-6-fluoropyridin-3-yl)-N-(ethylsulfonyl)-3-methoxybenzamide (1.265 g, 3.39 mmol, 90% yield). MS m/z: $[M+1]^+$=372.9. $^1$H NMR (400 MHz, DMSO-$d_6$) 8.43-8.35 (m, 2H), 7.71 (d, J=1.6 Hz, 1H), 7.66 (dd, J=1.6, 7.9 Hz, 1H), 7.59 (d, J=7.9 Hz, 1H), 3.90 (s, 3H), 3.57-3.50 (m, 2H), 1.27 (t, J=7.3 Hz, 3H).

Step 3: 4-(5-Chloro-6-(2,3,6-Trifluorophenoxy)Pyridin-3-yl)-N-(Ethylsulfonyl)-3-Methoxybenzamide A vial was charged with 4-(5-chloro-6-fluoropyridin-3-yl)-N-(ethylsulfonyl)-2-fluoro-5-methoxybenzamide (Intermediate AM) (100 mg, 0.268 mmol), cesium carbonate (218 mg, 0.671 mmol), 2,3,6-trifluorophenol (60 mg, 0.402 mmol) and 1.5 mL DMSO. The vial was sealed, and the reaction mixture was heated at 120° C. for 15 h. The mixture was filtered through a frit, which was washed with MeOH and DCM. The filtrate was concentrated, and the crude material was purified by reverse phase chromatography, PREP LC/MS-2 System Column: XBridge Prep Shield RP18 19×100 mm 104|131331GG 03 Mobile phase: 0.1% $NH_4OH$ in water/acetonitrile Flow rate: 40 ml/min Inj: 2500 µL Gradient: 10 min, 10-40%_LV_$NH_3$. 4-(5-chloro-6-(2,3,6-trifluorophenoxy)pyridin-3-yl)-N-(ethylsulfonyl)-3-methoxybenzamide was isolated as an off-white solid (40 mg, 30% yield). MS (ESI, MH+) m/z 501.0; 1H NMR (500 MHz, DMSO-$d_6$) δ ppm 1.10 (t, J=7.43 Hz, 3H) 3.09 (q, J=7.31 Hz, 2H) 3.82 (s, 3H) 7.31-7.43 (m, 2H) 7.46-7.58 (m, 1H) 7.62 (d, J=7.73 Hz, 1H) 7.67 (s, 1H) 8.22 (d, J=1.95 Hz, 1H) 8.28 (d, J=1.95 Hz, 1H).

Method XXXX: Preparation by Using Intermediate AN

Example 794: 3-Bromo-4-(5-Chloro-6-(2,4-Dichloro-6-Methylphenoxy)-3-Pyridinyl)-N-(Methylsulfonyl)Benzamide

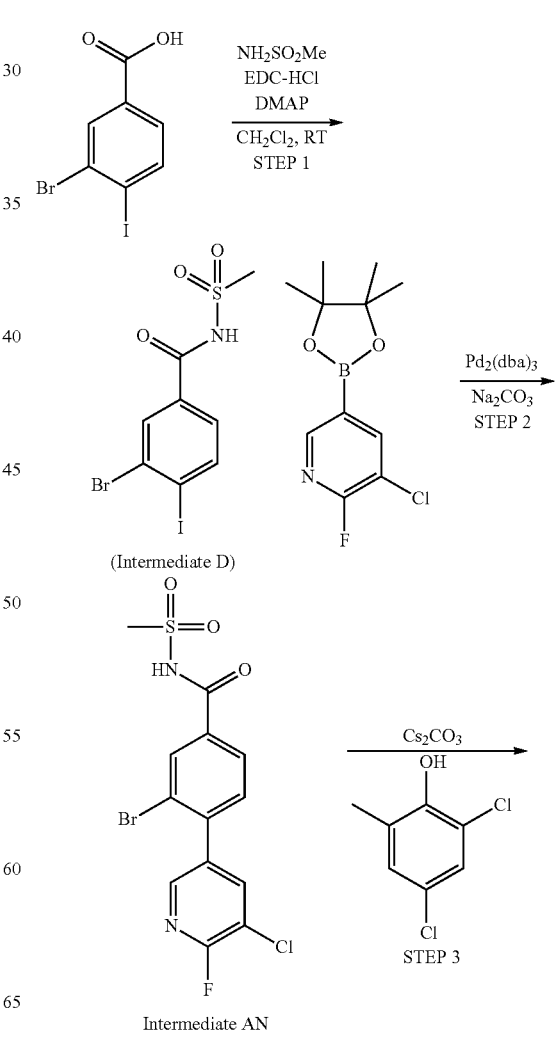

Intermediate AN

Step 1: 3-Bromo-4-Iodo-N-(Methylsulfonyl)Benzamide (Intermediate D)

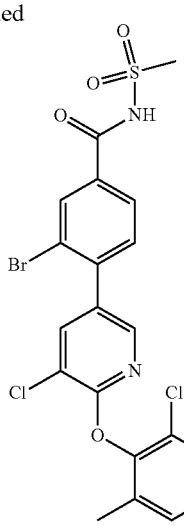

A suspension of 1-(3-dimethylaminopropyl)-3-ethylcarbodiimide hydrochloride (0.586 g, 3.06 mmol), 4-(dimethylamino)pyridine (0.561 g, 4.59 mmol), methanesulfonamide (0.128 ml, 1.835 mmol) and 3-bromo-4-iodobenzoic acid (0.5 g, 1.529 mmol, HDH Pharma) was shaken at ambient temperature for 16 h. The reaction mixture was purified by reverse phase HPLC using water and acetonitrile and TFA as modifier to obtain Intermediate D (0.268 g, 0.663 mmol, 43.4% yield) as a white sticky, solid. MS (ESI, positive ion) m/z 405.0.

Step 2: 3-Bromo-4-(5-Chloro-6-Fluoropyridin-3-yl)-N-(Methylsulfonyl)-Benzamide To a vial charged with 3-bromo-4-iodo-N-(methylsulfonyl)benzamide (Intermediate D) (7.5 g, 18.56 mmol), 3-chloro-2-fluoro-5-(4,4,5,5-tetramethyl-1,3,2-dioxaborolan-2-yl)pyridine (4.78 g, 18.56 mmol), Pd$_2$(dba)$_3$ (1.700 g, 1.856 mmol) and 1,4-dioxane (74.3 ml) was added Na$_2$CO$_3$ (2M) (46.4 ml, 93 mmol). The mixture was stirred overnight at 40° C. then cooled to rt. The mixture was filtered through CELITE and dried under reduced pressure. The crude residue was purified via column chromatography eluting with DCM:MeOH (90:10) in DCM (0-15%, isocratic at 15%, then to 40%, isocratic at 40%) affording 3-bromo-4-(5-chloro-6-fluoropyridin-3-yl)-N-(methylsulfonyl)benzamide (4.81 g, 11.80 mmol, 63.6% yield) as a light yellow solid. MS (ESI, MH+) m/z 406.8/408.9.

Step 3: 3-Bromo-4-(5-Chloro-6-(2,4-Dichloro-6-Methylphenoxy)-3-Pyridinyl)-N-(Methylsulfonyl)Benzamide A 2 dram resealable vial was charged with 2,4-dichloro-6-methylphenol (80 mg, 0.452 mmol), cesium carbonate (276 mg, 0.847 mmol), and 3-bromo-4-(5-chloro-6-fluoropyridin-3-yl)-N-(methylsulfonyl)benzamide (115 mg, 0.282 mmol, Intermediate AN) and DMSO (2 mL) was added. The vial was sealed and heated at 90° C. for 40 h. The reaction mixture was then filtered through a frit, washing with DCM and MeOH. After concentration, the crude residue was purified using preparative reverse phase LCMS (0.1% NH$_4$OH in water/acetonitrile; Flow rate: 40 ml/min; Gradient: 10 min 20-50% NH$_3$) to afford 3-bromo-4-(5-chloro-6-(2,4-dichloro-6-methylphenoxy)-3-pyridinyl)-N-(methylsulfonyl)benzamide (88 mg). MS m/z (ESI, negative ion) 563.0.

Example 702: 4-(5-Chloro-6-Cyclobutoxypyridin-3-yl)-2-Fluoro-5-Methoxy-N-(Methylsulfonyl)Benzamide To a vial charged with 4-(5-chloro-6-fluoropyridin-3-yl)-2-fluoro-5-methoxy-N-(methylsulfonyl)benzamide (65 mg, 0.173 mmol) and Cs$_2$CO$_3$ (169 mg, 0.518 mmol) was added cyclobutanol (0.242 mmol, 1.4 eq) and DMSO (0.3 M). The resulting suspension was heated with shaking at 90° C. overnight. The resulting suspension was filtered through a frit, rinsing with isopropanol. The isopropanol was removed in-vacuo and the crude material purified Waters-Xbridge C18, 19×100 mm, 10 μm column with a gradient 5-95% acetonitrile and water with 0.1% NH$_4$OH to afford 4-(5-chloro-6-cyclobutoxypyridin-3-yl)-2-fluoro-5-methoxy-N-(methylsulfonyl)benzamide (35 mg, 33%). LC-MS m/z (ESI, negative ion) 427.0. $^1$H NMR (500 MHz, DMSO-d$_6$) δ ppm 1.70-1.80 (m, 1H) 1.90 (q, J=10.10 Hz, 1H) 2.15-2.25 (m, 2H) 2.50-2.56 (m, 2H) 3.10 (s, 3H) 3.88 (s, 3H) 5.32 (quin, J=7.35 Hz, 1H) 7.34 (d, J=10.70 Hz, 1H) 7.42 (d, J=6.03 Hz, 1H) 8.14 (d, J=2.08 Hz, 1H) 8.34 (d, J=2.08 Hz, 1H).

Example 704: 4-(5-Chloro-6-(3-Chloro-2-Methylphenoxy)Pyridin-3-yl)-2-Fluoro-5-Methoxy-N-(Methylsulfonyl)Benzamide

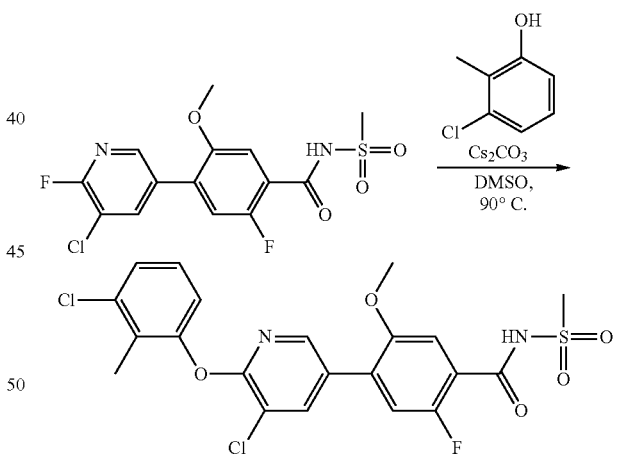

To a vial charged with 4-(5-chloro-6-fluoropyridin-3-yl)-2-fluoro-5-methoxy-N-(methylsulfonyl)benzamide (65 mg, 0.173 mmol) and Cs$_2$CO$_3$ (169 mg, 0.518 mmol) was added 3-chloro-2-methylphenol (0.242 mmol, 1.4 eq, Sigma Aldrich) and DMSO (0.3 M). The resulting suspension was heated with shaking at 90° C. overnight. The resulting suspension was filtered through a frit, rinsing with isopropanol. The isopropanol was removed in-vacuo and the crude material purified Waters-Xbridge C18, 19×100 mm, 10 μm column with a gradient 5-95% acetonitrile and water with 0.1% NH$_4$OH to afford 4-(5-chloro-6-(3-chloro-2-methylphenoxy)pyridin-3-yl)-2-fluoro-5-methoxy-N-(methylsulfonyl)benzamide (49 mg, 40%). LC-MS m/z (ESI, negative ion) 496.9. $^1$H NMR (500 MHz, DMSO-d$_6$) δ ppm 2.15 (s, 3H) 2.99 (s, 3H) 3.81 (s, 3H) 7.18 (d, J=7.91 Hz, 2H) 7.25-7.41 (m, 4H) 8.21 (d, J=2.01 Hz, 1H) 8.26 (d, J=2.01 Hz, 1H).

Example 825: 4-(6-(3,5-Dichlorophenoxy)-5-(Trifluoromethyl)Pyridin-3-yl)-3-Methoxy-N-(Methylsulfonyl)Benzamide

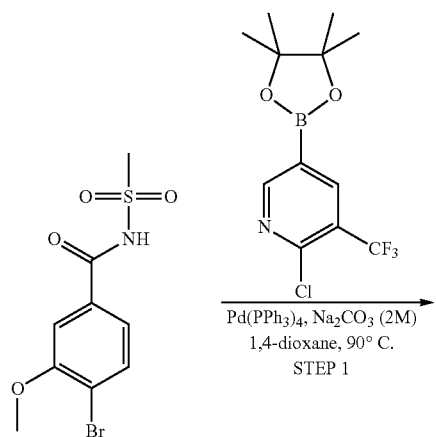

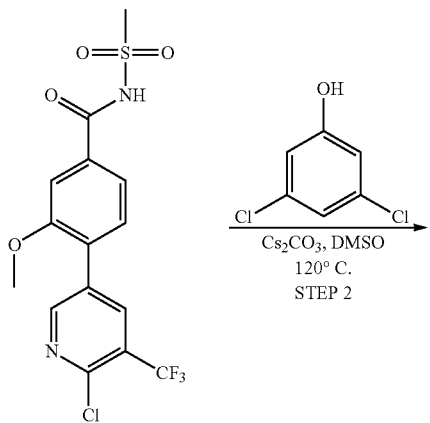

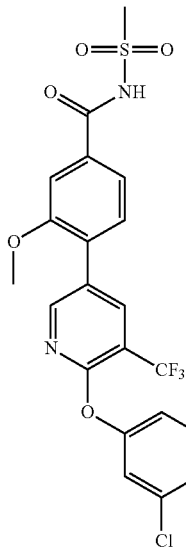

Step 1: 4-(6-Chloro-5-(Trifluoromethyl)Pyridin-3-yl)-3-Methoxy-N-(Methylsulfonyl)Benzamide To a flask charged with 4-bromo-3-methoxy-N-(methylsulfonyl)benzamide (0.97 g, 3.15 mmol), 2-chloro-5-(4,4,5,5-tetramethyl-1,3,2-dioxaborolan-2-yl)-3-(trifluoromethyl)pyridine (0.968 g, 3.15 mmol, CombiBlocks), Pd(PPh$_3$)$_4$ (0.182 g, 0.157 mmol) was added 1,4-dioxane (12.59 ml) and Na$_2$CO$_3$ (2M) (7.87 ml, 15.74 mmol) and the mixture purged with nitrogen for 5 mins then heated for 3 nights at 90° C. affording about 20% conversion to product relative to starting aryl bromide. The solid in the resulting suspension was collected by vacuum filtration but the LC-MS of this solid was similar to the crude LC-MS. The solid and reaction mixture was transferred to a sep funnel and extracted with EtOAc (2×). The combined organics were dried with Na$_2$SO$_4$, filtered, and dried under reduced pressure. The crude residue was purified with a 50 g ultra snap column ramping EtOAc in heptane (0-100%, 5% DCM throughout) affording product (~80% pure by LC-MS) with peak slicing as the last eluting species obtained as a colorless oil which will be used without further purification. MS (ESI, positive ion) m/z 409.1 (m/z).

Step 2: 4-(6-(3,5-Dichlorophenoxy)-5-(Trifluoromethyl)Pyridin-3-yl)-3-Methoxy-N-(Methylsulfonyl)Benzamide To a vial charged with 4-(6-chloro-5-(trifluoromethyl)pyridin-3-yl)-3-methoxy-N-(methylsulfonyl)benzamide (118 mg, 0.289 mmol), 3,5-dichlorophenol (47.1 mg, 0.289 mmol) and Cs$_2$CO$_3$ (282 mg, 0.866 mmol) was added DMSO (1155 µl) and the mixture heated overnight at 120° C. affording a brown suspension with product as a major species according to LC-MS. The mixture was cooled to room temperature, filtered through celite, and the filtrate dried under reduced pressure. The crude oil (containing DMSO) was filtered through a filter with MeOH rinsing and purified with the Gilson RP-HPLC ramping ACN in H$_2$O (35-95%, 0.1% TFA throughout). The product containing eluents were directly lyophilized affording product as a white solid, 4-(6-(3,5-dichlorophenoxy)-5-(trifluoromethyl)pyridin-3-yl)-3-methoxy-N-(methylsulfonyl)benzamide (31 mg, 0.058 mmol, 20.06% yield). $^1$H NMR (400 MHz, DMSO-d$_6$) δ ppm J=1.9 Hz, 1H), 8.42 (d, J=1.8 Hz, 1H), 7.71 (d, J=1.6 Hz, 1H), 7.67 (dd, J=7.9 Hz, 1H), 7.61 (d, J=7.9 Hz, 1H), 7.57 (t, J=1.9 Hz, 1H), 7.48 (d, J=1.9 Hz, 2H), 3.90 (s, 3H), 3.40 (s, 3H). MS (ESI, positive ion) m/z 535.1 (m/z).

Example 826: 4-(5-Chloro-6-(3-Chloro-4-Methylphenoxy)Pyridin-3-yl)-N-(Methylsulfonyl)-3-(Oxetan-3-yloxy)Benzamide

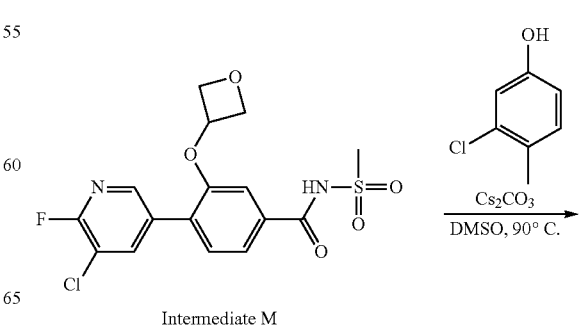

Intermediate M

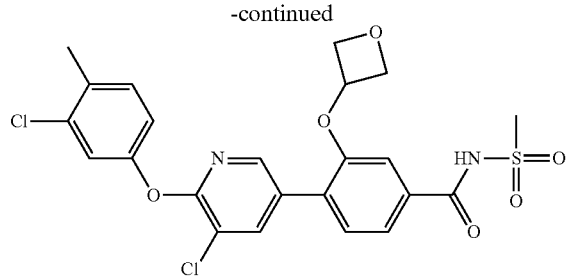

To a vial charged with 4-(5-chloro-6-fluoropyridin-3-yl)-N-(methylsulfonyl)-3-(oxetan-3-yloxy)benzamide (50 mg, 0.125 mmol) and Cs$_2$CO$_3$ (122 mg, 0.374 mmol) was added 3-chloro-4-methylphenol (0.343 mmol, 2.75 eq) and DMSO (0.3 M). The resulting suspension was heated with shaking at 90° C. overnight. The resulting suspension was filtered through a frit, rinsing with isopropanol. The isopropanol was removed in-vacuo and the crude material purified Waters-Xbridge C18, 19×100 mm, 10 μm column with a gradient 5-95% acetonitrile and water with 0.1% NH$_4$OH to afford 4-(5-chloro-6-(3-chloro-4-methylphenoxy)pyridin-3-yl)-N-(methylsulfonyl)-3-(oxetan-3-yloxy)benzamide (38 mg, 47%). LC-MS m/z (ESI, positive ion) 524.4. $^1$H NMR (500 MHz, DMSO-d$_6$) δ ppm 2.35 (s, 3H) 3.39 (s, 3H) 4.53 (dd, J=7.21, 4.97 Hz, 2H) 4.95 (t, J=6.68 Hz, 2H) 5.45 (quin, J=5.29 Hz, 1H) 7.14 (dd, J=8.28, 2.35 Hz, 1H) 7.23 (s, 1H) 7.38 (d, J=2.30 Hz, 1H) 7.43 (d, J=8.39 Hz, 1H) 7.61 (d, J=7.96 Hz, 1H) 7.65-7.79 (m, 1H) 8.29-8.47 (m, 2H).

Example 827: 4-(5-Chloro-6-(3,5-Dichlorophenoxy) Pyridin-3-yl)-3-Methoxy-N-(Methylsulfonyl)Benzamide

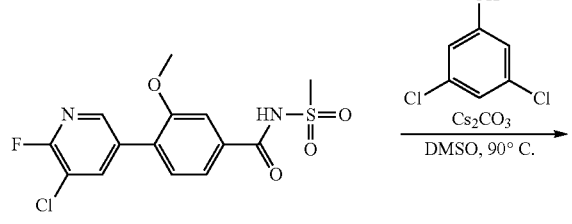

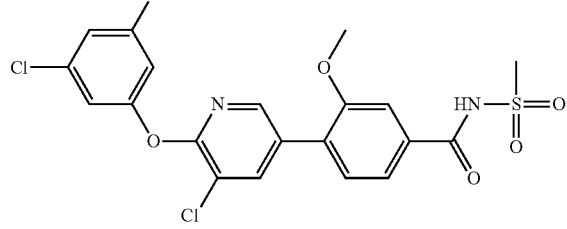

To a vial charged with 4-(5-chloro-6-fluoropyridin-3-yl)-3-methoxy-N-(methylsulfonyl)benzamide (50 mg, 0.139 mmol) and Cs$_2$CO$_3$ (136 mg, 0.418 mmol) was added 3,5-dichlorophenol (0.348 mmol, 2.5 eq) and DMSO (0.3 M). The resulting suspension was heated with shaking at 90° C. overnight. The resulting suspension was filtered through a frit, rinsing with isopropanol. The isopropanol was removed in-vacuo and the crude material purified Waters-Xbridge C18, 19×100 mm, 10 μm column with a gradient 5-95% acetonitrile and water with 0.1% NH$_4$OH to afford 4-(5-chloro-6-(3,5-dichlorophenoxy)pyridin-3-yl)-3-methoxy-N-(methylsulfonyl)benzamide (46 mg, 66%). LC-MS m/z (ESI, positive ion) 502.8. $^1$H NMR (500 MHz, DMSO-d$_6$) δ ppm 8.24-8.31 (m, 2H), 7.69 (d, J=1.56 Hz, 1H), 7.62-7.67 (m, 1H), 7.52-7.59 (m, 2H), 7.46 (d, J=1.86 Hz, 2H), 3.89 (s, 3H), 3.41 (s, 3H).

Example 828: 4-(5-Chloro-6-(2-Chloro-5-Methyl-phenoxy)Pyridin-3-yl)-N-(Methylsulfonyl)-3-(Oxetan-3-yloxy)Benzamide

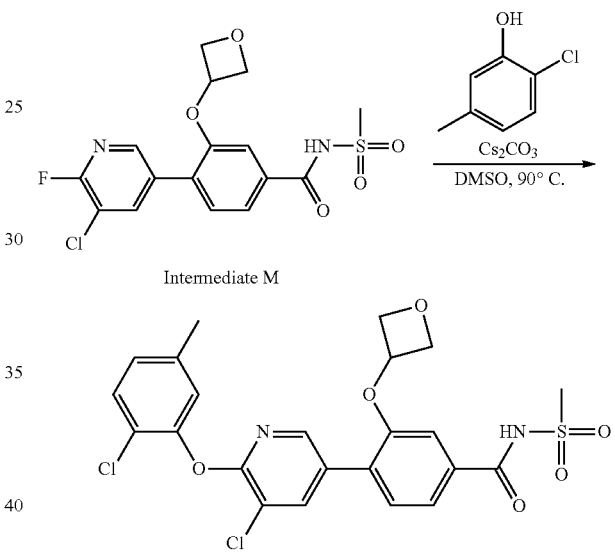

To a vial charged with 4-(5-chloro-6-fluoropyridin-3-yl)-N-(methylsulfonyl)-3-(oxetan-3-yloxy)benzamide (Intermediate M, see Method XII above, 50 mg, 0.125 mmol) and Cs$_2$CO$_3$ (122 mg, 0.374 mmol) was added 2-chloro-5-methylphenol (0.343 mmol, 2.75 eq) and DMSO (0.3 M). The resulting suspension was heated with shaking at 90° C. overnight. The resulting suspension was filtered through a frit, rinsing with isopropanol. The isopropanol was removed in-vacuo and the crude material purified Waters-Xbridge C18, 19×100 mm, 10 μm column with a gradient 5-95% acetonitrile and water with 0.1% NH$_4$OH to afford 4-(5-chloro-6-(2-chloro-5-methylphenoxy)pyridin-3-yl)-N-(methylsulfonyl)-3-(oxetan-3-yloxy)benzamide (35 mg, 43%). LC-MS m/z (ESI, positive ion) 524.7. $^1$H NMR (500 MHz, DMSO-d$_6$) δ ppm 2.34 (s, 3H) 3.39 (s, 5H) 4.53 (dd, J=7.19, 4.94 Hz, 2H) 4.95 (t, J=6.68 Hz, 2H) 5.45 (dq, J=5.50, 5.36 Hz, 1H) 7.15 (d, J=8.01 Hz, 1H) 7.26 (s, 1H) 7.23 (s, 1H) 7.48 (d, J=8.23 Hz, 1H) 7.57-7.65 (m, 1H) 7.65-7.76 (m, 1H) 8.28 (d, J=1.98 Hz, 1H) 8.37 (d, J=1.98 Hz, 1H) 12.20 (br. s., 1H).

Example 829: 4-(6-(3-Chloro-4-Methylphenoxy)-5-Cyanopyridin-3-yl)-3-Methoxy-N-(Methylsulfonyl)Benzamide

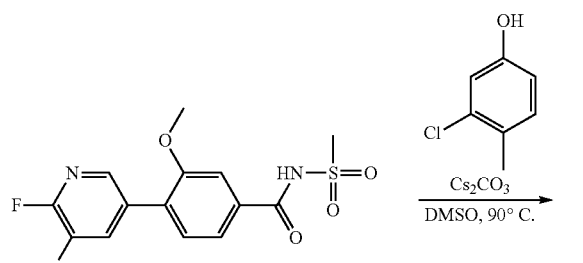

Intermediate Q

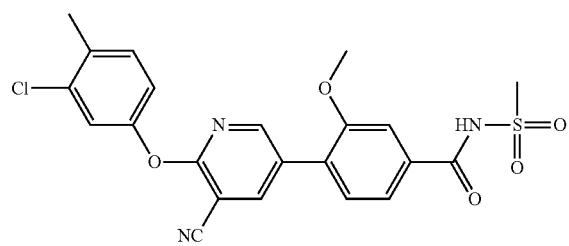

To a vial charged with 4-(5-cyano-6-fluoropyridin-3-yl)-3-methoxy-N-(methylsulfonyl)benzamide (75 mg, 0.215 mmol) and Cs$_2$CO$_3$ (210 mg, 0.644 mmol) was added 3-chloro-4-methylphenol (0.344 mmol, 1.6 eq) and DMSO (0.3 M). The resulting suspension was heated with shaking at 90° C. overnight. The resulting suspension was filtered through a frit, rinsing with isopropanol. The isopropanol was removed in-vacuo and the crude material purified Waters-Xbridge C18, 19×100 mm, 10 μm column with a gradient 5-95% acetonitrile and water with 0.1% NH$_4$OH to afford 4-(6-(3-chloro-4-methylphenoxy)-5-cyanopyridin-3-yl)-3-methoxy-N-(methylsulfonyl)benzamide (35 mg, 34%). LC-MS m/z (ESI, negative ion) 470.2. $^1$H NMR (500 MHz, DMSO-d$_6$) δ ppm 2.36 (s, 3H) 3.40 (s, 3H) 3.89 (s, 3H) 7.21 (dd, J=8.31, 2.32 Hz, 1H) 7.39-7.52 (m, 2H) 7.57 (d, J=7.92 Hz, 1H) 7.61-7.71 (m, 2H) 8.55 (d, J=2.32 Hz, 1H) 8.60 (d, J=2.32 Hz, 1H) 12.24 (br. s., 1H).

Example 830: 4-(6-(3,5-Dichlorophenoxy)-5-(Difluoromethyl)-Pyridin-3-yl)-3-Methoxy-N-(Methylsulfonyl)Benzamide

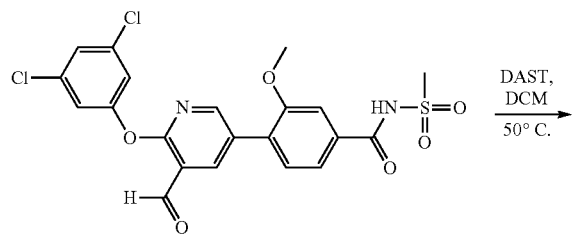

Example 823

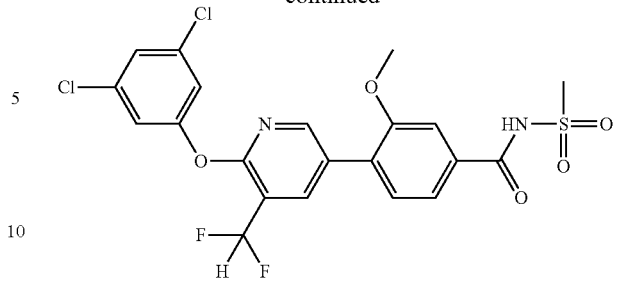

To a suspension of 4-(6-(3,5-dichlorophenoxy)-5-formylpyridin-3-yl)-2-fluoro-5-methyl-N-(methylsulfonyl)benzamide (Example 823 above, 150 mg, 0.302 mmol) in DCM (1206 μl) was added (diethylamino)sulfur trifluoride (100 μl, 0.754 mmol). The mixture was shaken at 50° C. for 30 mins affording a yellowish solution. To the mixture was added MeOH (~1 ml) and the solution dried under reduced pressure and purified with a 25 g ultra snap column ramping EtOAc:EtOH (76:24) in heptane (0-100%) affording product with about 75% purity (75 mg) which was repurified with RP-HPLC ramping ACN in H$_2$O (5-95%, 0.1% NH$_4$OH throughout) affording product as a white solid 4-(6-(3,5-dichlorophenoxy)-5-(difluoromethyl)pyridin-3-yl)-2-fluoro-5-methyl-N-(methylsulfonyl)benzamide (34 mg, 0.065 mmol, 21.71% yield). MS m/z: [M−1]$^-$=517.0. $^1$H NMR (500 MHz, DMSO-d$_6$) δ ppm 2.23 (s, 3H) 2.98 (s, 3H) 6.95-7.16 (m, 1H) 7.19 (s, 1H) 7.29 (s, 1H) 7.45 (d, J=1.75 Hz, 1H) 7.54 (t, J=1.72 Hz, 1H) 7.62 (d, J=7.46 Hz, 1H) 8.16 (s, 1H) 8.36 (s, 1H).

Example 831: 4-(5-Chloro-6-(2,3,6-Trifluorophenoxy)Pyridin-3-yl)-3-Methoxy-N-(Methylsulfonyl)Benzamide

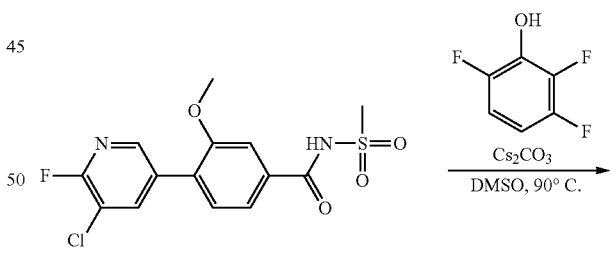

Intermediate L

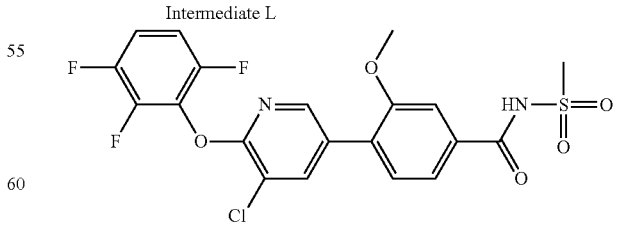

To a vial charged with 4-(5-chloro-6-fluoropyridin-3-yl)-3-methoxy-N-(methylsulfonyl)benzamide (INTERMEDIATE L, see above Method XI, 50 mg, 0.139 mmol) and Cs$_2$CO$_3$ (136 mg, 0.418 mmol) was added 2,3,6-trifluorophenol (0.348 mmol, 2.5 eq) and DMSO (0.3 M). The resulting suspension was heated with shaking at 90° C. overnight. The resulting suspension was filtered through a frit, rinsing with isopropanol. The isopropanol was removed in-vacuo and the crude material purified Waters-Xbridge C18, 19×100 mm, 10 μm column with a gradient 5-95% acetonitrile and water with 0.1% NH$_4$OH to afford 4-(5-chloro-6-(2,3,6-trifluorophenoxy)pyridin-3-yl)-3-methoxy-N-(methylsulfonyl)benzamide (14 mg, 21%). LC-MS m/z (ESI, positive ion) 487.0. $^1$H NMR (500 MHz, DMSO-d$_6$) 12.24 (br. s., 1H), 8.48 (s, 1H), 8.28 (s, 1H), 7.70 (s, 1H), 7.66 (dd, J=1.4, 8.0 Hz, 1H), 7.60-7.53 (m, 2H), 7.45 (m, 2H), 7.30 (s, 1H), 3.89 (s, 3H), 3.40 (s, 3H).

Example 832: 4-(5-Chloro-6-((3-Chloro-2-Methoxy-pyridin-4-yl)Oxy)Pyridin-3-yl)-3-Methoxy-N-(Methylsulfonyl)Benzamide

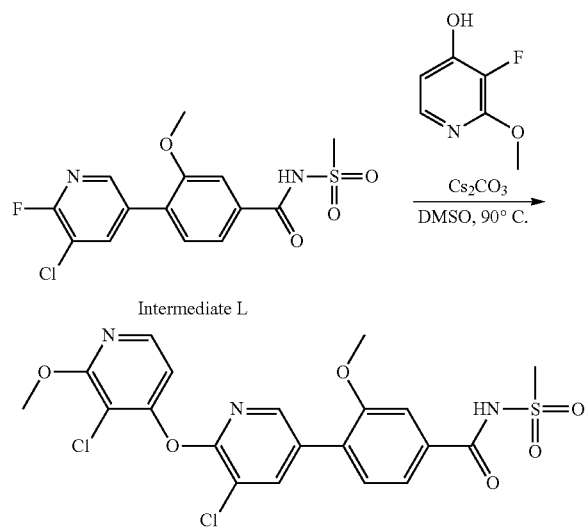

Intermediate L

To a vial charged with 4-(5-chloro-6-fluoropyridin-3-yl)-3-methoxy-N-(methylsulfonyl)benzamide (INTERMEDIATE L, see above Method XI, 50 mg, 0.139 mmol) and Cs$_2$CO$_3$ (136 mg, 0.418 mmol) was added 3-chloro-2-methoxypyridin-4-ol (0.348 mmol, 2.5 eq, Frontier Scientific) and DMSO (0.3 M). The resulting suspension was heated with shaking at 90° C. overnight. The resulting suspension was filtered through a frit, rinsing with isopropanol. The isopropanol was removed in-vacuo and the crude material purified with a Waters-Xbridge C18, 19×100 mm, 10 μm column with a gradient 5-95% acetonitrile and water with 0.1% NH$_4$OH to afford 4-(5-chloro-6-((3-chloro-2-methoxypyridin-4-yl)oxy)pyridin-3-yl)-3-methoxy-N-(methylsulfonyl)benzamide (23 mg, 33%). LC-MS m/z (ESI, positive ion) 498.4. $^1$H NMR (500 MHz, DMSO-d$_6$) δ ppm (hidden under D$_2$O, 3H), 3.88 (s, 4H) 4.00 (s, 3H) 7.09 (d, =5.54 Hz, 1H) 7.53 (d, J=7.92 Hz, 1H) 7.61-7.71 (m, 2H) 8.18 (d, J=5.60 Hz, 1H) 8.25-8.33 (m, 2H).

Example 833: 4-(5-Chloro-6-(2-Isopropylpyrrolidin-1-yl)Pyridin-3-yl)-3-(Difluoromethoxy)-N-(Methylsulfonyl)Benzamide

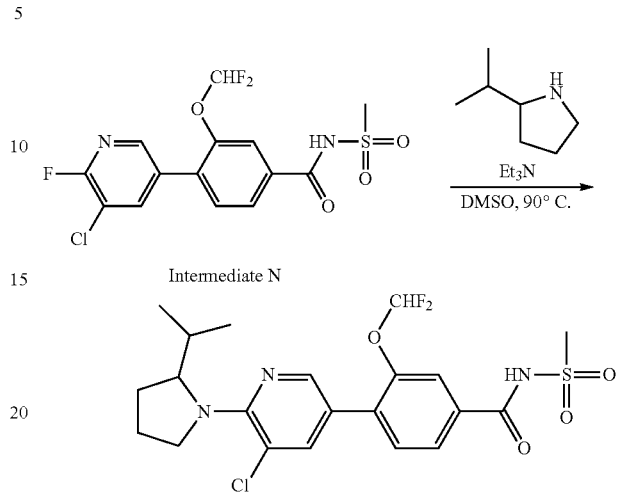

To a vial charged with 4-(5-chloro-6-fluoropyridin-3-yl)-3-(difluoromethoxy)-N-(methylsulfonyl)benzamide (Intermediate N, see Method XIII, 50 mg, 0.127 mmol) was added triethylamine (38.5 mg, 0.38 mmol), DMSO (0.507 ml) and 2-isopropylpyrrolidine (0.317 mmol, 2.5 eq, Frontier Scientific). The resulting mixture was heated with shaking at 90° C. overnight. The crude solution was purified with a Waters-Xbridge C18, 19×100 mm, 10 μm column with a gradient 5-95% acetonitrile and water with 0.1% NH$_4$OH to afford 4-(5-chloro-6-(2-isopropylpyrrolidin-1-yl)pyridin-3-yl)-3-methoxy-N-(methylsulfonyl)benzamide (30 mg, 44%). LC-MS m/z (ESI, positive ion) 489.0. $^1$H NMR (500 MHz, DMSO-d$_6$) δ ppm 0.92 (d, J=6.73 Hz, 3H) 0.97 (d, J=6.62 Hz, 3H) 1.46-1.58 (m, 1H) 1.75-1.97 (m, 2H) 2.90 (s, 3H) 3.02-3.10 (m, 1H) 3.42-3.49 (m, 1H) 3.72-3.80 (m, 1H) 4.45 (d, J=5.02 Hz, 1H) 7.06-7.39 (m, 1H) 7.49 (d, J=7.96 Hz, 1H) 7.52-7.65 (m, 2H) 7.76-7.89 (m, 3H) 8.24 (d, J=2.03 Hz, 1H).

Examples 804 and 805: 4-(5-Chloro-6-((1R)-2,2,2-Trifluoro-1-Methyl-1-Phenylethoxy)-3-Pyridinyl)-2,5-Difluoro-N-(Methylsulfonyl)Benzamide, and 4-(5-Chloro-6-((1S)-2,2,2-Trifluoro-1-Methyl-1-Phenylethoxy)-3-Pyridinyl)-2,5-Difluoro-N-(Methylsulfonyl)Benzamide Examples 804 and 805 were derived from resolution of Compounds of Example 566 by using SFC: Chiralpak OJ-H, 20% methanol to afford each enantiomer in >99% ee. Absolute stereochemistry was arbitrarily assigned.

Table A below tabulates exemplified compounds of formula (I) and sub genus thereof (Examples Nos. 327, 329, 344, 348, 350, 355, 357, 361-365, 368-374, 376-377, 379, 382, 402, 412-413, 419, 422-426, 436, 446, 449, 452-453, 455-457, 459-462, 464-468, 539, 547, 549 and 566 to 841). Each compound was prepared according to the above described Methods by using the identified reagent. The LCMS and NMR data (where available) are provided. LCMS (neg) means the chromatography was run in a negative ionization mode, i.e., mass observed is M−1 rather than the standard M+1 seen in the positive ionization mode.

Table A: The following data including $^1$H NMR data may also have been provided in the above written experimental section.

TABLE A

| EX. NO. | NAME | LCMS | METHODS | INTERMEDIATE | REAGENT | ¹H NMR DATA |
|---|---|---|---|---|---|---|
| 327 | 4-(5-chloro-6-(2-chloro-6-methylphenoxy)-3-pyridinyl)-3-methoxy-N-(methylsulfonyl)benzamide | 481.35 | II and XI | L | 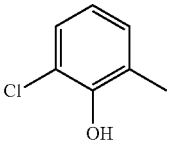 | |
| 329 | 4-(5-chloro-6-(3-chloro-4-methylphenoxy)-3-pyridinyl)-3-methoxy-N-(methylsulfonyl)benzamide | 481.35 | II and XI | L | 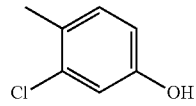 | |
| 344 | 4-(5-chloro-6-(2-chloro-4-methylphenoxy)-3-pyridinyl)-3-methoxy-N-(methylsulfonyl)benzamide | 481.35 | II and XI | L | 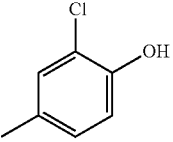 | |
| 348 | 4-(5-chloro-6-(3,5-dichlorophenoxy)-3-pyridinyl)-3-methoxy-N-(methylsulfonyl)benzamide | 501.77 | II and XI | L | 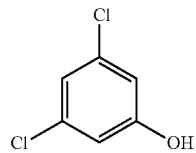 | |
| 350 | 4-(5-chloro-6-(4-chlorophenoxy)-3-pyridinyl)-3-methoxy-N-(methylsulfonyl)benzamide | 467.33 | II and XI | L | 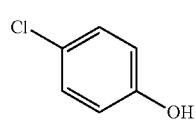 | |
| 355 | 4-(5-chloro-6-((2S)-2-(1-methylethyl)-1-pyrrolidinyl)-3-pyridinyl)-3-methoxy-N-(methylsulfonyl)benzamide | 451.97 | VIII and XI | L | 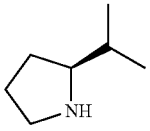 | |
| 357 | 4-(5-chloro-6-(2,3,4-trifluorophenoxy)-3-pyridinyl)-3-methoxy-N-(methylsulfonyl)benzamide | 486.85 | II and XI | L | 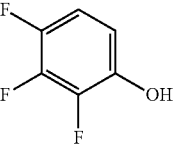 | |
| 361 | 4-(5-chloro-6-(4-fluoro-2-methylphenoxy)-3-pyridinyl)-3-methoxy-N-(methylsulfonyl)benzamide | 464.9 | II and XI | L | 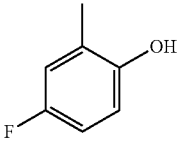 | |
| 362 | 4-(5-chloro-6-(2,3,6-trifluorophenoxy)-3-pyridinyl)-3-methoxy-N-(methylsulfonyl)benzamide | 486.85 | II and XI | L | 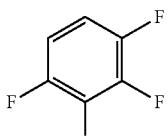 | |
| 363 | 4-(5-chloro-6-(2,5-difluorophenoxy)-3-pyridinyl)-3-methoxy-N-(methylsulfonyl)benzamide | 468.86 | II and XI | L | 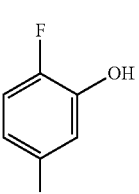 | |

TABLE A-continued

| EX. NO. | NAME | LCMS | METHODS | INTERMEDIATE | REAGENT | $^1$H NMR DATA |
|---|---|---|---|---|---|---|
| 364 | 4-(5-chloro-6-(4-chloro-3,5-dimethylphenoxy)-3-pyridinyl)-3-methoxy-N-(methylsulfonyl)benzamide | 495.38 | II and XI | L | | |
| 365 | 4-(5-chloro-6-(2-chloro-4-methoxyphenoxy)-3-pyridinyl)-3-methoxy-N-(methylsulfonyl)benzamide | 497.35 | II and XI | L | | |
| 368 | 4-(5-chloro-6-(4-chloro-3-methylphenoxy)-3-pyridinyl)-3-methoxy-N-(methylsulfonyl)benzamide | 495.38 | II and XI | L | | |
| 369 | 4-(5-chloro-6-(2-chloro-5-methoxyphenoxy)-3-pyridinyl)-3-methoxy-N-(methylsulfonyl)benzamide | 497.35 | II and XI | L | | |
| 370 | 4-(5-chloro-6-(4-chloro-3-(trifluoromethyl)phenoxy)-3-pyridinyl)-3-methoxy-N-(methylsulfonyl)benzamide | 535.33 | II and XI | L | | |
| 371 | 4-(5-chloro-6-(2-chloro-5-fluorophenoxy)-3-pyridinyl)-3-methoxy-N-(methylsulfonyl)benzamide | 485.32 | II and XI | L | | |
| 372 | 4-(5-chloro-6-(3-chloro-5-(trifluoromethoxy)phenoxy)-3-pyridinyl)-3-methoxy-N-(methylsulfonyl)benzamide | 551.32 | II and XI | L | | |
| 373 | 4-(5-chloro-6-(4-chloro-3-(trifluoromethoxy)phenoxy)-3-pyridinyl)-3-methoxy-N-(methylsulfonyl)benzamide | 551.32 | II and XI | L | | |
| 374 | 4-(5-chloro-6-(3-chloro-5-(trifluoromethyl)phenoxy)-3-pyridinyl)-3-methoxy-N-(methylsulfonyl)benzamide | 535.33 | II and XI | L | | |

TABLE A-continued

| EX. NO. | NAME | LCMS | METHODS | INTERMEDIATE | REAGENT | ¹H NMR DATA |
|---|---|---|---|---|---|---|
| 376 | 4-(5-chloro-6-(4-chloro-2-fluorophenoxy)-3-pyridinyl)-3-methoxy-N-(methylsulfonyl)benzamide | 485.32 | II and XI | L | 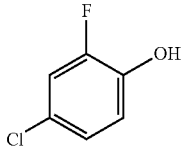 | |
| 377 | 4-(5-chloro-6-(2-chloro-4-fluorophenoxy)-3-pyridinyl)-3-methoxy-N-(methylsulfonyl)benzamide | 485.32 | II and XI | L | 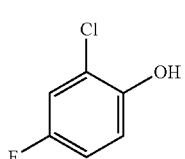 | |
| 379 | 4-(5-chloro-6-(5-chloro-2-methylphenoxy)-3-pyridinyl)-3-methoxy-N-(methylsulfonyl)benzamide | 481.35 | II and XI | L | 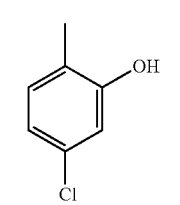 | |
| 382 | 4-(6-(3,5-dichlorophenoxy)-5-(difluoromethyl)-3-pyridinyl)-3-methoxy-N-(methylsulfonyl)benzamide | 517.33 | II and XI | L | 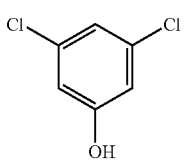 | |
| 402 | 4-(5-chloro-6-(2,3-difluorophenoxy)-3-pyridinyl)-3-methoxy-N-(methylsulfonyl)benzamide | 468.86 | II and XI | L | 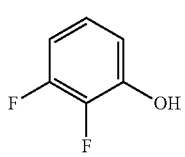 | |
| 566 | Mixture of 4-(5-chloro-6-((1R)-2,2,2-trifluoro-1-methyl-1-phenylethoxy)-3-pyridinyl)-2,5-difluoro-N-(methylsulfonyl)benzamide and 4-(5-chloro-6-((1S)-2,2,2-trifluoro-1-methyl-1-phenylethoxy)-3-pyridinyl)-2,5-difluoro-N-(methylsulfonyl)benzamide | 533.0 | II | C | 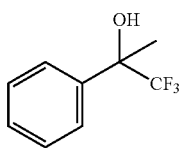 | |
| 567 | 4-(5-chloro-6-(2,4-dichloro-6-methylphenoxy)-3-pyridinyl)-2,5-difluoro-N-(methylsulfonyl)benzamide | 520 (neg) | II | C | 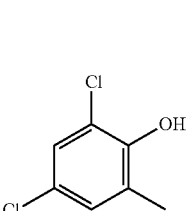 | |
| 568 | 4-(5-chloro-6-(2,4,6-trichlorophenoxy)-3-pyridinyl)-2,5-difluoro-N-(methylsulfonyl)benzamide | 540.8 | II | C | 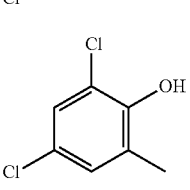 | |
| 569 | 4-(5-chloro-6-(2,3-difluoro-4-methylphenoxy)-3-pyridinyl)-2,5-difluoro-N-(methylsulfonyl)benzamide | 486.9 | II | C | 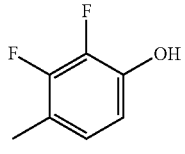 | |

TABLE A-continued

| EX. NO. | NAME | LCMS | METHODS | INTERMEDIATE | REAGENT | ¹H NMR DATA |
|---|---|---|---|---|---|---|
| 570 | 4-(5-chloro-6-(3,4-dichlorophenoxy)-3-pyridinyl)-2,5-difluoro-N-(methylsulfonyl)benzamide | 507.0 | II | C | 3,4-dichlorophenol | |
| 571 | 4-(5-chloro-6-(5-chloro-2-methylphenoxy)-3-pyridinyl)-2,5-difluoro-N-(methylsulfonyl)benzamide | 487.0 | II | C | 5-chloro-2-methylphenol | |
| 572 | 4-(5-chloro-6-(2,6-dichloro-4-fluorophenoxy)-3-pyridinyl)-2,5-difluoro-N-(methylsulfonyl)benzamide | 524.9 | II | C | 2,6-dichloro-4-fluorophenol | |
| 573 | 4-(5-chloro-6-((7-fluoro-2,3-dihydro-1H-inden-4-yl)oxy)-3-pyridinyl)-2,5-difluoro-N-(methylsulfonyl)benzamide | 477.0 | II | C | 7-fluoro-2,3-dihydro-1H-inden-4-ol | |
| 574 | 4-(5-chloro-6-((1R)-1-(2,4-difluorophenyl)ethoxy)-3-pyridinyl)-2,5-difluoro-N-(methylsulfonyl)benzamide | 503.0 | II | C | (1R)-1-(2,4-difluorophenyl)ethanol | |
| 575 | 4-(5-bromo-6-(2,4-dichloro-6-methylphenoxy)-3-pyridinyl)-2,5-difluoro-N-(methylsulfonyl)benzamide | 564.8 (neg) | II | U | 2,4-dichloro-6-methylphenol; and Example 559 (see priority document page 237) | |
| 576 | 4-(5-chloro-6-((4-chlorobenzyl)oxy)-3-pyridinyl)-3-methoxy-N-(methylsulfonyl)benzamide | 479.0 (−) | II and XI | L | (4-chlorophenyl)methanol | ¹H NMR (500 MHz, DMSO-d$_6$) δ ppm 2.88 (s, 3H) 3.82 (s, 3H) 5.48 (s, 2H) 7.34 (d, J = 7.80 Hz, 1H) 7.44-7.55 (m, 4H) 7.62 (d, J = 7.75 Hz, 1H) 7.67 (s, 1H) 8.07 (d, J = 2.04 Hz, 1H) 8.27 (d, J = 1.98 Hz, 1H) |
| 577 | 4-(5-chloro-6-((2-chlorobenzyl)oxy)-3-pyridinyl)-3-methoxy-N-(methylsulfonyl)benzamide | 479.0 (−) | II and XI | L | (2-chlorophenyl)methanol | |

TABLE A-continued

| EX. NO. | NAME | LCMS | METHODS | INTERMEDIATE | REAGENT | ¹H NMR DATA |
|---|---|---|---|---|---|---|
| 578 | 4-(5-chloro-6-(2,4-dichloro-6-methylphenoxy)-3-pyridinyl)-3-methoxy-N-(methylsulfonyl)benzamide | 514 (neg) | II and XI | L | 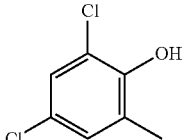 | 1H NMR (500 MHz, DMSO-d6) δ 8.24-8.28 (m, 1H), 8.15-8.19 (m, 1H) 7.66-7.70 (m 1H) 7.59-7.65 (m, 2H), 7.46-7.50 (m, 1H), 7.38-7.43 (m 1H) 3.84 (s, 3H) 3.01 (s, 3H), 2.15 (s, 3H) |
| 579 | 4-(5-chloro-6-(3-chloro-2-methylphenoxy)-3-pyridinyl)-3-methoxy-N-(methylsulfonyl)benzamide | 481.0 | II and XI | L | 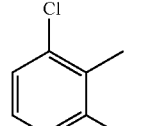 | 1H NMR (500 MHz, DMSO-d6) δ 8.20 (dd, J = 1.98, 19.43 Hz, 2H), 7.67 (s, 1H), 7.61 (dd, J = 1.07, 7.82 Hz, 1H), 7.29-7.42 (m, 3H), 7.18 (d, J = 8.04 Hz, 1H), 3.82 (s, 3H), 2.88 (s, 3H), 2.16 (s, 3H) |
| 580 | 4-(5-chloro-6-(2,3-dihydro-1H-inden-5-yloxy)-3-pyridinyl)-3-methoxy-N-(methylsulfonyl)benzamide | 473.0 | II and XI | L | 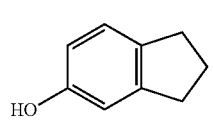 | |
| 581 | 4-(5-chloro-6-(2,6-dichlorophenoxy)-3-pyridinyl)-3-methoxy-N-(methylsulfonyl)benzamide | 501.0 | II and XI | L |  | |
| 582 | 4-(5-chloro-6-(2,5-dichlorophenoxy)-3-pyridinyl)-3-methoxy-N-(methylsulfonyl)benzamide | 503.0 | II and XI | L | 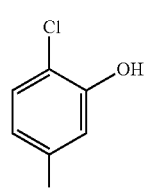 | |
| 583 | 4-(5-chloro-6-(2,3-dichlorophenoxy)-3-pyridinyl)-3-methoxy-N-(methylsulfonyl)benzamide | 503.0 | II and XI | L | 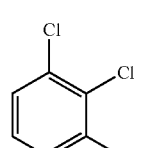 | ¹H NMR (500 MHz, DMSO-d6) δ ppm 2.94 (s, 3H), 3.79-3.88 (m, 3H), 7.38 (d, J = 7.96 Hz, 1H), 7.42-7.51 (m, 2H), 7.58-7.64 (m, 2H), 7.67 (s, 1H), 8.20 (d, J = 1.88 Hz, 1H), 8.25 (s, 1H). |
| 412 | 4-(5-chloro-6-((5-chloro-6-methoxy-3-pyridinyl)oxy)-3-pyridinyl)-N-(methylsulfonyl)-3-(3-oxetanyloxy)benzamide | 540.38 | II and XII | M | 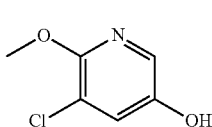 | |
| 413 | 4-(5-chloro-6-(4-chloro-3-methylphenoxy)-3-pyridinyl)-N-(methylsulfonyl)-3-(3-oxetanyloxy)benzamide | 523.39 | II and XII | M | 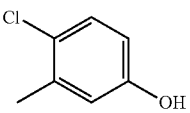 | |
| 419 | 4-(5-chloro-6-(1-naphthalenyloxy)-3-pyridinyl)-N-(methylsulfonyl)-3-(3-oxetanyloxy)benzamide | 524.98 | II and XII | M | 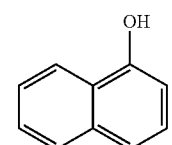 | |
| 422 | 4-(5-chloro-6-(3,5-dichlorophenoxy)-3-pyridinyl)-N-(methylsulfonyl)-3-(3-oxetanyloxy)benzamide | 543.81 | II and XII | M | 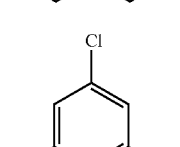 | |

TABLE A-continued

| EX. NO. | NAME | LCMS | METH-ODS | INTER-MEDI-ATE | REAGENT | ¹H NMR DATA |
|---|---|---|---|---|---|---|
| 423 | 4-(5-chloro-6-(2-chloro-5-methylphenoxy)-3-pyridinyl)-N-(methylsulfonyl)-3-(3-oxetanyloxy)benzamide | 523.39 | II and XII | M | | |
| 424 | 4-(5-chloro-6-(2-naphthalenyloxy)-3-pyridinyl)-N-(methylsulfonyl)-3-(3-oxetanyloxy)benzamide | 524.98 | II and XII | M | | |
| 425 | 4-(5-chloro-6-(3-chloro-4-methylphenoxy)-3-pyridinyl)-N-(methylsulfonyl)-3-(3-oxetanyloxy)benzamide | 523.39 | II and XII | M | | |
| 426 | 4-(5-chloro-6-(2-chloro-6-methylphenoxy)-3-pyridinyl)-N-(methylsulfonyl)-3-(3-oxetanyloxy)benzamide | 523.39 | II and XII | M | | |
| 584 | 4-(5-chloro-6-(2,4-dichloro-6-methylphenoxy)-3-pyridinyl)-N-(methylsulfonyl)-3-(3-oxetanyloxy)benzamide | 555 (neg) | II and XII | M | | |
| 436 | 4-(5-chloro-6-((5-chloro-6-methoxy-3-pyridinyl)oxy)-3-pyridinyl)-3-(difluoromethoxy)-N-(methylsulfonyl)benzamide | 534.32 | II and XIII | N | | |
| 446 | 4-(5-chloro-6-(2-naphthalenyloxy)-3-pyridinyl)-3-(difluoromethoxy)-N-(methylsulfonyl)benzamide | 518.92 | II and XIII | N | | |
| 449 | 4-(5-chloro-6-(3-chloro-4-methylphenoxy)-3-pyridinyl)-3-(difluoromethoxy)-N-(methylsulfonyl)benzamide | 517.33 | II and XIII | N | | |
| 452 | 4-(5-chloro-6-(1-naphthalenyloxy)-3-pyridinyl)-3-(difluoromethoxy)-N-(methylsulfonyl)benzamide | 518.92 | II and XIII | N | | |
| 453 | 4-(5-chloro-6-(4-chloro-3-methylphenoxy)-3-pyridinyl)-3-(difluoromethoxy)-N-(methylsulfonyl)benzamide | 517.33 | II and XIII | N | | |
| 455 | 4-(5-chloro-6-((1R)-1-phenylethoxy)-3-pyridinyl)-3-(difluoromethoxy)-N-(methylsulfonyl)benzamide | 496.92 | II and XIII | N | | |

TABLE A-continued

| EX. NO. | NAME | LCMS | METHODS | INTERMEDIATE | REAGENT | ¹H NMR DATA |
|---|---|---|---|---|---|---|
| 456 | 4-(5-chloro-6-(3-(trifluoromethyl)phenoxy)-3-pyridinyl)-3-(difluoromethoxy)-N-(methylsulfonyl)benzamide | 536.86 | II and XIII | N | | |
| 457 | 4-(5-chloro-6-((1S)-1-phenylethoxy)-3-pyridinyl)-3-(difluoromethoxy)-N-(methylsulfonyl)benzamide | 496.92 | II and XIII | N | | |
| 459 | 4-(5-chloro-6-(3,4-dimethylphenoxy)-3-pyridinyl)-3-(difluoromethoxy)-N-(methylsulfonyl)benzamide | 496.92 | II and XIII | N | | |
| 460 | 4-(5-chloro-6-(4-chloro-3-fluorophenoxy)-3-pyridinyl)-3-(difluoromethoxy)-N-(methylsulfonyl)benzamide | 521.3 | II and XIII | N | | |
| 461 | 4-(5-chloro-6-(3,5-dichlorophenoxy)-3-pyridinyl)-3-(difluoromethoxy)-N-(methylsulfonyl)benzamide | 537.75 | II and XIII | N | | |
| 462 | 4-(5-chloro-6-(2-chloro-5-methylphenoxy)-3-pyridinyl)-3-(difluoromethoxy)-N-(methylsulfonyl)benzamide | 517.33 | II and XIII | N | | |
| 464 | 4-(5-chloro-6-(2-(trifluoromethyl)phenoxy)-3-pyridinyl)-3-(difluoromethoxy)-N-(methylsulfonyl)benzamide | 536.86 | II and XIII | N | | |
| 465 | 4-(5-chloro-6-(2-chloro-4-methylphenoxy)-3-pyridinyl)-3-(difluoromethoxy)-N-(methylsulfonyl)benzamide | 517.33 | II and XIII | N | | |
| 466 | 4-(5-chloro-6-(4-chlorophenoxy)-3-pyridinyl)-3-(difluoromethoxy)-N-(methylsulfonyl)benzamide | 503.31 | II and XIII | N | | |
| 467 | 4-(5-chloro-6-(2-phenylethoxy)-3-pyridinyl)-3-(difluoromethoxy)-N-(methylsulfonyl)benzamide | 496.92 | II and XIII | N | | |

TABLE A-continued

| EX. NO. | NAME | LCMS | METHODS | INTER-MEDIATE | REAGENT | $^1$H NMR DATA |
|---|---|---|---|---|---|---|
| 468 | 4-(5-chloro-6-(2-chloro-6-methylphenoxy)-3-pyridinyl)-3-(difluoromethoxy)-N-(methylsulfonyl)benzamide | 517.33 | II and XIII | N | 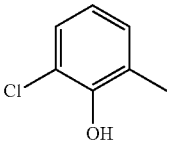 | |
| 585 | 4-(5-chloro-6-(2,4-dichloro-6-methylphenoxy)-3-pyridinyl)-3-(difluoromethoxy)-N-(methylsulfonyl)benzamide | 550 (neg) | II and XIII | N | 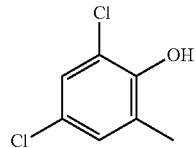 | |
| 586 | 4-(5-chloro-6-(3-chloro-2-methylphenoxy)-3-pyridinyl)-3-(difluoromethoxy)-N-(methylsulfonyl)benzamide | 517, 519, | II and XIII | N | 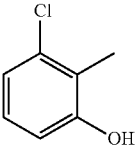 | |
| 587 | Mixture of 4-(5-chloro-6-((1R)-2,2,2-trifluoro-1-methyl-1-phenylethoxy)-3-pyridinyl)-2-fluoro-5-methyl-N-(methylsulfonyl)benzamide and (5-chloro-6-((1S)-2,2,2-trifluoro-1-methyl-1-phenylethoxy)-3-pyridinyl)-2-fluoro-5-methyl-N-(methylsulfonyl)benzamide | 533.0 | II and XIX | W | 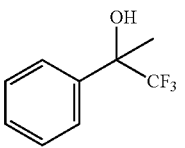 | $^1$H NMR (500 MHz, DMSO-$d_6$) δ ppm 2.14 (s, 3H) 2.30 (s, 3H) 2.99 (s, 3H) 7.04 (s, 1H) 7.06 (s, 1H) 7.25-7.45 (m, 3H) 7.45-7.50 (m, 2H) 7.55 (d, J = 7.53 Hz, 1H) 7.88 (d, J = 2.08 Hz, 1H) 8.08 d, J = 2.14 Hz, 1H) |
| 588 | 5-chloro-4-(5-chloro-6-(2,3,4-trifluorophenoxy)-3-pyridinyl)-2-fluoro-N-(methylsulfonyl)benzamide | 506.8 (−) | II and XIX | W | 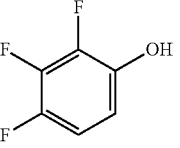 | $^1$H NMR (500 MHz, DMSO-$d_6$) δ ppm 2.99 (s, 3H) 7.37-7.50 (m, 3H) 7.84 (d, J = 6.62 Hz, 1H) 8.20 (d, J = 2.01 Hz, 1H) 8.32 (d, J = 2.08 Hz, 1H) |
| 589 | 5-chloro-4-(5-chloro-6-(2,3,5-trifluorophenoxy)-3-pyridinyl)-2-fluoro-N-(methylsulfonyl)benzamide | 506.9 (−) | II and XIX | W | 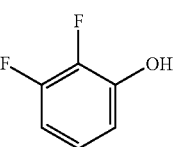 | $^1$H NMR (500 MHz, DMSO-$d_6$) δ ppm 2.91 (s, 3H) 7.38-7.47 (m, 2H) 7.55 (br. s., 1H) 7.82 (d, J = 6.68 Hz, 1H) 8.22 (d, J = 2.01 Hz, 1H) 8.33 (d, J = 2.01 Hz, 1H) |
| 590 | 5-chloro-4-(5-chloro-6-(5-chloro-2-methylphenoxy)-3-pyridinyl)-2-fluoro-N-(methylsulfonyl)benzamide | 500.8 (−) | II and XIX | W | 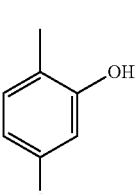 | $^1$H NMR (500 MHz, DMSO-$d_6$) δ ppm 2.09 (s, 3H) 2.87 (s, 3H) 7.08 (br. s., 1H) 7.28 (dd, J = 8.17, 2.01 Hz, 1H) 7.32-7.42 (m, 3H) 7.81 (d, J = 6.75 Hz, 1H) 8.17 (d, J = 2.08 Hz, 1H) 8.27 (d, J = 2.08 Hz, 1H) |
| 591 | 5-chloro-4-(5-chloro-6-(3-fluoro-4-methylphenoxy)-3-pyridinyl)-2-fluoro-N-(methylsulfonyl)benzamide | 485.0 (−) | II and XIX | W | 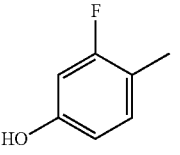 | |

TABLE A-continued

| EX. NO. | NAME | LCMS | METHODS | INTERMEDIATE | REAGENT | $^1$H NMR DATA |
|---|---|---|---|---|---|---|
| 592 | 5-chloro-4-(5-chloro-6-(2,6-dichlorophenoxy)-3-pyridinyl)-2-fluoro-N-(methylsulfonyl)benzamide | 522.8 (−) | II and XIX | W | 2,6-dichlorophenol | $^1$H NMR (500 MHz, DMSO-d$_6$) δ ppm 2.85 (s, 3H) 7.35-7.43 (m, 2H) 7.65 (d, J = 8.17 Hz, 2H) 7.80 (d, J = 6.75 Hz, 1H) 8.16 (d, J = 2.01 Hz, 1H) 8.32 (d, J = 2.08 Hz, 1H) |
| 593 | Mixture of 4-(6-(((1R)-1-benzylpropyl)oxy)-5-chloro-3-pyridinyl)-5-chloro-2-fluoro-N-(methylsulfonyl)benzamide and 4-(6-(((1S)-1-benzylpropyl)oxy)-5-chloro-3-pyridinyl)-5-chloro-2-fluoro-N-(methylsulfonyl)benzamide | 509.0 (−) | II and XIX | W | 1-phenylbutan-2-ol | |
| 594 | Mixture of 5-chloro-4-(5-chloro-6-(((1R)-2-methyl-1-phenylpropyl)oxy)-3-pyridinyl)-2-fluoro-N-(methylsulfonyl)benzamide and 5-chloro-4-(5-chloro-6-(((1S)-2-methyl-1-phenylpropyl)oxy)-3-pyridinyl)-2-fluoro-N-(methylsulfonyl)benzamide | 509.0 (−) | II and XIX | W | 2-methyl-1-phenylpropan-1-ol | |
| 595 | 5-chloro-4-(5-chloro-6-(2-chloro-5-fluorophenoxy)-3-pyridinyl)-2-fluoro-N-(methylsulfonyl)benzamide | 506.8 (−) | II and XIX | W | 2-chloro-5-fluorophenol | $^1$H NMR (500 MHz, DMSO-d$_6$) δ ppm 2.86 (s, 3 H) 7.26 (td, J = 8.51, 2.95 Hz, 1 H) 7.37 (d, J = 10.51 Hz, 1H) 7.53 (dd, J = 9.15, 2.92 Hz, 1H) 7.68 (dd, J = 8.92, 5.81 Hz, 1H) 7.81 (d, J = 6.75 Hz, 1H) 8.19 (d, J = 2.01 Hz, 1H) 8.30 (d, J = 2.08 Hz, 1H) |
| 596 | Mixture of 5-chloro-4-(5-chloro-6-(41R)-1-(4-fluorophenyl)propyl)oxy)-3-pyridinyl)-2-fluoro-N-(methylsulfonyl)benzamide and 5-chloro-4-(5-chloro-6-(((1S)-1-(4-fluorophenyl)propyl)oxy)-3-pyridinyl)-2-fluoro-N-(methylsulfonyl)benzamide | 513.0 (−) | II and XIX | W | 1-(4-fluorophenyl)propan-1-ol | |
| 597 | 5-chloro-4-(5-chloro-6-(2,5-difluorophenoxy)-3-pyridinyl)-2-fluoro-N-(methylsulfonyl)benzamide | 488.8 (−) | II and XIX | W | 2,5-difluorophenol | $^1$H NMR (500 MHz, DMSO-d$_6$) δ ppm 2.86 (s, 3H) 7.18-7.26 (m, 1H) 7.37 (d, J = 10.51 Hz, 1H) 7.44-7.55 (m, 2H) 7.81 (d, J = 6.75 Hz, 1H) 8.19 (d, J = 2.01 Hz, 1H) 8.29 (d, J = 2.01 Hz, 1H) |
| 598 | 5-chloro-4-(5-chloro-6-(2,4-dichloro-6-methylphenoxy)-3-pyridinyl)-2-fluoro-N-(methylsulfonyl)benzamide | 536.8 (−) | II and XIX | W | 2,4-dichloro-6-methylphenol | $^1$H NMR (500 MHz, DMSO-d$_6$) δ ppm 2.15 (s, 3H) 2.89 (s, 3H) 7.40 (d, J = 10.51 Hz, 1H) 7.45-7.54 (m, 1H) 7.63 (d, J = 2.14 Hz, 1H) 7.81 (d, J = 6.68 Hz, 1H) 8.15 (d, J = 2.01 Hz, 1H) 8.30 (d, J = 2.01 Hz, 1H) |
| 599 | 5-chloro-4-(5-chloro-6-(2-chloro-3,5-difluorophenoxy)-3-pyridinyl)-2-fluoro-N-(methylsulfonyl)benzamide | 524.8 (−) | II and XIX | W | 2-chloro-3,5-difluorophenol | |
| 600 | 5-chloro-4-(5-chloro-6-(cyclopentylmethoxy)-3-pyridinyl)-2-fluoro-N-(methylsulfonyl)benzamide | 461.0 | II and XIX | W | cyclopentylmethanol | |

TABLE A-continued

| EX. NO. | NAME | LCMS | METHODS | INTERMEDIATE | REAGENT | ¹H NMR DATA |
|---|---|---|---|---|---|---|
| 601 | 5-chloro-4-(5-chloro-6-(1-ethylpropoxy)-3-pyridinyl)-2-fluoro-N-(methylsulfonyl)benzamide | 447 (neg) | II and XIX | W | pentan-3-ol | |
| 602 | 5-chloro-4-(5-chloro-6-((1-methylcyclobutyl)oxy)-3-pyridinyl)-2-fluoro-N-(methylsulfonyl)benzamide | 445 (neg) | II and XIX | W | 1-methylcyclobutanol | |
| 603 | 4-(5-chloro-6-(2,4-difluorophenoxy)-3-pyridinyl)-2-fluoro-5-methyl-N-(methylsulfonyl)benzamide | 469.0 (−) | II and XV | P | 2,4-difluorophenol | |
| 604 | 4-(5-chloro-6-(2,3-difluorophenoxy)-3-pyridinyl)-2-fluoro-5-methyl-N-(methylsulfonyl)benzamide | 469.0 (−) | II and XV | P | 2,3-difluorophenol | |
| 605 | 4-(5-chloro-6-(2,5-difluorophenoxy)-3-pyridinyl)-2-fluoro-5-methyl-N-(methylsulfonyl)benzamide | 469.0 (−) | II and XV | P | 2,5-difluorophenol | ¹H NMR (500 MHz, DMSO-d₆) δ ppm 2.26 (s, 3H) 3.37 (s, 3H) 7.22 (t, J = 8.62 Hz, 1H) 7.35 (d, J = 10.86 Hz, 1H) 7.43-7.53 (m, 2H) 7.63 (d, J = 7.18 Hz, 1H) 8.14 (d, J = 1.92 Hz, 1H) 8.25 (d, J = 1.98 Hz, 1H) 12.28 (br. s., 1H) |
| 606 | 4-(6-(4-bromo-2-chloro-5-fluorophenoxy)-5-chloro-3-pyridinyl)-2-fluoro-5-methyl-N-(methylsulfonyl)benzamide | 564.8 (−) | II and XV | P | 4-bromo-2-chloro-5-fluorophenol | |
| 607 | 4-(6-(3-bromophenoxy)-5-chloro-3-pyridinyl)-2-fluoro-5-methyl-N-(methylsulfonyl)benzamide | 512.9 (−) | II and XV | P | 3-bromophenol | |
| 608 | 4-(5-chloro-6-((2-methyl-1-naphthalenyl)oxy)-3-pyridinyl)-2-fluoro-5-methyl-N-(methylsulfonyl)benzamide | 497.0 | II and XV | P | 2-methylnaphthalen-1-ol | |
| 609 | 4-(6-(4-bromophenoxy)-5-chloro-3-pyridinyl)-2-fluoro-5-methyl-N-(methylsulfonyl)benzamide | 513.0 (−) | II and XV | P | 4-bromophenol | |

| EX. NO. | NAME | LCMS | METHODS | INTER-MEDIATE | REAGENT | ¹H NMR DATA |
|---|---|---|---|---|---|---|
| 610 | 4-(5-chloro-6-(5,6,7,8-tetrahydro-1-naphthalenyloxy)-3-pyridinyl)-2-fluoro-5-methyl-N-(methylsulfonyl)benzamide | 487.0 | II and XV | P | | |
| 611 | 4-(6-(4-tert-butyl-2-chlorophenoxy)-5-chloro-3-pyridinyl)-2-fluoro-5-methyl-N-(methylsulfonyl)benzamide | 523.0 (−) | II and XV | P | | |
| 612 | 4-(6-(2-biphenylyloxy)-5-chloro-3-pyridinyl)-2-fluoro-5-methyl-N-(methylsulfonyl)benzamide | 509.0 (−) | II and XV | P | | |
| 613 | 4-(5-chloro-6-((4-chloro-1-naphthalenyl)oxy)-3-pyridinyl)-2-fluoro-5-methyl-N-(methylsulfonyl)benzamide | 517.0 (−) | II and XV | P | | |
| 614 | 4-(6-(4-bromo-2-methylphenoxy)-5-chloro-3-pyridinyl)-2-fluoro-5-methyl-N-(methylsulfonyl)benzamide | 526.8 (−) | II and XV | P | | |
| 615 | 4-(5-chloro-6-(2,3,4-trifluorophenoxy)-3-pyridinyl)-2-fluoro-5-methyl-N-(methylsulfonyl)benzamide | 487.0 (−) | II and XV | P | | ¹H NMR (500 MHz, DMSO-d₆) δ ppm 2.20 (s, 3H) 2.85 (s, 3H) 7.05 (d, J = 10.97 Hz, 1H) 7.32-7.48 (m, 2H) 7.59 (d, J = 7.58 Hz, 1H) 8.10 (d, J = 2.04 Hz, 1H) 8.21 (d, J = 1.98 Hz, 1H) |
| 616 | 4-(5-chloro-6-(5-chloro-2-methylphenoxy)-3-pyridinyl)-2-fluoro-5-methyl-N-(methylsulfonyl)benzamide | 481.0 (−) | II and XV | P | | |
| 617 | 4-(5-chloro-6-(5-chloro-2-fluorophenoxy)-3-pyridinyl)-2-fluoro-5-methyl-N-(methylsulfonyl)benzamide | 485.0 (−) | II and XV | P | | |
| 618 | 4-(5-chloro-6-(2-fluoro-3-methylphenoxy)-3-pyridinyl)-2-fluoro-5-methyl-N-(methylsulfonyl)benzamide | 465.0 (−) | II and XV | P | | |

TABLE A-continued

| EX. NO. | NAME | LCMS | METHODS | INTERMEDIATE | REAGENT | ¹H NMR DATA |
|---|---|---|---|---|---|---|
| 619 | 4-(5-chloro-6-(3-chloro-2-fluorophenoxy)-3-pyridinyl)-2-fluoro-5-methyl-N-(methylsulfonyl)benzamide | 484.8 (−) | II and XV | P | 3-chloro-2-fluorophenol | |
| 620 | 4-(5-chloro-6-(4-chloro-2-methylphenoxy)-3-pyridinyl)-2-fluoro-5-methyl-N-(methylsulfonyl)benzamide | 481.0 (−) | II and XV | P | 4-chloro-2-methylphenol | ¹H NMR (500 MHz, DMSO-$d_6$) δ ppm 2.11 (s, 3H) 2.22 (s, 3H) 2.97 (s, 3 H) 7.11 (d, J = 10.97 Hz, 1H) 7.21 (d, J = 8.59 Hz, 1H) 7.32 (dd, J = 8.59, 2.37 Hz, 1H) 7.44 (d, J = 2.09 Hz, 1H) 7.59 (d, J = 7.52 Hz, 1H) 8.06 (d, J = 2.04 Hz, 1H) 8.17 (d, J = 2.04 Hz, 1H) |
| 621 | 4-(5-chloro-6-(3-methylphenoxy)-3-pyridinyl)-2-fluoro-5-methyl-N-(methylsulfonyl)benzamide | 447.0 (−) | II and XV | P | 3-methylphenol | |
| 622 | 4-(5-chloro-6-(2,4,6-trifluorophenoxy)-3-pyridinyl)-2-fluoro-5-methyl-N-(methylsulfonyl)benzamide | 487.0 | II and XV | P | 2,4,6-trifluorophenol | |
| 623 | 4-(5-chloro-6-(3-fluoro-4-methylphenoxy)-3-pyridinyl)-2-fluoro-5-methyl-N-(methylsulfonyl)benzamide | 465.0 (−) | II and XV | P | 3-fluoro-4-methylphenol | ¹H NMR (500 MHz, DMSO-$d_6$) δ ppm 2.25 (s, 3H) 2.22 (s, 3H) 2.87 (s, 3H) 6.98 (dd, J = 8.26, 2.04 Hz, 1H) 7.01-7.17 (m, 2H) 7.34 (t, J = 8.57 Hz, 1H) 7.59 (d, J = 7.58 Hz, 1H) 8.09 (d, J = 2.04 Hz, 1H) 8.15 (d, J = 2.04 Hz, 1H) |
| 624 | 4-(6-(2-tert-butyl-5-methylphenoxy)-5-chloro-3-pyridinyl)-2-fluoro-5-methyl-N-(methylsulfonyl)benzamide | 503.0 (−) | II and XV | P | 2-tert-butyl-5-methylphenol | |
| 625 | 4-(5-chloro-6-(3-chloro-2,6-difluorophenoxy)-3-pyridinyl)-2-fluoro-5-methyl-N-(methylsulfonyl)benzamide | 502.8 (−) | II and XV | P | 3-chloro-2,6-difluorophenol | |
| 626 | 4-(5-chloro-6-(3-chloro-4-fluorophenoxy)-3-pyridinyl)-2-fluoro-5-methyl-N-(methylsulfonyl)benzamide | 486.9 | II and XV | P | 3-chloro-4-fluorophenol | |
| 627 | 4-(5-chloro-6-(2,6-dichlorophenoxy)-3-pyridinyl)-2-fluoro-5-methyl-N-(methylsulfonyl)benzamide | 502.9 | II and XV | P | 2,6-dichlorophenol | ¹H NMR (500 MHz, DMSO-$d_6$) δ ppm 2.25 (s, 3H) 3.35 (s, 3H) 7.26-7.45 (m 2H) 7.57-7.69 (m, 3 H) 8.12 (d, J = 1.98 Hz, 1H) 8.27 (d, J = 1.98 Hz, 1H) 12.29 (br. s., 1H) |

TABLE A-continued

| EX. NO. | NAME | LCMS | METHODS | INTERMEDIATE | REAGENT | ¹H NMR DATA |
|---|---|---|---|---|---|---|
| 628 | 4-(5-chloro-6-(2,4-dichloro-6-methylphenoxy)-3-pyridinyl)-2-fluoro-5-methyl-N-(methylsulfonyl)benzamide | 516.9 | II and XV | P | 2-methyl-4,6-dichlorophenol | ¹H NMR (500 MHz, DMSO-d$_6$) δ ppm 2.15 (s, 3 H) 2.26 (s, 3H) 3.37 (s, 3H) 7.36 (d, J = 10.91 Hz, 1H) 7.49 (d, J = 1.81 Hz, 1H) 7.59-7.65 (m, 2H) 8.09 (d, J = 2.04 Hz, 1H) 8.25 (d, J = 2.04 Hz, 1H) 12.28 (br. s., 1H) |
| 629 | 4-(5-chloro-6-(2,3,5-trifluorophenoxy)-3-pyridinyl)-2-fluoro-5-methyl-N-(methylsulfonyl)benzamide | 488.9 | II and XV | P | 2,3,5-trifluorophenol | ¹H NMR (500 MHz, DMSO-d$_6$) δ ppm 2.27 (s, 3H) 3.37 (s, 3H) 7.36 (d, J = 10.86 Hz, 1H) 7.43 (dd, J = 5.60, 3.39 Hz, 1H) 7.51-7.61 (m, 1H) 7.64 (d, J = 7.12 Hz, 1H) 8.17 (d, J = 2.04 Hz, 1H) 8.28 (d, J = 2.04 Hz, 1H) 12.29 (br. s., 1H) |
| 630 | 4-(5-chloro-6-(3,5-difluorophenoxy)-3-pyridinyl)-2-fluoro-5-methyl-N-(methylsulfonyl)benzamide | 471.0 | II an XV | P | 3,5-difluorophenol | ¹H NMR (500 MHz, DMSO-d$_6$) δ ppm 2.28 (s, 3H) 3.37 (s, 3H) 7.08-7.20 (m, 3H) 7.33 (d, J = 10.86 Hz, 1H) 7.64 (d, J = 7.18 Hz, 1H) 8.18 (d, J = 2.09 Hz, 1H) 8.24 (d, J = 2.04 Hz, 1H) 12.28 (br. s., 1H) |
| 631 | 4-(5-chloro-6-(2-chloro-3,5-difluorophenoxy)-3-pyridinyl)-2-fluoro-5-methyl-N-(methylsulfonyl)benzamide | 504.9 | II and XV | P | 2-chloro-3,5-difluorophenol | |
| 632 | 4-(5-chloro-6-(2-chloro-4,5-dimethylphenoxy)-3-pyridinyl)-2-fluoro-5-methyl-N-(methylsulfonyl)benzamide | 496.9 | II and XV | P | 2-chloro-4,5-dimethylphenol | |
| 633 | 4-(6-(2-tert-butyl-6-methylphenoxy)-5-chloro-3-pyridinyl)-2-fluoro-5-methyl-N-(methylsulfonyl)benzamide | 505.0 | II and XV | P | 2-tert-butyl-6-methylphenol | |
| 634 | 4-(6-(2-tert-butyl-4-methylphenoxy)-5-chloro-3-pyridinyl)-2-fluoro-5-methyl-N-(methylsulfonyl)benzamide | 505.0 | II and XV | P | 2-tert-butyl-4-methylphenol | |
| 635 | 4-(6-4-((1R,2S,4S)-bicyclo[2.2.1]hept-2-yloxy)-5-chloro-3-pyridinyl)-2-fluoro-5-methyl-N-(methylsulfonyl)benzamide | 451.0 (−) | II and XV | P | bicyclo[2.2.1]heptan-2-ol | |
| 636 | 4-(6-(1,3-benzothiazol-2-ylmethoxy)-5-chloro-3-pyridinyl)-2-fluoro-5-methyl-N-(methylsulfonyl)benzamide | 504.0 (−) | II and XV | P | benzothiazol-2-ylmethanol | |

TABLE A-continued

| EX. NO. | NAME | LCMS | METHODS | INTER-MEDIATE | REAGENT | ¹H NMR DATA |
|---|---|---|---|---|---|---|
| 637 | 4-(5-chloro-6-(3-methylbutoxy)-3-pyridinyl)-2-fluoro-5-methyl-N-(methylsulfonyl)benzamide | 427.0 (−) | II and XV | P | 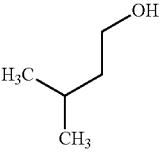 | |
| 638 | Mixture of 4-(5-chloro-6-(((1R)-1-methyl-3-phenylpropyl)oxy)-3-pyridinyl)-2-fluoro-5-methyl-N-(methylsulfonyl)benzamide and 4-(5-chloro-6-(((1S)-1-methyl-3-phenylpropyl)oxy)-3-pyridinyl)-2-fluoro-5-methyl-N-(methylsulfonyl)benzamide | 489.0 (−) | II and XV | P | 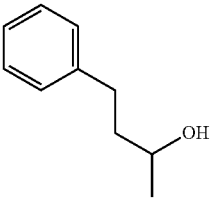 | |
| 639 | Mixture of 4-(5-chloro-6-(((1R)-1-(4-fluorophenyl)propyl)oxy)-3-pyridinyl)-2-fluoro-5-methyl-N-(methylsulfonyl)benzamide and 4-(5-chloro-6-(((1S)-1-(4-fluorophenyl)propyl)oxy)-3-pyridinyl)-2-fluoro-5-methyl-N-(methylsulfonyl)benzamide | 493.0 (−) | II and XV | P | 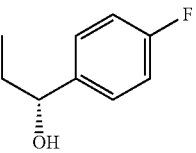 | |
| 640 | Mixture of 4-(5-chloro-6-(((1R)-1-(4-chlorophenyl)propyl)oxy)-3-pyridinyl)-2-fluoro-5-methyl-N-(methylsulfonyl)benzamide and 4-(5-chloro-6-(((1S)-1-(4-chlorophenyl)propyl)oxy)-3-pyridinyl)-2-fluoro-5-methyl-N-(methylsulfonyl)benzamide | 509.0 (−) | II and XV | P | 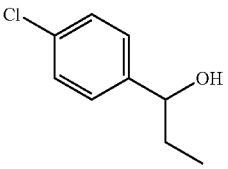 | |
| 641 | Mixture of 4-(5-chloro-6-((1R)-1-cyclobutylethoxy)-3-pyridinyl)-2-fluoro-5-methyl-N-(methylsulfonyl)benzamide and 4-(5-chloro-6-((1S)-1-cyclobutylethoxy)-3-pyridinyl)-2-fluoro-5-methyl-N-(methylsulfonyl)benzamide | 439.0 (−) | II and XV | P | 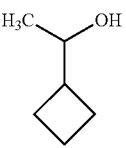 | |
| 642 | 4-(5-chloro-6-(2-chloro-5-(trifluoromethyl)phenoxy)-3-pyridinyl)-2-fluoro-5-methyl-N-(methylsulfonyl)benzamide | 535.0 (−) | II and XV | P | 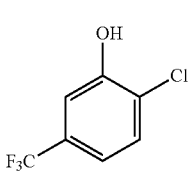 | ¹H NMR (500 MHz, DMSO-d₆) δ ppm 2.21 (s, 3H) 2.84 (s, 3H) 7.04 (d, J = 10.97 Hz, 1H) 7.59 (d, J = 7.58 Hz, 1H) 7.73 (d, J = 8.37 Hz, 1H) 7.89 (d, J = 8.42 Hz, 1H) 7.97 (s, 1H) 8.09 (d, J = 1.98 Hz, 1H) 8.21 (d, J = 2.04 Hz, 1H) |
| 643 | 4-(5-chloro-6-(2,3-difluoro-4-methylphenoxy)-3-pyridinyl)-2-fluoro-5-methyl-N-(methylsulfonyl)benzamide | 483.0 (−) | II and XV | P | 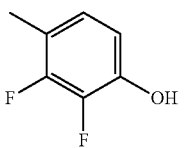 | ¹H NMR (500 MHz, DMSO-d₆) δ ppm 2.20 (s, 3H) 2.32 (s, 3H) 2.84 (s, 3H) 7.05 (d, J = 10.97 Hz, 1H) 7.13-7.22 (m, 2H) 7.59 (d, J = 7.63 Hz, 1H) 8.09 (d, J = 1.98 Hz, 1H) 8.19 (d, J = 2.04 Hz, 1H) |
| 644 | 4-(5-chloro-6-(2,6-dichloro-4-fluorophenoxy)-3-pyridinyl)-2-fluoro-5-methyl-N-(methylsulfonyl)benzamide | 518.9 (−) | II and XV | P | 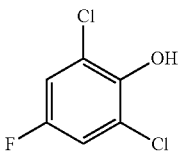 | ¹H NMR (500 MHz, DMSO-d₆) δ ppm 2.20 (s, 3H) 2.84 (s, 3H) 7.06 (d, J = 10.86 Hz, 1H) 7.58 (d, J = 7.63 Hz, 1H) 7.73 (d, J = 8.31 Hz, 2H) 8.08 (d, J = 1.98 Hz, 1H) 8.23 (d, J = 1.98 Hz, 1H) |
| 645 | 4-(5-chloro-6-(4-ethoxy-3-fluorophenoxy)-3-pyridinyl)-2-fluoro-5-methyl-N-(methylsulfonyl)benzamide | 495.0 (−) | II and XV | P | 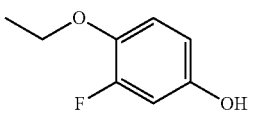 | |

TABLE A-continued

| EX. NO. | NAME | LCMS | METHODS | INTERMEDIATE | REAGENT | $^1$H NMR DATA |
|---|---|---|---|---|---|---|
| 646 | 4-(5-chloro-6-((2S)-2-phenyl-1-pyrrolidinyl)-3-pyridinyl)-2-fluoro-5-methyl-N-(methylsulfonyl)benzamide | | II and XV | P | 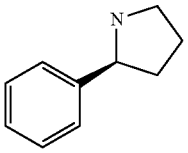 [SMILES: c1ccc([C@@H]2CCCN2)cc1] | |
| 647 | Mixture of 4-(6-((1R)-1-(1,3-benzothiazol-2-yl)ethoxy)-5-chloro-3-pyridinyl)-2-fluoro-5-methyl-N-(methylsulfonyl)benzamide and 4-(6-((1S)-1-(1,3-benzothiazol-2-yl)ethoxy)-5-chloro-3-pyridinyl)-2-fluoro-5-methyl-N-(methylsulfonyl)benzamide | 520.0 | II and XV | P | 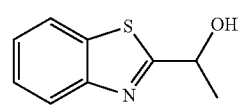 | |
| 648 | Mixture of 4-(5-chloro-6-(((1R)-1-(2-chlorophenyl)pentypoxy)-3-pyridinyl)-2-fluoro-5-methyl-N-(methylsulfonyl)benzamide and 4-(5-chloro-6-(((1S)-1-(2-chlorophenyl)pentyl)oxy)-3-pyridinyl)-2-fluoro-5-methyl-N-(methylsulfonyl)benzamide | 539.0 | II and XV | P | 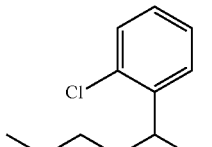 | $^1$H NMR (500 MHz, DMSO-d$_6$) δ ppm 0.83-0.92 (m, 3H) 1.29-1.51 (m, 4H) 1.90-2.00 (m, 2H) 2.20 (s, 3 H) 3.20 (s, 3 H) 6.47 (t, J = 6.47 Hz, 1H) 7.15-7.27 (m, 1H) H) 7.27-7.40 (m, 3H) 7.46 (d, J = 7.91 Hz, 1H) 7.49 (d, J = 7.79 Hz, 1 H) 7.53 - 7.63 (m, 1 H) 8.03 (d, J = 2.08 Hz, 1H) 8.06 (d, J = 2.01 Hz, 1H) |
| 649 | Mixture of 4-(5-chloro-6-((1R)-2-(2-methoxyphenyl)-1-methylethoxy)-3-pyridinyl)-2-fluoro-5-methyl-N-(methylsulfonyl)benzamide and 4-(5-chloro-6-((1S)-2-(2-methoxyphenyl)-1-methylethoxy)-3-pyridinyl)-2-fluoro-5-methyl-N-(methylsulfonyl)benzamide | 505.0 | II and XV | P | 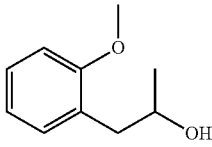 | |
| 650 | 4-(5-chloro-6-(((1R)-1-(4-fluorophenyl)propyl)oxy)-3-pyridinyl)-2-fluoro-5-methyl-N-(methylsulfonyl)benzamide | 493.0 | II and XV | P | 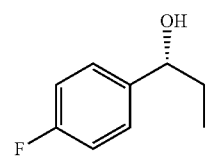 | $^1$H NMR (500 MHz, DMSO-d$_6$) δ ppm 0.91 (t, J = 7.33 Hz, 3H) 2.90-2.06 (m, 2H) 2.18 (s, 3H) 2.90 (s, 3H) 6.12 (t, J = 6.42 Hz, 1H) 7.01-7.03 (m, 1H) 7.06-7.14 (m, 1H) 7.19 (t, J = 8.39 Hz, 2H) 7.47 (dd, J = 8.47, 5.61 Hz, 2H) 7.53-7.64 (m, 1H) 7.98 (d, J = 2.01 Hz, 1H) 8.05 (d, J = 2.08 Hz, 1H) |
| 651 | 4-(5-chloro-6-(((1S)-1-(4-fluorophenyl)propyl)oxy)-3-pyridinyl)-2-fluoro-5-methyl-N-(methylsulfonyl)benzamide | 493.0 | II and XV | P | 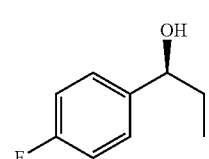 | $^1$H NMR (500 MHz, DMSO-d$_6$) δ ppm 0.87-0.96 (m, 3H) 1.87-2.05 (m, 2H) 2.18 (s, 3H) 2.91 (s, 3H) 6.12 (t, J = 6.46 Hz, 1H) 7.01-7.04 (m, 1H) 7.06-7.14 (m, 1H) 7.19 (t, J = 8.45 Hz, 2H) 7.47 (t, J = 6.76 Hz, 2H) 7.53-7.64 (m, 1H) 7.98 (d, J = 2.08 Hz, 1H) 8.05 (d, J = 2.08 Hz, 1H) |
| 652 | Mixture of 4-(5-chloro-6-((1R)-1-(2-chloro-4-fluorophenyl)ethoxy)-3-pyridinyl)-2-fluoro-5-methyl-N-(methylsulfonyl)benzamide and, 4-(5-chloro-6-((1S)-1-(2-chloro-4-fluorophenyl)ethoxy)-3-pyridinyl)-2-fluoro-5-methyl-N-(methylsulfonyl)benzamide | 515.0 | II and XV | P | 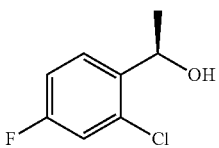 | $^1$H NMR (500 MHz, DMSO-d$_6$) δ ppm 1.63 (d, J = 6.49 Hz, 3H) 2.19 (s, 3H) 2.93 (s, 3H) 6.51 (q, J = 6.42 Hz, 1H) 7.03-7.06 (m, 1H) 7.13-7.35 (m, 1H) 7.47 (dd, J = 8.76, 2.53 Hz, 1H) 7.52-7.65 (m, 3H) 8.01 (d, J = 2.01 Hz, 1H) 8.09 (d, J = 2.01 Hz, 1H) |

TABLE A-continued

| EX. NO. | NAME | LCMS | METHODS | INTERMEDIATE | REAGENT | ¹H NMR DATA |
|---|---|---|---|---|---|---|
| 653 | Mixture of 4-(5-chloro-6-((1R)-1-(5-chloro-1,3-benzothiazol-2-yl)ethoxy)-3-pyridinyl)-2-fluoro-5-methyl-N-(methylsulfonyl)benzamide and 4-(5-chloro-6-((1S)-1-(5-chloro-1,3-benzothiazol-2-yl)ethoxy)-3-pyridinyl)-2-fluoro-5-methyl-N-(methylsulfonyl)benzamide | 554.0 | II and XV | P | 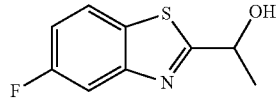 | |
| 654 | 4-(5-chloro-6-(5-quinolinylmethoxy)-3-pyridinyl)-2-fluoro-5-methyl-N-(methylsulfonyl)benzamide | 500.0 | II and XV | P | 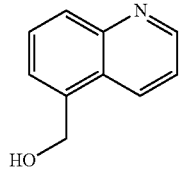 | |
| 655 | Mixture of 4-(5-chloro-6-((2R)-2-(3-(trifluoromethyl)phenyl)-1-pyrrolidinyl)-3-pyridinyl)-2-fluoro-5-methyl-N-(methylsulfonyl)benzamide and 4-(5-chloro-6-((2S)-2-(3-(trifluoromethyl)phenyl)-1-pyrrolidinyl)-3-pyridinyl)-2-fluoro-5-methyl-N-(methylsulfonyl)benzamide | 556.1 | II and XV | P | 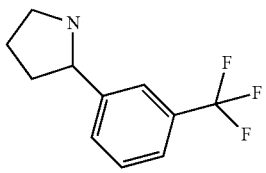 [SMILES: FC(F)(F)c1cccc(C2CCCN2)c1] | |
| 656 | Mixture of 4-(5-chloro-6-((2R)-2-(3-chlorophenyl)-1-pyrrolidinyl)-3-pyridinyl)-2-fluoro-5-methyl-N-(methylsulfonyl)benzamide and 4-(5-chloro-6-((2S)-2-(3-chlorophenyl)-1-pyrrolidinyl)-3-pyridinyl)-2-fluoro-5-methyl-N-(methylsulfonyl)benzamide | 522.0 | II and XV | P | 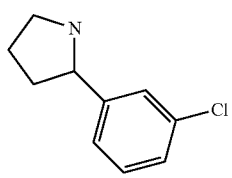 [SMILES: Clc1cccc(C2CCCN2)c1] | ¹H NMR (500 MHz, DMSO-d₆) δ ppm 1.72-1.82 (m, 1H) 1.85-2.03 (m, 2H) 2.21 (s, 3H) 2.39-2.45 (m, 1H) 3.19 (s, 3H) 3.52-3.73 (m, 1H) 4.12-4.22 (m, 1H) 5.47 (t, J = 7.43 Hz, 1H) 7.15 (d, J = 11.16 Hz, 1H) 7.23 (t, J = 8.33 Hz, 2H) 7.30 (t, J = 7.80 Hz, 2H) 7.49-7.65 (m, 1H) 7.75 (d, J = 2.01 Hz, 1H) 8.02 (d, J = 1.95 Hz, 1H) |
| 657 | Mixture of 4-(5-chloro-6-((2R)-2-(4-methylphenyl)-1-pyrrolidinyl)-3-pyridinyl)-2-fluoro-5-methyl-N-(methylsulfonyl)benzamide and 4-(5-chloro-6-((2S)-2-(4-methylphenyl)-1-pyrrolidinyl)-3-pyridinyl)-2-fluoro-5-methyl-N-(methylsulfonyl)benzamide | 502.2 | II and XV | P | 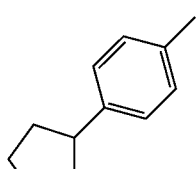 | |
| 658 | Mixture of 4-(5-chloro-6-((2R)-2-(3,4-dichlorophenyl)-1-pyrrolidinyl)-3-pyridinyl)-2-fluoro-5-methyl-N-(methylsulfonyl)benzamide and 4-(5-chloro-6-((2S)-2-(3,4-dichlorophenyl)-1-pyrrolidinyl)-3-pyridinyl)-2-fluoro-5-methyl-N-(methylsulfonyl)benzamide | 554.0 | II and XV | P | 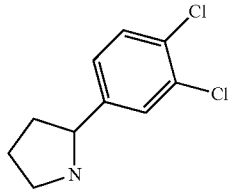 [SMILES: Clc1ccc(C2CCCN2)cc1Cl] | |
| 659 | Mixture of 4-(5-chloro-6-((2R)-2-(2-(trifluoromethyl)phenyl)-1-pyrrolidinyl)-3-pyridinyl)-2-fluoro-5-methyl-N-(methylsulfonyl)benzamide and 4-(5-chloro-6-((2S)-2-(2-(trifluoromethyl)phenyl)-1-pyrrolidinyl)-3-pyridinyl)-2-fluoro-5-methyl-N-(methylsulfonyl)benzamide | 556.0 | II and XV | P | 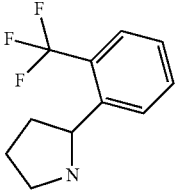 | |

TABLE A-continued

| EX. NO. | NAME | LCMS | METHODS | INTERMEDIATE | REAGENT | ¹H NMR DATA |
|---|---|---|---|---|---|---|
| 660 | Mixture of 4-(5-chloro-6-((1R)-1-(2,4,5-trifluorophenyl)ethoxy)-3-pyridinyl)-2-fluoro-5-methyl-N-(methylsulfonyl)benzamide and 4-(5-chloro-6-((1S)-1-(2,4,5-trifluorophenyl)ethoxy)-3-pyridinyl)-2-fluoro-5-methyl-N-(methylsulfonyl)benzamide | 515.0 | II and XV | P | 2,4,5-trifluoro-α-methylbenzyl alcohol | |
| 661 | Mixture of 4-(5-chloro-6-((1R)-1-(2,4,6-trifluorophenyl)ethoxy)-3-pyridinyl)-2-fluoro-5-methyl-N-(methylsulfonyl)benzamide and 4-(5-chloro-6-((1S)-1-(2,4,6-trifluorophenyl)ethoxy)-3-pyridinyl)-2-fluoro-5-methyl-N-(methylsulfonyl)benzamide | 515.0 | II and XV | P | 2,4,6-trifluoro-α-methylbenzyl alcohol | ¹H NMR (500 MHz, DMSO-d₆) δ ppm 1.74 (d, J = 6.68 Hz, 3H) 2.18 (s, 3H) 2.89 (s, 3H) 6.48 (q, J = 6.66 Hz, 1H) 7.02 (d, J = 4.97, 1H) 7.20 (t, J = 8.99 Hz, 2H) 7.57 (d, J = 7.59 Hz, 1H) 7.98 (d, J = 2.08 Hz, 1H) 8.07 (d, J = 2.08 Hz, 1H) |
| 662 | 4-(5-chloro-6-((7-methyl-2,3-dihydro-1H-inden-4-yl)oxy)-3-pyridinyl)-2-fluoro-5-methyl-N-(methylsulfonyl)benzamide | 487.0 | II and XV | P | 7-methyl-4-hydroxyindane | |
| 663 | 4-(5-chloro-6-(4-(1-methylethoxy)phenoxy)-3-pyridinyl)-2-fluoro-5-methyl-N-(methylsulfonyl)benzamide | 491.0 | II and XV | P | 4-isopropoxyphenol | |
| 664 | 4-(5-chloro-6-(3,4-dichlorophenoxy)-3-pyridinyl)-2-fluoro-5-methyl-N-(methylsulfonyl)benzamide | 502.8 | II and XV | P | 3,4-dichlorophenol | |
| 665 | 4-(5-chloro-6-(2,4-dichlorophenoxy)-3-pyridinyl)-2-fluoro-5-methyl-N-(methylsulfonyl)benzamide | 502.9 | II and XV | P | 2,4-dichlorophenol | ¹H NMR (500 MHz, DMSO-d₆) δ ppm 2.26 (s, 3H) 3.34 (s, 4H) 7.33 (d, J = 10.83 Hz, 1H) 7.47-7.57 (m, 2 H) 7.63 (d, J = 7.20 Hz, 1H) 7.82 (d, J = 2.40 Hz, 1H) 8.11 (d, J = 2.08 Hz, 1H) 8.24 (d, J = 2.01 Hz, 1H |
| 666 | 4-(5-chloro-6-(2-chloro-4,6-difluorophenoxy)-3-pyridinyl)-2-fluoro-5-methyl-N-(methylsulfonyl)benzamide | 504.8 | II and XV | P | 2-chloro-4,6-difluorophenol | ¹H NMR (500 MHz, DMSO-d₆) δ ppm 2.22 (s, 3H) 3.05 (s, 3H) 7.18 (s, 1H) 7.20 (s, J = 7.04, 7.04 Hz, 1H) 7.56-7.64 (m, 2H) 8.11 (d, J = 2.01 Hz, 1H) 8.25 (d, J = 2.01 Hz, 1H) |
| 667 | 4-(5-chloro-6-(2,4,5-trichlorophenoxy)-3-pyridinyl)-2-fluoro-5-methyl-N-(methylsulfonyl)benzamide | 536.8 | II and XV | P | 2,4,5-trichlorophenol | ¹H NMR (500 MHz, DMSO-d₆) δ ppm 2.24 (s, 3H) 3.11 (s, 3H) 7.20 (d, J = 10.77 Hz, 1H) 7.53-7.66 (m, 2H) 7.95 (s, 1H) 8.07 (s, 1H) 8.12 (d, J = 2.08 Hz, 1H) 8.24 (d, J = 2.01 Hz, 1H) |

TABLE A-continued

| EX. NO. | NAME | LCMS | METHODS | INTERMEDIATE | REAGENT | $^1$H NMR DATA |
|---|---|---|---|---|---|---|
| 668 | 4-(5-chloro-6-(4-chloro-3,5-difluorophenoxy)-3-pyridinyl)-2-fluoro-5-methyl-N-(methylsulfonyl)benzamide | 504.9 | II and XV | P | 3,5-difluoro-4-chlorophenol | |
| 669 | 4-(5-chloro-6-(4-chloro-2,6-dimethylphenoxy)-3-pyridinyl)-2-fluoro-5-methyl-N-(methylsulfonyl)benzamide | 497.0 | II and XV | P | 4-chloro-2,6-dimethylphenol | $^1$H NMR (500 MHz, DMSO-d$_6$) δ ppm 2.07 (s, 6H) 2.22 (s, 3H) 3.03 (s, 3H) 7.16 (d, J = 13.78 Hz, 1H) 7.26 (s, 2H) 7.59 (d, J = 7.53 Hz, 1H) 8.04 (d, J = 2.08 Hz, 1H) 8.18 (d, J = 2.08 Hz, 1H) |
| 670 | 4-(5-chloro-6-(6-chloro-2-fluoro-3-methylphenoxy)-3-pyridinyl)-2-fluoro-5-methyl-N-(methylsulfonyl)benzamide | 501.0 | II and XV | P | 6-chloro-2-fluoro-3-methylphenol | |
| 671 | 4-(5-chloro-6-(3-fluoro-4-(trifluoromethyl)phenoxy)-3-pyridinyl)-2-fluoro-5-methyl-N-(methylsulfonyl)benzamide | 519.0 | II and XV | P | 3-fluoro-4-(trifluoromethyl)phenol | |
| 672 | 4-(5-chloro-6-((7-fluoro-2,3-dihydro-1H-inden-4-yl)oxy)-3-pyridinyl)-2-fluoro-5-methyl-N-(methylsulfonyl)benzamide | 491.0 | II and XV | P | 7-fluoro-2,3-dihydro-1H-inden-4-ol | |
| 673 | 4-(5-chloro-6-((1R)-1-(2,5-dichlorophenyl)ethoxy)-3-pyridinyl)-2-fluoro-5-methyl-N-(methylsulfonyl)benzamide | 531.0 | II and XV | P | (1R)-1-(2,5-dichlorophenyl)ethanol | 1H NMR (500 MHz, DMSO-d$_6$) δ 8.09 (d, J = 2.08 Hz, 1H), 8.03 (d, J = 2.08 Hz, 1H), 7.50-7.60 (m, 3H), 7.42 (dd, J = 2.53, 8.56 Hz, 1H), 7.03 (d, J = 11.09 Hz, 1H), 6.49 (q, J = 6.36 Hz, 1H), 2.87 (s, 3H), 2.18 (s, 3H), 1.64 (d, J = 6.42 Hz, 3H) |
| 674 | 4-(5-chloro-6-((1S)-1-(2,5-dichlorophenyl)ethoxy)-3-pyridinyl)-2-fluoro-5-methyl-N-(methylsulfonyl)benzamide | 531.0 | II and XV | P | (1S)-1-(2,5-dichlorophenyl)ethanol | |
| 675 | 4-(5-chloro-6-(((1R)-1-(4-fluoro-3-methylphenyl)propyl)oxy)-3-pyridinyl)-2-fluoro-5-methyl-N-(methylsulfonyl)benzamide | 507.0 | II and XV | P | (1R)-1-(4-fluoro-3-methylphenyl)propan-1-ol | |

TABLE A-continued

| EX. NO. | NAME | LCMS | METHODS | INTERMEDIATE | REAGENT | $^1$H NMR DATA |
|---|---|---|---|---|---|---|
| 676 | 4-(5-chloro-6-(((1S)-1-(3-chlorophenyl)propyl)oxy)-3-pyridinyl)-2-fluoro-5-methyl-N-(methylsulfonyl)benzamide | 509, 511 (neg) | II and XV | P | | |
| 677 | 4-(5-chloro-6-(2-methyl-3-(trifluoromethyl)phenoxy)-3-pyridinyl)-2-fluoro-5-methyl-N-(methylsulfonyl)benzamide | 515 (neg) | II and XV | P | | |
| 678 | 4-(5-chloro-6-(4-fluoro-2-(trifluoromethyl)phenoxy)-3-pyridinyl)-2-fluoro-5-methyl-N-(methylsulfonyl)benzamide | 519 (neg) | II and XV | P | | |
| 679 | 4-(5-chloro-6-(4-chloro-2-(trifluoromethyl)phenoxy)-3-pyridinyl)-2-fluoro-5-methyl-N-(methylsulfonyl)benzamide | 537.0 | II and XV | P | | |
| 680 | 4-(5-chloro-6-(2-ethyl-5-methylphenoxy)-3-pyridinyl)-2-fluoro-5-methyl-N-(methylsulfonyl)benzamide | 475 (neg) | II and XV | P | | |
| 681 | 4-(5-chloro-6-((4-chloro-2-methylbenzyl)oxy)-3-pyridinyl)-2-fluoro-5-methyl-N-(methylsulfonyl)benzamide | 495 (neg) | II and XV | P | | |
| 682 | 4-(5-chloro-6-((1S)-1-(1-naphthalenypethoxy)-3-pyridinyl)-2-fluoro-5-methyl-N-(methylsulfonyl)benzamide | 511 (neg) | II and XV | P | | |
| 683 | 4-(5-chloro-6-(2-cyclopropylethoxy)-3-pyridinyl)-2-fluoro-5-methyl-N-(methylsulfonyl)benzamide | 425 (neg) | II and XV | P | | |

TABLE A-continued

| EX. NO. | NAME | LCMS | METHODS | INTERMEDIATE | REAGENT | ¹H NMR DATA |
|---|---|---|---|---|---|---|
| 684 | 4-(5-chloro-6-((1S)-2,2,2-trifluoro-1-phenylethoxy)-3-pyridinyl)-2-fluoro-5-methyl-N-(methylsulfonyl)benzamide | 515 (neg) | II and XV | P | | |
| 685 | Mixture of 4-(5-chloro-6-(((1R)-1-(4-methylphenyl)propyl)oxy)-3-pyridinyl)-2-fluoro-5-methyl-N-(methylsulfonyl)benzamide and 4-(5-chloro-6-(41S)-1-(4-methylphenyl)propyl)oxy)-3-pyridinyl)-2-fluoro-5-methyl-N-(methylsulfonyl)benzamide | 489 (neg) | II and XV | P | | |
| 686 | 4-(5-chloro-6-(2,2,2-trifluoro-1-(trifluoromethyl)ethoxy)-3-pyridinyl)-2-fluoro-5-methyl-N-(methylsulfonyl)benzamide | 507 (neg) | II and XV | P | | |
| 687 | Mixture of 4-(5-chloro-6-(((1R)-3,3-dimethylcyclohexyl)oxy)-3-pyridinyl)-2-fluoro-5-methyl-N-(methylsulfonyl)benzamide and 4-(5-chloro-6-(((1S)-3,3-dimethylcyclohexyl)oxy)-3-pyridinyl)-2-fluoro-5-methyl-N-(methylsulfonyl)benzamide | 467 (neg) | II and XV | P | | |
| 688 | Mixture of 4-(5-chloro-6-((1R)-1-(2-(trifluoromethyl)phenyl)ethoxy)-3-pyridinyl)-2-fluoro-5-methyl-N-(methylsulfonyl)benzamide, and 4-(5-chloro-6-((1S)-1-(2-(trifluoromethyl)phenyl)ethoxy)-3-pyridinyl)-2-fluoro-5-methyl-N-(methylsulfonyl)benzamide | 529 (neg) | II and XV | P | | |
| 539 | 4-(5-cyano-6-(2-phenylethoxy)-3-pyridinyl)-3-methoxy-N-(methylsulfonyl)benzamide | 451.5 | II and XVI | Q | | |
| 547 | 4-(5-cyano-6-(3,5-dichlorophenoxy)-3-pyridinyl)-3-methoxy-N-(methylsulfonyl)benzamide | 492.34 | II and XVI | Q | | |
| 549 | 4-(6-(3-chloro-4-methylphenoxy)-5-cyano-3-pyridinyl)-3-methoxy-N-(methylsulfonyl)benzamide | 471.92 | II and XVI | Q | | |
| 689 | 4-(5-cyano-6-(2,4-dichloro-6-methylphenoxy)-3-pyridinyl)-3-methoxy-N-(methylsulfonyl)benzamide | 506 (neg) | II and XVI | Q | | |

TABLE A-continued

| EX. NO. | NAME | LCMS | METHODS | INTERMEDIATE | REAGENT | ¹H NMR DATA |
|---|---|---|---|---|---|---|
| 690 | 4-(6-(3-chloro-2-methylphenoxy)-5-cyano-3-pyridinyl)-3-methoxy-N-(methylsulfonyl)benzamide | 472.0 | II and XVI | Q | 3-chloro-2-methylphenol | ¹H NMR (500 MHz, DMSO-d₆) δ 8.59 (d, J = 2.34 Hz, 1H), 8.51 (d, J = 2.34 Hz, 1H), 7.68 (s, 1H), 7.63 (d, J = 7.90 Hz, 1H), 7.25-7.45 (m, 4H), 7.12 (br. s., 1H), 3.83 (s, 3H), 2.90 (s, 3H), 2.18 (s, 3H) |
| 691 | 4-(5-cyano-6-(2,4-dichlorophenoxy)-3-pyridinyl)-3-methoxy-N-(methylsulfonyl)benzamide | 490.0 (−) | II and XVI | Q | 2,4-dichlorophenol | |
| 692 | 4-(5-cyano-6-(3,4-dichlorophenoxy)-3-pyridinyl)-3-methoxy-N-(methylsulfonyl)benzamide | 490.0 (−) | II and XVI | Q | 3,4-dichlorophenol | |
| 693 | 4-(5-cyano-6-(2,6-dichloro-4-methylphenoxy)-3-pyridinyl)-3-methoxy-N-(methylsulfonyl)benzamide | 508.0 (+) | II and XVI | Q | 2,6-dichloro-4-methylphenol | |
| 694 | 4-(5-cyano-6-(3,6-dichloro-2-methylphenoxy)-3-pyridinyl)-3-methoxy-N-(methylsulfonyl)benzamide | 504.0 (−) | II and XVI | Q | 3,6-dichloro-2-methylphenol | 1H NMR (500 MHz, DMSO-d₆) δ ppm 2.23 (s, 3H) 3.89 (s, 3H) 7.47-7.60 (m, 3H) 7.64 (d, J = 7.77 Hz, 1H) 7.69 (s, 1H) 8.56 (d, J = 2.27 Hz, 1H) 8.70 (d, J = 2.27 Hz, 1H). |
| 695 | 4-(5-chloro-6-(3,5-dichlorophenoxy)-3-pyridinyl)-2-fluoro-5-methoxy-N-(methylsulfonyl)benzamide | 518.9 (−) | II and XVIII | V | 3,5-dichlorophenol | ¹H NMR (500 MHz, DMSO-d₆) δ ppm 2.95 (s, 3H) 3.80 (s, 3H) 7.26 (d, J = 10.63 Hz, 1H) 7.35 (d, J = 6.05 Hz, 1H) 7.44 (d, J = 1.70 Hz, 2H) 7.53 (s, 1H) 8.27 (dd, J = 9.95, 2.04 Hz, 2H) |
| 696 | Mixture of 4-(5-chloro-6-((1R)-1-phenylethoxy)-3-pyridinyl)-2-fluoro-5-methoxy-N-(methylsulfonyl)benzamide and 4-(5-chloro-6-((1S)-1-phenylethoxy)-3-pyridinyl)-2-fluoro-5-methoxy-N-(methylsulfonyl)benzamide | 477.0 (−) | II and XVIII | V | 1-phenylethanol | |
| 697 | 4-(5-chloro-6-(cyclobutyl(methyl)amino)-3-pyridinyl)-2-fluoro-5-methoxy-N-(methylsulfonyl)benzamide | 442.2 | VIII and XVIII | V | N-methylcyclobutylamine | |
| 698 | 4-(5-chloro-6-(3-fluoro-4-methylphenoxy)-3-pyridinyl)-2-fluoro-5-methoxy-N-(methylsulfonyl)benzamide | 481.0 (−) | II and XVIII | V | 3-fluoro-4-methylphenol | |

TABLE A-continued

| EX. NO. | NAME | LCMS | METHODS | INTER-MEDIATE | REAGENT | $^1$H NMR DATA |
|---|---|---|---|---|---|---|
| 699 | 4-(5-chloro-6-(5-chloro-2-methylphenoxy)-3-pyridinyl)-2-fluoro-5-methoxy-N-(methylsulfonyl)benzamide | 496.9 (−) | II and XVIII | V | 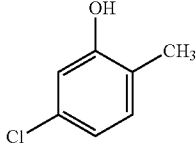 | |
| 700 | 4-(5-chloro-6-(2,3,5-trifluorophenoxy)-3-pyridinyl)-2-fluoro-5-methoxy-N-(methylsulfonyl)benzamide | 503.0 (−) | II and XVIII | V | 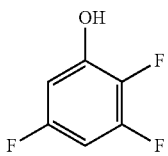 | |
| 701 | 4-(5-chloro-6-(2,3,4-trifluorophenoxy)-3-pyridinyl)-2-fluoro-5-methoxy-N-(methylsulfonyl)benzamide | 503.0 (−) | II and XVIII | V |  | |
| 702 | 4-(5-chloro-6-(cyclobutyloxy)-3-pyridinyl)-2-fluoro-5-methoxy-N-(methylsulfonyl)benzamide | 427.0 (−) | II and XVIII | V |  | $^1$H NMR (500 MHz, DMSO-d$_6$) δ ppm 1.70-1.80 (m, 1H) 1.90 (q, J = 10.10 Hz, 1H) 2.15-2.25 (m, 2H) 2.50-2.56 (m, 2H) 3.10 (s, 3H) 3.88 (s, 3H) 5.32 (quin, J = 7.35 Hz 1 H) 7.34 (d, J = 10.70 Hz, 1H) 7.42 (d, J = 6.03 Hz, 1H) 8.14 (d, J = 2.08 Hz, 1H) 8.34 (d, J = 2.08 Hz, 1H) |
| 703 | 4-(6-(((1R,2S,4S)-bicyclo[2.2.1]hept-2-yloxy)-5-chloro-3-pyridinyl)-2-fluoro-5-methoxy-N-(methylsulfonyl)benzamide | 467.0 (−) | II and XVIII | V |  | $^1$H NMR (500 MHz, DMSO-d$_6$) δ ppm 1.04 (dt, J = 13.09, 3.22 Hz, 1H) 1.29-1.42 (m, 3H) 1.48 (d, J = 9.86 Hz, 1H) 1.53-1.64 (m, 1H) H) 1.84-1.93 (m, 1H) 2.07-2.15 (m, 1H) 2.25 (br. s., 1H) 2.61 (br. s., 1H) 3.16 (s, 3H) 3.82 (s, 3H) 5.23-5.32 (m, 1H) 7.33 (m, 1H) 7.52-7.65 (m, 2H) 8.06 (d, J = 2.08 Hz, 1H) 8.27 (d, J = 2.08 Hz, 1H) |
| 704 | 4-(5-chloro-6-(3-chloro-2-methylphenoxy)-3-pyridinyl)-2-fluoro-5-methoxy-N-(methylsulfonyl)benzamide | 496.9 (−) | II and XVIII | V | 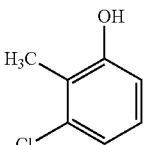 | $^1$H NMR (500 MHz, DMSO-d$_6$) δ ppm 2.15 (s, 3H) 2.99 (s, 3H) 3.81 (s, 3 H) 7.18 (d, J = 7.91 Hz, 2H) 7.25-7.41 (m, 4H) 8.21 (d, J = 2.01 Hz, 1H) 8.26 (d, J = 2.01 Hz, 1H). |
| 705 | 4-(5-chloro-6-((1-methylcyclopropyl)methoxy)-3-pyridinyl)-2-fluoro-5-methoxy-N-(methylsulfonyl)benzamide | 441.0 (−) | II and XVIII | V | 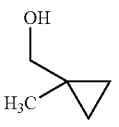 | $^1$H NMR (500 MHz, DMSO-d$_6$) δ ppm 0.36-0.46 (m, 2H) 0.51-0.63 (m 2H) 1.20 (s, 3H) 3.01 (s, 3H) 3.80 (s, 3H) 4.20 (s, 2H) 7.26 (d, J = 10.70 Hz, 1H) 7.34 (d, J = 6.10 Hz, 1H) 8.06 (d, J = 2.08 Hz, 1H) 8.25 (d, J = 2.08 Hz, 1H) |
| 706 | 4-(5-chloro-6-(2,5-difluorophenoxy)-3-pyridinyl)-2-fluoro-5-methoxy-N-(methylsulfonyl)benzamide | 484.8 (−) | II and XVIII | V | 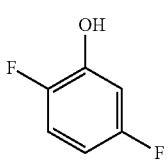 | $^1$H NMR (500 MHz, DMSO-d$_6$) δ ppm 2.95 (s, 3H) 3.80 (s, 3H) 7.17-7.31 (m, 2H) 7.35 (d, J = 6.03 Hz, 1H) 7.40-7.54 (m, 2H) 8.23 (d, J = 1.95 Hz, 1H) 8.27 (d, J = Hz, 1H) |

TABLE A-continued

| EX. NO. | NAME | LCMS | METHODS | INTERMEDIATE | REAGENT | ¹H NMR DATA |
|---|---|---|---|---|---|---|
| 707 | Mixture of 4-(5-chloro-6-((1R)-1-methyl-2-phenylethoxy)-3-pyridinyl)-2-fluoro-5-methoxy-N-(methylsulfonyl)benzamide and 4-(5-chloro-6-((1S)-1-methyl-2-phenylethoxy)-3-pyridinyl)-2-fluoro-5-methoxy-N-(methylsulfonyl)benzamide | 491.0 (−) | II and XVIII | V | | |
| 708 | 4-(5-chloro-6-(2-chloro-3,5-difluorophenoxy)-3-pyridinyl)-2-fluoro-5-methoxy-N-(methylsulfonyl)benzamide | 520.8 (−) | II and XVIII | V | | |
| 709 | 4-(6-(1,3-benzothiazol-2-ylmethoxy)-5-chloro-3-pyridinyl)-2-fluoro-5-methoxy-N-(methylsulfonyl)benzamide | 520.0 (−) | II and XVIII | V | | ¹H NMR (500 MHz, DMSO-d₆) δ ppm 3.14 (s, 3H) 3.82 (s, 3H) 5.94 (s, 2H) 7.30-7.41 (m, 2H) 7.46 (t, J = 7.70 Hz, 1H) 7.54 (t, J = 7.10 Hz, 1H) 8.02 (d, J = 8.04 Hz, 1H) 8.08-8.17 (m, 1H) 8.20 (d, J = 2.01 Hz, 1H) 8.34 (d, J = 2.01 Hz, 1H) |
| 710 | 4-(6-((1R)-1-(1,3-benzothiazol-2-yl)ethoxy)-5-chloro-3-pyridinyl)-2-fluoro-5-methyl-N-(methylsulfonyl)benzamide | 520.1 | II and XVIII | V | | |
| 711 | 4-(6-((1S)-1-(1,3-benzothiazol-2-yl)ethoxy)-5-chloro-3-pyridinyl)-2-fluoro-5-methyl-N-(methylsulfonyl)benzamide | 520.1 | II and XVIII | V | | |
| 712 | 4-(5-chloro-6-(2,4-dichloro-6-methylphenoxy)-3-pyridinyl)-2-fluoro-5-methoxy-N-(methylsulfonyl)benzamide | 534.8 | II and XVIII | V | | ¹H NMR (500 MHz, DMSO-d₆) δ ppm 2.14 (s, 3H) 3.01 (s, 3H) 3.81 (s, 3H) 7.19-7.38 (m, 1H) 7.48-7.68 (m, 3H) 8.19 (d, J = 2.01 Hz, 1H) 8.29 (d, J = 2.01 Hz, 1H) |
| 713 | Mixture of 4-(6-(((1R)-1-benzylpropyl)oxy)-5-chloro-3-pyridinyl)-2-fluoro-5-methoxy- and 4-(6-(((1S)-1-benzylpropyl)oxy)-5-chloro-3-pyridinyl)-2-fluoro-5-methoxy-N-(methylsulfonyl)benzamide | 507.2 | II and XVIII | V | | |
| 714 | 4-(5-chloro-6-((1-methylcyclohexyl)methoxy)-3-pyridinyl)-2-fluoro-5-methoxy-N-(methylsulfonyl)benzamide | 483 (neg) | II and XVIII | V | | |
| 715 | 4-(5-chloro-6-((3-chloro-2-naphthalenyl)oxy)-3-pyridinyl)-2-fluoro-5-methoxy-N-(methylsulfonyl)benzamide | 535.0 | II and XVIII | V | | |

TABLE A-continued

| EX. NO. | NAME | LCMS | METHODS | INTERMEDIATE | REAGENT | ¹H NMR DATA |
|---|---|---|---|---|---|---|
| 716 | 4-(5-chloro-6-(2,4-dichloro-5-methoxyphenoxy)-3-pyridinyl)-2-fluoro-5-methoxy-N-(methylsulfonyl)benzamide | 549.0 | II and XVIII | V | | |
| 717 | 4-(5-chloro-6-((l-chloro-2-naphthalenyl)oxy)-3-pyridinyl)-2-fluoro-5-methoxy-N-(methylsulfonyl)benzamide | 535.0 | II and XVIII | V | | |
| 718 | 4-(5-chloro-6-((2,2,3,3-tetramethylcyclopropyl)methoxy)-3-pyridinyl)-2-fluoro-5-methoxy-N-(methylsulfonyl)benzamide | 483 (neg) | II and XVIII | V | | |
| 732 | Mixture of 4-(5-chloro-6-(((1R)-1-(trifluoromethyl)propyl)oxy)-3-pyridinyl)-2-fluoro-5-methoxy-N-(methylsulfonyl)benzamide and 4-(5-chloro-6-(((1S)-1-(trifluoromethyl)propyl)oxy)-3-pyridinyl)-2-fluoro-5-methoxy-N-(methylsulfonyl)benzamide | 483 (neg) | II and XVIII | V | | |
| 720 | Mixture of 4-(5-chloro-6-((1R)-spiro[2.4]hept-1-ylamino)-3-pyridinyl)-2-fluoro-5-methoxy-N-(methylsulfonyl)benzamide and 4-(5-chloro-6-((1S)-spiro[2.4]hept-1-ylamino)-3-pyridinyl)-2-fluoro-5-methoxy-N-(methylsulfonyl)benzamide | 466 (neg) | VIII and XVIII | V | | |
| 721 | 4-(5-chloro-6-(((4,4-dimethylcyclohexyl)methyl)amino)-3-pyridinyl)-2-fluoro-5-methoxy-N-(methylsulfonyl)benzamide | 498.0 | VIII and XVIII | V | | |
| 722 | Mixture of 4-(5-chloro-6-((1R)-spiro[3.3]hept-1-ylamino)-3-pyridinyl)-2-fluoro-5-methoxy-N-(methylsulfonyl)benzamide and 4-(5-chloro-6-((1S)-spiro[3.3]hept-1-ylamino)-3-pyridinyl)-2-fluoro-5-methoxy-N-(methylsulfonyl)benzamide | 466 (neg) | VIII and XVIII | V | | |
| 723 | 4-(5-chloro-6-4(3,3-dimethylcyclobutyl)methyl)amino)-3-pyridinyl)-2-fluoro-5-methoxy-N-(methylsulfonyl)benzamide | 468 (neg) | VIII and XVIII | V | | |

TABLE A-continued

| EX. NO. | NAME | LCMS | METHODS | INTERMEDIATE | REAGENT | ¹H NMR DATA |
|---|---|---|---|---|---|---|
| 724 | 4-(5-chloro-6-((4,4-dimethylcyclohexyl)amino)-3-pyridinyl)-2-fluoro-5-methoxy-N-(methylsulfonyl)benzamide | 482 (neg) | VIII and XVIII | V | 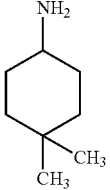 | |
| 725 | 4-(5-chloro-6-((1-ethylpropyl)amino)-3-pyridinyl)-2-fluoro-5-methoxy-N-(methylsulfonyl)benzamide | 444.0 | VIII and XVIII | V | 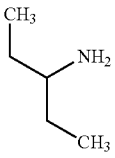 | |
| 726 | 4-(5-chloro-6-(((1S)-1,3-dimethylbutyl)oxy)-3-pyridinyl)-2-fluoro-5-methoxy-N-(methylsulfonyl)benzamide | 457 (neg) | II and XVIII | V | 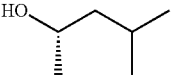 | |
| 727 | 4-(5-chloro-6-(((1R,2R)-2-methylcyclopentyl)oxy)-3-pyridinyl)-2-fluoro-5-methoxy-N-(methylsulfonyl)benzamide | 456.0 | II and XVIII | V | 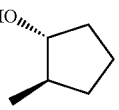 | |
| 728 | 4-(5-chloro-6-((4-methylphenyl)sulfanyl)-3-pyridinyl)-2-fluoro-5-methoxy-N-((methylsulfonyl)benzamide | 479 (neg) | XXIX and XVIII | V | 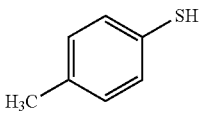 | |
| 729 | 4-(5-chloro-6-((3,5-dimethylphenyl)sulfanyl)-3-pyridinyl)-2-fluoro-5-methoxy-N-(methylsulfonyl)benzamide | 493 (neg) | XXIX and XVIII | V | 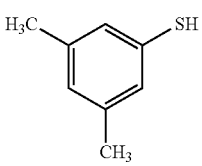 | |
| 730 | 4-(5-chloro-6-((2,5-difluorobenzyl)sulfanyl)-3-pyridinyl)-2-fluoro-5-methoxy-N-(methylsulfonyl)benzamide | 515 (neg) | XXIX and XVIII | V | 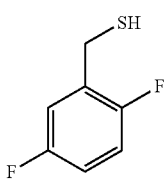 | |
| 731 | 4-(5-chloro-6-((2-cyclopentylethyl)amino)-3-pyridinyl)-2-fluoro-5-methoxy-N-(methylsulfonyl)benzamide | 468 (neg) | VIII and XVIII | V | 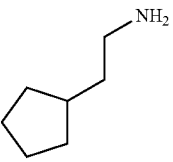 | |
| 719 | Mixture of 4-(5-chloro-6-((1S)-1-cyclobutylethoxy)-3-pyridinyl)-2-fluoro-5-methoxy-N-(methylsulfonyl)benzamide and 4-(5-chloro-6-((1R)-1-cyclobutylethoxy)-3-pyridinyl)-2-fluoro-5-methoxy-N-(methylsulfonyl)benzamide | 457.0 | II and XVIII | V | 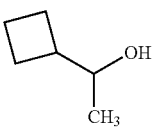 | |

TABLE A-continued

| EX. NO. | NAME | LCMS | METHODS | INTERMEDIATE | REAGENT | ¹H NMR DATA |
|---|---|---|---|---|---|---|
| 733 | Mixture of 4-(5-chloro-6-(((1R,2R)-2-methylcyclobutypoxy)-3-pyridinyl)-2-fluoro-5-methoxy-N-(methylsulfonyl)benzamide and 4-(5-chloro-6-(((1S,2S)-2-methylcyclobutyl)oxy)-3-pyridinyl)-2-fluoro-5-methoxy-N-(methylsulfonyl)benzamide | 442 (neg) | II and XVIII | V | cyclobutanol with CH₃ | |
| 734 | 4-(5-chloro-6-((1-(trifluoromethyl)cyclobutyl)oxy)-3-pyridinyl)-2-fluoro-5-methoxy-N-(methylsulfonyl)benzamide | 497.0 | II and XVIII | V | F₃C-cyclobutanol-OH | ¹H NMR (500 MHz, DMSO-d₆) δ 8.29 (d, J = 2.08 Hz, 1H), 8.14 (d, J = 2.01 Hz, 1H), 7.34 (d, J = 6.03 Hz 1H) 7.26 (d, J = 10.70 Hz, 1H), 3.80 (s, 3H), 2.96 (s, 3H), 2.82-2.94 (m, 2H), 2.61-2.70 (m, 2H), 1.94-2.04 (m, 1H), 1.79-1.90 (m, 1H) |
| 735 | 4-(5-chloro-6-((trans-3-methylcyclobutyl)oxy)-3-pyridinyl)-2-fluoro-5-methoxy-N-(methylsulfonyl)benzamide | 443.0 | II and XVIII | V | HO-cyclobutyl-CH₃ (trans) | ¹H NMR (500 MHz, DMSO-d₆) δ 8.24 (d, J = 6.85 Hz, 1H), 8.03 (d, J = 7.05 Hz, 1H), 7.33 (d, J = 6.16 Hz, 1H), 7.17 (d, J = 10.77 Hz, 1H), 5.07 (quin, J = 7.43 Hz, 1H), 3.78 (s, 3H), 2.86 (s, 3H), 2.56-2.73 (m, 2H), 1.98-2.08 (m, 1H), 1.64-1.74 (m, 2H), 1.12 (d, J = 6.55 Hz, 3H) |
| 769 | 4-(5-chloro-6-((1R)-1-cyclobutylethoxy)-3-pyridinyl)-2-fluoro-5-methoxy-N-(methylsulfonyl)benzamide | 455 (neg) | II and XVIII | V | HO-CH(CH₃)-cyclobutyl | ¹H NMR (500 MHz, DMSO-d₆) δ 8.32 (d, J = 2.01 Hz, 1H), 8.17 (d, J = 1.95 Hz, 1H), 7.35 (d, J = 6.10 Hz, 1H), 7.24 (d, J = 10.64 Hz, 1H), 5.89-5.98 (m, 1H), 3.80 (s, 3H), 2.89 (s, 3H), 1.83-2.03 (m, 2H), 0.99 (t, J = 7.40 Hz, 3H) |
| 737 | 4-(5-chloro-6-(2,6-dichloro-4-fluorophenoxy)-3-pyridinyl)-2-fluoro-5-methoxy-N-(methylsulfonyl)benzamide | 537.0 | II and XVIII | V | 2,6-dichloro-4-fluorophenol | |
| 738 | 4-(5-chloro-6-(2,4-dichlorophenoxy)-3-pyridinyl)-2-fluoro-5-methoxy-N-(methylsulfonyl)benzamide | 516.9 (−) | II and XVIII | V | 2,4-dichlorophenol | |
| 739 | 4-(5-chloro-6-(2,4,5-trichlorophenoxy)-3-pyridinyl)-2-fluoro-5-methoxy-N-(methylsulfonyl)benzamide | 552.8 (−)G | II and XVIII | V | 2,4,5-trichlorophenol | |
| 740 | 4-(5-chloro-6-(3,5-difluorophenoxy)-3-pyridinyl)-2-fluoro-5-methoxy-N-(methylsulfonyl)benzamide | 485.0 (−) | II and XVIII | V | 3,5-difluorophenol | |
| 741 | 4-(5-chloro-6-(3-chloro-4-fluorophenoxy)-3-pyridinyl)-2-fluoro-5-methoxy-N-(methylsulfonyl)benzamide | 500.9 (−) | II and XVIII | V | 3-chloro-4-fluorophenol | |

TABLE A-continued

| EX. NO. | NAME | LCMS | METHODS | INTERMEDIATE | REAGENT | ¹H NMR DATA |
|---|---|---|---|---|---|---|
| 742 | 4-(5-chloro-6-(2,4-difluorophenoxy)-3-pyridinyl)-2-fluoro-5-methoxy-N-(methylsulfonyl)benzamide | 485.0 (−) | II and XVIII | V | 2,4-difluorophenol | |
| 743 | 4-(5-chloro-6-(5-fluoro-2-methylphenoxy)-3-pyridinyl)-2-fluoro-5-methoxy-N-(methylsulfonyl)benzamide | 481.0 (−) | II and XVIII | V | 5-fluoro-2-methylphenol | |
| 744 | 4-(5-chloro-6-(3-chloro-2,6-difluorophenoxy)-3-pyridinyl)-2-fluoro-5-methoxy-N-(methylsulfonyl)benzamide | 519.0 (−) | II and XVIII | V | 3-chloro-2,6-difluorophenol | |
| 745 | 4-(5-chloro-6-(3-chloro-2-fluorophenoxy)-3-pyridinyl)-2-fluoro-5-methoxy-N-(methylsulfonyl)benzamide | 500.9 (−) | II and XVIII | V | 3-chloro-2-fluorophenol | |
| 746 | 4-(5-chloro-6-(2,3-difluoro-4-methylphenoxy)-3-pyridinyl)-2-fluoro-5-methoxy-N-(methylsulfonyl)benzamide | 499.0 (−) | II and XVIII | V | 2,3-difluoro-4-methylphenol | |
| 747 | 4-(5-chloro-6-(5-chloro-2-fluorophenoxy)-3-pyridinyl)-2-fluoro-5-methoxy-N-(methylsulfonyl)benzamide | 500.9 (−) | II and XVIII | V | 5-chloro-2-fluorophenol | |
| 748 | 4-(5-chloro-6-(2-chloro-6-methylphenoxy)-3-pyridinyl)-2-fluoro-5-methoxy-N-(methylsulfonyl)benzamide | 497.0 (−) | II and XVIII | V | 2-chloro-6-methylphenol | |
| 749 | 4-(5-chloro-6-((1R)-1-phenylethoxy)-3-pyridinyl)-2-fluoro-5-methoxy-N-(methylsulfonyl)benzamide | 477.0 (−) | II and XVIII | V | (1R)-1-phenylethanol | |
| 750 | 4-(5-chloro-6-((4-chlorobenzy)oxy)-3-pyridinyl)-2-fluoro-5-methoxy-N-(methylsulfonyl)benzamide | 497.0 (−) | II and XVIII | V | (4-chlorophenyl)methanol | |
| 751 | 4-(5-chloro-6-(3-chloro-4-methylphenoxy)-3-pyridinyl)-2-fluoro-5-methoxy-N-(methylsulfonyl)benzamide | 497.0 (−) | II and XVIII | V | 3-chloro-4-methylphenol | |

TABLE A-continued

| EX. NO. | NAME | LCMS | METHODS | INTERMEDIATE | REAGENT | ¹H NMR DATA |
|---|---|---|---|---|---|---|
| 752 | 4-(5-chloro-6-(2-chloro-5-methylphenoxy)-3-pyridinyl)-2-fluoro-5-methoxy-N-(methylsulfonyl)benzamide | 497.0 (−) | II and XVIII | V | 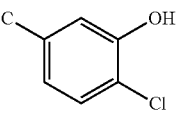 | 1H NMR (500 MHz, DMSO-d6) δ ppm 2.33 (s, 3H) 2.87 (s, 3H) 3.76-3.83 (m, 3 H) 7.04-7.18 (m,2H) 7.18-7.27 (m, 1H) 7.35 (d, J = 6.10 Hz, 1H) 7.47 (d, J = 8.17 Hz, 1H) 8.17-8.27 (m, 2H) |
| 753 | 4-(5-chloro-6-(4-chloro-2-fluorophenoxy)-3-pyridinyl)-2-fluoro-5-methoxy-N-(methylsulfonyl)benzamide | 500.9 (−) | II and XVIII | V | 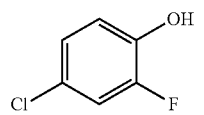 | |
| 754 | 4-(5-chloro-6-(4-fluoro-3-methylphenoxy)-3-pyridinyl)-2-fluoro-5-methoxy-N-(methylsulfonyl)benzamide | 481.0 (−) | II and XVIII | V | 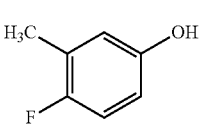 | |
| 755 | 4-(5-chloro-6-(3,4-dichlorophenoxy)-3-pyridinyl)-2-fluoro-5-methoxy-N-(methylsulfonyl)benzamide | 516.8 (−) | II and XVIII | V | 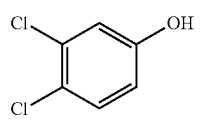 | |
| 756 | 4-(5-chloro-6-((1R)-1-methyl-2-phenylethoxy)-3-pyridinyl)-2-fluoro-5-methoxy-N-(methylsulfonyl)benzamide | 491.0 (−) | II and XVIII | V | 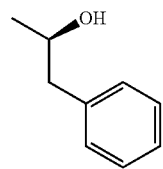 | |
| 757 | 4-(5-chloro-6-((7-fluoro-2,3-dihydro-1H-inden-4-yl)oxy)-3-pyridinyl)-2-fluoro-5-methoxy-N-(methylsulfonyl)benzamide | 507.0 (−) | II and XVIII | V | 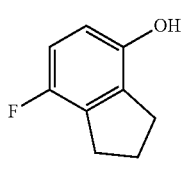 | |
| 758 | 4-(5-chloro-6-((1S)-1-methyl-2-phenylethoxy)-3-pyridinyl)-2-fluoro-5-methoxy-N-(methylsulfonyl)benzamide | 493.0 (+) | II and XVIII | V | 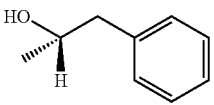 | |
| 759 | 4-(5-chloro-6-(2,6-difluoro-3-methylphenoxy)-3-pyridinyl)-2-fluoro-5-methoxy-N-(methylsulfonyl)benzamide | 501.0 (+) | II and XVIII | V | 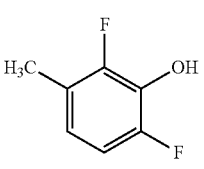 | |
| 760 | 4-(5-chloro-6-(2-chloro-3-methylphenoxy)-3-pyridinyl)-2-fluoro-5-methoxy-N-(methylsulfonyl)benzamide | 501.0 (+) | II and XVIII | V | 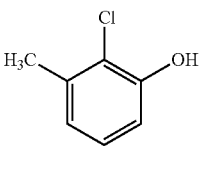 | |
| 761 | 4-(5-chloro-6-((1R)-1-(2-chloro-4-fluorophenyl)ethoxy)-3-pyridinyl)-2-fluoro-5-methoxy-N-(methylsulfonyl)benzamide | 529.0 (−) | II and XVIII | V | 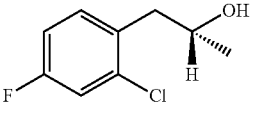 | |

TABLE A-continued

| EX. NO. | NAME | LCMS | METHODS | INTERMEDIATE | REAGENT | ¹H NMR DATA |
|---|---|---|---|---|---|---|
| 762 | 4-(5-chloro-6-(6-chloro-2-fluoro-3-methylphenoxy)-3-pyridinyl)-2-fluoro-5-methoxy-N-(methylsulfonyl)benzamide | 517.0 (+) | II and XVIII | V | 6-chloro-2-fluoro-3-methylphenol | |
| 763 | 4-(5-chloro-6-(4-chloro-3,5-difluorophenoxy)-3-pyridinyl)-2-fluoro-5-methoxy-N-(methylsulfonyl)benzamide | 521.0 (−) | II and XVIII | V | 4-chloro-3,5-difluorophenol | |
| 764 | 4-(5-chloro-6-(2,6-dichlorophenoxy)-3-pyridinyl)-2-fluoro-5-methoxy-N-(methylsulfonyl)benzamide | 521.0 (+) | II and XVIII | V | 2,6-dichlorophenol | |
| 765 | 4-(5-chloro-6-(3-chlorophenoxy)-3-pyridinyl)-2-fluoro-5-methoxy-N-(methylsulfonyl)benzamide | 485.0 (+) | II and XVIII | V | 3-chlorophenol | |
| 766 | 4-(5-chloro-6-(2,3,6-trifluorophenoxy)-3-pyridinyl)-2-fluoro-5-methoxy-N-(methylsulfonyl)benzamide | 503.0 (−) | II and XVIII | V | 2,3,6-trifluorophenol | |
| 768 | 4-(5-chloro-6-(((1S)-1-(trifluoromethyl)propyl)oxy)-3-pyridinyl)-2-fluoro-5-methoxy-N-(methylsulfonyl)benzamide | 484.0 | II and XVIII; followed by SFC: Chiralpak OJ—H, 15% methanol (Peak 1-23 mg > 98% ee | V | 1,1,1-trifluoro-2-butanol | |
| 767 | 4-(5-chloro-6-((1S)-1-cyclobutylethoxy)-3-pyridinyl)-2-fluoro-5-methoxy-N-(methylsulfonyl)benzamide | 456.0 | II and XVIII; followed by resolution by SFC: Chiralpak OJ—H, 15% methanol (Peak 1-8 mg > 96% ee). | V | 1-cyclobutylethanol | |

TABLE A-continued

| EX. NO. | NAME | LCMS | METHODS | INTERMEDIATE | REAGENT | ¹H NMR DATA |
|---|---|---|---|---|---|---|
| 736 | 4-(5-chloro-6-(((1R)-1-(trifluoromethyl)propyl)oxy)-3-pyridinyl)-2-fluoro-5-methoxy-N-(methylsulfonyl)benzamide | 484.0 | II and XVIII; followed by resolution by SFC: Chiralpak OJ—H, 15% methanol (Peak 2-20 mg > 98% ee). | V | 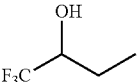 | |
| 770 | 4-(5-chloro-6-(((1R,2S)-2-methylcyclobutyl)oxy)-3-pyridinyl)-2-fluoro-5-methoxy-N-(methylsulfonyl)benzamide | 441 (neg) | II and XVIII; followed by resolution by SFC: Chiralpak OJ—H, 15% methanol (Peak 2 of cis-98.8% ee). | V | 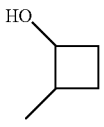 | |
| 771 | 4-(5-chloro-6-((1S)-spiro[2.4]hept-1-ylamino)-3-pyridinyl)-2-fluoro-5-methoxy-N-(methylsulfonyl)benzamide | 466 (neg) | VIII and XVIII; followed by resolution by SFC: Chiralpak OJ—H, 15% methanol (Peak 2 of cis-98.8% ee). | V | 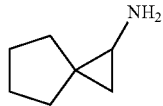 | |
| 772 | 4-(5-chloro-6-(3,5-dichlorophenoxy)-3-pyridinyl)-3-methoxy-N-(methylsulfamoyl)benzamide | 514.0 (−) | XX | X | 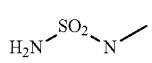 | ¹H NMR (500 MHz, DMSO-d₆) δ ppm 2.52 (d, J = 4.64 Hz, 3H) 3.88 (m, 3H) 7.24 (br. s., 1H) 7.45 (d, J = 1.70 Hz, 2H) 7.48-7.54 (m, 2H) H) 7.64 (d, J = 7.92 Hz, 1H) 7.69 (s, 1H) 8.26 (dd, J = 9.67, 1.98 Hz, 2H) |
| 773 | N-(1-azetidinylsulfonyl)-4-(5-chloro-6-(3,5-dichlorophenoxy)-3-pyridinyl)-3-methoxybenzamide | 542.0 (−) | XX | X | 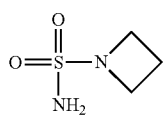 | |
| 774 | 4-(5-chloro-6-((3,4-dichlorophenoxy)methyl)-3-pyridinyl)-3-methoxy-N-(methylsulfonyl)benzamide | 517.0 | XXVII | AC | 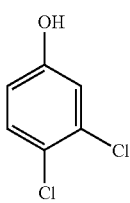 | |

TABLE A-continued

| EX. NO. | NAME | LCMS | METHODS | INTERMEDIATE | REAGENT | ¹H NMR DATA |
|---|---|---|---|---|---|---|
| 775 | 4-(5-chloro-6-(2,4-dichloro-6-methylphenoxy)-3-pyridinyl)-3-methyl-N-(methylsulfonyl)benzamide | 498.8 (neg) | XXX | AD | | |
| 776 | 3-chloro-4-(5-chloro-6-(2,4-dichloro-6-methylphenoxy)-3-pydinyl)-N-(methylsulfonyl)benzamide | 518.8, 520.8 (neg) | XXXI | AE | | |
| 777 | 3-chloro-4-(5-chloro-6-(3,5-dichlorophenoxy)-3-pyridinyl)-N-(methylsulfonyl)benzamide | 507.0 (+) | XXXI | AE | | ¹H NMR (500 MHz, DMSO-d₆) δ ppm 2.87 (s, 3H) 7.45-7.50 (m, 3H) 7.53 (t, J = 7.49 Hz, 1H) 7.94 (dd, J = 7.91, 1.36 Hz, 1H) 8.05 (d, J = 1.23 Hz, 1H) 8.21 (d, J = 2.08 Hz, 1H) 8.25 (d, J = 2.01 Hz, 1H). |
| 778 | 3-chloro-4-(5-chloro-6-(2,3,6-trifluorophenoxy)-3-pyridinyl)-N-(methylsulfonyl)benzamide | 491.0 (+) | XXXI | AE | | |
| 779 | 4-(5-chloro-6-(3-chloro-2-methylphenoxy)-3-pyridinyl)-5-ethoxy-2-fluoro-N-(methylsulfonyl)benzamide | 513, 515 | XXXII | AF | | |
| 780 | 4-(5-chloro-6-(3-chloro-2-methylphenoxy)-3-pyridinyl)-5-(difluoromethoxy)-2-fluoro-N-(methylsulfonyl)benzamide | 535.0, 537.0 | XXXIII | AG | | |
| 781 | 4-(5-chloro-6-(cyclobutyloxy)-3-pyridinyl)-5-(difluoromethoxy)-2-fluoro-N-(methylsulfonyl)benzamide | 465.0 | XXXIII | AG | | |
| 782 | 4-(5-chloro-6-(2,4-dichloro-6-methylphenoxy)-3-pydinyl)-5-(difluoromethoxy)-2-fluoro-N-(methylsulfonyl)benzamide | 569.0 | XXXIII | AG | | 1H NMR (500 MHz, DMSO-d₆) δ 8.29 (d, J = 2.01 Hz, 1H), 8.17 (d, J = 1.95 Hz, 1H), 7.63 (d, J = 2.14 Hz, 1H), 7.58 (d, J = 6.10 Hz, 1H), 7.49 (d, J = 1.82 Hz, 1H), 7.44 (d, J = 10.51 Hz, 1H), 7.01-7.33 (m, 1H), 2.93 (s, 3H), 2.14 (s, 3H) |
| 783 | 4-(6-((1S,2R,4S)-bicyclo[2.2.1]hept-2-yloxy)-5-chloro-3-pyridinyl)-5-(difluoromethoxy)-2-fluoro-N-(methylsulfonyl)benzamide | 505.0 | XXXIII | AG | | |

TABLE A-continued

| EX. NO. | NAME | LCMS | METHODS | INTERMEDIATE | REAGENT | ¹H NMR DATA |
|---|---|---|---|---|---|---|
| 784 | 4-(5-chloro-6-(3,5-dichlorophenoxy)-3-pyridinyl)-5-(difluoromethoxy)-2-fluoro-N-(methylsulfonyl)benzamide | 556.0 | XXXIII | AG | 3,5-dichlorophenol | 1H NMR (500 MHz, DMSO-$d_6$) δ 8.28 (dd, J = 2.01, 9.02 Hz, 2H), 7.60 (d, J = 6.29 Hz, 1H), 7.54 (t, J = 14.59 Hz, 1H), 7.39-7.51 (m, 3H), 7.03-7.35 (m, 1H), 3.01 (s, 3H) |
| 785 | 4-(5-chloro-6-(2,3,6-trifluorophenoxy)-3-pyridinyl)-5-(difluoromethoxy)-2-fluoro-N-(methylsulfonyl)benzamide | 540 (neg) | XXXIII | AG | 2,3,6-trifluorophenol | |
| 786 | 4-(5-chloro-6-((4-chlorobenzyl)oxy)-3-pyridinyl)-5-(difluoromethoxy)-2-fluoro-N-(methylsulfonyl)benzamide | 535.0 | XXXIII | AG | (4-chlorophenyl)methanol | |
| 787 | 4-(5-cyano-6-(2,4-dichloro-6-methylphenoxy)-3-pyridinyl)-2,5-difluoro-N-(methylsulfonyl)benzamide | 514.0 | XXXIV | AH | 2,4-dichloro-6-methylphenol | |
| 788 | 4-(5-chloro-6-(2,4-dichloro-6-methylphenoxy)-3-pyridinyl)-N-(ethylsulfonyl)-3-methoxybenzamide | 528 (neg) | XXXIX | AM | 2,4-dichloro-6-methylphenol | |
| 789 | 4-(5-chloro-6-(3-chloro-2-methylphenoxy)-3-pyridinyl)-N-(ethylsulfonyl)-3-methoxybenzamide | 495 | XXXIX | AM | 3-chloro-2-methylphenol | |
| 790 | 4-(5-chloro-6-(cyclobutyloxy)-3-pyridinyl)-N-(ethylsulfonyl)-3-methoxybenzamide | 425.0 | XXXIX | AM | cyclobutanol | |
| 791 | 4-(5-chloro-6-(2,3,6-trifluorophenoxy)-3-pyridinyl)-N-(ethylsulfonyl)-3-methoxybenzamide | 501.0 (+) | XXXIX | AM | 2,3,6-trifluorophenol | 1H NMR (500 MHz, DMSO-$d_6$) δ ppm 1.10 (t, J = 7.43 Hz, 3H) 3.09 (q, J = 7.31 Hz, 2H) 3.82 (s, 3H) 7.31-7.43 (m, 2H) 7.46-7.58 (m, 1H) 7.62 (d, J = 7.73 Hz, 1H) 7.67 (s, 1H) 8.22 (d, J = 1.95 Hz, 1H) 8.28 (d, J = 1.95 Hz, 1H). |
| 792 | 4-(6-(((1R,2S,4S)-bicyclo[2.2.1]hept-2-yl)oxy)-5-chloro-3-pyridinyl)-N-(ethylsulfonyl)-3-methoxybenzamide | 463.0 (−) | XXXIX | AM | (1R,2S,4S)-bicyclo[2.2.1]heptan-2-ol | |

TABLE A-continued

| EX. NO. | NAME | LCMS | METH-ODS | INTER-MEDI-ATE | REAGENT | $^1$H NMR DATA |
|---|---|---|---|---|---|---|
| 793 | 4-(5-chloro-6-(3,4-dichlorobenzyl)-3-pyridinyl)-3-methoxy-N-(methylsulfonyl)benzamide | 498.1 | XXXV | AI | (3,4-dichlorobenzyl)zinc chloride | |
| 794 | 3-bromo-4-(5-chloro-6-(2,4-dichloro-6-methylphenoxy)-3-pyridinyl)-N-(methylsulfonyl)benzamide | 563 (neg) | XXXX | AN | 2,4-dichloro-6-methylphenol | |
| 795 | 4-(5-chloro-6-(cyclobutyloxy)-3-pyridinyl)-2-fluoro-5-methyl-N-(1,3-thiazol-2-ylsulfonyl)benzamide | 482 | XXXVI | AJ | thiazole-2-sulfonamide | $^1$H NMR (500 MHz, DMSO-d$_6$) ä ppm 1.28 (br. s., 1H) 1.67-1.76 (m, 1 H) 1.86 (q, J = 10.06 Hz, 1H) 2.15-2.29 (m, 4H) 2.50-2.57 (m, 6H) 2.80 (br. s., 1H) 3.23 (s, 1H) 5.26-5.33 (m, 1H) 7.02 (br. s., 1H) 7.04-7.16 (m, 2H) 7.22 (br. s., 1H) 7.69 (d, J = 7.66 Hz, 1H) 7.85 (q, J = 5.67 Hz, 1H) 8.01 (d, J = 2.08 Hz, 1H) 8.14 (s, 1H) |
| 796 | 4-(5-chloro-6-(cyclobutyloxy)-3-pyridinyl)-2-fluoro-5-methyl-N-(propylsulfonyl)benzamide | 439.0 (neg) | XXXVI | AJ | propanesulfonamide | $^1$H NMR (500 MHz, DMSO-d$_6$) ä ppm 1.03 (t, J = 7.46 Hz, 1H) 1.08-1.24 (m, 1H) 1.74 (dq, J = 14.86, 7.48 Hz, 2H) 1.81-1.95 (m, 1H) 2.15-2.25 (m, 1H) 2.28 (s, 1H) 2.53-2.60 (m, 3H) 2.66-2.87 (m, 2H) 3.07-3.20 (m, 1H) 3.26-3.35 (m, 2H) 3.39 (br. s., 3H) 5.31 (quin, J = 7.44 Hz, 1H) 7.20 (d, J = 10.96 Hz, 1H) 7.64 (d, J = 7.40 Hz, 1H) 8.04 (d, J = 2.08 Hz, 1H) 8.17 (d, J = 2.08 Hz, 1H) |
| 797 | 4-(5-chloro-6-(cyclobutyloxy)-3-pyridinyl)-N-(cyclopropylsulfonyl)-2-fluoro-5-methylbenzamide | 437.1 (neg) | XXXVI | AJ | cyclopropanesulfonamide | $^1$H NMR (400 MHz, DMSO-d$_6$) δ ppm 1.09-1.18 (m, 3H) 1.23 (br. s., 1H) 1.59-1.74 (m, 1H) 1.82 (q, J = 9.95 Hz, 1H) 2.07-2.19 (m, 2H) 2.25 (s, 3H) 2.39-2.48 (m, 2H) 3.02-3.15 (m, 1H) 5.24 (quin, J = 7.23 Hz, 1H) 7.26-7.34 (m, 1H) 7.60 (d, J = 7.26 Hz, 1H) 7.98-8.04 (m, 1H) 8.10-8.18 (m, 1H) 12.20 (br. s., 1H) |
| 798 | 4-(5-chloro-6-(cyclobutyloxy)-3-pyridinyl)-N-(cyclobutylsulfonyl)-2-fluoro-5-methylbenzamide | 451.1 (neg) | XXXVI | AJ | cyclobutanesulfonamide | $^1$H NMR (500 MHz, DMSO-d$_6$) δ ppm 1.23 (br. s., 2H) 1.61-1.73 (m, 1H) 1.77-1.86 (m, 1H) 1.88-2.05 (m, 2H) 2.13 (quin, J = 9.97 Hz, 2H) 2.24 (s, 3H) 2.28 (d, J = 9.02 Hz, 2H) 2.35-2.47 (m, 2H) 4.37 (quin, J = 8.16 Hz, 1H) 5.24 (quin, J = 10.90 Hz, 1H) 7.57 (d, (d, J = 10.90 Hz, 1H) 7.57 (d, J = 7.14 Hz, 1H) 8.00 (d, J = 2.08 Hz, 1H) 8.12 (d, J = 2.08 Hz, 1H) 12.09 (br. s., 1H) |
| 799 | 4-(5-chloro-6-(2,4-dichloro-6-methylphenoxy)-3-pyridinyl)-2-fluoro-5-methyl-N-(1,3-thiazol-2-ylsulfonyl)benzamide | 584.1 (neg) | XXXVII | AK | thiazole-2-sulfonamide | $^1$H NMR (400 MHz, DMSO-d$_6$) δ ppm 2.14 (s, 3H) 2.20 (s, 3H) 7.08 (d, J = 11.20 Hz, 1H) 7.40-7.56 (m, 1H) 7.58-7.68 (m, 3H) 7.80 (q, J = 3.14 Hz, 2H) 8.05 (d, J = 2.07 Hz, 1H) 8.21 (d, J = 2.13 Hz, 1H). |

TABLE A-continued

| EX. NO. | NAME | LCMS | METHODS | INTER- MEDI- ATE | REAGENT | $^1$H NMR DATA |
|---|---|---|---|---|---|---|
| 800 | 4-(5-chloro-6-(2,4-dichloro-6-methylphenoxy)-3-pyridinyl)-N-(ethylsulfonyl)-2-fluoro-5-methylbenzamide | 530.8 (neg) | XXXVII | AK | | $^1$H NMR (400 MHz, DMSO-d$_6$) ä 12.20 (br. s., 1H), 8.18-8.32 (m, 1H) 8.10 (d, J = 2.07 Hz, 1H), 7.57-7.70 (m, 2H), 7.49 (d, J = 1.76 Hz, 1H), 7.37 (d, J = 10.68 Hz, 1H), 3.42-3.58 (m, 2H), 2.26 (s, 3H), 2.15 (s, 3H), 1.22-1.34 (m, 3H) |
| 801 | 4-(5-chloro-6-(2,4-dichloro-6-methylphenoxy)-3-pyridinyl)-N-(cyclopropylsulfonyl)-2-fluoro-5-methylbenzamide | 544.8 | XXXVII | AK | | $^1$H NMR (400 MHz, DMSO-d$_6$) ä 12.23 (br. s., 1H), 8.21-8.29 (m, 1H), 8.07-8.12 (m, 1H), 7.59-7.66 (m, 2H), 7.46-7.53 (m, 1H), 7.33-7.41 (m, 1H), 3.04-3.14 (m, 1H), 2.23-2.30 (m, 3H), 2.15 (s, 3H), 1.10-1.19 (m, 4H). |
| 802 | 4-(5-chloro-6-(cyclobutyloxy)-3-pyridinyl)-5-cyclopropyl-2-fluoro-N-(methylsulfonyl)benzamide | 439.0 | XXXVIII | AL | | |
| 803 | 4-(2-chloro-6-(3,5-dichlorophenoxy)-4-pyridinyl)-3-methoxy-N-(methylsulfonyl)benzamide | 498.9 | II and XI | | | $^1$H NMR (500 MHz, DMSO-d$_6$) δ 12.29 (br. s., 1H), 7.72 (s, 1H), 7.60-7.69 (m, 3H), 7.53 (t, J = 1.68 Hz, 1H), 7.50 (d, J = 0.85 Hz, 1H), 7.42 (d, J = 1.71 Hz, 2H), 7.30 (d, J = 0.80 Hz, 1H), 3.92 (s, 3H), 3.41 (s, 3H) |
| 804 | 4-(5-chloro-6-((1S)-2,2,2-trifluoro-1-methyl-1-phenylethoxy)-3-pyridinyl)-2,5-difluoro-N-(methylsulfonyl)benzamide | 533.1 | II, followed by resolution of Example 566 | C | | $^1$H NMR (400 MHz, DMSO-d$_6$) d 8.28 (s, 1H), 8.11 (s, 1H), 7.55 (d, J = 5.49 Hz, 3H), 7.48 (d, J = 6.63 Hz, 2H), 7.40 (d, J = 7.46 Hz, 2H), 3.09 (s, 3H), 2.31 (s, 3H) |
| 805 | 4-(5-chloro-6-((1R)-2,2,2-trifluoro-1-methyl-1-phenylethoxy)-3-pyridinyl)-2,5-difluoro-N-(methylsulfonyl)benzamide | 533.1 | II, followed by resolution of Example 566 | C | | $^1$H NMR (400 MHz, DMSO-d$_6$) d 8.28 (s, 1H), 8.11 (s, 1H), 7.38-7.58 (m, 7H), 3.12 (s, 3H), 2.31 (s, 3H) |
| 806 | 4'-chloro-5-fluoro-2-methyl-N-(methylsulfonyl)-3'-(trifluoromethyl)-4-biphenylcarboxamide | 407.9 | XXII | | | |
| 807 | 3'-chloro-5-fluoro-2-methyl-N-(methylsulfonyl)-4'-(trifluoromethyl)-4-biphenylcarboxamide | 408.0 | XXII | | | |
| 808 | 4-(5-chloro-6-(2,2-difluoroethoxy)-3-pyridinyl)-2-fluoro-5-methyl-N-(methylsulfonyl)benzamide | 421.0 | XXII | | | |

TABLE A-continued

| EX. NO. | NAME | LCMS | METHODS | INTERMEDIATE | REAGENT | ¹H NMR DATA |
|---|---|---|---|---|---|---|
| 809 | 4-(2,2-difluoro-1,3-benzodioxol-5-yl)-2-fluoro-5-methyl-N-(methylsulfonyl)benzamide | 386.0 | XXII | | 5-bromo-2,2-difluoro-1,3-benzodioxole | |
| 810 | 5-fluoro-2-methyl-N-(methylsulfonyl)-4'-(2,2,2-trifluoroethoxy)-4-biphenylcarboxamide | 404.0 | XXII | | 1-bromo-4-(2,2,2-trifluoroethoxy)benzene | |
| 811 | 5-fluoro-2-methyl-N-(methylsulfonyl)-4'-(1,1,2,2-tetrafluoroethoxy)-4-biphenylcarboxamide | 422.0 | XXII | | 1-bromo-4-(1,1,2,2-tetrafluoroethoxy)benzene | |
| 812 | 5-fluoro-2-methyl-N-(methylsulfonyl)-3'-(1,1,2,2-tetrafluoroethoxy)-4-biphenylcarboxamide | 422.0 | XXII | | 1-bromo-3-(1,1,2,2-tetrafluoroethoxy)benzene | |
| 813 | 3'-chloro-4'-(cyclopropylmethyl)-5-fluoro-2-methyl-N-(methylsulfonyl)-4-biphenylcarboxamide | 394.0 | XXII | | 4-bromo-2-chloro-1-(cyclopropylmethyl)benzene | |
| 814 | 3'-chloro-4'-ethyl-5-fluoro-2-methyl-N-(methylsulfonyl)-4-biphenylcarboxamide | 368.0 | XXII | | 4-bromo-2-chloro-1-ethylbenzene | |
| 815 | 4-(6-(tert-butylamino)-5-chloro-3-pyridinyl)-2-fluoro-5-methyl-N-(methylsulfonyl)benzamide | 412.0 | XXII | | 5-bromo-N-tert-butylpyridin-2-amine | |
| 816 | 4-(6-tert-butoxy-5-chloro-3-pyridinyl)-2-fluoro-5-methyl-N-(methylsulfonyl)benzamide | 413.1 | XXII | | 5-bromo-2-tert-butoxypyridine | |
| 817 | 4-(6-(3,5-dichlorophenoxy)-5-(trifluoromethyl)-3-pyridinyl)-2-fluoro-5-methyl-N-(methylsulfonyl)benzamide | 537.0 | | | 3,5-dichlorophenol | |

TABLE A-continued

| EX. NO. | NAME | LCMS | METHODS | INTERMEDIATE | REAGENT | $^1$H NMR DATA |
|---|---|---|---|---|---|---|
| 818 | 4-(5-chloro-6-((3-methoxybenzyl)sulfanyl)-3-pyridinyl)-2-fluoro-5-methyl-N-(methylsulfonyl)benzamide | 495.0 | XXIX | P | | |
| 819 | 4-(5-chloro-6-((4-cyanophenoxy)methyl)-3-pyridinyl)-3-methoxy-N-(methylsulfonyl)benzamide | 472.0 | XXVI | AB | | |
| 825 | 4-(6-(3,5-dichlorophenoxy)-5-(trifluoromethyl)-3-pyridinyl)-3-methoxy-N-(methylsulfonyl)benzamide | 535.1 | | | | $^1$H NMR (400 MHz, DMSO-d$_6$) δ = 8.60 (d, J = 1.9 Hz, 1H), 8.42 (d, J = 1.8 Hz, 1H), 7.71 (d, J = 1.6 Hz, 1H), 7.67 (dd, J = 1.6, 7.9 Hz, 1H), 7.61 (d, J = 7.9 Hz, 1H), 7.57 (t, J = 1.9 Hz, 1H), 7.48 (d, J = 1.9 Hz, 2H), 3.90 (s, 3H), 3.40 (s, 3H). |
| 832 | 4-(5-chloro-6-((3-chloro-2-methoxy-4-pyridinyl)oxy)-3-pyridinyl)-3-methoxy-N-(methylsulfonyl)benzamide | 498.34 | II and XI | L | | |
| 833 | Mixture of 4-(5-chloro-6-((2R)-2-(1-methylethyl)-1-pyrrolidinyl)-3-pyridinyl)-3-(difluoromethoxy)-N-4-(5-chloro-6-((2S)-2-(1-methylethyl)-1-pyrrolidinyl)-3-pyridinyl)-3-(difluoromethoxy)-N-(methylsulfonyl)benzamide | 487.95 | VIII and XIII | N | | |
| 835 | 4-(5-chloro-6-(3,4-dichlorophenyl)-3-pyridinyl)-2-fluoro-5-methyl-N-(methylsulfonyl)benzamid | 486.9 | XXIII | Y | | |
| 838 | 4-(5-(3,5-difluorophenyl)-6-(2-methylpropoxy)-3-pyridinyl)-2,5-difluoro-N-(methylsulfonyl)benzamide | 495.0 | XXIV | | | |
| 841 | 4-(6-(3,5-dichlorophenoxy)-5-methyl-3-pyridinyl)-3-methoxy-N-(methylsulfonyl)benzamide | 481 | XXV | | | |

Biological Examples

The following assays were used in testing the exemplary compounds of the invention. Data for those examples tested in accordance with the procedures described below are presented in Table B below.

Nav 1.7 or Nav 1.5 Ion Works Quattro (IWQ) In Vitro Assay

HEK 293 Cells stably transfected with either human Nav 1.7 or human Nav 1.5 were recorded in population patch-clamp mode with the IonWorks® Quattro automated electrophysiology system in accordance with the manufacturer's specifications (Molecular Devices, LLC, Sunnyvale, Calif.).

Sodium channel currents were measured in response to a train of depolarizations that induced successively greater inactivation.

Cells were held at −110 mV for three seconds (Nav 1.7) or half a second (Nav 1.5) from a holding voltage of −15 mV, then put through a series of 26 pulses of 150 msec duration to −20 mV at a frequency of 5 Hz. Cells were then left unclamped for a period of 3 to 8 minutes while a single concentration of test compound was added. Cells were then reclamped and put through the same voltage protocol. Current at the end of the $26^{th}$ pulse to −20 mV was subtracted from the peak current evoked by the $26^{th}$ pulse to −20 mV to correct for leak current. Percent block was calculated for each concentration in duplicate, and $IC_{50}$ curves were fitted to percent block as a function of concentration.

Nav 1.7 In Vitro Patch Express (PX) Assay

HEK 293 cells stably transfected with human Nav1.7 were recorded in whole cell voltage clamp mode with the PatchXpress automated electrophysiology system (Molecular Devices, LLC, Sunnyvale, Calif.). Compound effects were measured on a partially inactivated state of the sodium channel. Cells were clamped to a holding potential yielding 20 to 50% inactivation. To elicit sodium current, channels were activated by pulsing to −10 mV for 20 msec. This voltage protocol was repeated at a rate of 0.1 Hz throughout the experiment. A single concentration of test compound was applied to cells for a duration of 3 minutes. Peak sodium current was measured at the end of the compound addition period to determine percent inhibition. Three to five cells were tested per concentration, and $IC_{50}$ curves were fitted to percent inhibition as a function of concentration. Data for compounds representative of the invention are presented in the Tables herein.

Nav 1.5 In Vitro PX Assay 293 cells stably transfected with human Nav 1.5 were recorded in whole cell voltage clamp mode with the PatchXpress automated electrophysiology system according to the manufacturer's specifications (Molecular Devices, LLC, Sunnyvale, Calif.). Cells were held at a holding potential of −50 mV to inactivate sodium channels. To elicit sodium currents the voltage was changed to −120 mV to recover a portion of the channels, followed by delivery of test pulses of 20 msec duration to 0 mV, at 0.1 Hz. A single concentration of test compound was applied to cells for a duration of 5 minutes. Peak sodium current was measured at the end of the compound addition period to determine percent inhibition. A minimum of two cells were tested per concentration. $IC_{50}$ curves were fitted to percent inhibition as a function of concentration. Data for compounds representative of the invention are presented in the Tables herein.

The compounds of the present invention may also be tested in the following in vivo assays.

Rat Formalin Model of Persistent Pain

On the test day, animals (Naïve, male Sprague Dawley rats) weighing between 260-300 g at the start of testing can be obtained from Harlan (Indianapolis, Ind.). All animals may be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. Animals are pretreated with the appropriate test compound either by oral gavage or intraperitoneal injection at the desired pretreatment time (typically two hours before test onset) and then returned to their home cages. After dosing and at least 30 minutes prior to test onset, animals can be acclimated to the individual testing chambers. At test time, each animal can be gently wrapped in a towel with the left hindpaw exposed. A dilute solution of formalin (2.5%) in phosphate buffered saline can be injected subcutaneously into the dorsal surface of the left hindpaw in a volume to 50 μL with a 30 g needle. Immediately following injection, a small metal band can be affixed to the plantar side of the left hindpaw with a drop of LOCTITE (adhesive). Animals may be then placed into the testing chambers and the number of flinches can be recorded between 10 to 40 minutes after formalin injection. A flinch is defined as a quick and spontaneous movement of the injected hindpaw not associated with ambulation. Flinches can be quantified with the aid of the Automated Nociception Analyzer built by the University of California, San Diego Department of Anesthesiology. Individual data can be expressed as a % maximal potential effect (% MPE) calculated with the following formula:

(−(Individual score−Vehicle average score)/Vehicle average score))*100=% MPE

Statistical analysis can be performed by analysis of variance (ANOVA), with post-hoc analysis using Bonferroni compared to the vehicle group for a significant main effect. Data can be represented as mean % MPE+/−standard error for each group.

Rat Open Field Assay

On the test day, animals (Naïve, male Sprague Dawley rats) weighing between 260-300 g at the start of testing may be obtained from Harlan (Indianapolis, Ind.). All animals can be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. In a room separate from the testing room, animals can be pretreated with the appropriate test compound either by oral gavage or intraperitoneal injection at the desired pretreatment time (typically two hours before test onset) and then can be returned to their home cages until the pretreatment has elapsed. At test time, animal can be transferred to the open field testing room in their home cages. Each animal may be placed in a separate testing chamber and the motion tracking system is started. The house lights in the testing room should be turned off and the animals can be allowed to explore the novel open field for 30 minutes. An automated motion tracker, made by San Diego Instruments, San Diego, Calif., can be used to capture animal exploration with the aid of infrared photo beams to detect animal movement. These behaviors include basic movement and vertical rearing, which can be used as the primary endpoints for this assay. At the end of the test, house lights can be turned on and the animals should be removed from the testing apparatus. Data can be expressed as a percent change from the vehicle control using the following equation.

(1−(Test mean/Vehicle mean))*100=% Change.

Statistical analysis can be performed by analysis of variance (ANOVA), with post-hoc analysis using Dunnett to follow up significant main effects.

Mouse Formalin Model of Persistent Pain

Mice (Naïve, male C57Bl/6) weighing between 22-30 g at the start of testing were obtained from Harlan (Indianapolis, Ind.). All animals were housed under a 12/12 h light/dark cycle with lights on at 0630. Mice were singly housed on solid bottom cages with corn cob bedding and had access to food and water ad libitum. Animals were allowed to habituate to the vivarium for at least five days before testing was begun and were brought into the testing room at least 30 minutes prior to dosing. Animals were pretreated with the appropriate test compound either by oral gavage or intraperitoneal injection at the desired pretreatment time (typically two hours before test onset) and then returned to their home cages. After dosing and at least 5 minutes prior to test onset, animals were acclimated to the individual testing chambers. At test time, each animal was gently wrapped in a cloth glove with the left hind paw exposed. A dilute solution of formalin (2%) in phosphate buffered saline was injected subcutaneously into the dorsal surface of the left hind paw in a volume to 20 µL with a 30 g needle. Animals were then placed into the observation chambers and the behaviors were recorded for 60 minutes following the formalin injection. A pain-like behavior was defined as licking and/or non-weight bearing of the injected hind paw not associated with ambulation.

Statistical analysis was performed by analysis of variance (ANOVA), with post-hoc analysis using the Dunnett post-hoc test compared to the vehicle group for any significant main effect. Data were represented as mean+/−standard error for each group.

Mouse Open Field Assay

Mice (Naïve, male C57Bl/6) weighing between 22-30 g at the start of testing were obtained from Harlan (Indianapolis, Ind.). All animals were housed under a 12/12 h light/dark cycle with lights on at 0630. Mice were singly housed on solid bottom cages with corn cob bedding and had access to food and water ad libitum. Animals were allowed to habituate to the vivarium for at least five days before testing was begun and were brought into the testing room at least 30 minutes prior to dosing. In a room separate from the testing room, animals were pretreated with the appropriate test compound either by oral gavage or intraperitoneal injection at the desired pretreatment time (typically two hours before test onset) and then returned to their home cages until the pretreatment has elapsed. At test time, animal were transferred to the open field testing room in their home cages. Each animal was placed in a separate testing chamber and the motion tracking system was started. The house lights in the testing room were turned off and the animals were allowed to explore the novel open field for 30 minutes. An automated motion tracker, made by Kinder Scientific, Poway, Calif., was used to capture animal exploration with the aid of infrared photo beams to detect animal movement. These behaviors include basic movement and vertical rearing, which were used as the primary endpoints for this assay. At the end of the test, house lights were turned on and the animals were removed from the testing apparatus.

Statistical analysis was performed by analysis of variance (ANOVA), with post-hoc analysis using the Dunnett post-hoc test compared to the vehicle group for any significant main effect. Data were represented as mean+/−standard error for each group. Data was also expressed as a percent change from the vehicle control using the following equation:

(1−(Test mean/Vehicle mean))*100=% Change.

CFA-Thermal Assay

Animals (Naïve, male Sprague Dawley rats) weighing between 260-300 g at the start of testing) can be obtained from Harlan (Indianapolis, Ind.). All animals can be housed under a 12/12 h light/dark cycle with lights on at 0600. Rodents may be housed two to a cage on solid bottom cages with corn cob bedding with access to food and water ad libitum. Animals can be allowed to habituate to the vivarium for at least five days before testing was begun and may be brought into the testing room at least 30 minutes prior to dosing. The Complete Freund's Adjuvant (CFA)-thermal assay may use a three continuous day testing schedule consisting of a habituation day, a baseline day, and a test day. On day 1, animals can be brought into the testing room, labeled, and placed in their individual testing boxes on the testing apparatus. Animals may be allowed to explore this environment for at least an hour without actually being tested. After habituating, animals can be placed back in their home cages and returned to the vivarium. On day 2, animals can be brought back into the testing room and placed on the testing apparatus and allowed to calm down (typically 30-45 minutes). A basal thermal threshold should be then taken with the following procedure: once calm, a Ugo Basile plantar device is placed under the animals left hindpaw; the start button is depressed turning on a steadily increasing thermal source and a timer; when the animal reaches its thermal threshold it will flinch its hindpaw, stopping the timer and the thermal stimulus. This latency to flinch can be recorded three times for each animal, with at least 5 minutes between trials, and the mean score can be used as the animal's baseline threshold. After testing, animals can be injected intraplantarly with a 25 µg/50 µl of complete Freund's adjuvant into the left hindpaw. Animals are then returned to their home cages and returned to the vivarium. On test day, animals can be again placed on the thermal testing apparatus and their post-CFA baselines obtained with the procedure outlined above. Animals can be pretreated with the appropriate test compound either by oral gavage or intraperitoneal injection at the desired pretreatment time (typically two hours before test onset) and then can be returned to their home cages. Thirty minutes prior to testing, animals can be placed on the apparatus again. Once the pretreatment time has elapsed, animals can be again tested with the procedure above. Data may be expressed as a percent maximal potential effect with the following formula:

((Post-Drug Mean−Pre-Drug Mean)/(Baseline Mean−Pre-Drug Mean))*100=% MPE

Statistical analysis can be performed by analysis of variance (ANOVA), with post-hoc analysis using Bonferroni compared to the vehicle group for a significant main effect. Data can be represented as mean % MPE+/−standard error for each group.

Spinal Nerve Ligation (CHUNG)

Animals (Naïve, male Sprague Dawley rats) weighing between 150-200 g at the start of first time testing can be obtained from Harlan (Indianapolis, Ind.). All animals may be housed under a 12/12 h light/dark cycle with lights on at 0600. Rodents can be housed two to a cage on solid bottom cages with corn cob bedding with access to food and water ad libitum. Animals may be allowed to habituate to the vivarium for at least five days before testing is begun. Surgery may be then performed based on the method described by Kim and Chung (1992). Briefly, animals can be placed under isoflurane anesthesia and placed in a sterile surgical field. The area of the lumbar spine is excised and the spinal nerves at L4-L5 are exposed. The L5 spinal nerve is identified and tightly ligated with 5-0 silk suture. The muscle may be closed with absorbable suture and the skin with wound clip. Animals may be returned to the vivarium for 7-14 days and monitored daily. On test day, animals can be brought into the testing room and placed on a wire mesh floor in individual testing chambers. They may be allowed to acclimate to the chambers until they are calm. A series of Semmes-Weinstein monofilaments (von Frey hairs) with calibrated bending forces are then applied to determine a hyperalgesic baseline following the method set forth by Chaplan et al. (1994). Briefly, filaments are applied with an increasing force (if there was not reaction to the previous stimulus) or decreasing force (if there was a reaction to the previous stimulus) until a baseline value is reached. Animals are then pretreated with the appropriate test compound either by oral gavage or intraperitoneal injection at the desired pretreatment time (typically two hours before test onset) and then returned to their home cages. Thirty minutes prior to testing, animals are placed on the apparatus again. After the pretreatment time had elapsed, the procedure above is repeated to determine drug efficacy. Data can be expressed as the mean gram force to elicit a nociceptive behavior. Statistical analysis can be performed by analysis of variance (ANOVA), with post-hoc analysis using Bonferroni compared to the vehicle group for a significant main effect.

Table B provides data for compounds exemplified in the present application and priority document thereof, as representative compounds of the present invention having Nav 1.7 PX $IC_{50}$ of 145 μM or lower, as follows: compound name (as named by ACD software, version 12; while the compound names in the written examples presented herein were named using ChemDraw Ultra version 12); and biological data including in-vitro Nav 1.7 PX data ($IC_{50}$ in uM) and Nav 1.5 IWQ data ($IC_{50}$ in uM), where available. Ex. # refers to Example No. All other compounds exemplified herein have Nav 1.7 PX $IC_{50}$, where available, as disclosed in the priority document U.S. Provisional Patent Application Nos. 61/885,372, filed on Oct. 1, 2013, Table 20, pages 241-291.

TABLE B

BIOLOGICAL DATA

| EX. NO. | COMPOUND NAME | NAV 1.7 PX $IC_{50}$ (μM) | NAV 1.5 IWQ $IC_{50}$ (μM) |
|---|---|---|---|
| 327 | 4-(5-chloro-6-(2-chloro-6-methylphenoxy)-3-pyridinyl)-3-methoxy-N-(methylsulfonyl)benzamide | 0.0823 | |
| 329 | 4-(5-chloro-6-(3-chloro-4-methylphenoxy)-3-pyridinyl)-3-methoxy-N-(methylsulfonyl)benzamide | 0.0847 | |
| 344 | 4-(5-chloro-6-(2-chloro-4-methylphenoxy)-3-pyridinyl)-3-methoxy-N-(methylsulfonyl)benzamide | 0.0915 | |
| 348 | 4-(5-chloro-6-(3,5-dichlorophenoxy)-3-pyridinyl)-3-methoxy-N-(methylsulfonyl)benzamide | 0.0345 | 5.74 |
| 350 | 4-(5-chloro-6-(4-chlorophenoxy)-3-pyridinyl)-3-methoxy-N-(methylsulfonyl)benzamide | 0.0926 | |
| 355 | 4-(5-chloro-6-((2S)-2-(1-methylethyl)-1-pyrrolidinyl)-3-pyridinyl)-3-methoxy-N-(methylsulfonyl)benzamide | 0.0877 | |
| 357 | 4-(5-chloro-6-(2,3,4-trifluorophenoxy)-3-pyridinyl)-3-methoxy-N-(methylsulfonyl)benzamide | 0.0882 | |
| 361 | 4-(5-chloro-6-(4-fluoro-2-methylphenoxy)-3-pyridinyl)-3-methoxy-N-(methylsulfonyl)benzamide | 0.0966 | |
| 362 | 4-(5-chloro-6-(2,3,6-trifluorophenoxy)-3-pyridinyl)-3-methoxy-N-(methylsulfonyl)benzamide | 0.0636 | |

TABLE B-continued

BIOLOGICAL DATA

| EX. NO. | COMPOUND NAME | NAV 1.7 PX $IC_{50}$ (μM) | NAV 1.5 IWQ $IC_{50}$ (μM) |
|---|---|---|---|
| 363 | 4-(5-chloro-6-(2,5-difluorophenoxy)-3-pyridinyl)-3-methoxy-N-(methylsulfonyl)benzamide | 0.1 | |
| 364 | 4-(5-chloro-6-(4-chloro-3,5-dimethylphenoxy)-3-pyridinyl)-3-methoxy-N-(methylsulfonyl)benzamide | 0.0643 | |
| 365 | 4-(5-chloro-6-(2-chloro-4-methoxyphenoxy)-3-pyridinyl)-3-methoxy-N-(methylsulfonyl)benzamide | 0.0914 | |
| 368 | 4-(5-chloro-6-(4-chloro-3-ethylphenoxy)-3-pyridinyl)-3-methoxy-N-(methylsulfonyl)benzamide | 0.0723 | |
| 369 | 4-(5-chloro-6-(2-chloro-5-methoxyphenoxy)-3-pyridinyl)-3-methoxy-N-(methylsulfonyl)benzamide | 0.0905 | |
| 370 | 4-(5-chloro-6-(4-chloro-3-(trifluoromethyl)phenoxy)-3-pyridinyl)-3-methoxy-N-(methylsulfonyl)benzamide | 0.057 | |
| 371 | 4-(5-chloro-6-(2-chloro-5-fluorophenoxy)-3-pyridinyl)-3-methoxy-N-(methylsulfonyl)benzamide | 0.08 | |
| 372 | 4-(5-chloro-6-(3-chloro-5-(trifluoromethoxy)phenoxy)-3-pyridinyl)-3-methoxy-N-(methylsulfonyl)benzamide | 0.0504 | |
| 373 | 4-(5-chloro-6-(4-chloro-3-(trifluoromethoxy)phenoxy)-3-pyridinyl)-3-methoxy-N-(methylsulfonyl)benzamide | 0.0662 | |
| 374 | 4-(5-chloro-6-(3-chloro-5-(trifluoromethyl)phenoxy)-3-pyridinyl)-3-methoxy-N-(methylsulfonyl)benzamide | 0.0584 | |
| 376 | 4-(5-chloro-6-(4-chloro-2-fluorophenoxy)-3-pyridinyl)-3-methoxy-N-(methylsulfonyl)benzamide | 0.0603 | |
| 377 | 4-(5-chloro-6-(2-chloro-4-fluorophenoxy)-3-pyridinyl)-3-methoxy-N-(methylsulfonyl)benzamide | 0.0612 | |
| 379 | 4-(5-chloro-6-(5-chloro-2-methylphenoxy)-3-pyridinyl)-3-methoxy-N-(methylsulfonyl)benzamide | 0.0546 | |
| 382 | 4-(6-(3,5-dichlorophenoxy)-5-(difluoromethyl)-3-pyridinyl)-3-methoxy-N-(methylsulfonyl)benzamide | 0.054 | |
| 402 | 4-(5-chloro-6-(2,3-difluorophenoxy)-3-pyridinyl)-3-methoxy-N-(methylsulfonyl)benzamide | 0.08 | |
| 412 | 4-(5-chloro-6-((5-chloro-6-methoxy-3-pyridinyl)oxy)-3-pyridinyl)-N-(methylsulfonyl)-3-(3-oxetanyloxy)benzamide | 0.0989 | |
| 413 | 4-(5-chloro-6-(4-chloro-3-methylphenoxy)-3-pyridinyl)-N-(methylsulfonyl)-3-(3-oxetanyloxy)benzamide | 0.0461 | |
| 419 | 4-(5-chloro-6-(1-naphthalenyloxy)-3-pyridinyl)-N-(methylsulfonyl)-3-(3-oxetanyloxy)benzamide | 0.098 | |
| 422 | 4-(5-chloro-6-(3,5-dichlorophenoxy)-3-pyridinyl)-N-(methylsulfonyl)-3-(3-oxetanyloxy)benzamide | 0.0313 | |

TABLE B-continued

BIOLOGICAL DATA

| EX. NO. | COMPOUND NAME | NAV 1.7 PX IC$_{50}$ (μM) | NAV 1.5 IWQ IC$_{50}$ (μM) |
|---|---|---|---|
| 423 | 4-(5-chloro-6-(2-chloro-5-methylphenoxy)-3-pyridinyl)-N-(methylsulfonyl)-3-(3-oxetanyloxy)benzamide | 0.0386 | |
| 424 | 4-chloro-6-(2-naphthalenyloxy)-3-pyridinyl)-N-(methylsulfonyl)-3-(3-oxetanyloxy)benzamide | 0.0994 | |
| 425 | 4-(5-chloro-6-(3-chloro-4-methylphenoxy)-3-pyridinyl)-N-(methylsulfonyl)-3-(3-oxetanyloxy)benzamide | 0.0322 | |
| 426 | 4-(5-chloro-6-(2-chloro-6-methylphenoxy)-3-pyridinyl)-N-(methylsulfonyl)-3-(3-oxetanyloxy)benzamide | 0.075 | |
| 436 | 4-(5-chloro-6-((5-chloro-6-methoxy-3-pyridinyl)oxy)-3-pyridinyl)-3-(difluoromethoxy)-N-(methylsulfonyl)benzamide | 0.0922 | |
| 446 | 4-(5-chloro-6-(2-naphthalenyloxy)-3-pyridinyl)-3-(difluoromethoxy)-N-(methylsulfonyl)benzamide | 0.0748 | |
| 449 | 4-(5-chloro-6-(3-chloro-4-methylphenoxy)-3-pyridinyl)-3-(difluoromethoxy)-N-(methylsulfonyl)benzamide | 0.0792 | |
| 452 | 4-(5-chloro-6-(1-naphthalenyloxy)-3-pyridinyl)-3-(difluoromethoxy)-N-(methylsulfonyl)benzamide | 0.0599 | |
| 453 | 4-(5-chloro-6-(4-chloro-3-methylphenoxy)-3-pyridinyl)-3-(difluoromethoxy)-N-(methylsulfonyl)benzamide | 0.0603 | |
| 455 | 4-(5-chloro-6-((1R)-1-phenylethoxy)-3-pyridinyl)-3-(difluoromethoxy)-N-(methylsulfonyl)benzamide | 0.058 | |
| 456 | 4-(5-chloro-6-(3-(trifluoromethyl)phenoxy)-3-pyridinyl)-3-(difluoromethoxy)-N-(methylsulfonyl)benzamide | 0.064 | |
| 457 | 4-(5-chloro-6-((1S)-1-phenylethoxy)-3-pyridinyl)-3-(difluoromethoxy)-N-(methylsulfonyl)benzamide | 0.08 | |
| 459 | 4-(5-chloro-6-(3,4-dimethylphenoxy)-3-pyridinyl)-3-(difluoromethoxy)-N-(methylsulfonyl)benzamide | 0.095 | |
| 460 | 4-(5-chloro-6-(4-chloro-3-fluorophenoxy)-3-pyridinyl)-3-(difluoromethoxy)-N-(methylsulfonyl)benzamide | 0.0962 | |
| 461 | 4-(5-chloro-6-(3,5-dichlorophenoxy)-3-pyridinyl)-3-(difluoromethoxy)-N-(methylsulfonyl)benzamide | 0.0337 | |
| 462 | 4-(5-chloro-6-(2-chloro-5-methylphenoxy)-3-pyridinyl)-3-(difluoromethoxy)-N-(methylsulfonyl)benzamide | 0.0683 | |
| 464 | 4-(5-chloro-6-(2-(trifluoromethyl)phenoxy)-3-pyridinyl)-3-(difluoromethoxy)-N-(methylsulfonyl)benzamide | 0.0924 | |
| 465 | 4-(5-chloro-6-(2-chloro-4-methylphenoxy)-3-pyridinyl)-3-(difluoromethoxy)-N-(methylsulfonyl)benzamide | 0.0697 | |
| 466 | 4-(5-chloro-6-(4-chlorophenoxy)-3-pyridinyl)-3-(difluoromethoxy)-N-(methylsulfonyl)benzamide | 0.0688 | |
| 467 | 4-(5-chloro-6-(2-phenylethoxy)-3-pyridinyl)-3-(difluoromethoxy)-N-(methylsulfonyl)benzamide | 0.0788 | |
| 468 | 4-(5-chloro-6-(2-chloro-6-methylphenoxy)-3-pyridinyl)-3-(difluoromethoxy)-N-(methylsulfonyl)benzamide | 0.0535 | |
| 539 | 4-(5-cyano-6-(2-phenylethoxy)-3-pyridinyl)-3-methoxy-N-(methylsulfonyl)benzamide | 0.0942 | |
| 547 | 4-(5-cyano-6-(3,5-dichlorophenoxy)-3-pyridinyl)-3-methoxy-N-(methylsulfonyl)benzamide | 0.0771 | |
| 549 | 4-(6-(3-chloro-4-methylphenoxy)-5-cyano-3-pyridinyl)-3-methoxy-N-(methylsulfonyl)benzamide | 0.0505 | |
| 566 | 4-(5-chloro-6-((1R)-2,2,2-trifluoro-1-methyl-1-phenylethoxy)-3-pyridinyl)-2,5-difluoro-N-(methylsulfonyl)benzamide, 4-(5-chloro-6-((1S)-2,2,2-trifluoro-1-methyl-1-phenylethoxy)-3-pyridinyl)-2,5-difluoro-N-(methylsulfonyl)benzamide | 0.07309 | >3.0 |
| 567 | 4-(5-chloro-6-(2,4-dichloro-6-methylphenoxy)-3-pyridinyl)-2,5-difluoro-N-(methylsulfonyl)benzamide | 0.0598 | >4.9 |
| 568 | 4-(5-chloro-6-(2,4,6-trichlorophenoxy)-3-pyridinyl)-2,5-difluoro-N-(methylsulfonyl)benzamide | 0.04851 | |
| 569 | 4-(5-chloro-6-(2,3-difluoro-4-methylphenoxy)-3-pyridinyl)-2,5-difluoro-N-(methylsulfonyl)benzamide | 0.05996 | |
| 570 | 4-(5-chloro-6-(3,4-dichlorophenoxy)-3-pyridinyl)-2,5-difluoro-N-(methylsulfonyl)benzamide | 0.06121 | |
| 571 | 4-(5-chloro-6-(5-chloro-2-methylphenoxy)-3-pyridinyl)-2,5-difluoro-N-(methylsulfonyl)benzamide | 0.09916 | |
| 572 | 4-(5-chloro-6-(2,6-dichloro-4-fluorophenoxy)-3-pyridinyl)-2,5-difluoro-N-(methylsulfonyl)benzamide | 0.057645 | |
| 573 | 4-(5-chloro-6-((7-fluoro-2,3-dihydro-1H-inden-4-yl)oxy)-3-pyridinyl)-2,5-difluoro-N-(methylsulfonyl)benzamide | 0.09652 | |
| 574 | 4-(5-chloro-6-((1R)-1-(2,4-difluorophenyl)ethoxy)-3-pyridinyl)-2,5-difluoro-N-(methylsulfonyl)benzamide | 0.08879 | |
| 575 | 4-(5-bromo-6-(2,4-dichloro-6-methylphenoxy)-3-pyridinyl)-2,5-difluoro-N-(methylsulfonyl)benzamide | 0.04235 | >4.9 |
| 576 | 4-(5-chloro-6-((4-chlorobenzyl)oxy)-3-pyridinyl)-3-methoxy-N-(methylsulfonyl)benzamide | 0.07 | >3.0 |
| 577 | 4-(5-chloro-6-((2-chlorobenzyl)oxy)-3-pyridinyl)-3-methoxy-N-(methylsulfonyl)benzamide | 0.09505 | >3.0 |
| 578 | 4-(5-chloro-6-(2,4-dichloro-6-methylphenoxy)-3-pyridinyl)-3-methoxy-N-(methylsulfonyl)benzamide | 0.029625 | |
| 579 | 4-(5-chloro-6-(3-chloro-2-methylphenoxy)-3-pyridinyl)-3-methoxy-N-(methylsulfonyl)benzamide | 0.0486 | |

TABLE B-continued

BIOLOGICAL DATA

| EX. NO. | COMPOUND NAME | NAV 1.7 PX IC$_{50}$ (μM) | NAV 1.5 IWQ IC$_{50}$ (μM) |
|---|---|---|---|
| 580 | 4-(5-chloro-6-(2,3-dihydro-1H-inden-5-yloxy)-3-pyridinyl)-3-methoxy-N-(methylsulfonyl)benzamide | 0.06607 | |
| 581 | 4-(5-chloro-6-(2,6-dichlorophenoxy)-3-pyridinyl)-3-methoxy-N-(methylsulfonyl)benzamide | 0.08456 | |
| 582 | 4-(5-chloro-6-(2,5-dichlorophenoxy)-3-pyridinyl)-3-methoxy-N-(methylsulfonyl)benzamide | 0.06143 | |
| 583 | 4-(5-chloro-6-(2,3-dichlorophenoxy)-3-pyridinyl)-3-methoxy-N-(methylsulfonyl)benzamide | 0.03053 | |
| 584 | 4-(5-chloro-6-(2,4-dichloro-6-methylphenoxy)-3-pyridinyl)-N-(methylsulfonyl)-3-(3-oxetanyloxy)benzamide | 0.059 | |
| 585 | 4-(5-chloro-6-(2,4-dichloro-6-methylphenoxy)-3-pyridinyl)-3-(difluoromethoxy)-N-(methylsulfonyl)benzamide | 0.04718 | 0.289 |
| 586 | 4-(5-chloro-6-(3-chloro-2-methylphenoxy)-3-pyridinyl)-3-(difluoromethoxy)-N-(methylsulfonyl)benzamide | 0.03463 | |
| 587 | 4-(5-chloro-6-((1R)-2,2,2-trifluoro-1-methyl-1-phenylethoxy)-3-pyridinyl)-2-fluoro-5-methyl-N-(methylsulfonyl)benzamide, 4-(5-chloro-6-((1S)-2,2,2-trifluoro-1-methyl-1-phenylethoxy)-3-pyridinyl)-2-fluoro-5-methyl-N-(methylsulfonyl)benzamide | 0.08153 | >3.0 |
| 588 | 5-chloro-4-(5-chloro-6-(2,3,4-trifluorophenoxy)-3-pyridinyl)-2-fluoro-N-(methylsulfonyl)benzamide | 0.08233 | >3.0 |
| 589 | 5-chloro-4-(5-chloro-6-(2,3,5-trifluorophenoxy)-3-pyridinyl)-2-fluoro-N-(methylsulfonyl)benzamide | 0.04994 | >3.0 |
| 590 | 5-chloro-4-(5-chloro-6-(5-chloro-2-methylphenoxy)-3-pyridinyl)-2-fluoro-N-(methylsulfonyl)benzamide | 0.06808 | >3.0 |
| 591 | 5-chloro-4-(5-chloro-6-(3-fluoro-4-methylphenoxy)-3-pyridinyl)-2-fluoro-N-(methylsulfonyl)benzamide | 0.08556 | >3.0 |
| 592 | 5-chloro-4-(5-chloro-6-(2,6-dichlorophenoxy)-3-pyridinyl)-2-fluoro-N-(methylsulfonyl)benzamide | 0.06606 | >3.0 |
| 593 | 4-(6-(((1R)-1-benzylpropyl)oxy)-5-chloro-3-pyridinyl)-5-chloro-2-fluoro-N-(methylsulfonyl)benzamide, 4-(6-(((1S)-1-benzylpropyl)oxy)-5-chloro-3-pyridinyl)-5-chloro-2-fluoro-N-(methylsulfonyl)benzamide | 0.09739 | >3.0 |
| 594 | 5-chloro-4-(5-chloro-6-(((1R)-2-methyl-1-phenylpropyl)oxy)-3-pyridinyl)-2-fluoro-N-(methylsulfonyl)benzamide, 5-chloro-4-(5-chloro-6-(((1S)-2-methyl-1-phenylpropyl)oxy)-3-pyridinyl)-2-fluoro-N-(methylsulfonyl)benzamide | 0.0488 | >3.0 |
| 595 | 5-chloro-4-(5-chloro-6-(2-chloro-5-fluorophenoxy)-3-pyridinyl)-2-fluoro-N-(methylsulfonyl)benzamide | 0.08144 | >3.0 |
| 596 | 5-chloro-4-(5-chloro-6-(((1R)-1-(4-fluorophenyl)propyl)oxy)-3-pyridinyl)-2-fluoro-N-(methylsulfonyl)benzamide, 5-chloro-4-(5-chloro-6-(((1S)-1-(4-fluorophenyl)propyl)oxy)-3-pyridinyl)-2-fluoro-N-(methylsulfonyl)benzamide | 0.08792 | >3.0 |
| 597 | 5-chloro-4-(5-chloro-6-(2,5-difluorophenoxy)-3-pyridinyl)-2-fluoro-N-(methylsulfonyl)benzamide | 0.0698 | 5.39 |
| 598 | 5-chloro-4-(5-chloro-6-(2,4-dichloro-6-methylphenoxy)-3-pyridinyl)-2-fluoro-N-(methylsulfonyl)benzamide | 0.01843 | |
| 599 | 5-chloro-4-(5-chloro-6-(2-chloro-3,5-difluorophenoxy)-3-pyridinyl)-2-fluoro-N-(methylsulfonyl)benzamide | 0.06268 | >3.0 |
| 600 | 5-chloro-4-(5-chloro-6-(cyclopentylmethoxy)-3-pyridinyl)-2-fluoro-N-(methylsulfonyl)benzamide | 0.09191 | |
| 601 | 5-chloro-4-(5-chloro-6-(1-ethylpropoxy)-3-pyridinyl)-2-fluoro-N-(methylsulfonyl)benzamide | 0.07544 | |
| 602 | 5-chloro-4-(5-chloro-6-((1-methylcyclobutyl)oxy)-3-pyridinyl)-2-fluoro-N-(methylsulfonyl)benzamide | 0.1 | |
| 603 | 4-(5-chloro-6-(2,4-difluorophenoxy)-3-pyridinyl)-2-fluoro-5-methyl-N-(methylsulfonyl)benzamide | 0.14295 | |
| 604 | 4-(5-chloro-6-(2,3-difluorophenoxy)-3-pyridinyl)-2-fluoro-5-methyl-N-(methylsulfonyl)benzamide | 0.1089 | |
| 605 | 4-(5-chloro-6-(2,5-difluorophenoxy)-3-pyridinyl)-2-fluoro-5-methyl-N-(methylsulfonyl)benzamide | 0.04547 | >3.0 |
| 606 | 4-(6-(4-bromo-2-chloro-5-fluorophenoxy)-5-chloro-3-pyridinyl)-2-fluoro-5-methyl-N-(methylsulfonyl)benzamide | 0.07167 | >3.0 |
| 607 | 4-(6-(3-bromophenoxy)-5-chloro-3-pyridinyl)-2-fluoro-5-methyl-N-(methylsulfonyl)benzamide | 0.06825 | >3.0 |
| 608 | 4-(5-chloro-6-((2-methyl-1-naphthalenyl)oxy)-3-pyridinyl)-2-fluoro-5-methyl-N-(methylsulfonyl)benzamide | 0.04805 | >3.0 |
| 609 | 4-(6-(4-bromophenoxy)-5-chloro-3-pyridinyl)-2-fluoro-5-methyl-N-(methylsulfonyl)benzamide | 0.07738 | >3.0 |
| 610 | 4-(5-chloro-6-(5,6,7,8-tetrahydro-1-naphthalenyloxy)-3-pyridinyl)-2-fluoro-5-methyl-N-(methylsulfonyl)benzamide | 0.1044 | |
| 611 | 4-(6-(4-tert-butyl-2-chlorophenoxy)-5-chloro-3-pyridinyl)-2-fluoro-5-methyl-N-(methylsulfonyl)benzamide | 0.07612 | >3.0 |
| 612 | 4-(6-(2-biphenylyloxy)-5-chloro-3-pyridinyl)-2-fluoro-5-methyl-N-(methylsulfonyl)benzamide | 0.08835 | >3.0 |
| 613 | 4-(5-chloro-6-((4-chloro-1-naphthalenyl)oxy)-3-pyridinyl)-2-fluoro-5-methyl-N-(methylsulfonyl)benzamide | 0.09266 | >3.0 |
| 614 | 4-(6-(4-bromo-2-methylphenoxy)-5-chloro-3-pyridinyl)-2-fluoro-5-methyl-N-(methylsulfonyl)benzamide | 0.06801 | >3.0 |
| 615 | 4-(5-chloro-6-(2,3,4-trifluorophenoxy)-3-pyridinyl)-2-fluoro-5-methyl-N-(methylsulfonyl)benzamide | 0.07518 | >3.0 |
| 616 | 4-(5-chloro-6-(5-chloro-2-methylphenoxy)-3-pyridinyl)-2-fluoro-5-methyl-N-(methylsulfonyl)benzamide | 0.07079 | >3.0 |
| 617 | 4-(5-chloro-6-(5-chloro-2-fluorophenoxy)-3-pyridinyl)-2-fluoro-5-methyl-N-(methylsulfonyl)benzamide | 0.0933 | >3.0 |

TABLE B-continued

BIOLOGICAL DATA

| EX. NO. | COMPOUND NAME | NAV 1.7 PX IC$_{50}$ (μM) | NAV 1.5 IWQ IC$_{50}$ (μM) |
|---|---|---|---|
| 618 | 4-(5-chloro-6-(2-fluoro-3-methylphenoxy)-3-pyridinyl)-2-fluoro-5-methyl-N-(methylsulfonyl)benzamide | 0.09501 | >3.0 |
| 619 | 4-(5-chloro-6-(3-chloro-2-fluorophenoxy)-3-pyridinyl)-2-fluoro-5-methyl-N-(methylsulfonyl)benzamide | 0.09367 | >3.0 |
| 620 | 4-(5-chloro-6-(4-chloro-2-methylphenoxy)-3-pyridinyl)-2-fluoro-5-methyl-N-(methylsulfonyl)benzamide | 0.07608 | >3.0 |
| 621 | 4-(5-chloro-6-(3-methylphenoxy)-3-pyridinyl)-2-fluoro-5-methyl-N-(methylsulfonyl)benzamide | 0.1075 | |
| 622 | 4-(5-chloro-6-(2,4,6-trifluorophenoxy)-3-pyridinyl)-2-fluoro-5-methyl-N-(methylsulfonyl)benzamide | 0.0873 | >3.0 |
| 623 | 4-(5-chloro-6-(3-fluoro-4-methylphenoxy)-3-pyridinyl)-2-fluoro-5-methyl-N-(methylsulfonyl)benzamide | 0.04853 | 4.837 |
| 624 | 4-(6-(2-tert-butyl-5-methylphenoxy)-5-chloro-3-pyridinyl)-2-fluoro-5-methyl-N-(methylsulfonyl)benzamide | 0.0827 | >3.0 |
| 625 | 4-(5-chloro-6-(3-chloro-2,6-difluorophenoxy)-3-pyridinyl)-2-fluoro-5-methyl-N-(methylsulfonyl)benzamide | 0.08369 | |
| 626 | 4-(5-chloro-6-(3-chloro-4-fluorophenoxy)-3-pyridinyl)-2-fluoro-5-methyl-N-(methylsulfonyl)benzamide | 0.1076 | |
| 627 | 4-(5-chloro-6-(2,6-dichlorophenoxy)-3-pyridinyl)-2-fluoro-5-methyl-N-(methylsulfonyl)benzamide | 0.06907 | >3.0 |
| 628 | 4-(5-chloro-6-(2,4-dichloro-6-methylphenoxy)-3-pyridinyl)-2-fluoro-5-methyl-N-(methylsulfonyl)benzamide | 0.05597 | 2.189 |
| 629 | 4-(5-chloro-6-(2,3,5-trifluorophenoxy)-3-pyridinyl)-2-fluoro-5-methyl-N-(methylsulfonyl)benzamide | 0.05783 | >3.0 |
| 630 | 4-(5-chloro-6-(3,5-difluorophenoxy)-3-pyridinyl)-2-fluoro-5-methyl-N-(methylsulfonyl)benzamide | 0.07781 | >3.0 |
| 631 | 4-(5-chloro-6-(2-chloro-3,5-difluorophenoxy)-3-pyridinyl)-2-fluoro-5-methyl-N-(methylsulfonyl)benzamide | 0.06278 | >3.0 |
| 632 | 4-(5-chloro-6-(2-chloro-4,5-dimethylphenoxy)-3-pyridinyl)-2-fluoro-5-methyl-N-(methylsulfonyl)benzamide | 0.08151 | >3.0 |
| 633 | 4-(6-(2-tert-butyl-6-methylphenoxy)-5-chloro-3-pyridinyl)-2-fluoro-5-methyl-N-(methylsulfonyl)benzamide | 0.08328 | >3.0 |
| 634 | 4-(6-(2-tert-butyl-4-methylphenoxy)-5-chloro-3-pyridinyl)-2-fluoro-5-methyl-N-(methylsulfonyl)benzamide | 0.09479 | >3.0 |
| 635 | 4-(6-((1R,2S,4S)-bicyclo[2.2.1]hept-2-yloxy)-5-chloro-3-pyridinyl)-2-fluoro-5-methyl-N-(methylsulfonyl)benzamide | 0.0809 | >3.0 |
| 636 | 4-(6-(1,3-benzothiazol-2-ylmethoxy)-5-chloro-3-pyridinyl)-2-fluoro-5-methyl-N-(methylsulfonyl)benzamide | 0.055745 | >3.0 |
| 637 | 4-(5-chloro-6-(3-methylbutoxy)-3-pyridinyl)-2-fluoro-5-methyl-N-(methylsulfonyl)benzamide | 0.0877 | >3.0 |
| 638 | 4-(5-chloro-6-(((1R)-1-methyl-3-phenylpropyl)oxy)-3-pyridinyl)-2-fluoro-5-methyl-N-(methylsulfonyl)benzamide, 4-(5-chloro-6-(((1S)-1-methyl-3-phenylpropyl)oxy)-3-pyridinyl)-2-fluoro-5-methyl-N-(methylsulfonyl)benzamide | 0.08 | >3.0 |
| 639 | 4-(5-chloro-6-(((1R)-1-(4-fluorophenyl)propyl)oxy)-3-pyridinyl)-2-fluoro-5-methyl-N-(methylsulfonyl)benzamide, 4-(5-chloro-6-(((1S)-1-(4-fluorophenyl)propyl)oxy)-3-pyridinyl)-2-fluoro-5-methyl-N-(methylsulfonyl)benzamide | 0.07041 | >3.0 |
| 640 | 4-(5-chloro-6-(((1R)-1-(4-chlorophenyl)propyl)oxy)-3-pyridinyl)-2-fluoro-5-methyl-N-(methylsulfonyl)benzamide, 4-(5-chloro-6-(((1S)-1-(4-chlorophenyl)propyl)oxy)-3-pyridinyl)-2-fluoro-5-methyl-N-(methylsulfonyl)benzamide | 0.09082 | >3.0 |
| 641 | 4-(5-chloro-6-(((1R)-1-cyclobutylethoxy)-3-pyridinyl)-2-fluoro-5-methyl-N-(methylsulfonyl)benzamide, 4-(5-chloro-6-(((1S)-1-cyclobutylethoxy)-3-pyridinyl)-2-fluoro-5-methyl-N-(methylsulfonyl)benzamide | 0.1106 | 9.325 |
| 642 | 4-(5-chloro-6-(2-chloro-5-(trifluoromethyl)phenoxy)-3-pyridinyl)-2-fluoro-5-methyl-N-(methylsulfonyl)benzamide | 0.07054 | >3.0 |
| 643 | 4-(5-chloro-6-(2,3-difluoro-4-methylphenoxy)-3-pyridinyl)-2-fluoro-5-methyl-N-(methylsulfonyl)benzamide | 0.0792 | 5.4425 |
| 644 | 4-(5-chloro-6-(2,6-dichloro-4-fluorophenoxy)-3-pyridinyl)-2-fluoro-5-methyl-N-(methylsulfonyl)benzamide | 0.0828 | >3.0 |
| 645 | 4-(5-chloro-6-(4-ethoxy-3-fluorophenoxy)-3-pyridinyl)-2-fluoro-5-methyl-N-(methylsulfonyl)benzamide | 0.09729 | >3.0 |
| 646 | 4-(5-chloro-6-((2S)-2-phenyl-1-pyrrolidinyl)-3-pyridinyl)-2-fluoro-5-methyl-N-(methylsulfonyl)benzamide | 0.09992 | >3.0 |
| 647 | 4-(6-((1R)-1-(1,3-benzothiazol-2-yl)ethoxy)-5-chloro-3-pyridinyl)-2-fluoro-5-methyl-N-(methylsulfonyl)benzamide, 4-(6-((1S)-1-(1,3-benzothiazol-2-yl)ethoxy)-5-chloro-3-pyridinyl)-2-fluoro-5-methyl-N-(methylsulfonyl)benzamide | 0.07595 | >3.0 |
| 648 | 4-(5-chloro-6-(((1R)-1-(2-chlorophenyl)pentyl)oxy)-3-pyridinyl)-2-fluoro-5-methyl-N-(methylsulfonyl)benzamide, 4-(5-chloro-6-(((1S)-1-(2-chlorophenyl)pentyl)oxy)-3-pyridinyl)-2-fluoro-5-methyl-N-(methylsulfonyl)benzamide | 0.04979 | 4.413 |

TABLE B-continued

BIOLOGICAL DATA

| EX. NO. | COMPOUND NAME | NAV 1.7 PX IC$_{50}$ (μM) | NAV 1.5 IWQ IC$_{50}$ (μM) |
|---|---|---|---|
| 649 | 4-(5-chloro-6-((1R)-2-(2-methoxyphenyl)-1-methylethoxy)-3-pyridinyl)-2-fluoro-5-methyl-N-(methylsulfonyl)benzamide, 4-(5-chloro-6-((1S)-2-(2-methoxyphenyl)-1-methylethoxy)-3-pyridinyl)-2-fluoro-5-methyl-N-(methylsulfonyl)benzamide | 0.09291 | >3.0 |
| 650 | 4-(5-chloro-6-(((1R)-1-(4-fluorophenyl)propyl)oxy)-3-pyridinyl)-2-fluoro-5-methyl-N-(methylsulfonyl)benzamide | 0.07866 | >3.0 |
| 651 | 4-(5-chloro-6-(((1S)-1-(4-fluorophenyl)propyl)oxy)-3-pyridinyl)-2-fluoro-5-methyl-N-(methylsulfonyl)benzamide | 0.07346 | >3.0 |
| 652 | 4-(5-chloro-6-((1R)-1-(2-chloro-4-fluorophenyl)ethoxy)-3-pyridinyl)-2-fluoro-5-methyl-N-(methylsulfonyl)benzamide, 4-(5-chloro-6-((1S)-1-(2-chloro-4-fluorophenyl)ethoxy)-3-pyridinyl)-2-fluoro-5-methyl-N-(methylsulfonyl)benzamide | 0.06641 | >3.0 |
| 653 | 4-(5-chloro-6-((1R)-1-(5-chloro-1,3-benzothiazol-2-yl)ethoxy)-3-pyridinyl)-2-fluoro-5-methyl-N-(methylsulfonyl)benzamide, 4-(5-chloro-6-((1S)-1-(5-chloro-1,3-benzothiazol-2-yl)ethoxy)-3-pyridinyl)-2-fluoro-5-methyl-N-(methylsulfonyl)benzamide | 0.0836 | >3.0 |
| 654 | 4-(5-chloro-6-(5-quinolinylmethoxy)-3-pyridinyl)-2-fluoro-5-methyl-N-(methylsulfonyl)benzamide | 0.09038 | >3.0 |
| 655 | 4-(5-chloro-6-((2R)-2-(3-(trifluoromethyl)phenyl)-1-pyrrolidinyl)-3-pyridinyl)-2-fluoro-5-methyl-N-(methylsulfonyl)benzamide, 4-(5-chloro-6-((2S)-2-(3-(trifluoromethyl)phenyl)-1-pyrrolidinyl)-3-pyridinyl)-2-fluoro-5-methyl-N-(methylsulfonyl)benzamide | 0.1023 | |
| 656 | 4-(5-chloro-6-((2R)-2-(3-chlorophenyl)-1-pyrrolidinyl)-3-pyridinyl)-2-fluoro-5-methyl-N-(methylsulfonyl)benzamide, 4-(5-chloro-6-((2S)-2-(3-chlorophenyl)-1-pyrrolidinyl)-3-pyridinyl)-2-fluoro-5-methyl-N-(methylsulfonyl)benzamide | 0.07381 | >3.0 |
| 657 | 4-(5-chloro-6-((2R)-2-(4-methylphenyl)-1-pyrrolidinyl)-3-pyridinyl)-2-fluoro-5-methyl-N-(methylsulfonyl)benzamide, 4-(5-chloro-6-((2S)-2-(4-methylphenyl)-1-pyrrolidinyl)-3-pyridinyl)-2-fluoro-5-methyl-N-(methylsulfonyl)benzamide | 0.0929 | >3.0 |
| 658 | 4-(5-chloro-6-((2R)-2-(3,4-dichlorophenyl)-1-pyrrolidinyl)-3-pyridinyl)-2-fluoro-5-methyl-N-(methylsulfonyl)benzamide, 4-(5-chloro-6-((2S)-2-(3,4-dichlorophenyl)-1-pyrrolidinyl)-3-pyridinyl)-2-fluoro-5-methyl-N-(methylsulfonyl)benzamide | 0.0899 | >3.0 |
| 659 | 4-(5-chloro-6-((2R)-2-(2-(trifluoromethyl)phenyl)-1-pyrrolidinyl)-3-pyridinyl)-2-fluoro-5-methyl-N-(methylsulfonyl)benzamide, 4-(5-chloro-6-((2S)-2-(2-(trifluoromethyl)phenyl)-1-pyrrolidinyl)-3-pyridinyl)-2-fluoro-5-methyl-N-(methylsulfonyl)benzamide | 0.1072 | |
| 660 | 4-(5-chloro-6-((1R)-1-(2,4,5-trifluorophenyl)ethoxy)-3-pyridinyl)-2-fluoro-5-methyl-N-(methylsulfonyl)benzamide, 4-(5-chloro-6-((1S)-1-(2,4,5-trifluorophenyl)ethoxy)-3-pyridinyl)-2-fluoro-5-methyl-N-(methylsulfonyl)benzamide | 0.09248 | 6.4395 |
| 661 | 4-(5-chloro-6-((1R)-1-(2,4,6-trifluorophenyl)ethoxy)-3-pyridinyl)-2-fluoro-5-methyl-N-(methylsulfonyl)benzamide, 4-(5-chloro-6-((1S)-1-(2,4,6-trifluorophenyl)ethoxy)-3-pyridinyl)-2-fluoro-5-methyl-N-(methylsulfonyl)benzamide | 0.07691 | >10.0 |
| 662 | 4-(5-chloro-6-((7-methyl-2,3-dihydro-1H-inden-4-yl)oxy)-3-pyridinyl)-2-fluoro-5-methyl-N-(methylsulfonyl)benzamide | 0.08822 | 3.7685 |
| 663 | 4-(5-chloro-6-(4-(1-methylethoxy)phenoxy)-3-pyridinyl)-2-fluoro-5-methyl-N-(methylsulfonyl)benzamide | 0.1081 | |
| 664 | 4-(5-chloro-6-(3,4-dichlorophenoxy)-3-pyridinyl)-2-fluoro-5-methyl-N-(methylsulfonyl)benzamide | 0.08057 | >10.0 |
| 665 | 4-(5-chloro-6-(2,4-dichlorophenoxy)-3-pyridinyl)-2-fluoro-5-methyl-N-(methylsulfonyl)benzamide | 0.03567 | 4.677 |
| 666 | 4-(5-chloro-6-(2-chloro-4,6-difluorophenoxy)-3-pyridinyl)-2-fluoro-5-methyl-N-(methylsulfonyl)benzamide | 0.0497 | 3.406 |
| 667 | 4-(5-chloro-6-(2,4,5-trichlorophenoxy)-3-pyridinyl)-2-fluoro-5-methyl-N-(methylsulfonyl)benzamide | 0.05046 | 7.453 |
| 668 | 4-(5-chloro-6-(4-chloro-3,5-difluorophenoxy)-3-pyridinyl)-2-fluoro-5-methyl-N-(methylsulfonyl)benzamide | 0.09702 | >10.0 |
| 669 | 4-(5-chloro-6-(4-chloro-2,6-dimethylphenoxy)-3-pyridinyl)-2-fluoro-5-methyl-N-(methylsulfonyl)benzamide | 0.06596 | 3.609 |
| 670 | 4-(5-chloro-6-(6-chloro-2-fluoro-3-methylphenoxy)-3-pyridinyl)-2-fluoro-5-methyl-N-(methylsulfonyl)benzamide | 0.0836 | >10.0 |
| 671 | 4-(5-chloro-6-(3-fluoro-4-(trifluoromethyl)phenoxy)-3-pyridinyl)-2-fluoro-5-methyl-N-(methylsulfonyl)benzamide | 0.1231 | |
| 672 | 4-(5-chloro-6-((7-fluoro-2,3-dihydro-1H-inden-4-yl)oxy)-3-pyridinyl)-2-fluoro-5-methyl-N-(methylsulfonyl)benzamide | 0.06753 | >10.0 |
| 673 | 4-(5-chloro-6-((1R)-1-(2,5-dichlorophenyl)ethoxy)-3-pyridinyl)-2-fluoro-5-methyl-N-(methylsulfonyl)benzamide | 0.04616 | >10.0 |
| 674 | 4-(5-chloro-6-((1S)-1-(2,5-dichlorophenyl)ethoxy)-3-pyridinyl)-2-fluoro-5-methyl-N-(methylsulfonyl)benzamide | 0.08337 | 4.8555 |

TABLE B-continued

BIOLOGICAL DATA

| EX. NO. | COMPOUND NAME | NAV 1.7 PX IC$_{50}$ (μM) | NAV 1.5 IWQ IC$_{50}$ (μM) |
|---|---|---|---|
| 675 | 4-(5-chloro-6-(((1R)-1-(4-fluoro-3-methylphenyl)propyl)oxy)-3-pyridinyl)-2-fluoro-5-methyl-N-(methylsulfonyl)benzamide | 0.05397 | >10.0 |
| 676 | 4-(5-chloro-6-(((1S)-1-(3-chlorophenyl)propyl)oxy)-3-pyridinyl)-2-fluoro-5-methyl-N-(methylsulfonyl)benzamide | 0.05865 | |
| 677 | 4-(5-chloro-6-(2-methyl-3-(trifluoromethyl)phenoxy)-3-pyridinyl)-2-fluoro-5-methyl-N-(methylsulfonyl)benzamide | 0.08365 | |
| 678 | 4-(5-chloro-6-(4-fluoro-2-(trifluoromethyl)phenoxy)-3-pyridinyl)-2-fluoro-5-methyl-N-(methylsulfonyl)benzamide | 0.07439 | |
| 679 | 4-(5-chloro-6-(4-chloro-2-(trifluoromethyl)phenoxy)-3-pyridinyl)-2-fluoro-5-methyl-N-(methylsulfonyl)benzamide | 0.0875 | |
| 680 | 4-(5-chloro-6-(2-ethyl-5-methylphenoxy)-3-pyridinyl)-2-fluoro-5-methyl-N-(methylsulfonyl)benzamide | 0.06629 | |
| 681 | 4-(5-chloro-6-((4-chloro-2-methylbenzyl)oxy)-3-pyridinyl)-2-fluoro-5-methyl-N-(methylsulfonyl)benzamide | 0.09857 | >4.9 |
| 682 | 4-(5-chloro-6-((1S)-1-(1-naphthalenyl)ethoxy)-3-pyridinyl)-2-fluoro-5-methyl-N-(methylsulfonyl)benzamide | 0.05509 | |
| 683 | 4-(5-chloro-6-(2-cyclopropylethoxy)-3-pyridinyl)-2-fluoro-5-methyl-N-(methylsulfonyl)benzamide | 0.111 | |
| 684 | 4-(5-chloro-6-((1S)-2,2,2-trifluoro-1-phenylethoxy)-3-pyridinyl)-2-fluoro-5-methyl-N-(methylsulfonyl)benzamide | 0.09413 | |
| 685 | 4-(5-chloro-6-(((1R)-1-(4-methylphenyl)propyl)oxy)-3-pyridinyl)-2-fluoro-5-methyl-N-(methylsulfonyl)benzamide, 4-(5-chloro-6-(((1S)-1-(4-methylphenyl)propyl)oxy)-3-pyridinyl)-2-fluoro-5-methyl-N-(methylsulfonyl)benzamide | 0.08812 | |
| 686 | 4-(5-chloro-6-(2,2,2-trifluoro-1-(trifluoromethyl)ethoxy)-3-pyridinyl)-2-fluoro-5-methyl-N-(methylsulfonyl)benzamide | 0.1148 | |
| 687 | 4-(5-chloro-6-(((1R)-3,3-dimethylcyclohexyl)oxy)-3-pyridinyl)-2-fluoro-5-methyl-N-(methylsulfonyl)benzamide, 4-(5-chloro-6-(((1S)-3,3-dimethylcyclohexyl)oxy)-3-pyridinyl)-2-fluoro-5-methyl-N-(methylsulfonyl)benzamide | 0.07593 | |
| 688 | 4-(5-chloro-6-((1R)-1-(2-(trifluoromethyl)phenyl)ethoxy)-3-pyridinyl)-2-fluoro-5-methyl-N-(methylsulfonyl)benzamide, 4-(5-chloro-6-((1S)-1-(2-(trifluoromethyl)phenyl)ethoxy)-3-pyridinyl)-2-fluoro-5-methyl-N-(methylsulfonyl)benzamide | 0.08626 | |
| 689 | 4-(5-cyano-6-(2,4-dichloro-6-methylphenoxy)-3-pyridinyl)-3-methoxy-N-(methylsulfonyl)benzamide | 0.028405 | 1 |
| 690 | 4-(6-(3-chloro-2-methylphenoxy)-5-cyano-3-pyridinyl)-3-methoxy-N-(methylsulfonyl)benzamide | 0.04686 | |
| 691 | 4-(5-cyano-6-(2,4-dichlorophenoxy)-3-pyridinyl)-3-methoxy-N-(methylsulfonyl)benzamide | 0.08385 | |
| 692 | 4-(5-cyano-6-(3,4-dichlorophenoxy)-3-pyridinyl)-3-methoxy-N-(methylsulfonyl)benzamide | 0.0603 | |
| 693 | 4-(5-cyano-6-(2,6-dichloro-4-methylphenoxy)-3-pyridinyl)-3-methoxy-N-(methylsulfonyl)benzamide | 0.02207 | |
| 694 | 4-(5-cyano-6-(3,6-dichloro-2-methylphenoxy)-3-pyridinyl)-3-methoxy-N-(methylsulfonyl)benzamide | 0.01718 | |
| 695 | 4-(5-chloro-6-(3,5-dichlorophenoxy)-3-pyridinyl)-2-fluoro-5-methoxy-N-(methylsulfonyl)benzamide | 0.05241 | >3.0 |
| 696 | 4-(5-chloro-6-((1R)-1-phenylethoxy)-3-pyridinyl)-2-fluoro-5-methoxy-N-(methylsulfonyl)benzamide, 4-(5-chloro-6-((1S)-1-phenylethoxy)-3-pyridinyl)-2-fluoro-5-methoxy-N-(methylsulfonyl)benzamide | 0.09302 | >3.0 |
| 697 | 4-(5-chloro-6-(cyclobutyl(methyl)amino)-3-pyridinyl)-2-fluoro-5-methoxy-N-(methylsulfonyl)benzamide | 0.1461 | |
| 698 | 4-(5-chloro-6-(3-fluoro-4-methylphenoxy)-3-pyridinyl)-2-fluoro-5-methoxy-N-(methylsulfonyl)benzamide | 0.05895 | 6.052 |
| 699 | 4-(5-chloro-6-(5-chloro-2-methylphenoxy)-3-pyridinyl)-2-fluoro-5-methoxy-N-(methylsulfonyl)benzamide | 0.05506 | >3.0 |
| 700 | 4-(5-chloro-6-(2,3,5-trifluorophenoxy)-3-pyridinyl)-2-fluoro-5-methoxy-N-(methylsulfonyl)benzamide | 0.09134 | >3.0 |
| 701 | 4-(5-chloro-6-(2,3,4-trifluorophenoxy)-3-pyridinyl)-2-fluoro-5-methoxy-N-(methylsulfonyl)benzamide | 0.070565 | >3.0 |
| 702 | 4-(5-chloro-6-(cyclobutyloxy)-3-pyridinyl)-2-fluoro-5-methoxy-N-(methylsulfonyl)benzamide | 0.06842 | >4.9 |
| 703 | 4-(6-((1R,2S,4S)-bicyclo[2.2.1]hept-2-yloxy)-5-chloro-3-pyridinyl)-2-fluoro-5-methoxy-N-(methylsulfonyl)benzamide | 0.07818 | >3.0 |
| 704 | 4-(5-chloro-6-(3-chloro-2-methylphenoxy)-3-pyridinyl)-2-fluoro-5-methoxy-N-(methylsulfonyl)benzamide | 0.046827 | |
| 705 | 4-(5-chloro-6-(2,5-difluorophenoxy)-3-pyridinyl)-2-fluoro-5-methoxy-N-(methylsulfonyl)benzamide | 0.13042 | 0.8409 |
| 706 | 4-(5-chloro-6-((1R)-1-methyl-2-phenylethoxy)-3-pyridinyl)-2-fluoro-5-methoxy-N-(methylsulfonyl)benzamide, 4-(5-chloro-6-((1S)-1-methyl-2-phenylethoxy)-3-pyridinyl)-2-fluoro-5-methoxy-N-(methylsulfonyl)benzamide | 0.0537 | >3.0 |
| 707 | 4-(5-chloro-6-(2-chloro-3,5-difluorophenoxy)-3-pyridinyl)-2-fluoro-5-methoxy-N-(methylsulfonyl)benzamide | 0.09463 | >3.0 |
| 708 | 4-(6-(1,3-benzothiazol-2-ylmethoxy)-5-chloro-3-pyridinyl)-2-fluoro-5-methoxy-N-(methylsulfonyl)benzamide | 0.03257 | >3.0 |

TABLE B-continued

BIOLOGICAL DATA

| EX. NO. | COMPOUND NAME | NAV 1.7 PX IC$_{50}$ (µM) | NAV 1.5 IWQ IC$_{50}$ (µM) |
|---|---|---|---|
| 709 | 4-(6-((1R)-1-(1,3-benzothiazol-2-yl)ethoxy)-5-chloro-3-pyridinyl)-2-fluoro-5-methyl-N-(methylsulfonyl)benzamide | 0.03489 | >3.0 |
| 710 | 4-(6-((1S)-1-(1,3-benzothiazol-2-yl)ethoxy)-5-chloro-3-pyridinyl)-2-fluoro-5-methyl-N-(methylsulfonyl)benzamide | 0.08732 | >3.0 |
| 711 | 4-(5-chloro-6-(2,4-dichloro-6-methylphenoxy)-3-pyridinyl)-2-fluoro-5-methoxy-N-(methylsulfonyl)benzamide | 0.060735 | >3.0 |
| 712 | 4-(6-(((1R)-1-benzylpropyl)oxy)-5-chloro-3-pyridinyl)-2-fluoro-5-methoxy-N-(methylsulfonyl)benzamide, 4-(6-(((1S)-1-benzylpropyl)oxy)-5-chloro-3-pyridinyl)-2-fluoro-5-methoxy-N-(methylsulfonyl)benzamide | 0.08789 | >3.0 |
| 714 | 4-(5-chloro-6-((1-methylcyclohexyl)methoxy)-3-pyridinyl)-2-fluoro-5-methoxy-N-(methylsulfonyl)benzamide | 0.09862 | |
| 715 | 4-(5-chloro-6-((3-chloro-2-naphthalenyl)oxy)-3-pyridinyl)-2-fluoro-5-methoxy-N-(methylsulfonyl)benzamide | 0.09884 | |
| 716 | 4-(5-chloro-6-(2,4-dichloro-5-methoxyphenoxy)-3-pyridinyl)-2-fluoro-5-methoxy-N-(methylsulfonyl)benzamide | 0.09167 | |
| 717 | 4-(5-chloro-6-((1-chloro-2-naphthalenyl)oxy)-3-pyridinyl)-2-fluoro-5-methoxy-N-(methylsulfonyl)benzamide | 0.09926 | |
| 718 | 4-(5-chloro-6-((2,2,3,3-tetramethylcyclopropyl)methoxy)-3-pyridinyl)-2-fluoro-5-methoxy-N-(methylsulfonyl)benzamide | 0.1451 | |
| 732 | 4-(5-chloro-6-(((1R)-1-(trifluoromethyl)propyl)oxy)-3-pyridinyl)-2-fluoro-5-methoxy-N-(methylsulfonyl)benzamide, 4-(5-chloro-6-(((1S)-1-(trifluoromethyl)propyl)oxy)-3-pyridinyl)-2-fluoro-5-methoxy-N-(methylsulfonyl)benzamide | 0.10418 | |
| 720 | 4-(5-chloro-6-((1R)-spiro[2.4]hept-1-ylamino)-3-pyridinyl)-2-fluoro-5-methoxy-N-(methylsulfonyl)benzamide, 4-(5-chloro-6-((1S)-spiro[2.4]hept-1-ylamino)-3-pyridinyl)-2-fluoro-5-methoxy-N-(methylsulfonyl)benzamide | 0.08439 | |
| 721 | 4-(5-chloro-6-(((4,4-dimethylcyclohexyl)methyl)amino)-3-pyridinyl)-2-fluoro-5-methoxy-N-(methylsulfonyl)benzamide | 0.08715 | |
| 722 | 4-(5-chloro-6-((1R)-spiro[3.3]hept-1-ylamino)-3-pyridinyl)-2-fluoro-5-methoxy-N-(methylsulfonyl)benzamide, 4-(5-chloro-6-((1S)-spiro[3.3]hept-1-ylamino)-3-pyridinyl)-2-fluoro-5-methoxy-N-(methylsulfonyl)benzamide | 0.1102 | |
| 723 | 4-(5-chloro-6-(((3,3-dimethylcyclobutyl)methyl)amino)-3-pyridinyl)-2-fluoro-5-methoxy-N-(methylsulfonyl)benzamide | 0.07477 | |
| 724 | 4-(5-chloro-6-((4,4-dimethylcyclohexyl)amino)-3-pyridinyl)-2-fluoro-5-methoxy-N-(methylsulfonyl)benzamide | 0.106 | |
| 725 | 4-(5-chloro-6-((1-ethylpropyl)amino)-3-pyridinyl)-2-fluoro-5-methoxy-N-(methylsulfonyl)benzamide | 0.09654 | |
| 726 | 4-(5-chloro-6-(((1S)-1,3-dimethylbutyl)oxy)-3-pyridinyl)-2-fluoro-5-methoxy-N-(methylsulfonyl)benzamide | 0.08055 | |
| 727 | 4-(5-chloro-6-(((1R,2R)-2-methylcyclopentyl)oxy)-3-pyridinyl)-2-fluoro-5-methoxy-N-(methylsulfonyl)benzamide | 0.1016 | |
| 728 | 4-(5-chloro-6-((4-methylphenyl)sulfanyl)-3-pyridinyl)-2-fluoro-5-methoxy-N-(methylsulfonyl)benzamide | 0.04949 | |
| 729 | 4-(5-chloro-6-((3,5-dimethylphenyl)sulfanyl)-3-pyridinyl)-2-fluoro-5-methoxy-N-(methylsulfonyl)benzamide | 0.06952 | |
| 730 | 4-(5-chloro-6-((2,5-difluorobenzyl)sulfanyl)-3-pyridinyl)-2-fluoro-5-methoxy-N-(methylsulfonyl)benzamide | 0.0585 | |
| 731 | 4-(5-chloro-6-((2-cyclopentylethyl)amino)-3-pyridinyl)-2-fluoro-5-methoxy-N-(methylsulfonyl)benzamide | 0.1064 | |
| 719 | 4-(5-chloro-6-((1R)-1-cyclobutylethoxy)-3-pyridinyl)-2-fluoro-5-methoxy-N-(methylsulfonyl)benzamide, 4-(5-chloro-6-((1S)-1-cyclobutylethoxy)-3-pyridinyl)-2-fluoro-5-methoxy-N-(methylsulfonyl)benzamide | 0.08904 | |
| 733 | 4-(5-chloro-6-(((1R,2R)-2-methylcyclobutyl)oxy)-3-pyridinyl)-2-fluoro-5-methoxy-N-(methylsulfonyl)benzamide, 4-(5-chloro-6-(((1S,2S)-2-methylcyclobutyl)oxy)-3-pyridinyl)-2-fluoro-5-methoxy-N-(methylsulfonyl)benzamide | 0.2201 | |
| 734 | 4-(5-chloro-6-((1-(trifluoromethyl)cyclobutyl)oxy)-3-pyridinyl)-2-fluoro-5-methoxy-N-(methylsulfonyl)benzamide | 0.0587 | |
| 735 | 4-(5-chloro-6-((trans-3-methylcyclobutyl)oxy)-3-pyridinyl)-2-fluoro-5-methoxy-N-(methylsulfonyl)benzamide | 0.0591 | |
| 736 | 4-(5-chloro-6-(((1R)-1-(trifluoromethyl)propyl)oxy)-3-pyridinyl)-2-fluoro-5-methoxy-N-(methylsulfonyl)benzamide | 0.08403 | |
| 737 | 4-(5-chloro-6-(2,6-dichloro-4-fluorophenoxy)-3-pyridinyl)-2-fluoro-5-methoxy-N-(methylsulfonyl)benzamide | 0.1004 | |
| 738 | 4-(5-chloro-6-(2,4-dichlorophenoxy)-3-pyridinyl)-2-fluoro-5-methoxy-N-(methylsulfonyl)benzamide | 0.037 | |
| 739 | 4-(5-chloro-6-(2,4,5-trichlorophenoxy)-3-pyridinyl)-2-fluoro-5-methoxy-N-(methylsulfonyl)benzamide | 0.051 | |

TABLE B-continued

BIOLOGICAL DATA

| EX. NO. | COMPOUND NAME | NAV 1.7 PX IC$_{50}$ (μM) | NAV 1.5 IWQ IC$_{50}$ (μM) |
|---|---|---|---|
| 740 | 4-(5-chloro-6-(3,5-difluorophenoxy)-3-pyridinyl)-2-fluoro-5-methoxy-N-(methylsulfonyl)benzamide | 0.087 | |
| 741 | 4-(5-chloro-6-(3-chloro-4-fluorophenoxy)-3-pyridinyl)-2-fluoro-5-methoxy-N-(methylsulfonyl)benzamide | 0.056 | |
| 742 | 4-(5-chloro-6-(2,4-difluorophenoxy)-3-pyridinyl)-2-fluoro-5-methoxy-N-(methylsulfonyl)benzamide | 0.094 | |
| 743 | 4-(5-chloro-6-(5-fluoro-2-methylphenoxy)-3-pyridinyl)-2-fluoro-5-methoxy-N-(methylsulfonyl)benzamide | 0.09623 | |
| 744 | 4-(5-chloro-6-(3-chloro-2,6-difluorophenoxy)-3-pyridinyl)-2-fluoro-5-methoxy-N-(methylsulfonyl)benzamide | 0.06777 | |
| 745 | 4-(5-chloro-6-(3-chloro-2-fluorophenoxy)-3-pyridinyl)-2-fluoro-5-methoxy-N-(methylsulfonyl)benzamide | 0.07245 | |
| 746 | 4-(5-chloro-6-(2,3-difluoro-4-methylphenoxy)-3-pyridinyl)-2-fluoro-5-methoxy-N-(methylsulfonyl)benzamide | 0.06282 | |
| 747 | 4-(5-chloro-6-(5-chloro-2-fluorophenoxy)-3-pyridinyl)-2-fluoro-5-methoxy-N-(methylsulfonyl)benzamide | 0.08358 | |
| 748 | 4-(5-chloro-6-(2-chloro-6-methylphenoxy)-3-pyridinyl)-2-fluoro-5-methoxy-N-(methylsulfonyl)benzamide | 0.07643 | |
| 749 | 4-(5-chloro-6-((1R)-1-phenylethoxy)-3-pyridinyl)-2-fluoro-5-methoxy-N-(methylsulfonyl)benzamide | 0.09358 | |
| 750 | 4-(5-chloro-6-((4-chlorobenzyl)oxy)-3-pyridinyl)-2-fluoro-5-methoxy-N-(methylsulfonyl)benzamide | 0.074685 | |
| 751 | 4-(5-chloro-6-(3-chloro-4-methylphenoxy)-3-pyridinyl)-2-fluoro-5-methoxy-N-(methylsulfonyl)benzamide | 0.09833 | |
| 752 | 4-(5-chloro-6-(2-chloro-5-methylphenoxy)-3-pyridinyl)-2-fluoro-5-methoxy-N-(methylsulfonyl)benzamide | 0.04213 | |
| 753 | 4-(5-chloro-6-(4-chloro-2-fluorophenoxy)-3-pyridinyl)-2-fluoro-5-methoxy-N-(methylsulfonyl)benzamide | 0.03687 | |
| 754 | 4-(5-chloro-6-(4-fluoro-3-methylphenoxy)-3-pyridinyl)-2-fluoro-5-methoxy-N-(methylsulfonyl)benzamide | 0.09218 | |
| 755 | 4-(5-chloro-6-(3,4-dichlorophenoxy)-3-pyridinyl)-2-fluoro-5-methoxy-N-(methylsulfonyl)benzamide | 0.05155 | |
| 756 | 4-(5-chloro-6-((1R)-1-methyl-2-phenylethoxy)-3-pyridinyl)-2-fluoro-5-methoxy-N-(methylsulfonyl)benzamide | 0.055285 | |
| 757 | 4-(5-chloro-6-((7-fluoro-2,3-dihydro-1H-inden-4-yl)oxy)-3-pyridinyl)-2-fluoro-5-methoxy-N-(methylsulfonyl)benzamide | 0.04769 | |
| 758 | 4-(5-chloro-6-((1S)-1-methyl-2-phenylethoxy)-3-pyridinyl)-2-fluoro-5-methoxy-N-(methylsulfonyl)benzamide | 0.08376 | |
| 759 | 4-(5-chloro-6-(2,6-difluoro-3-methylphenoxy)-3-pyridinyl)-2-fluoro-5-methoxy-N-(methylsulfonyl)benzamide | 0.09539 | |
| 760 | 4-(5-chloro-6-(2-chloro-3-methylphenoxy)-3-pyridinyl)-2-fluoro-5-methoxy-N-(methylsulfonyl)benzamide | 0.06235 | |
| 761 | 4-(5-chloro-6-((1R)-1-(2-chloro-4-fluorophenyl)ethoxy)-3-pyridinyl)-2-fluoro-5-methoxy-N-(methylsulfonyl)benzamide | 0.08206 | |
| 762 | 4-(5-chloro-6-(6-chloro-2-fluoro-3-methylphenoxy)-3-pyridinyl)-2-fluoro-5-methoxy-N-(methylsulfonyl)benzamide | 0.07524 | |
| 763 | 4-(5-chloro-6-(4-chloro-3,5-difluorophenoxy)-3-pyridinyl)-2-fluoro-5-methoxy-N-(methylsulfonyl)benzamide | 0.04715 | |
| 764 | 4-(5-chloro-6-(2,6-dichlorophenoxy)-3-pyridinyl)-2-fluoro-5-methoxy-N-(methylsulfonyl)benzamide | 0.03669 | |
| 765 | 4-(5-chloro-6-(3-chlorophenoxy)-3-pyridinyl)-2-fluoro-5-methoxy-N-(methylsulfonyl)benzamide | 0.08488 | |
| 766 | 4-(5-chloro-6-(2,3,6-trifluorophenoxy)-3-pyridinyl)-2-fluoro-5-methoxy-N-(methylsulfonyl)benzamide | 0.09634 | |
| 767 | 4-(5-chloro-6-((1S)-1-cyclobutylethoxy)-3-pyridinyl)-2-fluoro-5-methoxy-N-(methylsulfonyl)benzamide | 0.07765 | |
| 768 | 4-(5-chloro-6-(((1S)-1-(trifluoromethyl)propyl)oxy)-3-pyridinyl)-2-fluoro-5-methoxy-N-(methylsulfonyl)benzamide | 0.09551 | |
| 769 | 4-(5-chloro-6-((1R)-1-cyclobutylethoxy)-3-pyridinyl)-2-fluoro-5-methoxy-N-(methylsulfonyl)benzamide | 0.05 | |
| 770 | 4-(5-chloro-6-(((1R,2S)-2-methylcyclobutyl)oxy)-3-pyridinyl)-2-fluoro-5-methoxy-N-(methylsulfonyl)benzamide | 0.1103 | |
| 771 | 4-(5-chloro-6-((1S)-spiro[2.4]hept-1-ylamino)-3-pyridinyl)-2-fluoro-5-methoxy-N-(methylsulfonyl)benzamide | 0.08681 | |
| 772 | 4-(5-chloro-6-(3,5-dichlorophenoxy)-3-pyridinyl)-3-methoxy-N-(methylsulfamoyl)benzamide | 0.08071 | >3.0 |
| 773 | N-(1-azetidinylsulfonyl)-4-(5-chloro-6-(3,5-dichlorophenoxy)-3-pyridinyl)-3-methoxybenzamide | 0.114 | |
| 774 | 4-(5-chloro-6-((3,4-dichlorophenoxy)methyl)-3-pyridinyl)-3-methoxy-N-(methylsulfonyl)benzamide | 0.08008 | >3.0 |
| 775 | 4-(5-chloro-6-(2,4-dichloro-6-methylphenoxy)-3-pyridinyl)-3-methyl-N-(methylsulfonyl)benzamide | 0.0782 | >4.9 |
| 776 | 3-chloro-4-(5-chloro-6-(2,4-dichloro-6-methylphenoxy)-3-pyridinyl)-N-(methylsulfonyl)benzamide | 0.0345 | |
| 777 | 3-chloro-4-(5-chloro-6-(3,5-dichlorophenoxy)-3-pyridinyl)-N-(methylsulfonyl)benzamide | 0.03997 | |
| 778 | 3-chloro-4-(5-chloro-6-(2,3,6-trifluorophenoxy)-3-pyridinyl)-N-(methylsulfonyl)benzamide | 0.07339 | |

TABLE B-continued

BIOLOGICAL DATA

| EX. NO. | COMPOUND NAME | NAV 1.7 PX IC$_{50}$ (μM) | NAV 1.5 IWQ IC$_{50}$ (μM) |
|---|---|---|---|
| 779 | 4-(5-chloro-6-(3-chloro-2-methylphenoxy)-3-pyridinyl)-5-ethoxy-2-fluoro-N-(methylsulfonyl)benzamide | 0.09473 | |
| 780 | 4-(5-chloro-6-(3-chloro-2-methylphenoxy)-3-pyridinyl)-5-(difluoromethoxy)-2-fluoro-N-(methylsulfonyl)benzamide | 0.04452 | |
| 781 | 4-(5-chloro-6-(cyclobutyloxy)-3-pyridinyl)-5-(difluoromethoxy)-2-fluoro-N-(methylsulfonyl)benzamide | 0.1451 | |
| 782 | 4-(5-chloro-6-(2,4-dichloro-6-methylphenoxy)-3-pyridinyl)-5-(difluoromethoxy)-2-fluoro-N-(methylsulfonyl)benzamide | 0.01607 | |
| 783 | 4-(6-((1S,2R,4S)-bicyclo[2.2.1]hept-2-yloxy)-5-chloro-3-pyridinyl)-5-(difluoromethoxy)-2-fluoro-N-(methylsulfonyl)benzamide | 0.07322 | |
| 784 | 4-(5-chloro-6-(3,5-dichlorophenoxy)-3-pyridinyl)-5-(difluoromethoxy)-2-(fluoro-N-methylsulfonyl)benzamide | 0.01402 | |
| 785 | 4-(5-chloro-6-(2,3,6-trifluorophenoxy)-3-pyridinyl)-5-(difluoromethoxy)-2-fluoro-N-(methylsulfonyl)benzamide | 0.07326 | |
| 786 | 4-(5-chloro-6-((4-chlorobenzyl)oxy)-3-pyridinyl)-5-(difluoromethoxy)-2-fluoro-N-(methylsulfonyl)benzamide | 0.05558 | |
| 787 | 4-(5-cyano-6-(2,4-dichloro-6-methylphenoxy)-3-pyridinyl)-2,5-difluoro-N-(methylsulfonyl)benzamide | 0.07889 | |
| 788 | 4-(5-chloro-6-(2,4-dichloro-6-methylphenoxy)-3-pyridinyl)-N-(ethylsulfonyl)-3-methoxybenzamide | 0.024805 | 1.38 |
| 789 | 4-(5-chloro-6-(3-chloro-2-methylphenoxy)-3-pyridinyl)-N-(ethylsulfonyl)-3-methoxybenzamide | 0.06692 | |
| 790 | 4-(5-chloro-6-(cyclobutyloxy)-3-pyridinyl)-N-(ethylsulfonyl)-3-methoxybenzamide | 0.123 | |
| 791 | 4-(5-chloro-6-(2,3,6-trifluorophenoxy)-3-pyridinyl)-N-(ethylsulfonyl)-3-methoxybenzamide | 0.03944 | |
| 792 | 4-(6-((1R,2S,4S)-bicyclo[2.2.1]hept-2-yloxy)-5-chloro-3-pyridinyl)-N-(ethylsulfonyl)-3-methoxybenzamide | 0.08531 | |
| 793 | 4-(5-chloro-6-(3,4-dichlorobenzyl)-3-pyridinyl)-3-methoxy-N-(methylsulfonyl)benzamide | 0.0504 | |
| 794 | 3-bromo-4-(5-chloro-6-(2,4-dichloro-6-methylphenoxy)-3-pyridinyl)-N-(methylsulfonyl)benzamide | 0.02751 | |
| 795 | 4-(5-chloro-6-(cyclobutyloxy)-3-pyridinyl)-2-fluoro-5-methyl-N-(1,3-thiazol-2-ylsulfonyl)benzamide | 0.0571 | |
| 796 | 4-(5-chloro-6-(cyclobutyloxy)-3-pyridinyl)-2-fluoro-5-methyl-N-(propylsulfonyl)benzamide | 0.1099 | 9.311 |
| 797 | 4-(5-chloro-6-(cyclobutyloxy)-3-pyridinyl)-N-(cyclopropylsulfonyl)-2-fluoro-5-methylbenzamide | 0.09878 | |
| 798 | 4-(5-chloro-6-(cyclobutyloxy)-3-pyridinyl)-N-(cyclobutylsulfonyl)-2-fluoro-5-methylbenzamide | 0.07388 | >4.9 |
| 799 | 4-(5-chloro-6-(2,4-dichloro-6-methylphenoxy)-3-pyridinyl)-2-fluoro-5-methyl-N-(1,3-thiazol-2-ylsulfonyl)benzamide | 0.023145 | 0.669 |
| 800 | 4-(5-chloro-6-(2,4-dichloro-6-methylphenoxy)-3-pyridinyl)-N-(ethylsulfonyl)-2-fluoro-5-methylbenzamide | 0.09601 | 1.25 |
| 801 | 4-(5-chloro-6-(2,4-dichloro-6-methylphenoxy)-3-pyridinyl)-N-(cyclopropylsulfonyl)-2-fluoro-5-methylbenzamide | 0.05625 | 0.485 |
| 802 | 4-(5-chloro-6-(cyclobutyloxy)-3-pyridinyl)-5-cyclopropyl-2-fluoro-N-(methylsulfonyl)benzamide | 0.1363 | |
| 803 | 4-(2-chloro-6-(3,5-dichlorophenoxy)-4-pyridinyl)-3-methoxy-N-(methylsulfonyl)benzamide | 0.09157 | >3.0 |
| 804 | 4-(5-chloro-6-((1S)-2,2,2-trifluoro-1-methyl-1-phenylethoxy)-3-pyridinyl)-2,5-difluoro-N-(methylsulfonyl)benzamide | 0.07694 | >3.0 |
| 805 | 4-(5-chloro-6-((1R)-2,2,2-trifluoro-1-methyl-1-phenylethoxy)-3-pyridinyl)-2,5-difluoro-N-(methylsulfonyl)benzamide | 0.0534 | >3.0 |
| 806 | 4'-chloro-5-fluoro-2-methyl-N-(methylsulfonyl)-3'-(trifluoromethyl)-4-biphenylcarboxamide | 0.618 | |
| 807 | 3'-chloro-5-fluoro-2-methyl-N-(methylsulfonyl)-4'-(trifluoromethyl)-4-biphenylcarboxamide | 0.4129 | |
| 808 | 4-(5-chloro-6-(2,2-difluoroethoxy)-3-pyridinyl)-2-fluoro-5-methyl-N-(methylsulfonyl)benzamide | 2.431 | |
| 809 | 4-(2,2-difluoro-1,3-benzodioxol-5-yl)-2-fluoro-5-methyl-N-(methylsulfonyl)benzamide | 0.6466 | |
| 810 | 5-fluoro-2-methyl-N-(methylsulfonyl)-4'-(2,2,2-trifluoroethoxy)-4-biphenylcarboxamide | 4.019 | |
| 811 | 5-fluoro-2-methyl-N-(methylsulfonyl)-4'-(1,1,2,2-tetrafluoroethoxy)-4-biphenylcarboxamide | 1.572 | |
| 812 | 5-fluoro-2-methyl-N-(methylsulfonyl)-3'-(1,1,2,2-tetrafluoroethoxy)-4-biphenylcarboxamide | 5.841 | |
| 813 | 3'-chloro-4'-(cyclopropylmethyl)-5-fluoro-2-methyl-N-(methylsulfonyl)-4-biphenylcarboxamide | 0.1411 | |
| 814 | 3'-chloro-4'-ethyl-5-fluoro-2-methyl-N-(methylsulfonyl)-4-biphenylcarboxamide | 0.3814 | |
| 815 | 4-(6-(tert-butylamino)-5-chloro-3-pyridinyl)-2-fluoro-5-methyl-N-(methylsulfonyl)benzamide | 0.2309 | |
| 816 | 4-(6-tert-butoxy-5-chloro-3-pyridinyl)-2-fluoro-5-methyl-N-(methylsulfonyl)benzamide | 0.1556 | |
| 817 | 4-(6-(3,5-dichlorophenoxy)-5-(trifluoromethyl)-3-pyridinyl)-2-fluoro-5-methyl-N-(methylsulfonyl)benzamide | 0.1691 | |
| 818 | 4-(5-chloro-6-((3-methoxybenzyl)sulfanyl)-3-pyridinyl)-2-fluoro-5-methyl-N-(methylsulfonyl)benzamide | 0.1686 | |
| 819 | 4-(5-chloro-6-((4-cyanophenoxy)methyl)-3-pyridinyl)-3-methoxy-N-(methylsulfonyl)benzamide | 6.558 | |
| 820 | 4-(5-chloro-6-isobutoxypyridin-3-yl)-3-(2-methoxy-4-methylpyridin-3-yl)-N-(methylsulfonyl)benzamide Atropisomer A | 23% inhibition at 5 μM | |
| 821 | 4-(5-chloro-6-isobutoxypyridin-3-yl)-3-(2-methoxy-4-methylpyridin-3-yl)-N-(methylsulfonyl)benzamide Atropisomer B | 31.98 | |

TABLE B-continued

BIOLOGICAL DATA

| EX. NO. | COMPOUND NAME | NAV 1.7 PX IC$_{50}$ (µM) | NAV 1.5 IWQ IC$_{50}$ (µM) |
|---|---|---|---|
| 822 | 4-(6-(3,5-dichlorophenoxy)-5-formyl-3-pyridinyl)-3-methoxy-N-(methylsulfonyl)benzamide | 0.1509 | |
| 823 | 4-(6-(3,5-dichlorophenoxy)-5-(difluoromethyl)-3-pyridinyl)-2-fluoro-5-methyl-N-(methylsulfonyl)benzamide | 0.1793 | |
| 829 | 4-(6-(3-chloro-4-methylphenoxy)-5-cyanopyridin-3-yl)-3-methoxy-N-(methylsulfonyl)benzamide | 0.0505 | |
| 832 | 4-(5-chloro-6-((3-chloro-2-methoxy-4-pyridinyl)oxy)-3-pyridinyl)-3-methoxy-N-(methylsulfonyl)benzamide | 0.0923 | |
| 833 | Mixture of 4-(5-chloro-6-((2R)-2-(1-methylethyl)-1-pyrrolidinyl)-3-pyridinyl)-3-(difluoromethoxy)-N-(methylsulfonyl)benzamide and 4-(5-chloro-6-((2S)-2-(1-methylethyl)-1-pyrrolidinyl)-3-pyridinyl)-3-(difluoromethoxy)-N-(methylsulfonyl)benzamide | 0.0721 | |
| 834 | 4-(5-chloro-6-(3,5-difluorophenyl)-3-pyridinyl)-2-fluoro-5-methyl-N-(methylsulfonyl)benzamide | 0.4979 | |
| 835 | 4-(5-chloro-6-(3,4-dichlorophenyl)-3-pyridinyl)-2-fluoro-5-methyl-N-(methylsulfonyl)benzamide | 0.1668 | |
| 836 | 4-(5-bromo-6-(2-methylpropoxy)-3-pyridinyl)-2,5-difluoro-N-(methylsulfonyl)benzamide | 0.5586 | |
| 837 | 2,5-difluoro-4-(5'-fluoro-2'-methoxy-2-(2-methylpropoxy)-3,3'-bipyridin-5-yl)-N-(methylsulfonyl)benzamide | 0.8096 | |
| 838 | 4-(5-(3,5-difluorophenyl)-6-(2-methylpropoxy)-3-pyridinyl)-2,5-difluoro-N-(methylsulfonyl)benzamide | 0.6416 | |
| 839 | 4-(3-chloro-2'-methoxy-4'-methyl-2,3'-bipyridin-5-yl)-2-fluoro-5-methyl-N-(methylsulfonyl)benzamide | 12.83 | |
| 840 | 4-(3-chloro-2'-methoxy-4'-methyl-2,3'-bipyridin-5-yl)-2-fluoro-5-methyl-N-(methylsulfonyl)benzamide | 8.353 | |
| 841 | 4-(6-(3,5-dichlorophenoxy)-5-methyl-3-pyridinyl)-3-methoxy-N-(methylsulfonyl)benzamide | 0.08283 | >3.0 |

The foregoing invention has been described in some detail by way of illustration and example, for purposes of clarity and understanding. Those skilled in the art understand that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited herein are hereby incorporated by reference in their entirety for all purposes to the same extent as if each individual patent, patent application or publication were so individually denoted.

What is claimed is:

1. A compound, or a pharmaceutically acceptable salt thereof, of Formula (Ia):

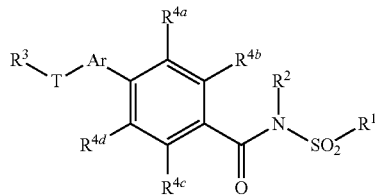

(Ia)

wherein:

Ar is a pyridinyl ring having a structure:

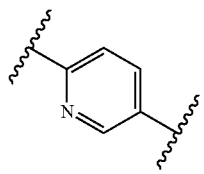 [SMILES: *c1ccc(*)nc1]

substituted by 1, 2, or 3 R$^5$ groups, wherein said pyridinyl ring is selected from the group consisting of:

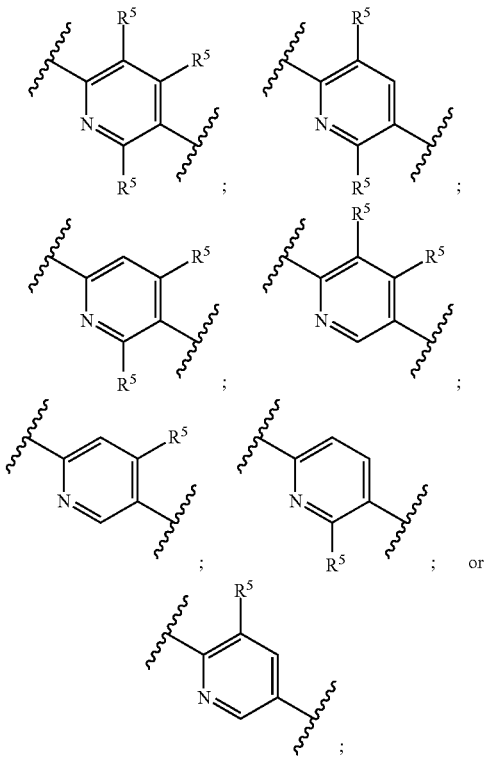

T is absent, —N(R$^f$)—, —(CR$^d$R$^d$)$_r$O(CR$^d$R$^d$)$_r$—, —O(CR$^d$R$^d$)$_p$O(CR$^d$R$^d$)$_p$—, —N(R$^d$)(CR$^d$R$^d$)$_p$—, S, S(=O), or S(=O)$_2$;

R$^1$ is —NHR$^e$, C$_{1-6}$alkyl, a 3- to 6-membered cycloalkyl group, a 4-, 5- to 6-membered heterocyclyl group, or a 4-, 5- to 6-membered heteroaryl group, wherein each C$_{1-6}$alkyl is independently substituted by 0, 1, 2, 3, or 4 R$^7$ groups; and each said heterocyclyl or heteroaryl group is independently substituted by 0, 1, 2, 3, or 4 C$_{1-6}$alkyl or R$^7$ groups;

$R^2$ is H or $C_{1-6}$alkyl;

$R^3$ is a —$(CR^eR^e)_q$(6- to 10-membered aryl) group, a —$(CR^eR^e)_q$(5- to 10-membered heteroaryl) group, a —$(CR^eR^e)_q$(3- to 8-membered cycloalkyl) group, or a —$C(R^eR^e)_q$(3- to 10-membered heterocycloalkyl) group, wherein each $R^3$ aryl, heteroaryl, cycloalkyl or heterocycloalkyl group is independently substituted by 0, 1, 2, 3, or 4 $R^8$ substituents independently selected from an A group, —O-A group, halo, —$CF_3$, —$CF_2H$, —$CFH_2$, —OH, —$OCF_3$, —$OCHF_2$, —$OCH_2F$, $C_{1-6}$alkyl, —$OC_{1-6}$alkyl, —CN, —$(CH_2)_nNR^cR^c$, —$O(CR^d R^d)_pOR^c$, —$N(R^c)_2$, —$NR^d(CH_2)_m$5- to 10-membered aryl, —$NR^d(CH_2)_m$5- to 10-membered heteroaryl, —$(CH_2)_mO(CH_2)_m$6-membered aryl, —$NR^d(CH_2)_m OR^c$, or oxo;

and each occurrence of $R^8$ $C_{1-6}$alkyl, —$OC_{1-6}$alkyl, aryl, or heteroaryl group is independently substituted by 0, 1, 2, 3, or 4 $R^9$ substituents independently selected from a B group, halo, $C_{1-6}$alkyl, —CN, —$CF_3$, —OH, —$OCHF_2$, —$OCH_2F$, —$OCF_3$, —$OC_{1-6}$alkyl, or —$(CH_2)_mNR^dR^d$;

Each $R^{4a}$, $R^{4b}$, $R^{4c}$, and $R^{4d}$ is independently H, halo, —CN, —$OC_{1-6}$alkyl, $C_{1-6}$alkyl, —$CF_3$, $CF_2H$, $CFH_2$, —$OCF_3$, —$OCF_2H$, —$OCFH_2$, or —O—$CH_2CF_3$; wherein each occurrence of said $R^{4a}$, $R^{4b}$, $R^{4c}$, and $R^{4d}$ $C_{1-6}$alkyl group is independently substituted by 0, 1, 2, 3, or 4 halo, CN, $C_{1-6}$alkyl, —$OC_{1-6}$alkyl, —$O(CR^dR^d)_pOR^c$, $NH_2$, OH, or —C(=O)$NH_2$;

each $R^5$ is independently halo, —CN, —$OC_{1-6}$alkyl, $C_{1-6}$alkyl, —$CF_3$, —OH, —$CF_2H$, —$CFH_2$, —$OCF_3$, —$OCF_2H$, or —$OCFH_2$;

an A group is a 5- to 6-membered aryl group, a 5- to 6-membered heteroaryl group, a 3- to 6-membered cycloalkyl group, or a 3- to 6-membered heterocycloalkyl group, wherein the aryl, heteroaryl, cycloalkyl, or heterocycloalkyl group is independently substituted by 0, 1, 2, 3, or 4 substituents independently selected from a B group or $R^6$;

a B group is a 5- to 6-membered aryl group, a 5- to 6-membered heteroaryl group, a 3- to 6-membered cycloalkyl group or a 3- to 6-membered heterocycloalkyl group, wherein the aryl, heteroaryl, cycloalkyl, or heterocycloalkyl group is independently substituted by 0, 1, 2, 3, or 4 substituents independently selected from $R^6$;

each $R^6$ is independently halo, halo$C_{1-6}$alkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, —$OC_{1-6}$alkyl, —O—B group, —$O(CH_2)_m$B group, —$(CH_2)_nNR^dR^d$, —$(CR^dR^d)_pOR^c$, —(C=O)$NR^dR^d$, —S(=O)$_2NR^d$, —$N(R^d)_2$, —$NR^d$(C=O)$NR^dR^d$, —$NR^dS$(=O)$_2NR^d$, —S(=O)$_2R^d$, —$NR^d(CH_2)_mOR^c$ or —$SC_{1-6}$alkyl, wherein each occurrence of $R^6$ $C_{1-6}$alkyl, $C_{2-6}$alkenyl, $C_{2-6}$alkynyl, or $C_{3-6}$cycloalkyl is independently substituted by 0, 1, 2, 3, 4, or 5 substituents independently selected from F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or oxetan-3-yl;

$R^7$ is a B group, halo, —CN, or —$C_{1-6}$alkyl-$OC_{1-6}$alkyl;

each $R^c$ and $R^d$ is independently H or $C_{1-6}$alkyl, and wherein the $C_{1-6}$alkyl is independently substituted by 0, 1, 2, 3, or 4 substituents independently selected from halo, —OH or —CN;

each $R^e$ is independently H, $C_{1-6}$alkyl or a 3- to 6-membered cycloalkyl group; wherein each of the $C_{1-6}$alkyl and the 3- to 6-membered cycloalkyl group is independently substituted by 0, 1, 2, 3, or 4 substituents independently selected from halo, —OH or —CN;

each $R^f$ is independently H or $C_{1-6}$alkyl, and wherein the $C_{1-6}$alkyl is independently substituted by 0, 1, 2, 3, or 4 substituents independently selected from halo, —OH or —CN;

or alternatively, $R^f$ and $R^3$ together with the nitrogen atom they attach to may form a four-membered, five-membered, or six-membered heterocycloalkyl or heteroaryl ring, each of which is independently substituted by 0, 1, 2, 3, or 4 substituents independently selected from halo, —OH or —CN;

each m is independently 0, 1, 2 or 3;
each n is independently 0, 1, 2 or 3;
each p is independently 1, 2, 3, or 4;
each q is independently 0, 1, 2 or 3; and
each r is independently 0, 1, 2 or 3.

2. The compound in accordance with claim 1, or a pharmaceutically acceptable salt thereof, wherein: T is absent, —$(CR^dR^d)_rO(CR^dR^d)_r$—, —$N(R^f)$—, or S, wherein r is 0, 1, or 2.

3. The compound in accordance with claim 1, or a pharmaceutically acceptable salt thereof, wherein: $R^2$ is H.

4. The compound in accordance with claim 1, or a pharmaceutically acceptable salt thereof, wherein each $R^{4a}$, $R^{4b}$, $R^{4c}$, and $R^{4d}$ is independently H, F, Cl, Br, methyl, ethyl, propyl, isopropyl, methoxy, ethoxy, CN, $CF_3$, —$OCF_2H$, or —O—$CF_2H$, wherein at least one of $R^{4a}$, $R^{4b}$, $R^{4c}$, and $R^{4d}$ is not H.

5. The compound in accordance with claim 1, or a pharmaceutically acceptable salt thereof, wherein: $R^{4a}$ is H, Br, —O—$CF_2H$, or methoxy.

6. The compound in accordance with claim 1, or a pharmaceutically acceptable salt thereof, wherein: $R^{4b}$ is H or F.

7. The compound in accordance with claim 1, or a pharmaceutically acceptable salt thereof, wherein: $R^{4c}$ is H or F.

8. The compound in accordance with claim 1, or a pharmaceutically acceptable salt thereof, wherein: $R^{4d}$ is H, F, Cl, methyl, isopropyl, or methoxy.

9. The compound in accordance with claim 1, or a pharmaceutically acceptable salt thereof, wherein: $R^5$ is Cl, CN, $CF_3$, $CHF_2$, or methyl.

10. The compound in accordance with claim 1, or a pharmaceutically acceptable salt thereof, wherein: le is methyl, ethyl, propyl, cyclopropyl, cyclobutyl, —$NH_2$, —$NHCH_3$, —$NHCH_2CH_3$, —$NHCH(CH_3)_2$, —NH-cyclopropyl, azetidinyl, or thiazolyl.

11. The compound in accordance with claim 1, or a pharmaceutically acceptable salt thereof, wherein: $R^f$ and $R^3$ together with the nitrogen atom they attach to form a four-membered or five-membered heterocycloalkyl or heteroaryl ring, each of which is independently substituted by 0, 1, 2, 3, or 4 substituents independently selected from halo, —OH or —CN.

12. The compound in accordance with claim 1, or a pharmaceutically acceptable salt thereof, wherein
$R^5$ is independently Cl, F, methyl, —CN, —$CF_3$, or —$CF_2H$.

13. The compound in accordance with claim 1, or a pharmaceutically acceptable salt thereof, wherein: $R^3$ is selected from:
(a) phenyl, naphthyl, or benzyl,
(b) pyridyl, pyrimidyl, pyrazinyl, pyridazinyl, pyrazolyl, pyridazinyl, triazolyl, piperazinyl, quinolinyl, or benzothiazolyl,
(c) cyclopropyl, cyclobutyl, cyclopentyl, cyclohexyl, spiro[2.4]heptyl, spiro[3.3]heptyl, —CH$_2$-cyclobutyl, —CH$_2$—CH$_2$-cyclopentyl, dihydroindenyl, tetrahydronaphthyl or bicyclo[2.2.1]heptyl, or
(d) piperidinyl, pyrrolidinyl, or azetidinyl,
wherein each $R^3$ is substituted by 0, 1, 2, or 3 $R^8$ substituents independently selected from F, Cl, Br, methyl, ethyl, isopropyl, tert-butyl, CF$_3$, methoxy, ethoxy, isopropoxy, —O—CF$_3$, —O-oxetanyl, or phenyl.

14. The compound in accordance with claim 1, or a pharmaceutically acceptable salt thereof, wherein: $R^3$ is phenyl or pyridyl substituted by 1, 2, or 3 $R^8$ substituents independently selected from F, Cl, Br, methyl, ethyl, isopropyl, tert-butyl, CF$_3$, methoxy, ethoxy, isopropoxy, —O—CF$_3$, —O-oxetanyl, or phenyl.

15. The compound in accordance with claim 1, or a pharmaceutically acceptable salt thereof, wherein: $R^9$ is CF$_3$, methyl, or chloro.

16. The compound in accordance with claim 1, or a pharmaceutically acceptable salt thereof, wherein: T is —O—.

17. The compound in accordance with claim 1, or a pharmaceutically acceptable salt thereof, wherein: $R^1$ is methyl.

18. The compound in accordance with claim 1, or a pharmaceutically acceptable salt thereof, wherein: $R^1$ is methyl or ethyl; $R^2$ is H; $R^3$ is phenyl, benzthiazolyl, cyclopropyl, cyclobutyl, or pyrrolidinyl; $R^{4a}$ is H or methoxy; $R^{4b}$ is H or F; $R^{4c}$ is H or F; $R^{4d}$ is H, Cl, methyl, methoxy, or —O—CHF$_2$; $R^5$ is Cl, CN, CF$_3$, or —CHF$_2$; T is absent, —O—, —O—CH$_2$—; or —O—(CH)(CH$_3$)—; and $R^8$ is H, F, Cl, methyl, methoxy, CF$_3$, or isopropyl.

19. The compound in accordance with claim 1, or a pharmaceutically acceptable salt thereof, selected from:
4-(5-chloro-6-((4-chlorobenzyl)oxy)-3-pyridinyl)-3-methoxy-N-(methylsulfonyl)benzamide;
4-(5-chloro-6-(3-chloro-2-methylphenoxy)-3-pyridinyl)-3-methoxy-N-(methylsulfonyl)benzamide;
5-chloro-4-(5-chloro-6-(2,3,5-trifluorophenoxy)-3-pyridinyl)-2-fluoro-N-(methylsulfonyl)benzamide;
5-chloro-4-(5-chloro-6-(2,4-dichloro-6-methylphenoxy)-3-pyridinyl)-2-fluoro-N-(methylsulfonyl)benzamide;
4-(5-chloro-6-(3-fluoro-4-methylphenoxy)-3-pyridinyl)-2-fluoro-5-methyl-N-(methyl sulfonyl)benzamide;
4-(5-chloro-6-((1R)-1-(2,5-dichlorophenyl)ethoxy)-3-pyridinyl)-2-fluoro-5-methyl-N-(methyl sulfonyl)benzamide;
4-(6-(3-chloro-2-methylphenoxy)-5-cyano-3-pyridinyl)-3-methoxy-N-(methyl sulfonyl)benzamide;
4-(5-cyano-6-(3,6-dichloro-2-methylphenoxy)-3-pyridinyl)-3-methoxy-N-(methyl sulfonyl)benzamide;
4-(5-chloro-6-(cyclobutyloxy)-3-pyridinyl)-2-fluoro-5-methoxy-N-(methyl sulfonyl)benzamide;
4-(5-chloro-6-(3-chloro-2-methylphenoxy)-3-pyridinyl)-2-fluoro-5-methoxy-N-(methyl sulfonyl)benzamide;
4-(5-chloro-6-((1-methylcyclopropyl)methoxy)-3-pyridinyl)-2-fluoro-5-methoxy-N-(methyl sulfonyl)benzamide;
4-(5-chloro-6-(2,5-difluorophenoxy)-3-pyridinyl)-2-fluoro-5-methoxy-N-(methyl sulfonyl)benzamide;
4-(6-(1,3-benzothiazol-2-ylmethoxy)-5-chloro-3-pyridinyl)-2-fluoro-5-methoxy-N-(methyl sulfonyl)benzamide;
4-(5-chloro-6-((1-(trifluoromethyl)cyclobutyl)oxy)-3-pyridinyl)-2-fluoro-5-methoxy-N-(methyl sulfonyl)benzamide;
4-(5-chloro-6-((trans-3-methylcyclobutyl)oxy)-3-pyridinyl)-2-fluoro-5-methoxy-N-(methyl sulfonyl)benzamide;
4-(5-chloro-6-((1R)-1-cyclobutylethoxy)-3-pyridinyl)-2-fluoro-5-methoxy-N-(methyl sulfonyl)benzamide;
4-(5-chloro-6-(2-chloro-5-methylphenoxy)-3-pyridinyl)-2-fluoro-5-methoxy-N-(methyl sulfonyl)benzamide;
3-chloro-4-(5-chloro-6-(3,5-dichlorophenoxy)-3-pyridinyl)-N-(methyl sulfonyl)benzamide;
4-(5-chloro-6-(2,4-dichloro-6-methylphenoxy)-3-pyridinyl)-5-(difluoromethoxy)-2-fluoro-N-(methylsulfonyl)benzamide;
4-(5-chloro-6-(3,5-dichlorophenoxy)-3-pyridinyl)-5-(difluoromethoxy)-2-fluoro-N-(methyl sulfonyl)benzamide;
4-(5-chloro-6-(2,3,6-trifluorophenoxy)-3-pyridinyl)-N-(ethylsulfonyl)-3-methoxybenzamide;
4-(6-(3,5-dichlorophenoxy)-5-(trifluoromethyl)-3-pyridinyl)-3-methoxy-N-(methyl sulfonyl)benzamide;
4-(5-chloro-6-(3,5-dichlorophenoxy)-3-pyridinyl)-3-methoxy-N-(methylsulfonyl)benzamide;
4-(6-(3-chloro-4-methylphenoxy)-5-cyano-3-pyridinyl)-3-methoxy-N-(methyl sulfonyl)benzamide;
4-(6-(3,5-dichlorophenoxy)-5-(difluoromethyl)-3-pyridinyl)-3-methoxy-N-(methyl sulfonyl)benzamide;
4-(5-chloro-6-(2,3,6-trifluorophenoxy)-3-pyridinyl)-3-methoxy-N-(methyl sulfonyl)benzamide;
4-(5-chloro-6-((3-chloro-2-methoxy-4-pyridinyl)oxy)-3-pyridinyl)-3-methoxy-N-(methyl sulfonyl)benzamide;
4-(5-chloro-6-((2R)-2-(1-methylethyl)-1-pyrrolidinyl)-3-pyridinyl)-3-(difluoromethoxy)-N-(methylsulfonyl)benzamide;
4-(5-chloro-6-((2S)-2-(1-methylethyl)-1-pyrrolidinyl)-3-pyridinyl)-3-(difluoromethoxy)-N-(methylsulfonyl)benzamide; or
4-(5-chloro-6-((4-chlorobenzyl)oxy)-3-pyridinyl)-3-methoxy-N-(methyl sulfonyl)benzamide.

20. A pharmaceutical composition comprising the compound in accordance with claim 1, or a pharmaceutically acceptable salt thereof, and a pharmaceutically acceptable excipient.

* * * * *